(12) United States Patent
Krumlauf et al.

(10) Patent No.: US 8,168,761 B2
(45) Date of Patent: May 1, 2012

(54) ANTIBODY TO SOST PEPTIDES

(75) Inventors: Robb Krumlauf, Mission Hills, KS (US); Debra Ellies, Kansas City, MO (US)

(73) Assignee: Stowers Institute for Medical Research, Kansas City, MO (US)

( * ) Notice: Subject to any disclaimer, the term of this patent is extended or adjusted under 35 U.S.C. 154(b) by 0 days.

(21) Appl. No.: 13/030,703

(22) Filed: Feb. 18, 2011

(65) Prior Publication Data

US 2012/0022237 A1  Jan. 26, 2012

Related U.S. Application Data

(60) Division of application No. 11/508,701, filed on Aug. 23, 2006, now Pat. No. 7,893,218, and a continuation-in-part of application No. 10/464,368, filed on Jun. 16, 2003, now abandoned.

(60) Provisional application No. 60/710,803, filed on Aug. 23, 2005, provisional application No. 60/388,970, filed on Jun. 14, 2002.

(51) Int. Cl.
 *C07K 16/26* (2006.01)
 *C07K 16/00* (2006.01)
(52) U.S. Cl. ............. 530/388.24; 530/387.1; 530/387.9; 530/388.1
(58) Field of Classification Search .................. None
 See application file for complete search history.

(56) References Cited

U.S. PATENT DOCUMENTS

| | | | |
|---|---|---|---|
| 5,780,263 A | 7/1998 | Hastings et al. | |
| 6,395,511 B1 | 5/2002 | Brunkow et al. | |
| 6,489,445 B1 | 12/2002 | Brunkow et al. | |
| 6,495,736 B1 | 12/2002 | Brunkow et al. | |
| 6,803,453 B1 | 10/2004 | Brunkow et al. | |
| 6,875,570 B2 | 4/2005 | Gerlach et al. | |
| 7,381,409 B2 | 6/2008 | Winkler et al. | |
| 7,578,999 B2 | 8/2009 | Winkler et al. | |
| 7,585,501 B2 | 9/2009 | Krumlauf et al. | |
| 7,914,786 B2 | 3/2011 | Krumlauf et al. | |
| 7,968,301 B2 | 6/2011 | Krumlauf et al. | |
| 2003/0166247 A1 | 9/2003 | Brunkow et al. | |
| 2004/0158045 A1 | 8/2004 | Brunkow et al. | |
| 2005/0106683 A1 | 5/2005 | Winkler et al. | |
| 2007/0072797 A1 | 3/2007 | Robinson et al. | |
| 2007/0110747 A1 | 5/2007 | Paszty et al. | |
| 2008/0160060 A1 | 7/2008 | Ellies | |

FOREIGN PATENT DOCUMENTS

| | | |
|---|---|---|
| WO | WO0032773 | 6/2000 |
| WO | WO0192308 | 12/2001 |
| WO | WO0224888 | 3/2002 |

OTHER PUBLICATIONS

Katagiri, T. et al., Skeletal Abnormalities in Doubly Heterozygous Bmp4 and Bmp7 Mice, Developmental Genetics 22:340-348 (1998).
Patel, KS. et al., Regulation of Bone Formation and Vision by LRP5, The New England Journal of Medicine 346 (20):1572-1574 (May 16, 2002).
Solloway, M.J. et al., Mice Lacking Bmp8 Function, Developmental Genetics 22321-339 (1998).
Winkler, D.G. et al., Osteocyte control of bone formation via sclerostin, a novel BMP antagonist, The European Molecular Biology Organization Journal 22(23):6287-6276 (2003).
Kusu, N. et al. Sclerostin is a novel secreted osteoclast-derived bone morphogenetic protein antagonist with unique ligand specificity. J Biol Chem 278, 24113-7 (2003).
Sasai, Y. et al. *Xenopus chordin*: a novel dorsalizing factor activated by organizer-specific homeobox genes. Cell 79, 779-90 (1994).
Hsu, D. R Economides, A. N., Wang, X., Eimon, P. M. & Harland, R. M. The *Xenopus* dorsalizing factor Gremlin identifies a novel family of secreted proteins that antagonize BMP activities. Mol Cell 1, 673-83 (1998).
Stanley, E. et al. DAN is a secreted glycoprotein related to *Xenopus cerberus*. Mech Dev 77, 173-84 (1998).
Yokouchi, Y., Vogan, K. J., Pearse, R. V., 2nd & Tabin, C. J. Antagonistic signaling by Caronte, a novel Cerberus-related gene, establishes left-right asymmetric gene expression, Cell 98, 573-83 (1999).
Abreu, J. G., Ketpura, N. I., Reversade, B. & De Robertis, E. M. Connective-tissue growth factor (CTGF) modulates cell signalling by BMP and TGF-beta. Nat Cell Biol. 4, 599-604 (2002).
Fullwood, P. et al. X linked exudative vitreoretinopathy: clinical features and genetic linkage analysis. Br J Ophthalmol. 77, 168-70 (1993).
Aberg, T. et al. Phenotypic changes in dentition of Runx2 homozygote-null mutant mice. J Histochem Cytochem 52, 131-9 (2004).
Karsenty, G. Minireview: transcriptional control of osteoblast differentiation. Endocrinology 142, 2731-3 (2001).
Sevetson, B., Taylor, S. & Pan, Y. Cbfal/RUNX2 directs specific expression of the sclerosteosis gene (SOST). J Biol Chem (2004).
Gall, C., Lauterborn, J. & Guthrie, K. in Autoradiography and Correlative Imaging (ed. W. E. Stumpf and H. F. Solomon) 379-399 (Academic Press, San Diego, 1995).
Kronenberg, H. M. Twist genes regulate runx2 and bone formation. Dev Cell 6,3 17-8 (2004). Albertsen et al., "A physical map and candidate genes in the BRCA1 region on chromosome 17q12-21," Nature Genetics, 7:472-479 (1994).
Balemans et al., "Localization of the Gene for Sclerosteosis to the van Buchem Disease-Gene Region on Chromosome 17q12-q21," Am. J. Hum. Genet., 64:1661-1669 (1999).
Bradley et al., "Modifying The Mouse: Design and Desire," Bio/Technology, 10:534-539 (1992).
Campbell et al., "Totipotency or Multipotentiality of Cultured Cells: Applications and Progress," Theriogenology, 47:63-72 (1997).
Chan et al., "New paradigm in the treatment of osteoporosis: Wnt pathway proteins and their antagonists," Current Opinion in Investigational Drugs, 8(4):293-298 (2007).

(Continued)

*Primary Examiner* — Sharon Wen
(74) *Attorney, Agent, or Firm* — Bryan Cave LLP

(57) ABSTRACT

The present invention is directed to isolated polypeptides and antibodies suitable for producing therapeutic preparations, methods, and kits relating to bone deposition. One objective of the present invention is to provide compositions that improve bone deposition. Yet another objective of the present invention is to provide methods and compositions to be utilized in diagnosing bone dysregulation. The therapeutic compositions and methods of the present invention are related to the regulation of Wise, Sost, and closely related sequences. In particular, the nucleic acid sequences and polypeptides include Wise and Sost as well as a family of molecules that express a cysteine knot polypeptide.

18 Claims, 33 Drawing Sheets

OTHER PUBLICATIONS

Cook et al., "Structural Basis for a Functional Antagonist in the Transforming Growth Factor β Superfamily," J. Biol. Chem., 280(48):40177-186 (2005).

Hoffman et al., "BMP Signaling Pathways in Cartilage and Bone Formation," Critical Review in Eukaryotic Gene Expression, 11(1-3):23-45 (2001).

Keller et al., "Molecular Recognition of BMP-2 and BMP Receptor IA," Nat. Struct. Mol. Biol., 11(5):481-488 (2004).

Li et al., "Sclerostin Binds to LRP5/6 and Antagonizes Canonical Wnt Signalling," Jour. Bio. Chem., 280(20); 19883-19887 (2005).

Lian et al., "Bone Formation: Osteoblast Lineage Cells, Growth Factors, Matrix Proteins, and the Mineralization Process," Primer on the Metabolic Bone Diseases and Disorders of Mineral Metabolism, 4th Edition, 14-29 (1999).

Mullins et al., "Transgenesis in the Rat and Larger Mammals," J. Clin. Invest., 97(7):1557-1560 (1996).

Oshima et al., "TGF-β Receptor Type II Deficiency Results in Defects of Yolk Sac Hematopoiesis and Vasculogenesis," Developmental Biology, 179:297-302 (1996).

Pittenger et al., "Multilineage Potential of Adult Human Mesenchymal Stem Cells," Science, 284:143-147 (1999).

Pockwinse et al., "Expression of Cell Growth and Bone Specific Genes at Single Cell Resolution During Development of Bone Tissue-Like Organization in Primary Osteoblast Cultures," Journal of Cellular Biochemistry, 49:310-323 (1992).

Schmitt et al., "Bone Morphogenetic Proteins: An Update on Basic Biology and Clinical Relevance," Journal of Orthopaedic Research,17:269-278 (1999).

Smith, "TGF β inhibitors, new and unexpected requirements in vertebrate development," TIG, 15(1):3-5 (1999).

Van Bezooijen et al., "Wnt but Not BMP Signaling is Involved in the Inhibitory Action of Sclerostin on BMP-Stimulated Bone Formation," J. Bone. Miner. Res., 22:19-28 (2007).

Lederman et al., Molecular Immunology, vol. 28, pp. 1171-1181 (1991).

Li et al., PNAS, vol. 77, pp. 3211-3214 (1980).

Houghten et al., New Approaches to Immunization, Vaccines 86, Cold Spring Harbor Laboratory, p. 21-25, 1986.

Campbell, Monoclonal Antibody Technology, 1984, Chapter 1, pp. 1-32.

McGrew, L.L., et al., Wnt and FGF pathways cooperatively pattern anteroposterior neural ectoderm in *Xenopus*, Mechanisms of Development 69:105-114 (1997).

Non-Final Office Action mailed Oct. 15, 2009 in U.S. Appl. No. 11/985,836 (Paper No. 20090930).

Response to Non-Final Office Action mailed Oct. 15, 2009 in U.S. Appl. No. 11/985,836.

Final Office Action mailed May 13, 2010 in U.S. Appl. No. 11/985,836 (Paper No. 20100426).

Response to Final Office Action mailed May 13, 2010 in U.S. Appl. No. 11/985,836.

Krumlauf et al., U.S. Appl. No. 13/030,753, filed Feb. 18, 2011.

Krumlauf et al., U.S. Appl. No. 13/030,863, filed Feb. 18, 2011.

Kolm, P.J. et al., Xenopus Hindbrain Patterning Requires Retinoid Signaling, Developmental Biology 192, 1-16 (1997).

Krieg, PA. et al., In Vitro RNA Synthesis with SP6 RNA Polymerase, Methods in Enzymology 155:397-415 (1988).

Lamb, T.M. et al., Fibroblast growth factor is a direct neural inducer, which combined with noggin generates anterior-posterior neural pattern, Development 121:3827-3636 (1995).

Lee, K.J. et al., The specification of dorsal cell fates in the vertebrate central nervous system, Annual Review of Neuroscience 22(1) 261-294 (1999).

Leyns, L. et al., Frzb-1 is a Secreted Antagonist of Wnt Signaling Expresses in the Spemann Organizer, Cell 88:747-756 (Mar. 21, 1997).

Liem, K.F. et al., A Role for the Roof Plate and Its Resident TGFβ-Related Proteins in Neuronal Patterning in the Dorsal Spinal Cord. Cell 91:127-138 (Oct. 3, 1997).

Liem, KF. et al., Dorsal Differentiation of Neural Plate Cells Induced by BMP-Mediated Signals from Epidermal Ectoderm, Cell 82:969-979 (Sep. 22, 1995).

Lin, X. et al., Daily cooperates with *Drosophila* Frizzled 2 to transduce Wingless signaling, Nature 400:281-284 (Jul. 15, 1999).

Lu, J. et al., Isolation and characterization of checker β-catenin, Gene 196:201-207 (1997).

Lumsden, A. et al., Patterning the Vertebrate Neuraxis, Science 274:1109-1115 (1996).

McGrew, L.L. et al., Specification of the Anteroposterior Neural Axis through Synergistic Interaction of the Wnt Signaling Cascade with noggin and follistatin, Developmental Biology 172:337-342 (1995).

McGrew, L.L. et al., Direct regulation of the Xenopus engrailed-2 promoter by the Wnt signaling pathway, and a molecular screen for Wnt-responsive genes, confirm a role for Wnt signaling during neural patterning in *Xenopus*, Mechanisms of Development 87:21-32 (1999).

McMahon, A.P. et al., The Midbrain-Hindbrain Phenotype of Wnt-1-/Wnt-1- Mice Results from Stepwise Deletion of engrailed-Expressing Cells by 9.5 Days Postcoitum, Cell 69:581-595 (1992).

Moon, R.T. et al., Structurally Related Receptors and Antagonists Compete for Secreted Wnt Ligands, Cell 88:725-728 (Mar. 21, 1997).

Muhr, J. et al., Convergent Inductive Signals Specify Midbrain, Hindbrain, and Spinal Cord Identity in Gastrula Stage Chick Embryos, Neuron 23:689-702 (Aug. 1999).

Muhr, J. et al., Assignment of Early Caudal Identity to Neural Plate Cells by a Signal from Caudal Paraxial Mesoderm, Neuron 19:487-502 (Sep. 1997).

Munsterberg, A.E. et al., Combinatorial signaling by Sonic hedgehog and Wnt family members induces myogenlc bHLH gene expression in the somite, Genes & Development 9:2911-2922 (1995).

Nieuwkoop, P.D. et al., Activation and organization of the central nervous system in amphibians, The Journal of Experimental Zoology 120(1):1-108 (Jun. 1952).

Pera, E.M. et al., A direct screen for secreted proteins in *Xenopus* embryos identifies distinct activities for the Wnt antagonists Crescent and Frzb-1, Mechanisms of Development 98:183-195 (2000).

Piccolo, S. et al., The head Inducer Cerberus is a multifunctional antagonist of Nodal, BMP and Wnt signals, Nature 397:707-710 (Feb. 25, 1999).

Piccolo, S. et al., Dorsoventral Patterning in *Xenopus*: Inhibition of Ventral Signals by Direct Binding of Chordin to BMP-4, Cell 86:589-598 (Aug. 23, 1996).

Pinson, K.I. et al., An LDL-receptor-related protein mediates Wnt signalling in mice, Nature 407:535-538 (Sep. 28, 2000).

Pownall, M.E. et al., eFGF, Xcad3 and Hox genes form a molecular pathway that establishes the anteroposterlor axis in *Xenopus*, Development 122:3881-3892 (1998).

Pownall, M.E. et al., Two phases of Hox gene regulation during early *Xenopus* development, Current Biology 8 (11):673-676.

Rasmussen, J.T. et al., Regulation of eye development by frizzled signaling in *Xenopus*, Proc Natl Acad Sci USA 98 (7):3881-3866 (Mar. 27, 2001).

Rothberg, J.M. et al., slit: an extracellular protein necessary for development of midline glia and commissural axon pathways contains both EGF and LRR domains, Genes & Development 4:2169-2187 (1990).

Ruiz i Altaba, A., Pattern formation in the vertebrate neural plate, TINS 17(6):233-243 (1994).

Salic, A.N. et al., Sizzled: a secreted Xwnt8 antagonist expressed in the ventral marginal zone of *Xenopus* embryos. Development 124:4739-4748 (1997).

Tada, M. et al., Xwnt 11 is a target of *Xenopus* Brachyury: regulation of gastrulation movements via Dishevelled, but not through the canonical Wnt pathway, Development 127:2227-2238 (2000).

Tamai, K. et al., LDL-receptor-related proteins in Wnt signal transduction, Nature 407:530-535 (Sep. 28, 2000).

Trainor, P. et al., Plasticity in mouse neural crest cells reveals a new patterning role for cranial mesoderm, Nature Cell Biology 2:96-102 (Feb. 2000).

Tsuda, M. et al., The cell-surface proteoglycan Daily regulates Wingless signalling in *Drosophila*, Nature 400:276-280 (Jul. 15, 1999).

Vleminckx, K. et al., The C-terminal transactivation domain of β-catenin is necessary and sufficient for signalling by the LEF-1/β-catenin complex in *Xenopus laevis*, Mechanisms of development 81:65-74 (1999).

von Heune, G., A new method for predicting signal sequence cleavage sites, Nucleic Acid Research 14:4683-4690 (1986).

Wallingford, J.B. et al., Disheveled controls cell polarity during *Xenopus* gastrulation, Nature 405:81-85 (May 4, 2000).

Wang, S. et al., Frzb, a Secreted Protein Expressed in the Spemann Organizer, Binds and inhibits Wnt-8, Cell 88:757-766 (Mar. 21, 1997).

Wehrli, M. et al., arrow encodes an LDL-receptor-related protein essential for Wingless signalling, Nature 407:527-530 (Sep. 28, 2000).

Yang, X. et al., CBFAI, OSF-1 Expression and Ex Vivo Mineralisation by Human Osteoprogenitors on 3-Dimensional Porous biodegradable Structures, Poster Session, 47th Annual Meeting, Orthopaedic Research Society, Feb. 25-28, 2001, San Francisco, CA.

Abreu, J.G. et al., Connective tissue growth factor modulates cell signalling by BMP and TGF-β (manuscript).

Beighton, P., Sclerosteosis, Journal of Medical Genetics 25:200-203 (1988).

Kadkhodayan, S. et al., Cloning, Expression, and One-Step Purification of the Minimal Essential Domain of the Light Chain of Botulinum Neurotoxin Type A. Protein Expression and Purification 19:125-130 (2000).
Laurikkala, J. et al., Identification of a secreted BMP antagonist, ectodin, integrating BMP, FGF, and SHH signals from the tooth enamel knot Developmental Biology 264 (1):91-105 (2003).
Marchler-Bauer, A. et al., COD: a curated Entrez database of conserved domain alignments, Nucleic Acids Research 31(1):383-387 (2003).
Stebbins, C.E. et al., Structure of the VHL-ElonginC-ElonginB Comples: Implications for VHL Tumor Suppressor Function, Science Magazine, 284:455-461 (Apr. 16, 1999).
Wood, R.E. et al., Jaw involvement in sclerosteosis: a case report, Dentomaxillofac. Radiol. 17:145-148 (1988).
Balemans, W. et al., Lack of Association Between the SOST Gene and Bone Mineral Density in Perimenopausal Women: Analysis of Five Polymorphisms, Bone, 31(4):515-519 (Oct. 2002).
Ebisawa, T. et al., Characterization of bone morphogenetic protein-6 signaling pathways in osteoblast differentiation, Journal of Cell Science 112:3519-3527 (1999).
Groppe, J. et al., Structural basis of BMP signalling inhibition by the cystine knot protein Noggin, Nature 420:636-642 (Dec. 12, 2002).
Jena, N. et al., BMP7 Null Mutation in Mice: Developmental Defects in Skeleton, Kidney, and Eye, Experimental Cell Research 230:28-37 (1997).
Karsenty, G. et al., Reaching a Genetic and Molecular Understanding of Skeletal Development 2:389-406 (Apr. 2002).
Capecchi, "Targeted Gene Replacement," Scientific American, vol. 270, No. 3, pp. 52-59 (1994).
Houdebine, "Production of Pharmaceutical Proteins From Transgenic Animals," J. Biotech, vol. 34, pp. 269-287 (1994).
Wall, "Transgenic Livestock: Progress and Prospects for the Future," Theriogenology, vol. 45, pp. 57-68 (1996).
Niemann, "Transgenic Farm Animals Get Off The Ground. Transgenic Animals in Agriculture," Transg. Res., vol. 7, pp. 73-75 (1998).
Keri et al., "Luteinizing Hormone Induction of Ovarian Tumors: Oligogenic Differences Between Mouse Strains Dictates Tumor Disposition," PNAS, vol. 97, No. 1, pp. 383-387 (2000).
Brunkow et al., "Bone Dysplasia Sclerosteosis Results From Loss of the SOST Gene Product, A Novel Cysteine Knot-Containing Protein," Am. J. Hum. Genet., vol. 68, pp. 577-589 (2001).
Balmain et al., "Cancer Resistance Genes in Mice: Models for the Study of Tumour Modifiers," Trends in Genetics, vol. 14, No. 4, pp. 139-144 (1998).
Cameron, "Recent Advances In Transgenic Technology," Molec. Biol., vol. 7, pp. 253-265 (1997).
Aubin. J.E. et al., Monoclonal Antibodies as Tools for Studying the Osteoblast Lineage, Microscopy Research and Technique, 33:128-140 (1996).
Bachiller D. et al., The organizer factors Chordin and Noggin are required for mouse forebrain development, Nature, vol. 403 (Feb. 10, 2000).
Balemans, W. et al., Extracellular Regulation of BMP Signaling in Vertebrates: A Cocktail of Modulators, Developmental Biology 250:231-250 (2002).
Balemans, W. et al., Increased bone density in sclerosteosis is due to the deficiency of a novel secreted protein (SOST), Human Molecular Genetics, vol. 10 (5): 537-543 (2001).
Bork, P., The modular architecture of a new family of growth regulators related to connective tissue growth factor, FEBS Letters 327(2):125-130 (Jul. 1993).
Boyden, L.M. et al., High Bone Density Due to a Mutation in LOL-Receptor-Related Protein 5, The New England Journal of Medicine. vol. 346(20). pp. 1513-1521 (May 16, 2002).
Bruder, S.P. et al., Monoclonal Antibodies Reactive With Human Osteogenic Cell Surface Antigens, Elsevier, Bone vol. 21, No. 3:225-235 (Sep. 1997).
Brunkow. M.E. et al., Bone Dysplasla Sclerosteosis Results from Loss of the SOST Gene Product, a Novel Cystine Knot-Containing Protein, Am. J. Hum. Genet. 68:577-589 (2001).
Chen, X. et al., Thy-1 Antigen Expression by Cells in the Osteoblast Lineage, Journal of Bone and Mineral Research, 14 (3): 362-375 (1999).
Dewitt, N., Bone and Cartilage, Nature 423:315 (May 2003).
Gong, Y. et al., LDL Receptor-Related Protein 5 (LRP5) Affects Bone Accrual and Eye Development, Cell 107: 513-523 (Nov. 16, 2001).
Hamersma, H. et al., The natural history of sclerosteosis, Clinical Genetics 63:192-197 (2003).
Harada, S. et al., Control of osteoblast function and regulation of bone mass, Nature 423:349-355 (2003).
Harris, S. et al. Human Fetal Osteoblast Progenitor Cell Lines (hFOB), http.//www.mayo.edutachcomm/93010.html, visited Jun. 11, 2003.
Hartley, K.O. et al., Targeted gene expression in transgenic *Xenopus* using the binary Ga14-UAS system, Proc. Natl. Acad. Sci. 99(3): 1377-1382.
Hartmann, C., Wnt-signaling and skeletogenesis, J. Musculoskel Neuron Interact 2(3):274-276 (2002).
Hemmati-Brivanlou, A., Vertebrate Neural Induction, Annual Review Neuroscience 20:43-60 (1997).
Hoppler, S., Wnt Signalling in *Xenopus* Development, http://www.personal.dundee.ac.uk/-sphopple/research.html, visited on May 1, 2002.
Itasaki, N. et al., Wise, a context-dependent activator and inhibitor of Wnt signaling, Development 130:4295 4305 (2003).
Ivkovic, S. et al., Connective tissue growth factor coordinates chondrogenesis and angiogenesis during skeletal development, Development 130:2779-2791 (2003).
Karsenty G., The complexities of skeletal biology, Nature 423:316-318 (2003).
Kato. M. et al., Cbfa1-Independent decrease in osteoblast proliferation, osteopenia, and persistent embryonic eye vascularization in mice deficient inLrp5, a Wnt coreceptor, The Journal of Cell Biology, 157 (2): 303-314 (Apr. 15, 2002).
Kerszberg, M. et al., A simple molecular model of neurulation, BioEssays 20:758-770 (1998), John Wiley & Sons, Inc.
Kronenberg. H.M. et al., Developmental regulation of the growth plate, Nature 423:332-338 (2003).
Kusu, N. et al., Sclerostin is a Novel Secreted Osteoclast-Derived Bone Morphogenetic Protein (BMP) Antagonist with Unique Ligand Specificity, The American Society for Biochemistry and Molecular Biology, Inc., published on Apr. 17, 2003 as Manuscript M301716200.
Latinkic, B.V. et. al., *Xenopus* Cyr61 regulates gastrulation movements and modulates Wnt signalling, Development 130:2429-2441 (2003).
Little, R.D. et. al., A Mutation in the LDL Receptor-Related Protein 5 Gene Results in the Autosomal Dominant High-Bone-Mass Trait, The American Journal of Human Genetics 70:11-19 (2002).
Little, R.D. et. al., High Bone Density Due to a Mutation in LDL-Receptor-Related Protein 5, The New England Journal of Medicine, vol. 347(12), pp. 943-944 (Sep. 19, 2002).

Mao, B. et. al., LDL-receptor-related protein 6 is a receptor for Dickkopf proteins, Nature 411:321-325 (May 17, 2001).
Mathis, J.R. et. al., Pre-Steady-State Study of Recombinant Sesquiterpene Cyclases, Biochemistry 38:8340-8348 (1997).
McClary, K. et al., The Effects of Ascorbic Acid on the Osteoblast Extracellular Matrix, http://lsvl.la.asu.edu/ubep2001/abstracts/mcclaryl, visted on Jun. 11, 2003.
McMahon, J.A. et al., Noggin-mediated antagonism of BMP signaling is required for growth and patterning of the neural tube and somite, Genes & Development 12:1438-1452.
Meitinger, T. et al., Molecular modelling of the Norrie disease protein predicts a cystine knot growth factor tertiary structure, Nature Genetics, vol. 5 (Dec. 1993).
Nijweide, P.J. et al., Identification of osteocytes in osteoblast-like cell cultures using a monoclonal antibody specifically directed against osteocytes, Histochemistry 84:342-347 (1986).
Prince, V.E. et al., Hox gene expression reveals regionalization along the anteroposterior axis of the zebrafish notochord, Dev Genes Evol 208:517-522 (1998).
Rosen, C.J. et al., Defining the Genetics of Osteoporosis: Using the Mouse to Understand Man, Osteoporosis International 12:803-810 (2001).
Segarini, P.R. et al., The Low Density Lipoprotein Receptor-Related Protein/alpha2-Macroglobulin Receptor is a Receptor for Connective Tissue Growth Factor (CTGF), The American Society for Biochemistry and Molecular Biology, Inc., Published on Aug. 22, 2001 as Manuscript M105180200.
Simmons, D.G. et al., Uterine Sensitization-Associated Gene-1: A Novel Gene Induced Within the Rat Endometrium at the Time of Uterine Receptivity/Sensitization for the Decidual Cell Reaction, Biology of Reproduction 67:1638-1645 (2002).
Stephen. L.X.G. et al., Dental and oral manifestations of Sclerosteosis, International Dental Journal 51:287-290 (2001).
Streit, A. et al., Neural induction a bird's eye view, Trends in Genetics 15(1): 20-24 (1999).
Tamai, K. et al., LDL-receptor-related proteins in Wnt signal transduction. Nature 407:530-535 (2000).
Thisse, B. et al., Activin-and Nodel-related factors control anteroposterior patterning of the zebrafish embryo, Nature, vol. 403 (Jan. 27, 2000).
Torres, R.M. et al., The Cologne Guide to Gene Targeting (manuscript) (1995).
Wu, W. et al., Mutual antagonism between dickkopf1 and dickkopf2 regulates Wnt/beta-catenin signaling, Current Biology 14-28; 10 (24) 1611-14 (2000).
Zelzer, E. et al., The genetic basis for skeletal diseases, Nature 423:343-348 (2003).
Amaya, E. et al., Expression of a Dominant Negative Mutant of the FGF Receptor Disrupts Mesoderm Formation in *Xenopus* Embryos, Cell 66:257-270 (Jul. 26, 1991).
Axelrod, J.D. et al., Differential recruitment of Dishevelled provides signaling specificity in the planar cell polarity and Wingless signaling pathways, Genes & Development 12:2610-2622 (1998).
Baker, J.C. et al., Wnt signaling in *Xenopus* Embryos Inhibits Bmp4 expression and activates neural development, Genes & Development 13:3149-3159 (1999).
Beddington, R. et al., Anterior patterning in mouse, Trends in Genetics 14:277-284 (Jul. 1998).
Beddington, R. et al., Axis Development and Early Asymmetry in Mammals, Cell 96:195-209 (Jan. 22, 1999).
Blumberg, B. et al., An essential role for retinoid signaling in anteroposterior neural patterning, Development 124:373-379 (1997).
Bourguignon, C. et al., XBF-1, a winged helix transcription factor with dual activity, has a role in positioning neurogenesis in *Xenopus* competent ectoderm, Development 125:4889-4900 (1998).
Bradley, L. et al., Different Activities of the Frizzled-Rotated Proteins frzb2 and sizzled2 during *Xenopus* Anteroposterior Patterning, Developmental Biology 227:118-132 (2000).
Brannon, M. et al., A β-catentn/XTcf-3 complex binds to the slamois promoter to regulate dorsal axis specification in *Xenopus*, Genes & Development 11:2359-2370 (1997).
Cadigan, K.M. et al., Wnt signaling: a common theme in animal development, Genes & Development 11:3286-3305 (1997).

Capdevila, J. et al., Control of Dorsoventral Somite Patterning by Wnt-1 and β-Catenin, Developmental Biology 193:182-194 (1998).
Christian, J.L. et al., Interactions between Xwnt-8 and Spemann organizer signaling pathways generate dorsoventral pattern in the embryonic mesoderm of *Xenopus*. Genes & Development 7:13-28 (1993).
Condie, B.G. et al., Most of the Homeobox-Containing Xhox 36 Transcripts in Early *Xenopus* Embryos Cannot Encode a Homeodomain Protein, Molecular and Cellular Biology 10:3376-3385 (Jul. 1990).
Cox, W.G. et al., Caudalization of neural fate by tissue recombination and bFGF, Development 121:4349.4358 (1995).
Danielian, P.S. et al., Engrailed-1 as a target of the Wnt-1 signalling pathway in vertebrate midbrain development, Nature 383:332-334 (Sep. 26, 1996).
Dickinson, ME. et al., Dorsalization of the neural tube by the nonneural ectoderm, Development 121: 2099-2106 (1995).
Doniach, T., Planar and Vertical induction of anteroposterior Pattern during the Development of the amphibian Central Nervous System, Journal of Neurobiology 24 (10):1256-1275 (1993).
Ensini, identity et al., The control of rostrocaudal pattern in the developing spinal cord: specification of motor neuron subtype identity is initiated by signals from paraxial mesoderm, Development 125:969-982 (1998).
Fagotto, F. et al., Induction of the primary dorsalizing center in *Xenopus* by the Wnt/GSK/β-catenin signaling pathway, but not by Vg1, Activin or Noggin, Development 124:453-460 (1997).
Fan, M.J. et al., A role for Siamois in Spemann organizer formation, Development 124:2581-2589 (1997).
Fredieu, J.R. et al., Xwnt-8 and Lithium Can Act upon either dorsal Mesodermal or Neurectodermal Cells to Cause a Loss of Forebrain in *Xenopus* Embryos, Developmental Biology 188: 100-114 (1997).
Gavalas, A. et al., Retinoid signalling and hindbrain patterning, Cur Opin Genet Dev 10:380-386 (2000).
Glinka, A. et al., Dickkopf-1 is a member of a new family of secreted proteins and functions in head induction, Nature 391:357-382 (Jan. 22, 1998).
Glinka, A. et al., Head induction by simultaneous repression of Bmp and Wnt signalling in *Xenopus*, Nature 389:517-519 (Oct. 2, 1997).
Gould, A. et al., Initiation of Rhombomeric Hoxb4 Expression Requires Induction by Somites and a Retinoid Pathway, Neuron 21:39-51 (Jul. 1998).
Grapin-Botton, A. et al., Hox gene Induction in the neural tube depends on three parameters: competence, signal supply and paralogue group, Development 124:849-859 (1997).
Hamburger, V. et al., A series of normal stages in the development of the chick embryo, J. Morph. 88:49-92 (1951).
He, X. et al., A Member of the Frizzled Protein Family Mediating Axis Induction by Wnt-5A, Science 275:1652-1654 (Mar. 14, 1997).
Heasman, J. et al., β-Catenin Signaling Activity Dissected in the Early *Xenopus* Embryo: A Novel Antisense Approach, Developmental Biology 222:124-134 (2000).
Heisenberg, C.P. et al., Silberblick/Wnt11 mediates convergent extension movements during zebrafish gastrulation, Nature 405:76-81 (May 4, 2000).
Hemmati-Brivanlou, A. et al., Follistatin, an Antagonist of Activin, is Expressed in the Spemann Organizer and Displays Direct Neuralizing Activity, Cell 77:283-295 (Apr. 22, 1994).
Hemmati-Brivanlou, A. et al., Vertebrate Embryonic Cells Will Become Nerve Cells Unless Told Otherwise, Cell 88:13-17 (Jan. 10, 1997).
Hemmati-Brivanlou, A. et al., Inhibition of Activin Receptor Signaling Promotes Neuralization in *Xenopus*, Cell 77:273-281 (Apr. 22, 1994).
Hoppler, S. et al., Expression of a dominant-negative Wnt blocks induction of MyoD in *Xenopus* embryos, Genes & Development 10:2805-2817 (1996).
Hsieh, J.C. et al., A new secreted protein that binds to Wnt proteins and inhibits their activities, Nature 398:431-436 (Apr. 1, 1999).
Itasaki, N. et al., Reprogramming Hox Expression in the Vertebrate Hindbrain: Influence of Paraxial Mesoderm and Rhombomere Transposition, Neuron 18:487-500 (Mar. 1996).

Itoh, K. et al., Graded amounts of *Xenopus* dishevelled specify discrete anteroposterior cell fates in prospective ectoderm, Mechanisms of Development 61:113-125 (1997).

Itoh, K. et al., Axis determination by inhibition of Wnt signaling in *Xenopus*, Genes & Development 13:2328-2338 (1999).

Itoh. K. et al., Specific modulation of ectodermal cell fates in *Xenopus* embryos by glycogen syntase kinase, Development 121:3979-3988 (1995).

Jones, C.M. et al., An Overview of *Xenopus* Development, Methods in Molecular Biology 97:331-340 (1999).

Jones, C.M. et al., Wholemount In Situ Hybridization to *Xenopus* Embryos, Methods in Molecular Biology 97:635-640 (1999).

Joyner, XL, Engrailed, Wnt and Pax genes regulate midbrain-hindbrain development, Trends in Genetics 12 (1):15-20 (1996).

Kintner, C., Molecular bases of early neural development in *Xenopus* embryos, Ann. Rev. Neurosci 15:251-284 (1992).

Reddi, A.H., Interplay between bone morphogenetic proteins and cognate binding proteins in bone and cartilage development: noggin, chordin and DAN, commentary available online http://arthritis-research.com/content/3/1/001. Arthritis Res., vol. 3, No. 1, 5 pages (2000).

Schweizer, L., et al., Wnt/Wingless signaling through β-catenin requires the function of both LRP/Arrow and frizzied, classes of receptors, BMC Cell Biology research article available at http://www.biomedcentral.com/1471-2121/4/4. BMC Cell Biology, vol. 4, 11 pages (2003).

Moon, R.T., et al., Overview of the role of beta-catenin in specification of the dorsal-ventral axis of Xenopus, http://www.ucalgary.ca/UofC/eduweb/virtualembryo/beta_catenin.html (1998).

Patel, Z., et al., The Role of Retinoic Acid in Patterning of the CNS in Xenopus, http://www.ucalgary.ca/UofC/eduwebg/virtualembryo/retinoic_CNS.html (1998).

FIG. 1E

WISE

SOST

ALP

TRAP

WISE

SOST

ALP

ALP

TRAP

TRAP

FIG. 5M
WISE
FIG. 5N
WISE
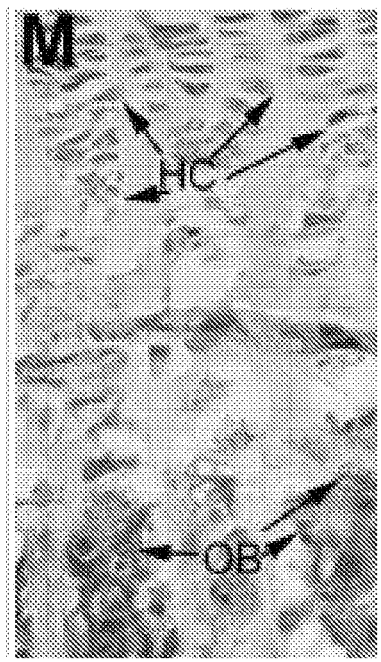
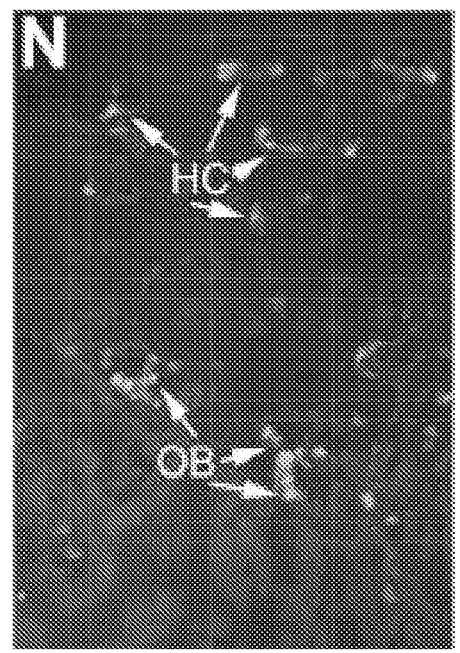

WILDTYPE

WISE -/-

WILDTYPE

WISE -/-

WILDTYPE

WISE -/-

WILDTYPE

WISE -/-

ANTIBODY TO SOST PEPTIDES

CROSS REFERENCES TO RELATED APPLICATIONS

The present application claims benefit to and is a divisional application of U.S. patent application Ser. No. 11/508,701, which was filed on Aug. 23, 2006, now U.S. Pat. No. 7,893, 218 which has now been allowed. The '701 application claims benefit to U.S. Provisional Application No. 60/710, 803 which was filed on Aug. 23, 2005 and is now expired. The '701 application also claims benefit, as a continuation-in-part, to U.S. application Ser. No. 10/464,368 filed on Jun. 16, 2003, now abandoned. The '368 application claims benefit to U.S. Provisional Application No. 60/308,970, which was filed on Jun. 14, 2002 and is now expired. The entire contents of all the above-identified applications are incorporated by reference in their entirety as if recited in full herein.

INCORPORATION BY REFERENCE OF SEQUENCE LISTING

This application contains references to amino acids and/or nucleic acid sequences that have been filed concurrently herewith as sequence listing text file "0209928_substitute_sequence_listing.txt", file size of 209 KB, created on Jan. 21, 2011. The aforementioned sequence listing is hereby incorporated by reference in its entirety pursuant to 37 C.F.R. §1.52(e)(5).

BACKGROUND

Osteoporosis is often referred to as the "silent disease" because bone loss occurs without symptoms. It affects 55% of Americans over the age of 50, and incurs a medical cost of $47 million a day. Osteoporosis is caused by a disruption in the fine equilibrium between bone resorption and bone deposition. Where osteoblasts control bone deposition and osteoclasts control its resorption. Our poor understanding on the molecular control of bone deposition has lead to many pharmaceutical drugs targeting bone resorption only, i.e. Oestrogen Therapy & Bisphosphonates. Bone deposition was thought to be regulated mainly by the Bone Morphogenetic Protein (BMP) pathway. However, recent data has lead to the discovery of another "bone deposition thermostat," called LRP5. This discovery began with positional cloning of the dominant High Bone Mass (HBM) trait found in Humans. In addition, a loss of LRP5 results in Osteoporosis Pseudoglioma (OPPG) Syndrome that is characterized by a decrease in bone mass. LRP5 is therefore an important player in the regulation of bone deposition. LRP5 has been shown to function as a membrane co-receptor for the WNT pathway. Only since the discovery of LRP5 has the WNT pathway been known to play a pivotal role in bone mass regulation.

SUMMARY OF THE INVENTION

One embodiment of the present invention is an isolated polypeptide suitable for producing a diagnostic or therapeutic preparation. This isolated polypeptide includes at least any 10 contiguous amino acids from a primary amino acid. The primary amino acid sequence is at least 75% homologous to an amino acid sequence selected from the group consisting of SEQ ID NOS: 37-87, 96-99, 101, 106-117, 134-157, 159-168 and 171-211.

In one aspect of the present embodiment, the amino acid sequence is selected from the group consisting of SEQ ID NOS: 159-168.

In another aspect of the present embodiment, the amino acid sequence selected from the group consisting of SEQ ID NOS: 171-211.

In another aspect of the present embodiment, the peptide binds to LRP5 or LRP6 with equal or greater affinity than to wtSOST at 4° C. in an isotonic solution.

In another aspect of the present embodiment, the polypeptide is capable of forming a complex with a wtSOST protein. The complex is incapable of inhibiting a wnt signal of a cell presenting LRP5 or LRP 6 and having a competent wnt pathway.

In another aspect of the present embodiment, the amino acid sequence is selected from the group consisting of SEQ ID NO: 159-168.

In another aspect of the present embodiment, the amino acid sequence is selected from the group consisting of SEQ ID NO: 134-157.

In a further aspect, at least 10 contiguous amino acids is an antigen for an antibody specifically recognizing wtSOST.

In another aspect of the present embodiment, the amino acid sequence is selected from the group consisting of SEQ ID NO: 171-211.

An additional embodiment of the present invention is a method of treating bone diseases. The method involves administering a pharmaceutical including a polypeptide comprising at least any 10 contiguous amino acids from a primary amino acid sequence. The primary amino acid sequence is at least 75% homologous to an amino acid sequence selected from the group consisting of SEQ ID NO: 134-157, 159-168 and 171-211.

In one aspect of the present embodiment, the pharmaceutical further includes a humanized antibody specifically recognizing an osteoblast-specific marker, and the polypeptide is coupled to the antibody.

In another aspect of the present embodiment, the osteoblast-specific marker is selected from the group consisting of LRP5, LRP 6 and SOST.

In another aspect of the present embodiment, the osteoblast-specific marker is selected from the group consisting of Collagen I, Runx2, ALP, osteoporitin, and Sox9.

In another aspect of the present embodiment, the antibody is non-covalently coupled to the polypeptide.

Another embodiment of the present invention is an isolated antibody specifically recognizing a polypeptide. The polypeptide includes at least any 10 contiguous amino acids from a primary amino acid sequence at least 75% homologous to an amino acid sequence selected from the group consisting of SEQ ID NOS: 37-87, 96-99, 101, 106-117, 134-157, 159-168 and 171-211.

In one aspect of the present embodiment, the amino acid sequence is selected from the group consisting of SEQ ID NO: 134-157 and 159-168.

In another aspect of the present embodiment, the antibody is a humanized antibody.

One embodiment of the present invention is a pharmaceutical preparation. The pharmaceutical preparation includes an isolated polypeptide comprising a primary amino acid and a pharmaceutically acceptable excipient. The primary amino acid sequence of the pharmaceutical preparation is at least 75% homologous to an amino acid sequence selected from the group consisting of SEQ ID NOS: 37-87, 96-99, 101, 106-117, 134-157, 159-168 and 171-211.

In one aspect of the present embodiment, the amino acid sequence is selected from the group consisting of SEQ ID NO: 159-168.

In another aspect of the present embodiment, the amino acid sequence is selected from the group consisting of SEQ ID NO: 171-211.

An embodiment of the present invention is also an isolated nucleic acid comprising a coding sequence encoding a polypeptide suitable for producing a diagnostic or therapeutic preparation. The polypeptide includes at least any 10 contiguous amino acids from a primary amino acid sequence at least 75% homologous to an amino acid sequence selected from the group consisting of SEQ ID NOS: 37-87, 96-99, 101, 106-117, 134-157, 159-168 and 171-211.

In one aspect of the present embodiment, the amino acid sequence is selected from the group consisting of SEQ ID NO: 159-168.

In another aspect of the present embodiment, the amino acid sequence selected from the group consisting of SEQ ID NO: 171-211.

In a further aspect, the amino acid sequence includes control sequences operably linked to the coding sequence, whereby translation of coding sequence directed by the control sequences produces the polypeptide.

An additional embodiment of the present invention is a recombinant cell system capable of synthesizing polypeptide suitable for producing a diagnostic or therapeutic preparation. The polypeptide includes at least any 10 contiguous amino acids from a primary amino acid sequence at least 75% homologous to an amino acid sequence selected from the group consisting of SEQ ID NO:106-117, 134-157, 159-168 and 171-211. The cell system also includes a recombinant nucleic acid with a coding sequence encoding the polypeptide, wherein the polypeptide is suitable for producing a diagnostic or therapeutic preparation.

In one aspect of the present embodiment, the cell system is a cell lysate.

In another aspect of the present embodiment, the cell system is a eukaryotic cell.

In another aspect of the present embodiment, the eukaryotic cell system is a mammalian cell.

In another aspect of the present embodiment, the recombinant nucleic acid further includes control sequences for modulating the expression of the polypeptide operably linked to the coding sequence.

Yet another embodiment of the present invention is method of identifying pharmaceutically-active compounds suitable for treatment of bone diseases. The method includes contacting a cell capable of producing a wnt or bmp signal with a compound of interest and a polypeptide. Specifically, the polypeptide includes at least any 10 contiguous amino acids from a primary amino acid sequence at least 75% homologous to an amino acid sequence selected from the group consisting of SEQ ID NO: 106-117, 134-157, 159-168 and 171-211. The method further includes determining if the compound blocks the wnt or bmp signal of the cell, wherein a determination that the writ or bmp signal is blocked indicates that the compound of interest may be suitable for treatment of bone diseases.

An additional embodiment of the present invention is a method of identifying pharmaceutically-active compounds suitable for treatment of bone diseases. The method includes contacting a solution comprising LRP5 or LRP6 with a compound of interest and a polypeptide. The polypeptide includes at least any 10 contiguous amino acids from a primary amino acid sequence at least 75% homologous to an amino acid sequence selected from the group consisting of SEQ ID NO: 171-211. The method further includes determining if the compound of interest blocks interaction of LRP5 or LRP6 with the polypeptide.

Another embodiment of the present invention is a method of identifying pharmaceutically-active compounds suitable for treatment of bone diseases. The method includes contacting a transgenic animal with a compound of interest. The method further includes the transgenic animal displaying a bone disease phenotype resulting from a deleterous mutation of an endogenous SOST gene and the transgenic animal having a nucleic acid comprising a coding sequence encoding an expressed polypeptide. The expressed polypeptide includes at least any 10 contiguous amino acids from a primary amino acid sequence at least 75% homologous to an amino acid sequence selected from the group consisting of SEQ ID NO: 106-117, 134-157, 159-168 and 171-211. The method also includes determining if the bone disease regresses to at least 50% of a normal phenotype over a period of two years or less. The determination that the bone disease has regressed to at least 10% of a normal phenotype indicates that the compound of interest may be suitable for treatment of bone malformation diseases.

Another embodiment of the present invention is a method for identifying a SOST protein in a biological sample. The method includes contacting the biological sample with an antibody specifically recognizing a polypeptide. The polypeptide includes at least any 10 contiguous amino acids from a primary amino acid sequence at least 75% homologous to an amino acid sequence selected from the group consisting of SEQ ID NO: 171-211. The method further includes detecting the presence or absence of the antibody complexed with the SOST protein.

Another embodiment of the present invention is a pharmaceutical preparation for modulating bone formation. The preparation includes an antibody specifically recognizing a polypeptide and a pharmaceutically acceptable excipient. The polypeptide includes at least any 10 contiguous amino acids from a primary amino acid sequence at least 75% homologous to an amino acid sequence selected from the group consisting of SEQ ID NO: NOS: 37-87, 96-99, 101, 106-117, 134-157, 159-168 and 171-211. Furthermore, the administering the pharmaceutical preparation to a subject attenuates inhibition of a wnt or bmp response by at least 10%.

In one aspect of the present embodiment, the amino acid sequence is selected from the group consisting of SEQ ID NO: 134-157 and 159-168.

In another aspect of the present embodiment, the pharmaceutical preparation further includes an adjuvant preparation.

Yet another embodiment of the present invention is a pharmaceutical preparation for modulating bone formation. The pharmaceutical preparation includes a polypeptide encoded by a nucleic acid comprising a set of at least 10 contiguous codons selected from, and in phase with the codon beginning with, the first nucleotide of a nucleotide sequence selected from the group consisting of 1-36, 88-95, 100, 102-105, 118-133, 158 and 169-170. The preparation also includes a pharmaceutically acceptable excipient, wherein administering the pharmaceutical preparation to a subject attenuates inhibition of a wnt or bmp response by at least 10%.

In one aspect of this embodiment, the nucleotide sequence is selected from the group consisting of SEQ ID NOS: 1-4, 6-22, 24-30, 33-39, 88-93, 105, 118-120, 125-133, 158.

In another aspect of this embodiment, the nucleotide sequence is from a human.

In another aspect of this embodiment, the pharmaceutical further includes an adjuvant preparation.

Another embodiment of the present invention is an isolated nucleic acid encoding a polypeptide suitable for producing a diagnostic or therapeutic preparation. The nucleic acid includes a set of at least 10 contiguous codons selected from, and in phase with the codon beginning with, the first nucleotide of a nucleotide sequence selected from the group consisting of 1-36, 88-95, 100, 102-105, 118-133, 158 and 169-170.

In one aspect of the present embodiment, the nucleotide sequence is selected from the group consisting of 1-4, 6-22, 24-30, 33-39, 88-93, 105, 118-120, 125-133, 158.

In another aspect of the present embodiment, the nucleotide sequence is from a human.

Another embodiment of the present invention is an isolated antibody specifically recognizing a polypeptide. The polypeptide is encoded by a nucleic acid comprising a set of at least 10 contiguous codons selected from, and in phase with the codon beginning with, the first nucleotide of a nucleotide sequence selected from the group consisting of 1-36, 88-95, 100, 102-105, 118-133, 158 and 169-170.

In one aspect of the present embodiment, the nucleotide sequence is selected from the group consisting of 1-4, 6-22, 24-30, 33-39, 88-93, 105, 118-120, 125-133, 158.

In another aspect of the present embodiment, the nucleotide sequence is from a human.

Yet another embodiment of the present invention is an isolated polypeptide suitable for producing a diagnostic or therapeutic preparation. The polypeptide is encoded by nucleic acid comprising a set of at least 10 contiguous codons selected from, and in phase with the codon beginning with, the first nucleotide of a nucleotide sequence selected from the group consisting of 1-36, 88-95, 100, 102-105, 118-133, 158 and 169-170.

In one aspect of the present embodiment, the nucleotide sequence is selected from the group consisting of 1-4, 6-22, 24-30, 33-39, 88-93, 105, 118-120, 125-133, 158.

In another aspect of the present embodiment, the nucleotide sequence is from a human.

Another embodiment of the present invention is a kit for the treatment of a bone disease. The kit includes a pharmaceutical preparation and an applicator. The pharmaceutical preparation includes an isolated polypeptide and an excipient. The isolated polypeptide includes at least any 10 contiguous amino acids from a primary amino acid sequence at least 75% homologous to an amino acid sequence selected from the group consisting of SEQ ID NOS: 37-87, 96-99, 101, 106-117, 134-157, 159-168 and 171-211.

In one aspect of the present embodiment, the amino acid sequence is selected from the group consisting of SEQ ID NO: 134-157 and 159-168.

In another aspect of the present embodiment, the kit further includes instructions for use of the kit.

In another aspect of the present embodiment, the kit further includes a container having instructions for use of the kit printed thereon, wherein the pharmaceutical preparation is housed in the container.

Another embodiment of the present invention is a kit for the treatment of a bone disease. The kit includes a pharmaceutical preparation and an applicator. The pharmaceutical preparation includes an antibody specifically recognizing a polypeptide and an exipient. The polypeptide recognized by the antibody includes at least any 10 contiguous amino acids from a primary amino acid sequence at least 75% homologous to an amino acid sequence selected from the group consisting of SEQ ID NOS: 37-87, 96-99, 101, 106-117, 134-157, 159-168 and 171-211.

In one aspect of the present embodiment, the amino acid sequence is selected from the group consisting of SEQ ID NO: 134-157 and 159-168.

In another aspect of the present embodiment, the kit further includes instructions for use of the kit.

In another aspect of the present embodiment, the kit further includes a container having instructions for use of the kit printed thereon, wherein the pharmaceutical preparation is housed in the container.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al. *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al, (eds.), Springer Verlag (1991); and Hale & Marham, *The Harper Collins Dictionary of Biology* (1991). As used herein, the following terms have the meanings ascribed to them unless specified otherwise.

As disclosed herein, proteins, particularly antibodies, muteins, nucleic acid aptamers, and peptide and nonpeptide small organic molecules that antagonize specific binding of SOST or WISE to their natural receptors may serve as "binding agents" and "SOST antagonists" of the present invention.

The phrase "specifically (or selectively) binds" or when referring to an antibody interaction, "specifically (or selectively) immunoreactive with," refers to a binding reaction between two molecules that is at least two times the background and more typically more than 10 to 100 times background molecular associations under physiological conditions. When using one or more detectable binding agents that are proteins, specific binding is determinative of the presence of the protein, in a heterogeneous population of proteins and other biologics. Thus, under designated immunoassay conditions, the specified antibodies bind to a particular protein sequence, thereby identifying its presence.

Specific binding to an antibody under such conditions requires an antibody that is selected for its specificity for a particular protein. For example, antibodies raised against a particular protein, polymorphic variants, alleles, orthologs, and conservatively modified variants, or splice variants, or portions thereof; can be selected to obtain only those polyclonal antibodies that are specifically immunoreactive with SOST, WISE or an LRP protein and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Methods for determining whether two molecules specifically interact are disclosed herein, and methods of determining binding affinity and specificity are well known in the art (see, for example, Harlow and Lane, Antibodies: A laboratory manual (Cold Spring Harbor Laboratory Press, 1988); Friefelder, "Physical Biochemistry: Applications to biochemistry and molecular biology" (W.H. Freeman and Co. 1976)).

Furthermore, an α5β1 integrin binding agent can interfere with the specific binding of a receptor and its ligand by various mechanism, including, for example, by binding to the ligand binding site, thereby interfering with ligand binding; by binding to a site other than the ligand binding site of the receptor, but sterically interfering with ligand binding to the receptor; by binding the receptor and causing a conformational or other change in the receptor, which interferes with binding of the ligand; or by other mechanisms. Similarly, the agent can bind to or otherwise interact with the ligand to interfere with its specifically interacting with the receptor. For purposes of the methods disclosed herein, an understanding of the mechanism by which the interference occurs is not required and no mechanism of action is proposed. An α5β1 binding agent, such as an anti-α5β1 antibody, or antigen binding fragment thereof, is characterized by having specific binding activity ($K_a$) for an α5β1 integrin of at least about $10^5$ $mol^{-1}$, $10^6$ $mol^{-1}$ or greater, preferably $10^7$ $mol^{-1}$ or greater, more preferably $10^8$ $mol^{-1}$ or greater, and most preferably $10^9$ $mol^{-1}$ or greater. The binding affinity of an antibody can be readily determined by one of ordinary skill in the art, for example, by Scatchard analysis (Scatchard, Ann. NY Acad. Sci. 51: 660-72, 1949).

The term "antibody" as used herein encompasses naturally occurring antibodies as well as non-naturally occurring antibodies, including, for example, single chain antibodies, chimeric, bifunctional and humanized antibodies, as well as antigen-binding fragments thereof, (e.g., Fab', F(ab')$_2$, Fab, Fv and rIgG). See also, Pierce Catalog and Handbook, 1994-1995 (Pierce Chemical Co., Rockford, Ill.). See also, e.g., Kuby, J., Immunology, 3rd Ed., W.H. Freeman & Co., New York (1998). Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

The term "antibody" includes both polyclonal and monoclonal antibodies. The term also includes genetically engineered forms such as chimeric antibodies (e.g., humanized murine antibodies) and heteroconjugate antibodies (e.g., bispecific antibodies). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547, Pack and Pluckthun (1992) Biochemistry 31:1579, Hollinger et al., 1993, supra, Gruber et al. (1994) J Immunol: 5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

Typically, an antibody has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" refer to the variable region of an immunoglobulin heavy chain of an antibody, including the heavy chain of an Fv, scFv, or Fab. References to "$V_L$" refer to the variable region of an immunoglobulin light chain, including the light chain of an Fv, scFv, dsFv or Fab.

Reference to "wtSOST" or similar notation is understood to refer to the wild type sequence encoding a given polypeptide. Thus, "wtSOST" refers to the wild type form of SOST.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule that contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., Nature 332: 323-329 (1988); and Presta, Curr. Op. Struct. Biol 2:593-596 (1992)). Humanization can be essentially performed following the method of Winter and co-workers (Jones et al., Nature 321:522-525 (1986); Riechmann et al., Nature 332:323-3'27 (1988); Verhoeyen et al., Science 239:1534-1536 (1988)), by substituting rodent CDRs or CDR sequences for the corresponding sequences of a human antibody. Accordingly, such humanized antibodies are chimeric antibodies (U.S. Pat. No.

4,816,567), wherein substantially less than an intact human variable domain has been substituted by the corresponding sequence from a non-human species.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996). A preferred method for epitope mapping is surface plasmon resonance, which has been used to identify preferred granulation inhibitors recognizing the same epitope region as the IIAI antibody disclosed herein.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (1), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Homologous," in relation to two Of more peptides, refers to two or more sequences or subsequences that have a specified percentage of amino acid residues that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids in length, or more preferably over a region that is 50-100 amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc, Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a peptide is considered similar to a reference sequence if the smallest sum probability in a comparison of the test peptide to the reference peptide is less than about 0.2, more preferably less than about 0.01, and most preferably less than about 0.001. Log values may be large negative numbers, e.g., 5, 10, 20, 30, 40, 40, 70, 90, 110, 150, 170, etc.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

DESCRIPTION OF THE DRAWINGS

FIG. 1E shows an alignment of known cystein knot containing proteins. Conserved cystein residues are highlighted in yellow and the consensus cystein knot sequence is CCCGC . . . CCG/PCC.

DETAILED DESCRIPTION

I. Introduction

The present invention is directed to compositions and methods that promote bone deposition in vertebrates. In particular, the present invention is directed to compositions and methods that antagonize the interaction between SOST and WISE proteins with their natural receptors particularly LRP5 and LRP 6. For example, any peptide of at least 20, preferably 25, 30, 35, 40, 50 or more amino acids encoded by SEQ ID NO:1, 3, 5, 7, 9, 11, 13, 19, 83, 84, 88, 89, 90, 92, 94, 96, 97, 99, 100, 102, 104, 106, 107 or 108, or any fragment of any sequence thereof, may be used to raise antibodies suitable for antagonizing the interaction between SOST and WISE proteins with their natural receptors. Preferably the immunogen selected is encoded by full length SEQ ID NO:1, 3, 5, 7, 9, 11, 13, 19, 83, 84, 88, 89, 90, 92, 94, 96, 97, 99, 100, 102, 104, 106, 107 or 108, preferably full length SEQ ID NO 1 or 3.

Alternatively the proteins and peptides of SEQ ID NO: 2, 4, 6, 8, 10, 12, 14-18, 20, 85-87, 91, 93, 95, 98, 101, 103, 105, 109-140 or 202-214 may be used to raise antagonists of the present invention. Preferable sequences in this regard are SEQ ID NO:113, 119 and most preferably 214.

A further embodiment are blocking peptides that antagonize the interaction between SOST and WISE proteins with their natural receptors. These include SEQ ID NO 21-82.

Figure 1A:
FIG. 1A shows a schematic depicting the genomic structure of Wise and SOST. Both genes include a 200 bp exon 1, 2.5 Kb intron, and 400 bp exon 2. The Wise mutant was created by insertion of a neoLacZ cassette (red) into exon 1.
Figure 1B:
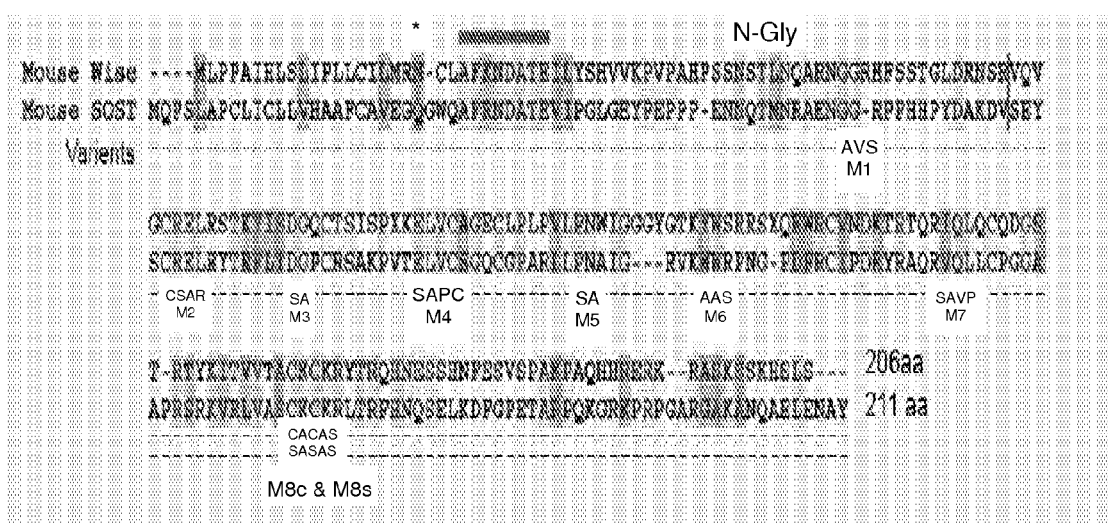
FIG. 1B is an alignment of SOST and Wise cDNA. A leader sequence cleavage site is denoted with a red bar, and a putative N-glycosylation (N-Gly) is also shown.
Figure 1C:
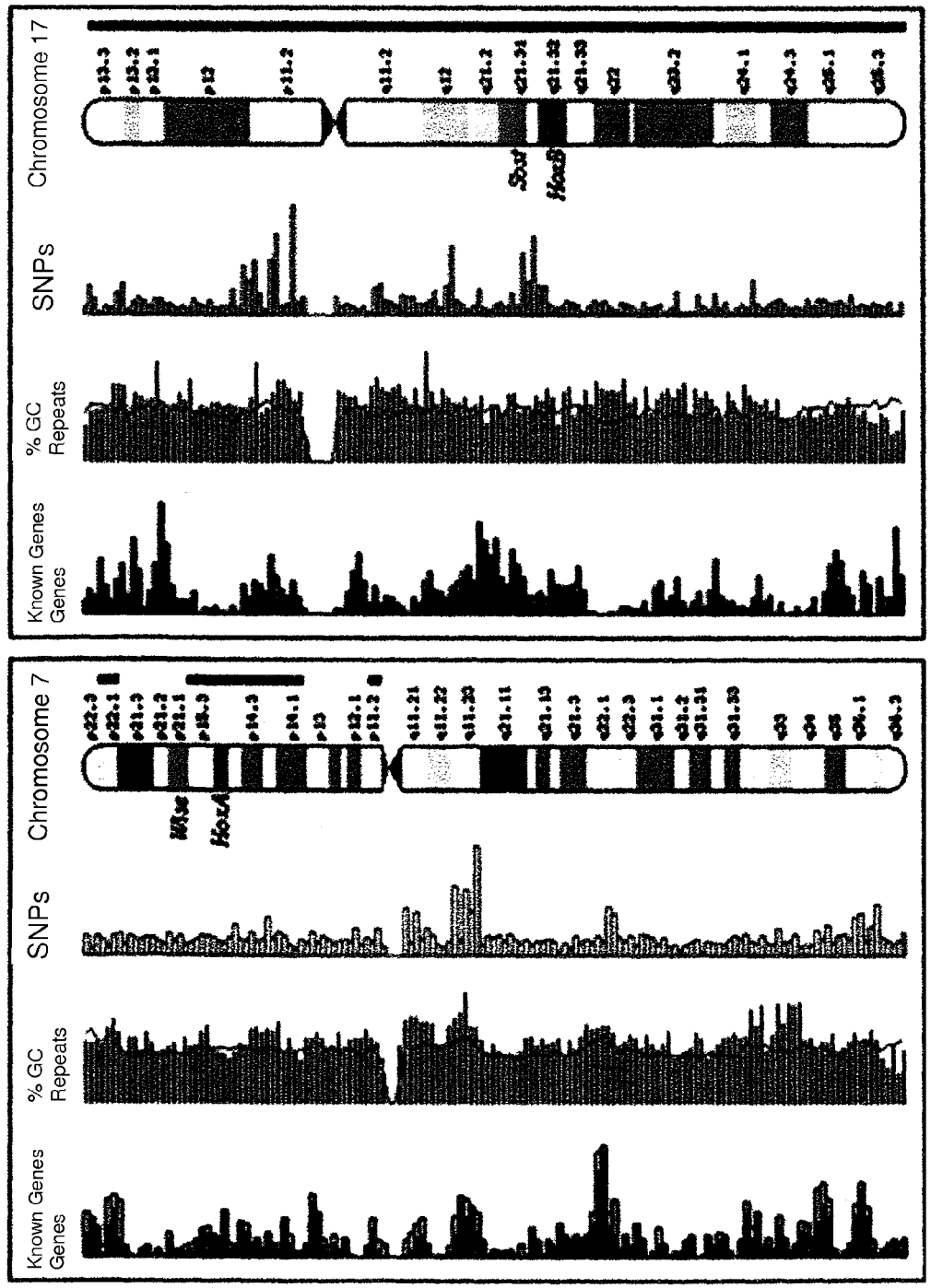
FIG. 1C is a schematic of human chromosomes 7 and 17 showing linkage of SOST with HOXB and Wise with HOX4 clusters.
Figure 1D:
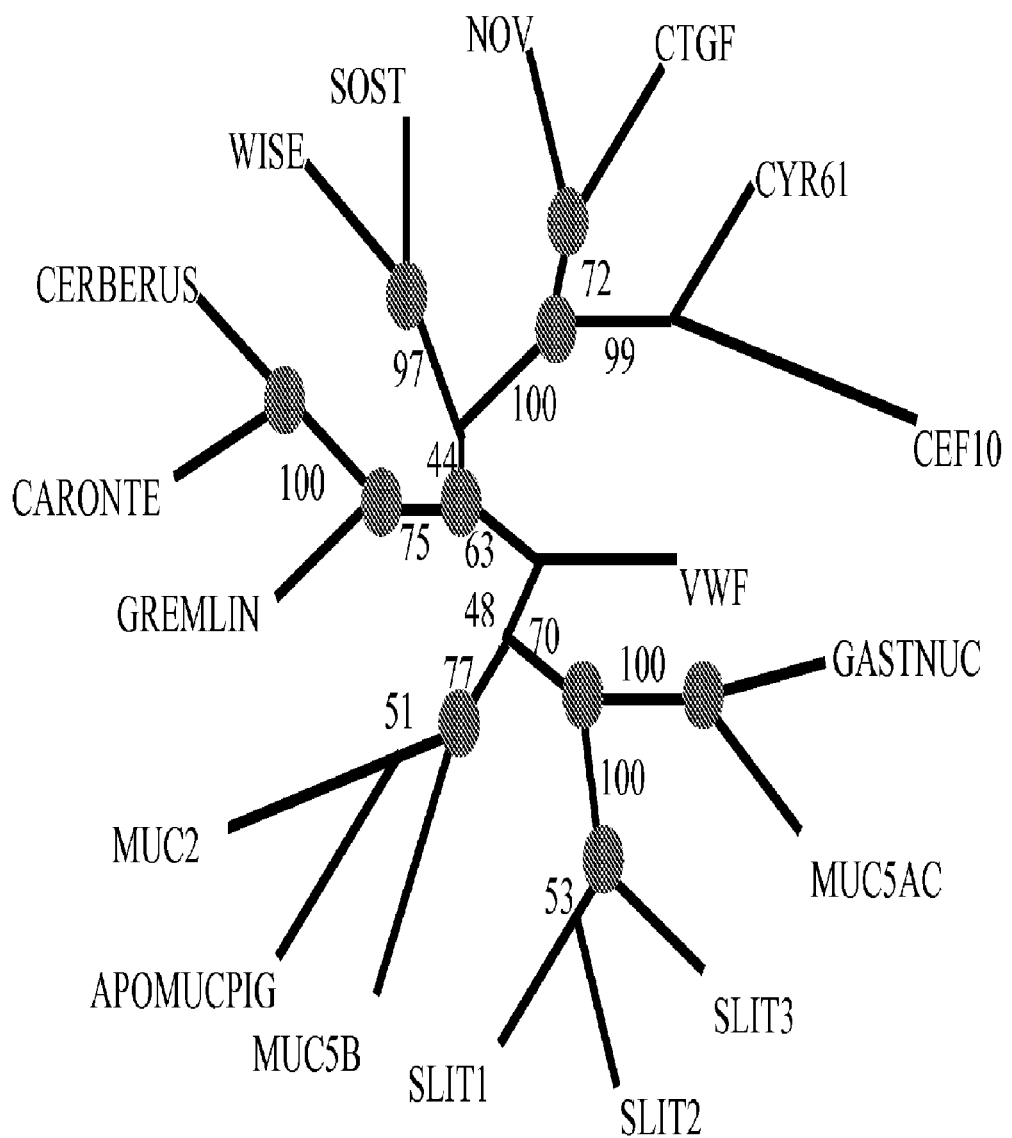
FIG. 1D shows a phylogenetic tree using known protein sequences containing cystein knots. Red dots depict significant branches within the tree. Wise and SOST exist in a branch between the CCN (NOV, CTGF, and CYR61) and DAN (Cereberus, DAN, gremlin, and caronte) families.
Figure 1E:
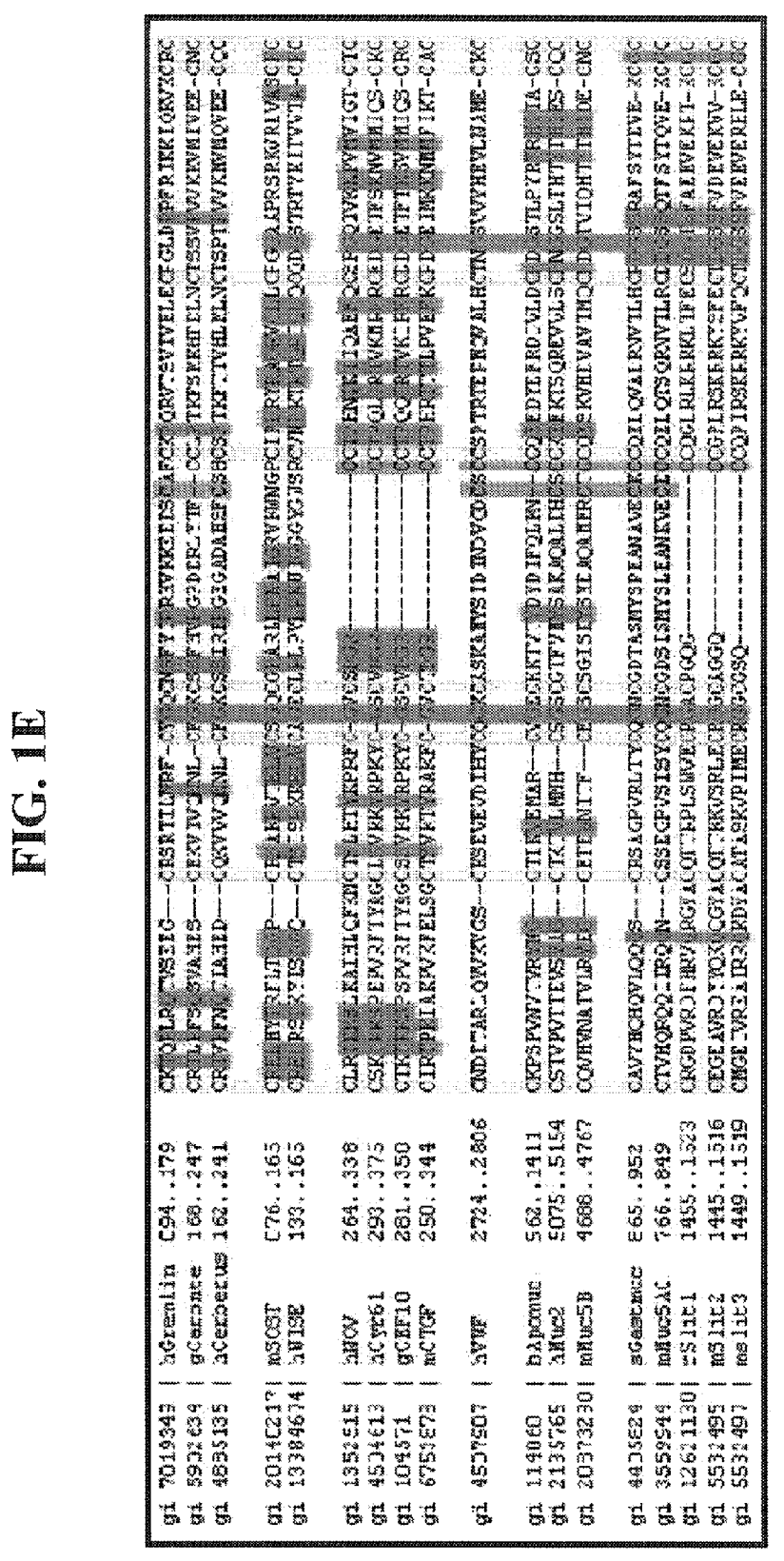

We have isolated the novel WNT inhibitor; Wise, that affects craniofacial anterior-posterior patterning, whose biochemical function we want to address. Wise is a secreted molecule with a genomic structure containing two exons (200 and 400 bp) and a large 2.5 Kb intron (FIG. 1A, 1B). The second exon encodes a cystein knot motif, which bears some homology to known DAN-, and CCN-family members (FIG. 1D, 1E). Wise is mapped to Human chromosome 7p21.1, which is linked to the HOXA cluster by 10.6 Mb (FIG. 1C). The four mammalian HOX clusters are thought to have evolved from a single cluster, as in Drosophila, we therefore searched other clusters for a possible Wise family member. We found that both HOXB and HOXC clusters had an ORF that was examined further. The HOXC cluster ORF, at 4 Mb upstream shares homology to the CCN family. The HOXB cluster contained an ORE at 5 Mb upstream. The HOXB ORF encodes a known gene, SOST (FIG. 1C). SOST was positionally cloned from a familial mutation affecting bone density. SOST and Wise both share the same gene structure, and produce a secreted protein whose second exon (70% homologous) encodes a cystein knot (FIG. 1B). Unlike the known cystein knot motifs from DAN- (Cerberus, DAN, Gremlin, Caronte) or CCN- (NOV, CTGF, Cyr61) family members, WISE and SOST cystein knots contain 8 cysteines instead of 9 (FIG. 1D). Other molecules, Mucin2 and VWF have cystein knots containing 10 cysteines, but are arranged in a manner similar to both the CCN- and DAN-family (FIGS. 1D and 1E). DAN and CCN cystein knots share about 50% homology to those of WISE and SOST (FIG. 1E). In addition to the cystein knot domain, CCN proteins also encode for Insulin binding, Von Willderbrand (BMP antagonist-like domain), and TSP1 domains. However, the DAN family appears to only encode for a cystein knot domain. Other genes that encode a cystein knot domain include Slits, VWF, Mucins, and NDP (FIGS. 1D and 1E).

Figure 2A:
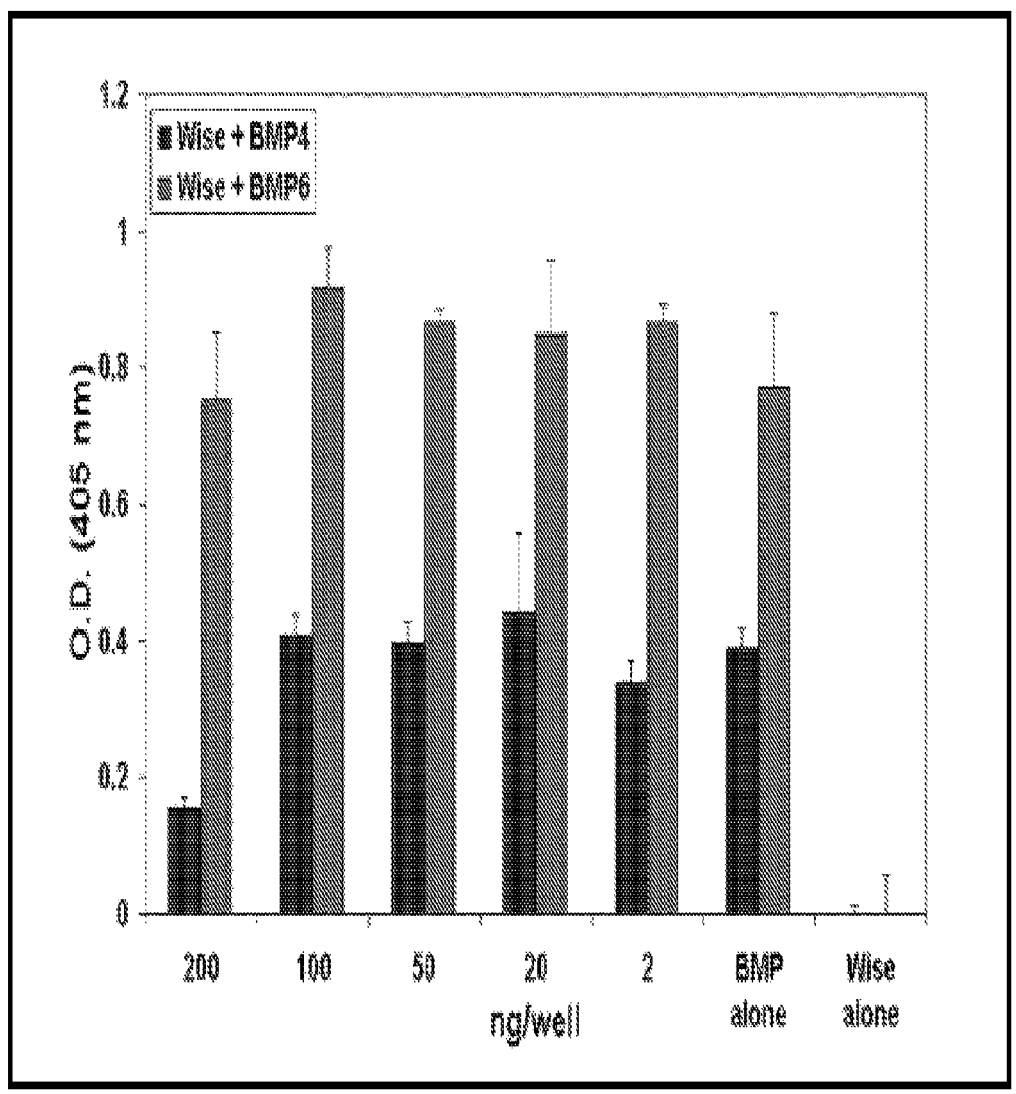
FIG. 2A graphically demonstrates that Wise does not inhibit the action of BMP4 or BMP6. These results were obtained from a BMP inhibition assay using ATDC-5 cells and exogenous Wise protein with BMP4 or BMP6 protein.
Figure 2B:
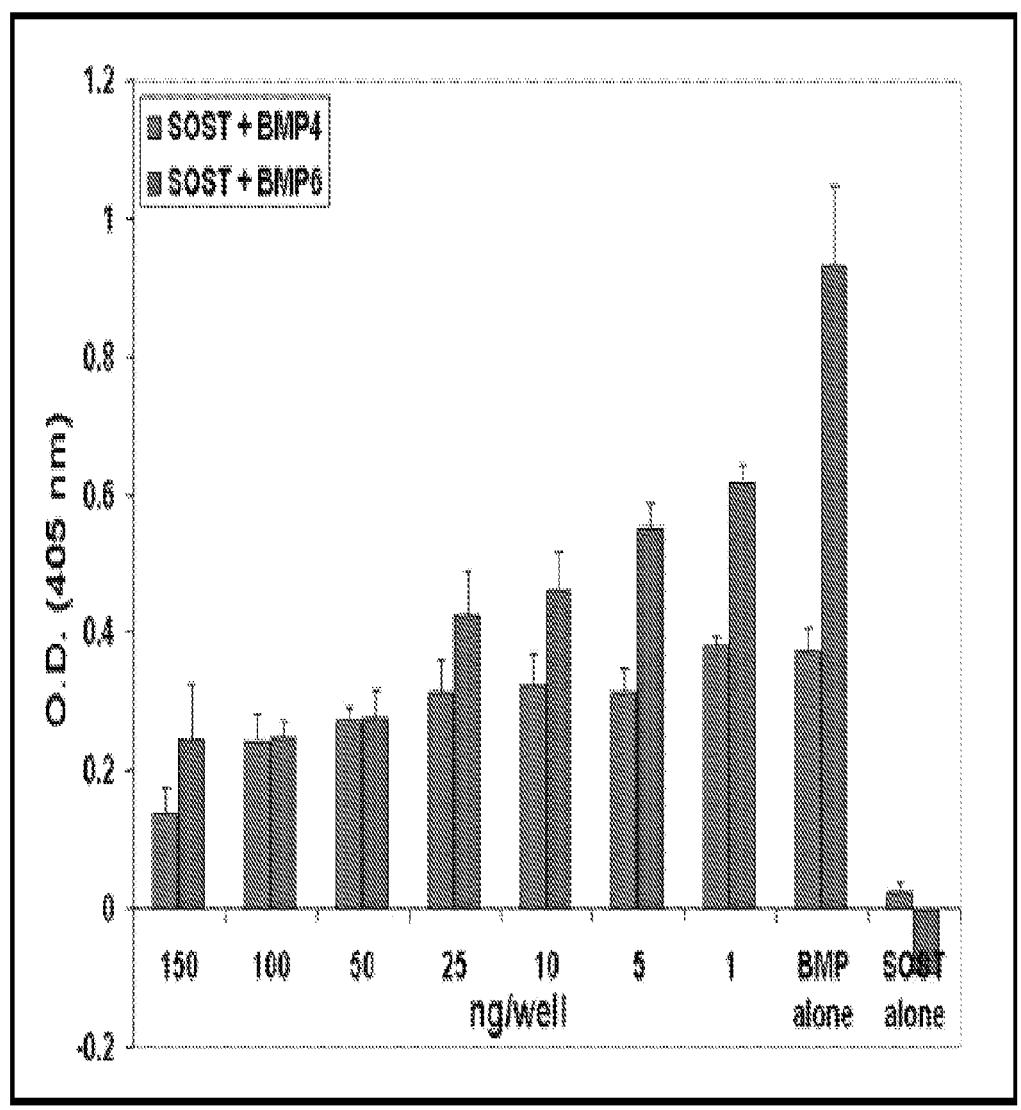
FIG. 2B graphically demonstrates that SOST inhibits the action of BMP6 but not that of BMP4. These results were obtained from a BMP inhibition assay using ATDC-5 cells and exogenous SOST protein with BMP4 or BMP6 protein. Using a *Xenopus* 2-axis formation assay in which injection of Wnt8 (FIG. 2D) causes 2-axis formation compared to wild-type *xenopus* formation (FIG. 2C), an injection of SOST inhibited the 2-axis formation caused by Wnt8, but unable to completely restore a normal axis (FIG. 2E). An animal Cap assay for En2 expression demonstrated that SOST injected alone was unable to induce the BMP inhibitor NCAM; however, SOST in combination with Noggin was able to induce NCAM (FIG. 2O. Further, SOST and Noggin injection also was unable to induce En2 (FIG. 2F), such as is known in the art for Wise and Wnt8 with Noggin injections. EF1 Alpha was used as a loading control for the western blot.

DAN-Family members are able to bind to and inhibit BMP proteins, and only CERBERUS has been shown, in addition, to bind and inhibit WNT activity. The cystein knots of SOST and WISE (also termed ECTODIN and USAG-1) are very similar to that of the DAN-family, thus not surprisingly that both, SOST and WISE, also function by binding to and inhibiting BMPs; where SOST binds and inhibits BMP6 strongly and BMP7 weakly (FIG. 2B). Whereas, WISE inhibits the activity of (strongest to weakest) BMP7; BMP2; BMP4; then BMP6 (FIG. 2A). Yet, WISE appears to bind BMP2 the strongest, then BMP7.

Figure 2C:
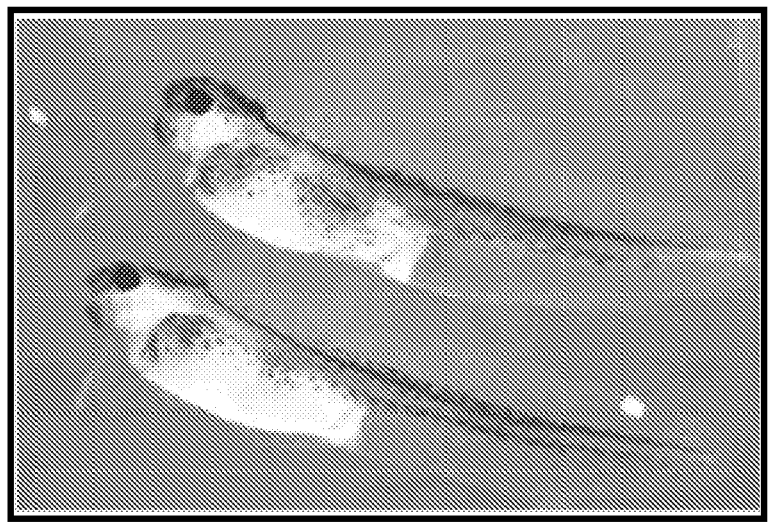
FIG. 2 demonstrates the SOST/WISE function of binding BMP and LRP to inhibit either WNT or BMP signaling, respectively.
FIG. 2G illustrates a Ventral Marginal Zone assay for early immediate WNT response genes Siamois and Xnr3. SOST alone was unable to induce Siamois and Xnr3; however, SOST was able to block the action of Wnt8 on Siamois and Xnr3. EF1Alpha was used as a loading control for the western blot.
FIG. 2H illustrates an immunoprecipitation of SOST and Wise proteins. SOST-Flag or Wise-Flag (~30 Kd) bound LRP6-IgG (160 kD) and LRP5-Myc (160 Kd), but not LRP6 G171V.
FIG. 2I graphically illustrates relative LRP6 binding to different SOST variants. Variants M1, M2, M3, and M8s exhibited a decrease in binding to LRP6.
Figure 2D:
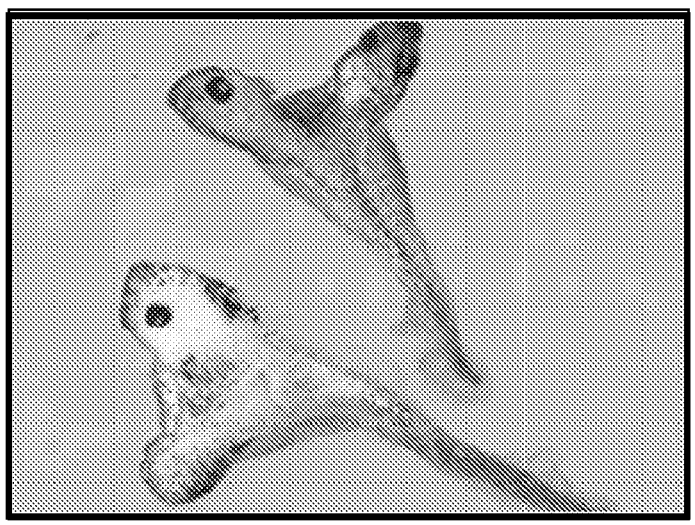
Figure 2E:
Figure 2F:
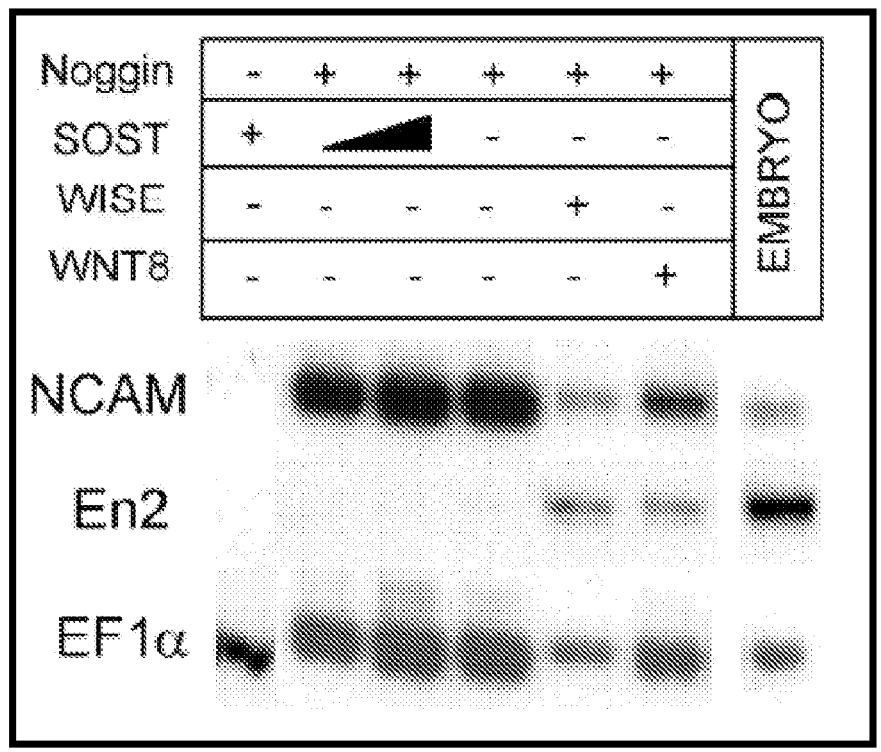

The actions of WISE as a BMP2 inhibitor is unclear as Xenopus Noggin (BMP4 & 2 inhibitor) injected animal cap assays tell a different story. Wise is able to induce En2 at a distance in Xenopus Noggin animal cap assays, through the activation of Wnt genes (data not shown). We wanted to test if Wise injections could induce the neural gene NCAM, like the BMP inhibitor Noggin (FIG. 2F). We found that Wise, alone, was unable to activate the expression of NCAM, and thus unable to inhibit BMP4 and 2 like the known BMP inhibitor Noggin. Therefore, WISE may function in vivo preferentially by binding to and inhibiting BMP7, instead of BMP2 and 4.

Figure 2G:
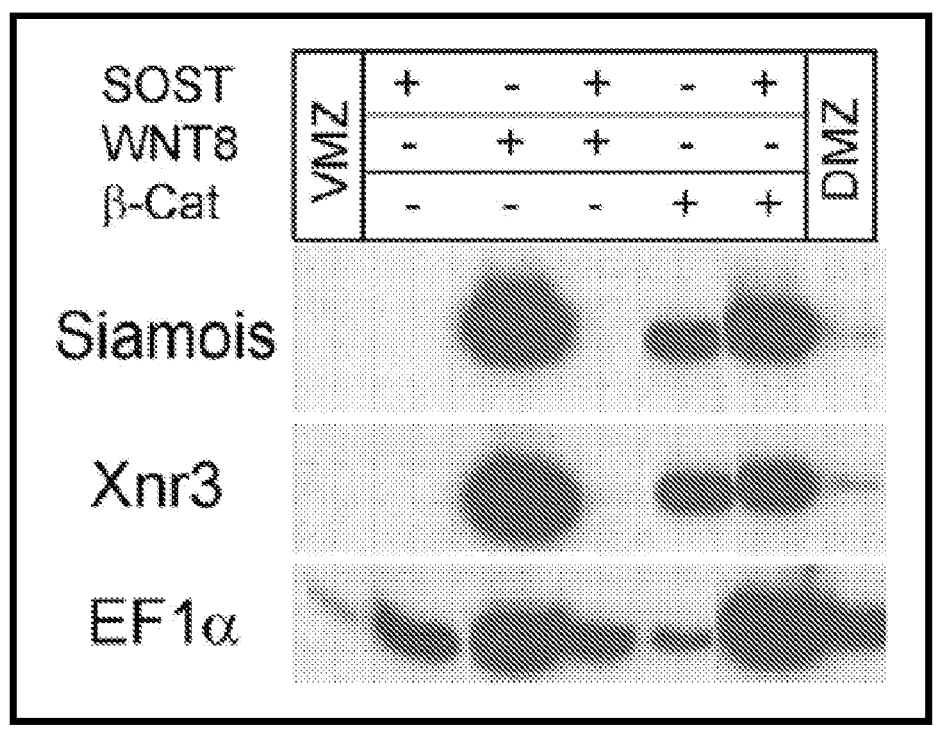
Figure 2H:
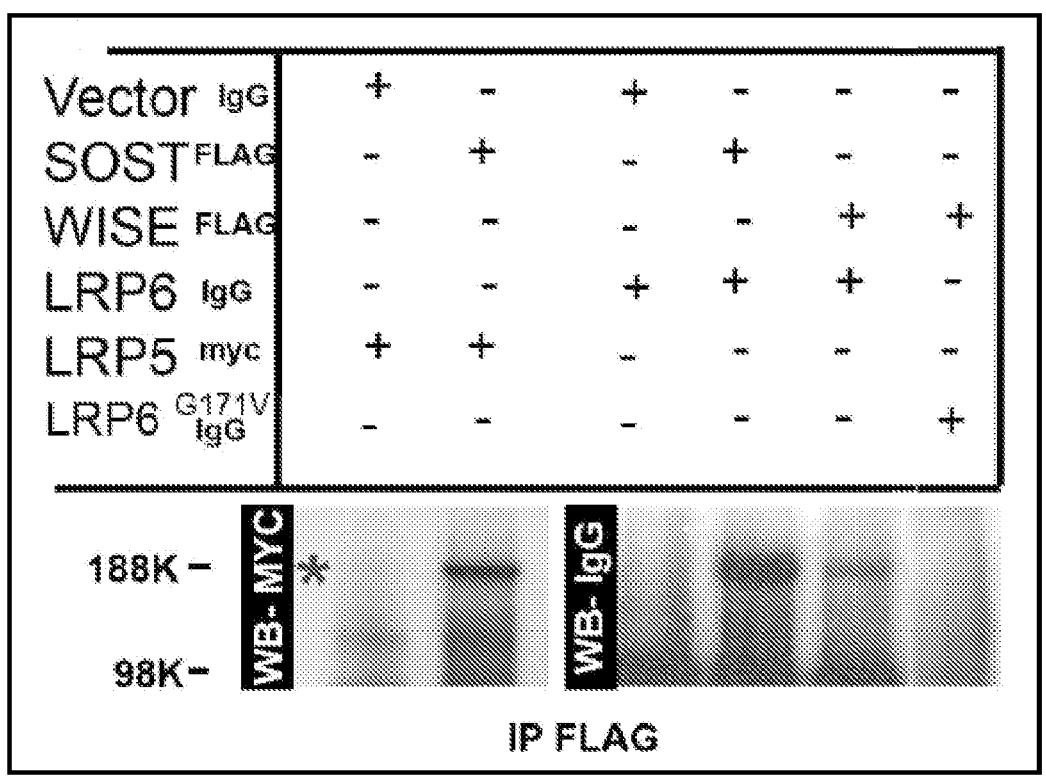
Figure 2I:
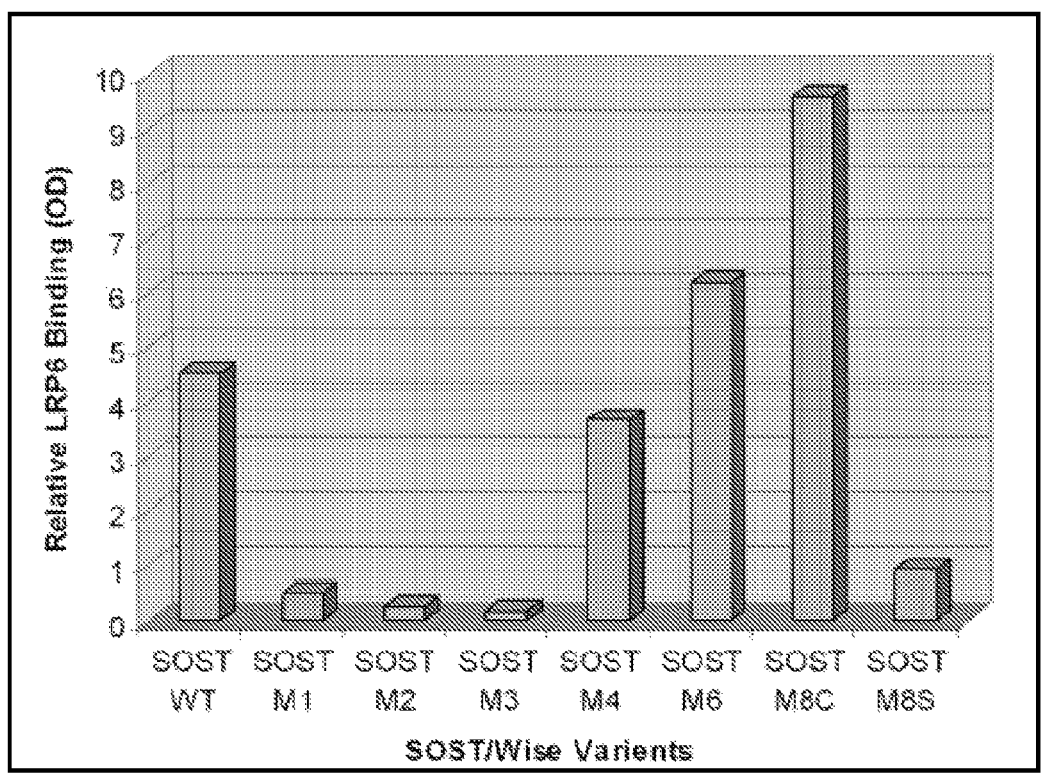

We then asked if SOST and WISE could be redundant by looking to see if SOST could also induce En2, like WISE. Xenopus embryos were either injected with Noggin and/or with SOST or Wise. We found that neither Wise nor SOST could induce En2 without the addition of Noggin. However, Wise and Noggin injected animal caps induced En2 expression; however SOST and Noggin injected caps did not (FIG. 2F). This unexpected finding leads us to examine these two genes more closely. Despite their similarity to the DAN-family, the cystein knots of WISE and SOST appear to be most similar to that of the CCN-family (FIGS. 1D, 1E). CCN-family members, CYR61 and CTGF, are known inhibitors of both WNT and BMP pathways. Interestingly, DAN-family member CERBERUS appears to bind WNT proteins directly, whereas CTGF binds the WNT co-receptor LRP1 and LRP6, and it is unknown as to how Cyr61 inhibits the pathways. Itasaki et al. (2003) showed that the cystein knot of WISE functioned to inhibit the WNT pathway by binding LRP6. We were curious if SOST could function in a similar fashion. SOST RNA was either microinjected alone or in combination with other factors into Xenopus embryos and dorsal marginal zones were assayed for early immediate WNT response genes, Siamois and Xnr3 (FIG. 2G). We found that, like Wise, SOST was able to inhibit the action of WNT on Siamois and Xnr3 (FIG. 2G). This WNT inhibition by SOST was found to be working upstream from Beta-Catenin (FIG. 2G). Like Wise, SOST was also able to rescue secondary axis formation by WNT (FIGS. 2C, 2D, 2E). However, unlike Wise, SOST was unable to completely restore a normal axis (FIG. 2E). The inhibition of WNT activity by WISE is from an interaction with the first two EGF/YWTD propeller repeats found in the amino-terminal of LRP6. We tested if SOST acted in a similar fashion to inhibit the WNT pathway and found that like WISE, SOST was able to bind to LRP6, and LRP5 (FIG. 2H). Interestingly, SOST is unable to bind to the Human HBM G171V mutation (FIG. 2H). Molecular dissection of SOST revealed putative LRP binding sites located in the first arm of the cystein knot (FIG. 2I and FIG. 1B). In addition, upon destruction of the cystein knot, M8s, SOST was unable to bind to LRP6 (FIG. 2I).

In conclusion, we find that SOST binds to and inhibits the activity of BMP6 strongly, and BMP7 weakly, whereas WISE binds to and inhibits BMP7 strongly, and possibly BMP2 more weakly. In addition to BMP modulation, WISE and SOST bind LRP-5 and -6 to also modulate the WNT pathway (FIG. 2I).

Figure 3A:
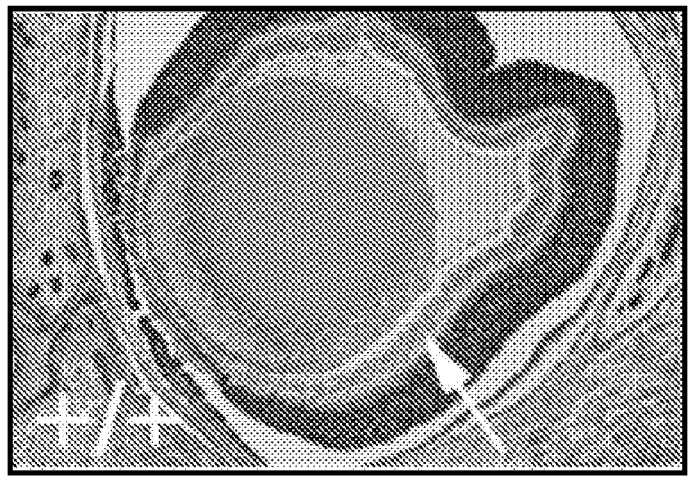
FIG. 3 demonstrates the retinal phenotype exhibited by the Wise mutant mouse model. Retinal sections from a P0 Wise mutant (FIG. 3B) and wildtype mouse (FIG. 3A) showed significant differences in the thickness of the inner neuroblastic layer (INL) (arrows). The Wise mutant INL was much thinner (FIG. 3B, arrow) compared to that of the wildtype (FIG. 3A, arrow). At 4 months the retina of the Wise mutant (FIG. 3D) displayed much undulation (asterisks) when compared to wildtype (FIG. 3C).
FIG. 3E is a schematic diagram depicting normal retinal layers including: 1) the optic nerve fibers; 2) ganglion cell layer; 3) inner plexiform layer; 4) integrating bipolar cell layer; 5) outer plexiform layer; 6) cell bodies of rods and cones; and 7) rods and cones. Retinal sections of a wildtype (FIG. 3F) and Wise mutant (FIG. 3G) at 4 months of age showed significant differences in the thinness of the optic nerve fiber layer (layer 1 in both FIGS. 3F and 3G) and increase in rod and cone layer (layer 7 in both FIGS. 3F and 3G). A cross-sections through the optic nerve of a 4 month old Wildtype (FIG. 3H) compared to a cross section of a Wise mutant mouse optic nerve (FIG. 3I) showed no difference in the overall width. Immunohistological staining of a 4 month old wildtype retina (FIG. 3J) and Wise mutant mouse retina (FIG. 3K) with the neurofilament marker 2H3 revealed the Wise mutant lacks horizontal cells in the integrating bipolar cell layer (FIGS. 3K, 4) PAX6 staining only showed a difference in neuronal cell body cellular shape. Neuronal cell bodies of Wise mutants (FIG. 3M) were more rounded compared to the elongated wildtype neuronal cell bodies (FIG. 3L). Wise immunohistological staining of wildtype retina (FIG. 3N) showed the WISE protein localized to the optic nerve (FIGS. 3N, 1), the ganglion cell lay (FIGS. 3N, 2), the integrating bipolar cell layer (FIGS. 3N, 4), and to the rods and cones layer (FIGS. 3N, 7). As expected, no Wise protein was detected in the Wise mutant mouse retina (FIG. 3O).
Figure 3B:
Figure 3C:
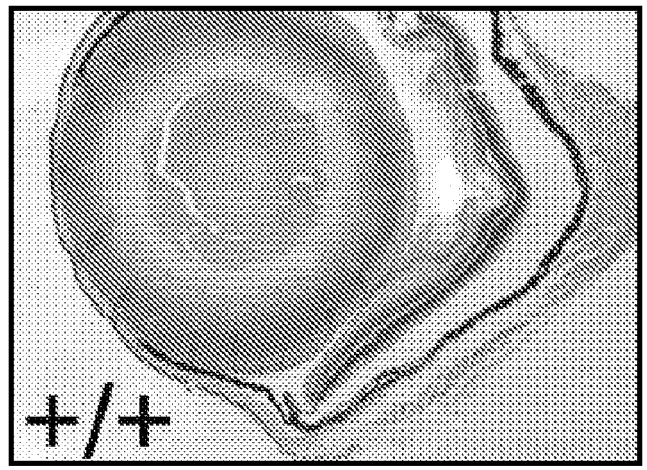
Figure 3D:
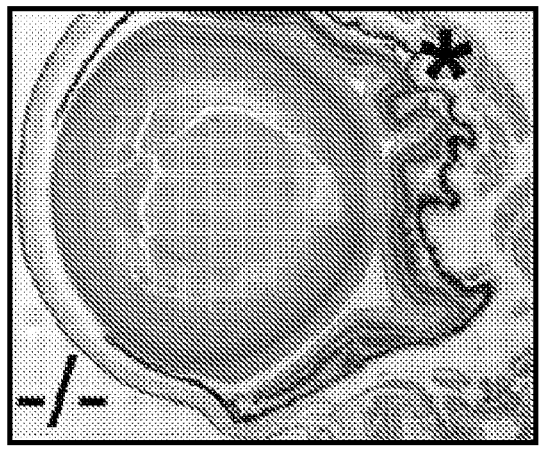
Figure 3E:
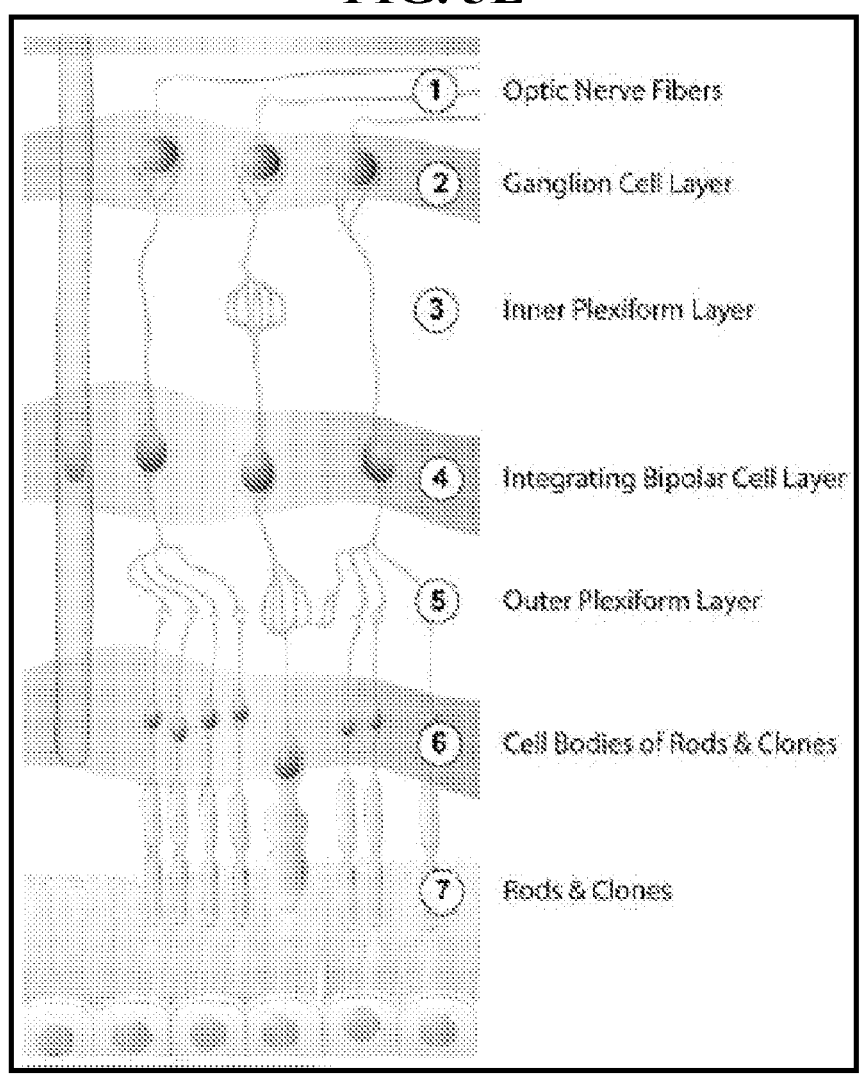
Figure 3F:
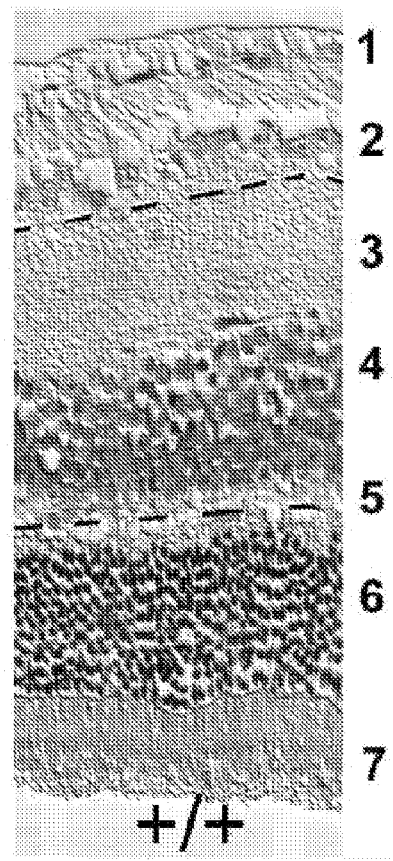
Figure 3G:
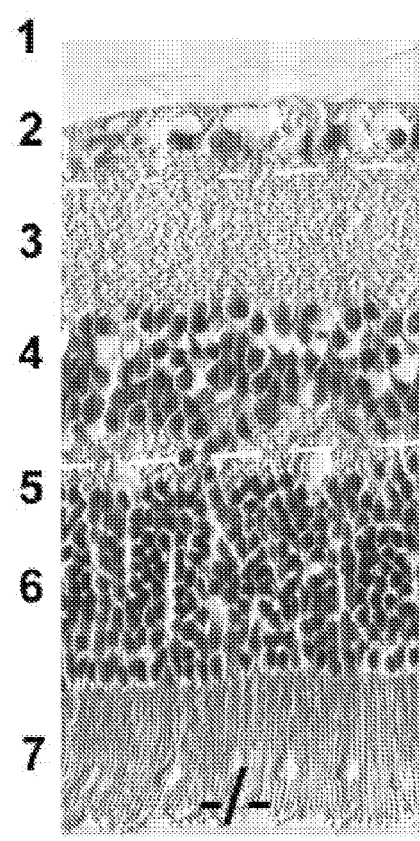
Figure 3H:
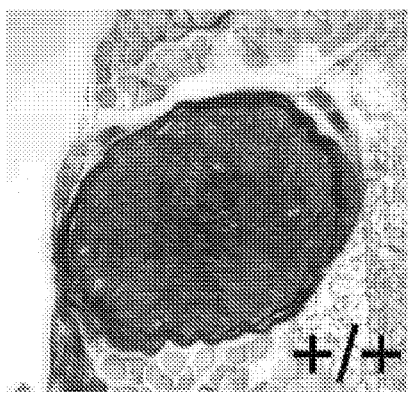
Figure 3I:
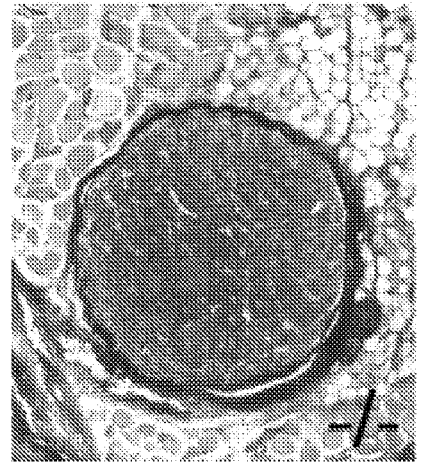
Figure 3J:
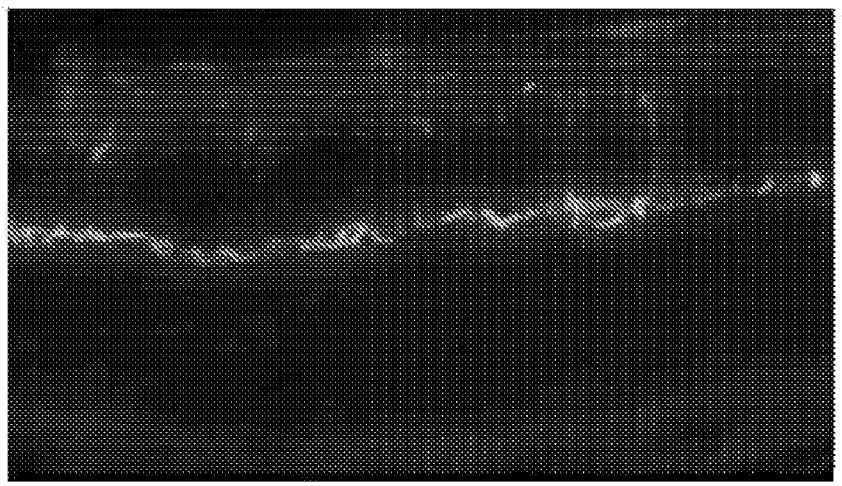
Figure 3K:
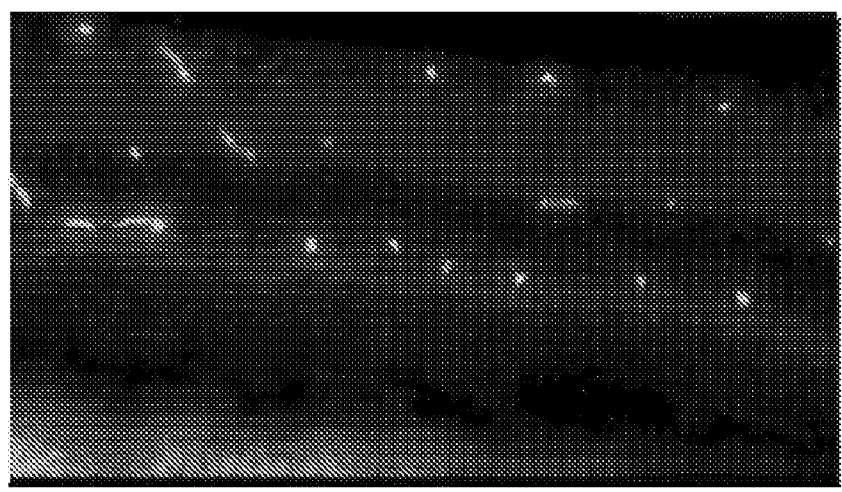
Figure 3L:
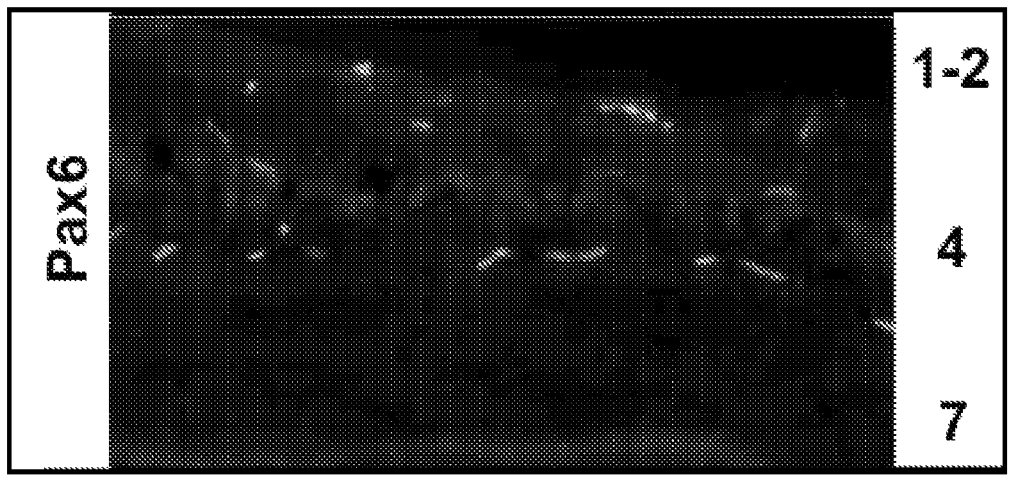
Figure 3M:
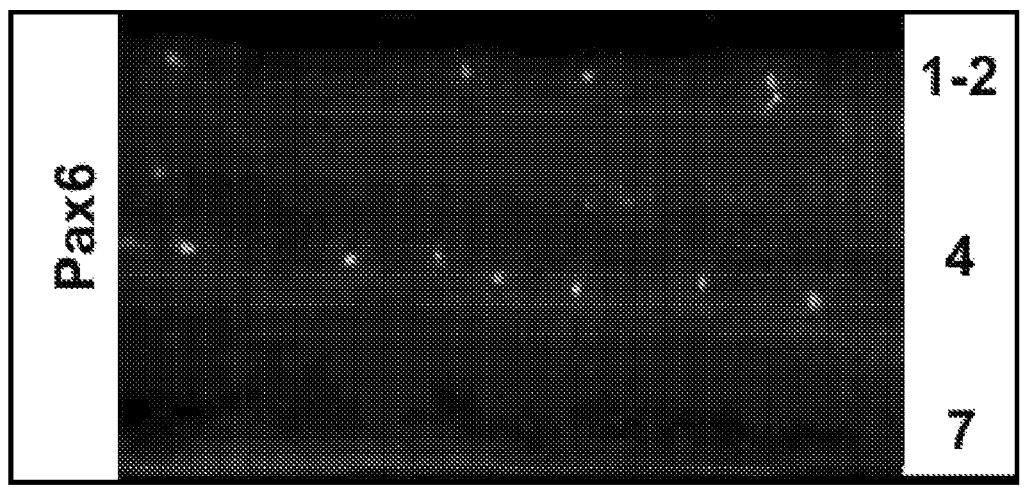
Figure 3N:
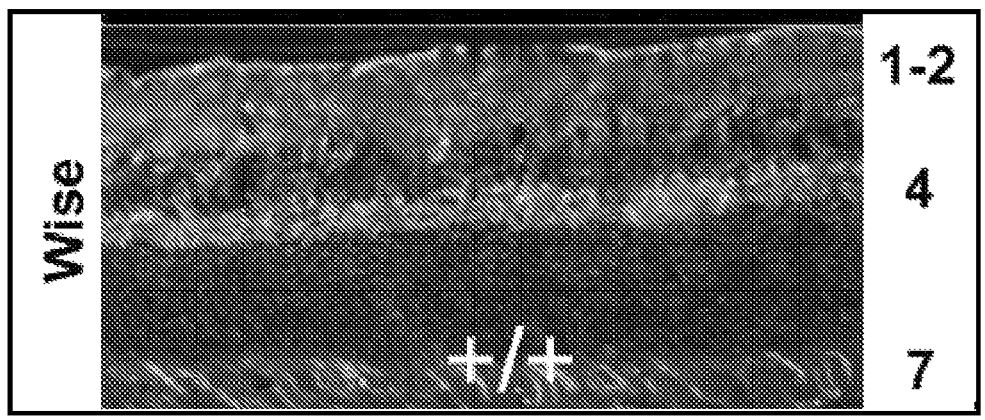
Figure 3O:
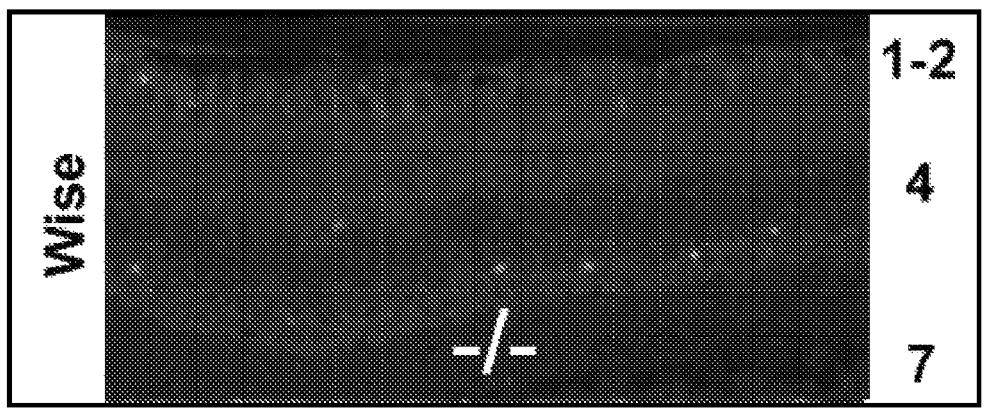

The Wise mutant mice are viable and appear to develop an undulated retina (FIG. 3D) similar to that seen in patients with Norrie-Disease.[15] The retina of Wise null mice have less optic nerve fibers (FIGS. 3F, 3G), however the optic nerve itself appears normal in diameter and trajectory (FIGS. 3H, 3I). Additionally, they have an increased thickness of rods and cones layer (FIGS. 3F, 3G). Neurofilament staining reveals a loss of horizontal cells within the inner nuclear bipolar cell layer (FIGS. 3J, 3K), which suggests that neighboring photoreceptors would be unable to communicate. Retinal ganglion cell marker, PAX6, stains elongated neuronal cell bodies of the inner nuclear layer (FIG. 3L). In Wise mutants, they appear rounded instead of elongated (FIG. 3M). WISE protein is found in the inner plexiform layer, ganglion cell layer, and in the rod and cone layer of a 2.5 month mouse retina (FIG. 3N). Unlike Wise, Sost is found in the tissues adjacent to the neuroepithelium of the diencephalon at E18dpc (data not shown).

Figure 4A:
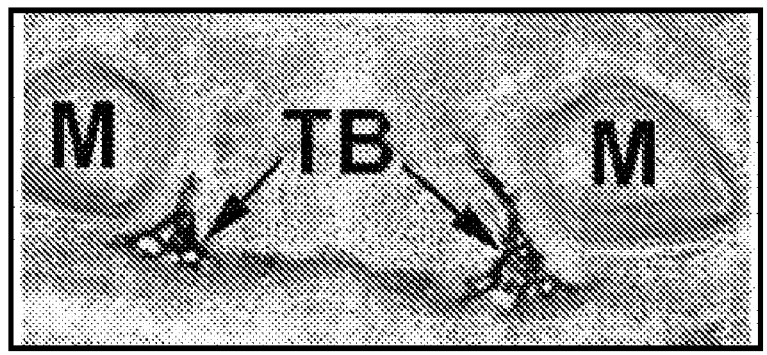
FIG. 4 demonstrates the abnormal tooth phenotypes associated with loss of Wise or SOST protein in the maxillary region. Wise mutant mice exhibited a supernumerary tooth phenotype, while SOST mutant mice exhibited a no teeth phenotype. Histological H&E staining of E16.5dpc wildtype mouse embryos showed molar (M) and trabecular bone (TB) (FIG. 4A); odontoblasts (Od), osteoblasts (OB), inner enamel epithelium (IeE), and dental follicle (DF) (FIG. 4D); and vibrissae (Vib) and incisors (i) (FIG. 4G) for orientation purposes. Radioactive in situs on E16.5dpc mouse embryos showed that SOST expression is found in osteoblasts and polarized odontoblasts (FIGS. 4B, 4E and 4H). SOST expression is not found in vibrissae or incisors (FIG. 4H). Radioactive in situs also showed that Wise expression is found in the inner enamel epithelium, dental follicle, vibrissae and incisors of the maxillary process (FIGS. 4C, 4F, 4I). X-rays of mouse maxilla showed duplicated incisors, and fusion of upper molar fields in Wise mutant mice (FIG. 4K) compared to wildtype mice (FIG. 4J). Molar patterning of mouse maxilla demonstrated a duplicate M1 in Wise mutant C57BL6 mice (FIG. 4M) compared to wildtype mice (FIG. 4L) (similar to the null Runx2 phenotype known in the art). Mandibular patterning of 1295V/EV mice demonstrated a reversal of molar pattern, M3-M1 instead of M1-M3, and a fusion of M1-M2 in Wise mutant mice (FIG. 4O) compared to wildtype mice (FIG. 4N).
Figure 4B:
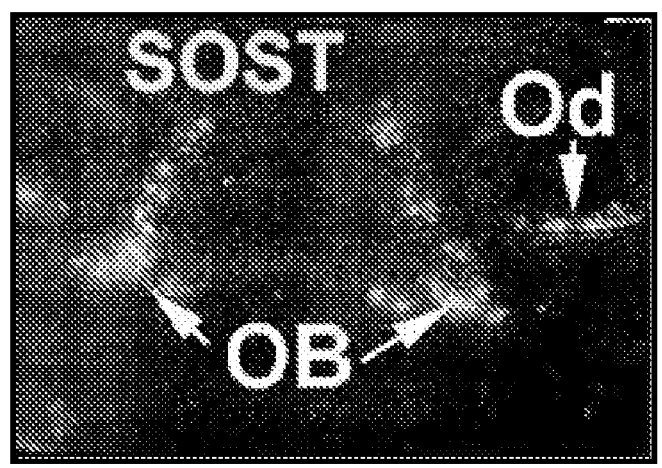
Figure 4C:
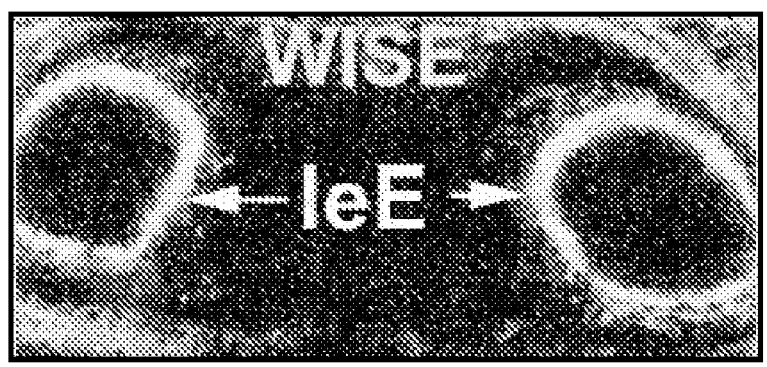
Figure 4D:
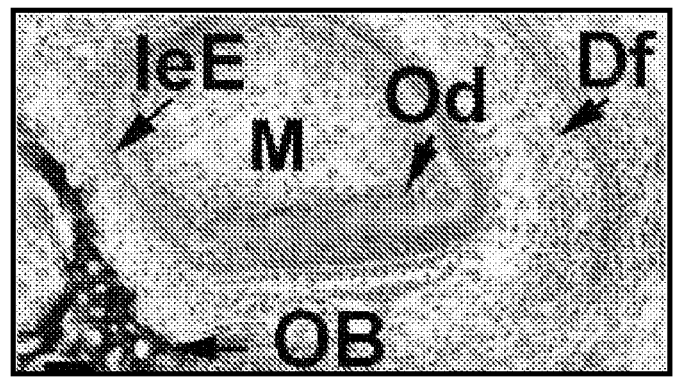
Figure 4E:
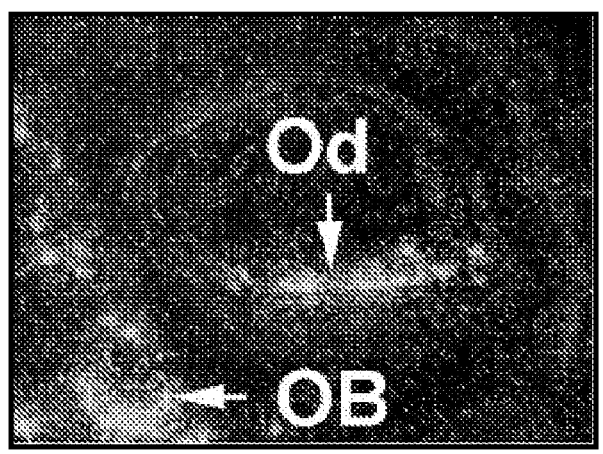
Figure 4F:
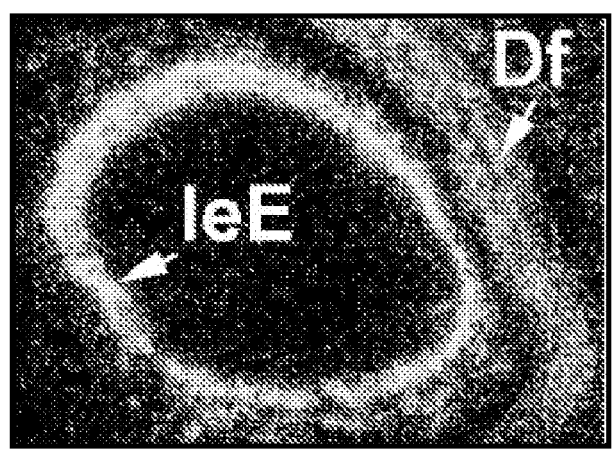
Figure 4G:
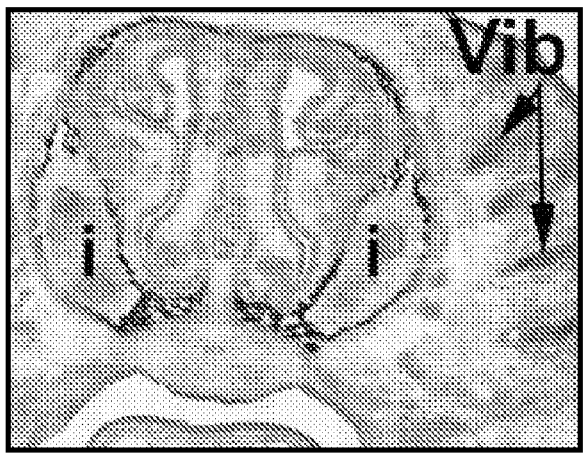
Figure 4H:
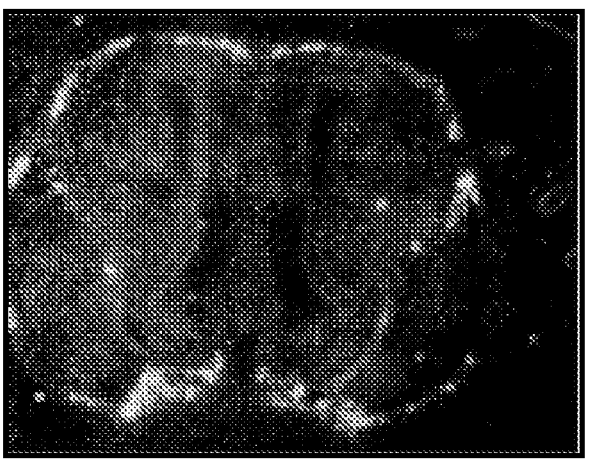
Figure 4I:
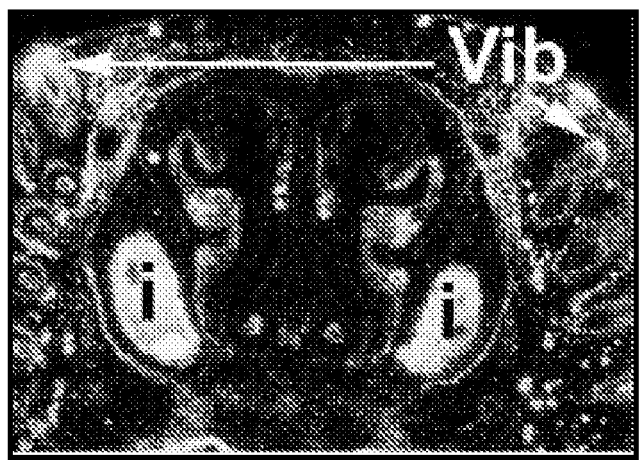
Figure 4J:
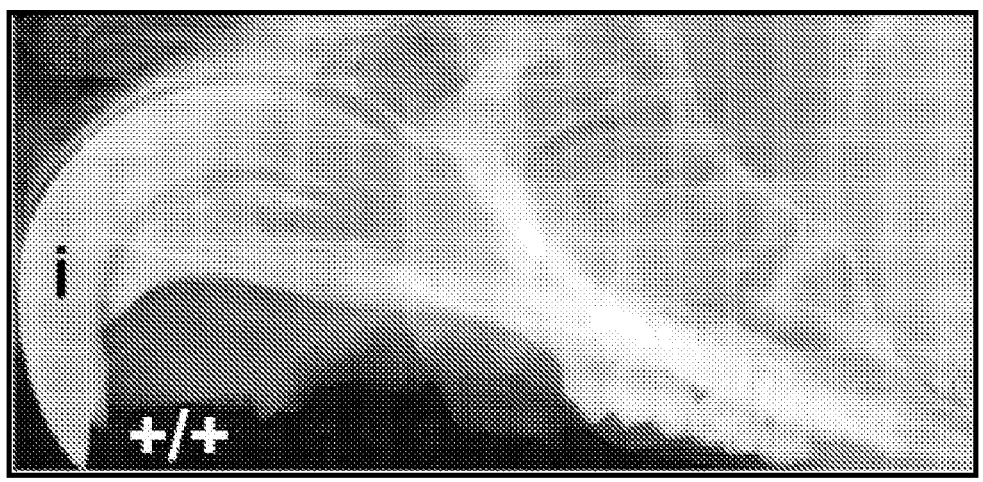
Figure 4K:
Figure 4L:
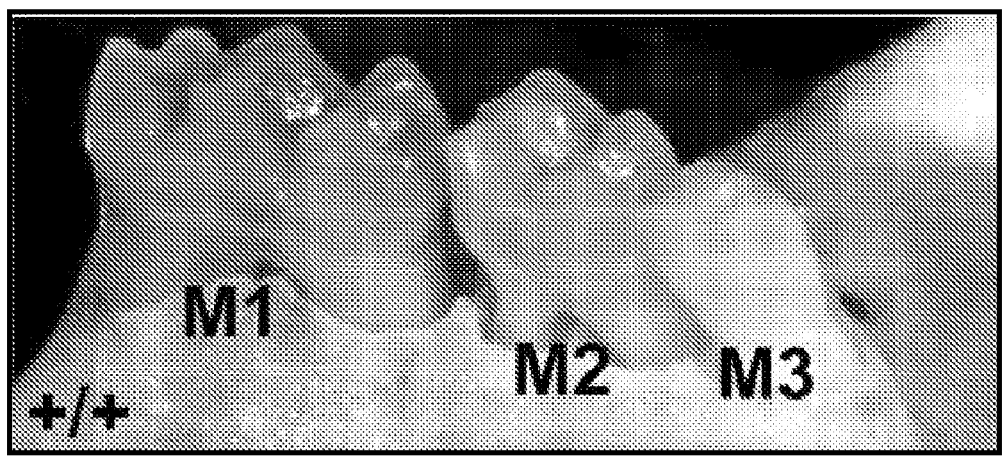
Figure 4M:
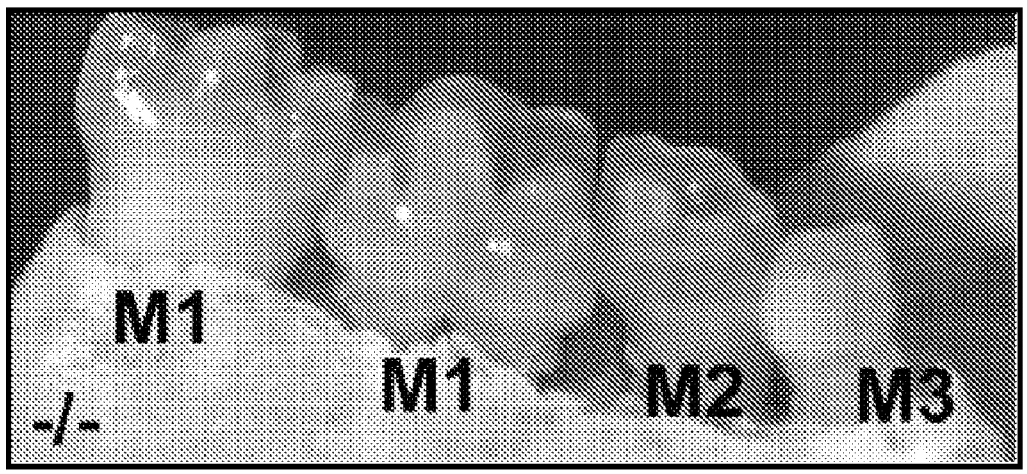
Figure 4N:
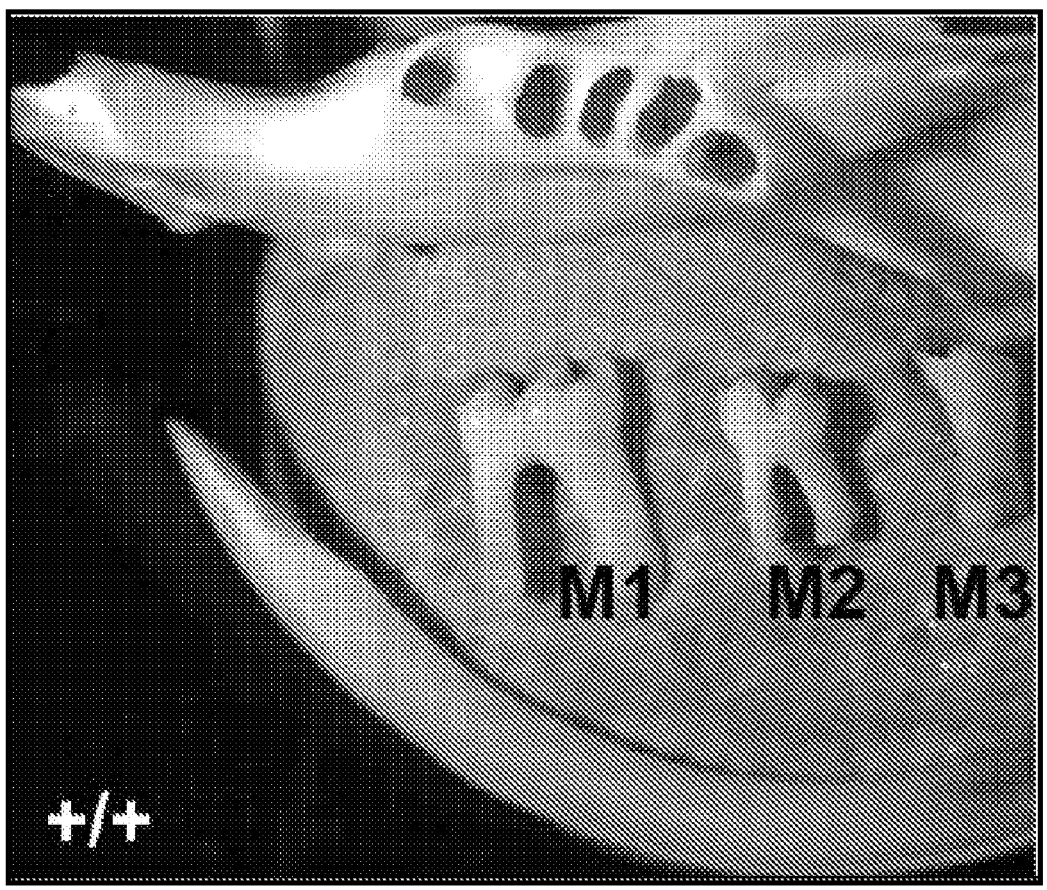
Figure 4O:
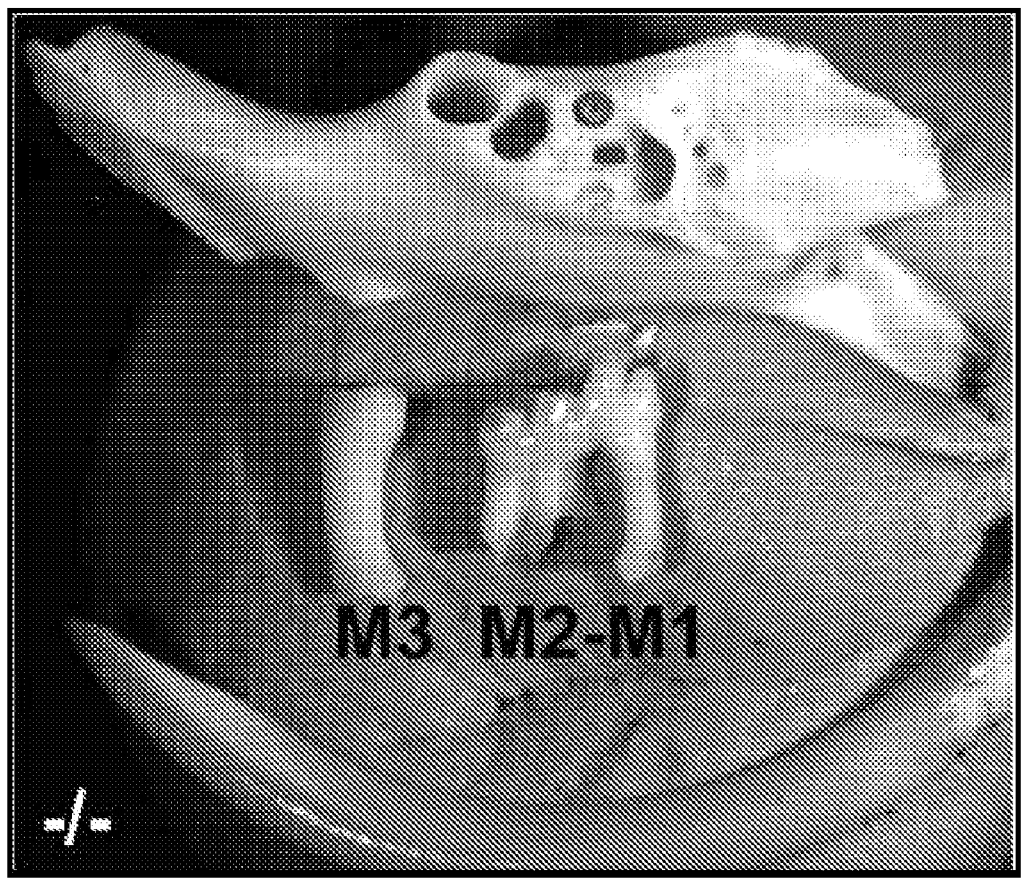

Development of the teeth in Wise mutants also shows abnormalities; the incisors need weekly clipping from weaning onwards and the maxillary incisors are supernumerary (FIG. 4K). The molars display abnormal patterning with or without supernumerary buds (FIGS. 4M, 4O). The most severe phenotype is seen in the 1295V/EV mouse where three molars are often found in reverse orientation and fusion of M1 and M2 (FIG. 4O). A less severe phenotype is seen in the C57BL6 mouse, which displays supernumerary M1 molars (FIG. 4M). The maxillary molars in both strains develop severe fusion of all molars (FIG. 4K). The SOST mutation does not present a tooth phenotype, probably because SOST is expressed in the polarized odontoblasts (which later gives rise to the periodontal ligament) and the surrounding osteoblasts (FIGS. 4B, 4E, 4H). Wise, on the other hand, is expressed in the inner enamel epithelium and dental follicle surrounding the tooth bud, as well as in the maxillary incisors (FIGS. 4C, 4F, 4I). Thus, SOST and Wise are expressed in complementary cell types and thus result with a different tooth phenotype.

Figure 5A:
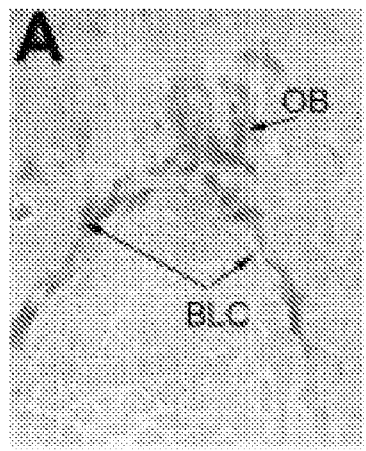
FIG. 5 demonstrates that Wise and SOST both function to regulate bone density. At E14.5dpc Wise was expressed in the Bone lining cells (BLC) and osteoblasts (OB) (FIG. 5A), while SOST was only expressed in the BLC (FIG. 5B). Wise and SOST staining resembled ALP staining (FIG. 5C) and not TRAP staining (FIG. 5D). Thus Wise and SOST were not expressed in Trap positive osteoclasts, but were expressed in alkaline phosphatase (ALP) positive OB and BLC. At 4 months of age, Wise was no longer expressed (FIG. 5E), whereas SOST was found in the osteoblasts (OB) and osteocytes (Oc) (FIG. 5F). Growth plates of a 4 month old wildtype (FIG. 5H) and Wise mutant (FIG. 5G) mouse femur stained with H&E showed an increase in metaphysis bone deposition (asterisks). ALP staining in a 4 month old Wise mutant revealed an increase in positive osteoblasts (asterisks) and also hypertrophic chondrocytes (line) (FIG. 5J) compared to wildtype ALP staining (FIG. 5I). TRAP staining did not show any significant difference between wildtype (FIG. 5K) and Wise mutant (FIG. 5L) at 4 months. Two-week old femurs from a wildtype mouse exhibited Wise protein localized to the hypertrophic chondrocytes and osteoblasts as shown by immunohistochemical Wise staining (FIG. 5N) and the accompanying H&E staining (FIG. 5M). Bone mineral density measurements of the Wise mutant mouse showed that lack of Wise resulted in a significant ($p<0.05$)~10% increase in bone density from birth to 3.5 months (FIG. 5O). At 4 months bone remodeling occurred and Wise mutants ceased to have an increase in BMD (FIG. 5O). Together these results demonstrated that early bone deposition by osteoblasts was modulated by Wise. Then during bone remodeling (occurs at 4 months), once the bone lining cells re-differentiate into osteoblasts, SOST modulated osteoblast bone deposition instead of Wise, as Wise is no longer expressed at this time
Figure 5B:
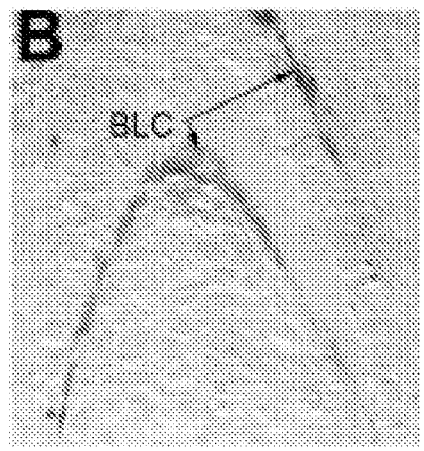
Figure 5C:
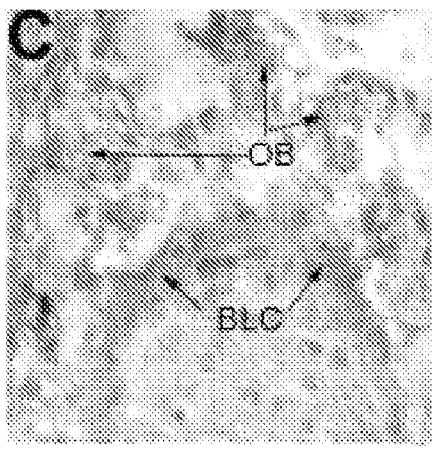
Figure 5D:
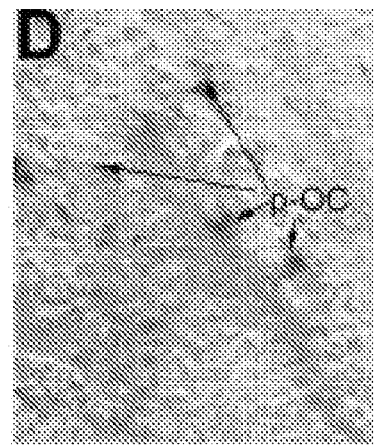
Figure 5E:
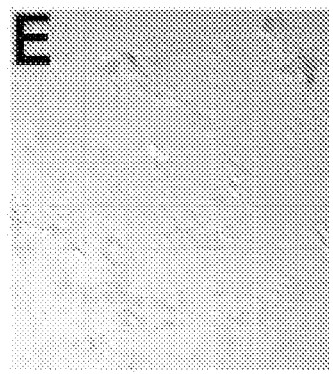
Figure 5F:
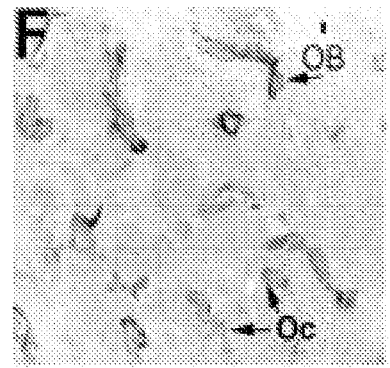
Figure 5G:
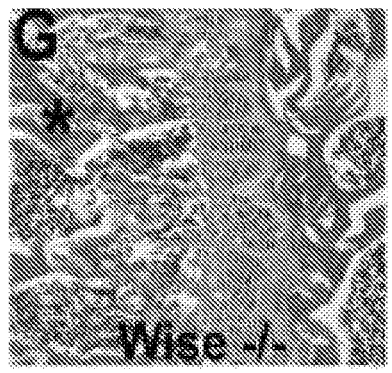
Figure 5H:
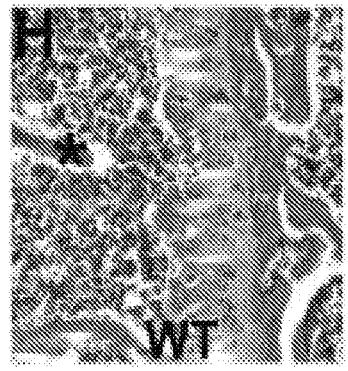
Figure 5I:
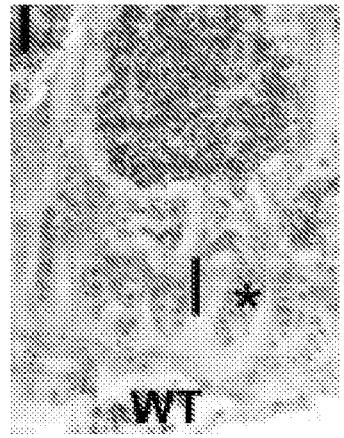
Figure 5J:
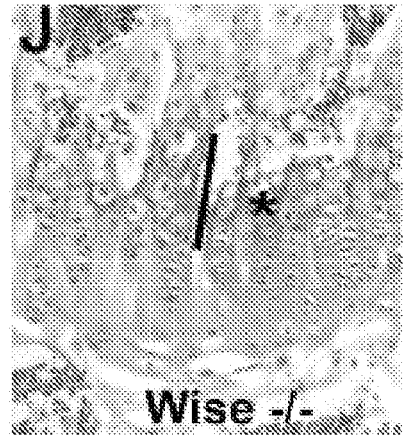
Figure 5K:
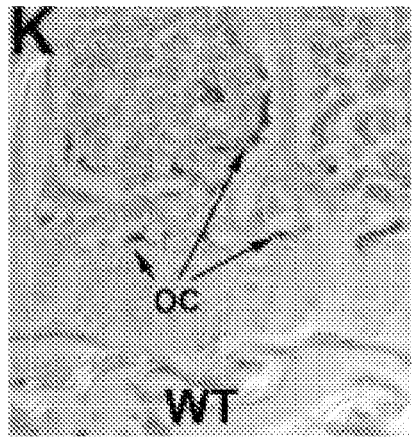
Figure 5L:
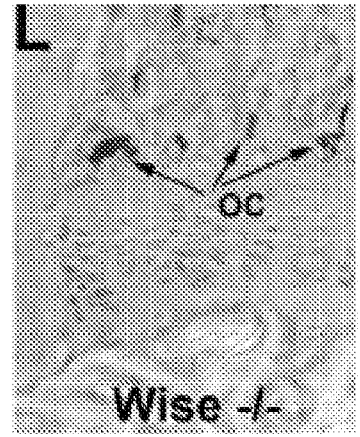
Figure 5O:
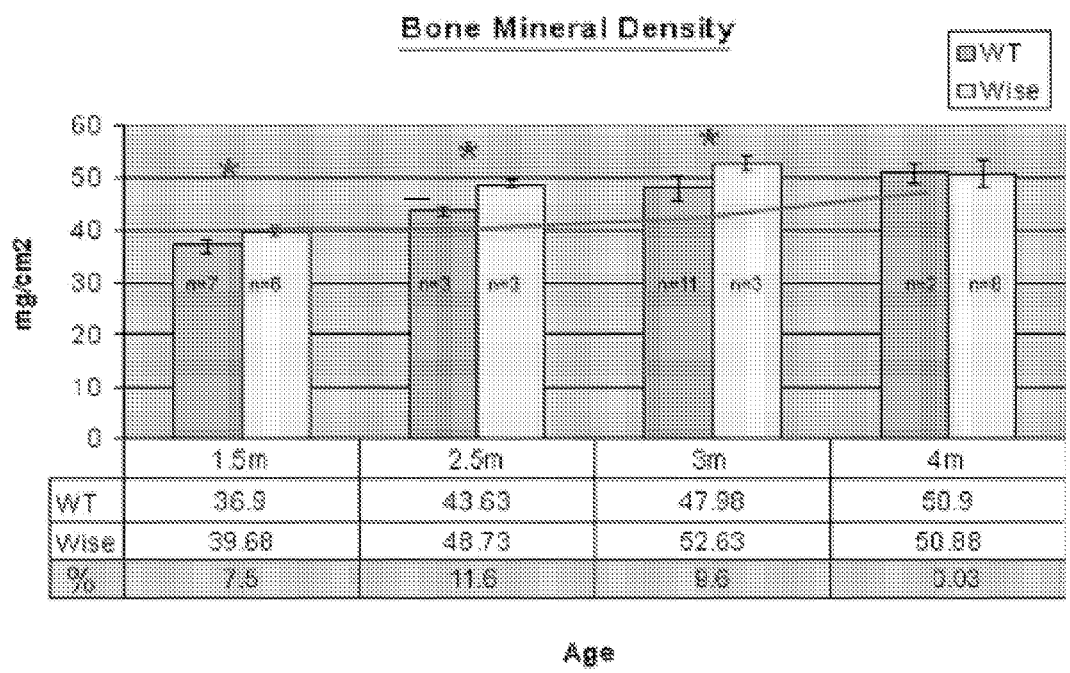
Figure 6A:
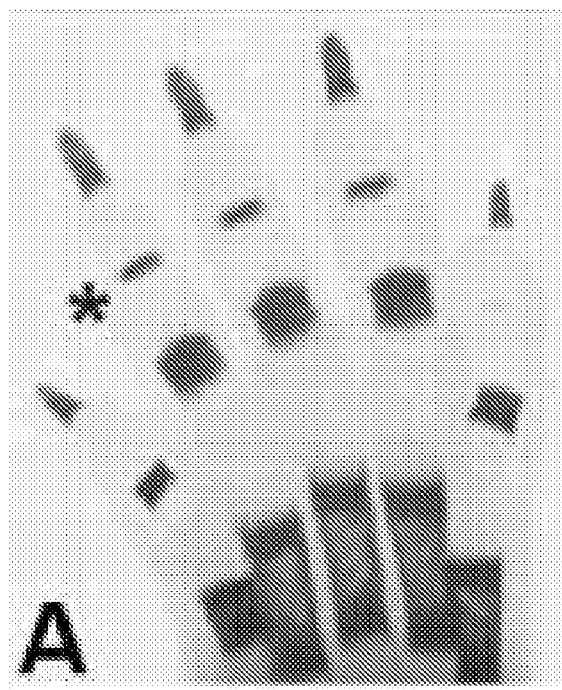
FIG. 6 shows skeletal stain at P0 demonstrating Fore-(FIGS. 6A and 6B) and Hind-(FIGS. 6E and 6F) limb development in the wildtype (FIGS. 6A and 6E) and Wise mutants (FIGS. 6B and 6F). Asterisks and yellow circles mark increased ossification in Wise mutants (FIGS. 6B and 6F) compared to wildtype ossification (FIGS. 6A and 6E). Alzarin red stain of vertebrae (FIGS. 6C and 6D) and femur (FIGS. 6G and 6H) showed that Wise mutants exhibited an increase in the cortical thickness of the femur (FIG. 6H), compared to wildtype femur (FIG. 6G).
FIG. 6I is a schematic showing the signaling responsible for regulating the osteoblastic lineage. Briefly, Twist negatively regulates CBFA.1 (Runx2) during osteoblast differentiation, which Cbfa.1 (Runx2) directly regulates SOST, and then SOST/Wise bind to LRP5/6 to regulate the WNT signaling pathway.
FIG. 6J is a schematic showing LRP5/6 4-YWTD propellers (green) and Wise/SOST binding to an area located within the first two YWTD motifs. This binding inhibits WNT signaling, whereas, DKK (red) binds to the third YWTD of LRP5/6 to inhibit WNT signaling. Wise and SOST (blue) also bind and inhibit BMPs, which signal through BMPRI and BMPRII.
Figure 6B:
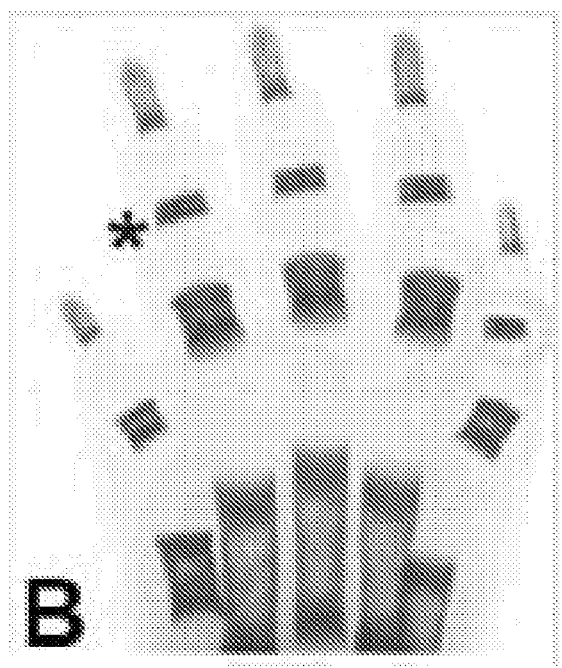
Figure 6C:
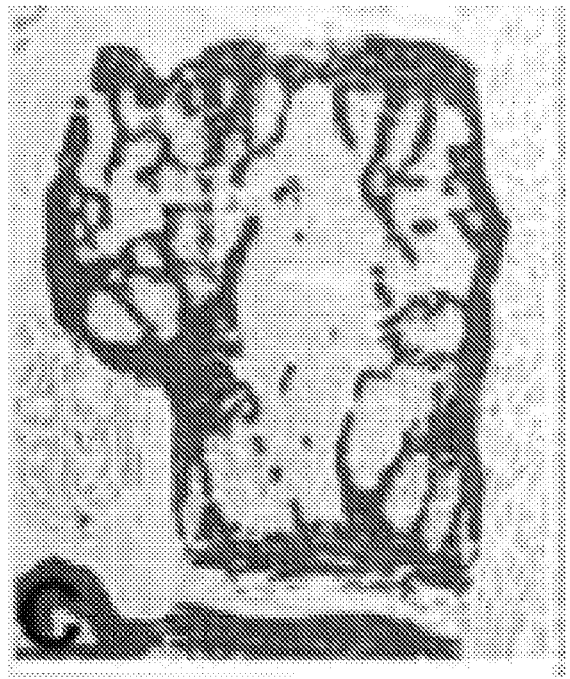
Figure 6D:
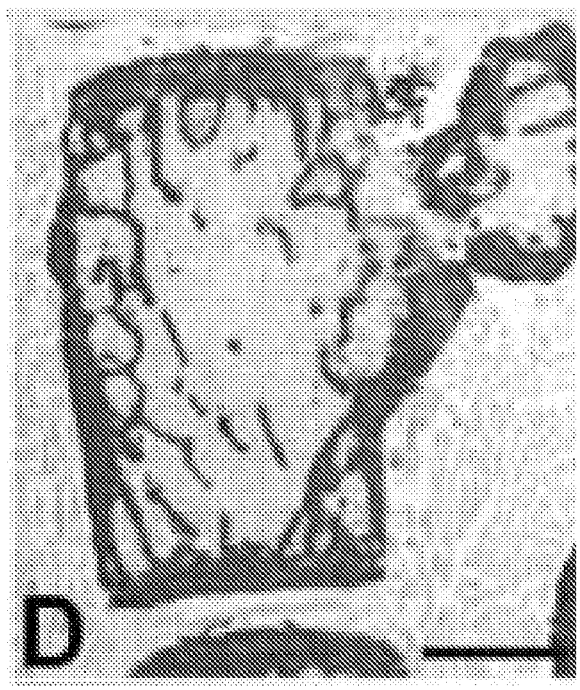
Figure 6E:
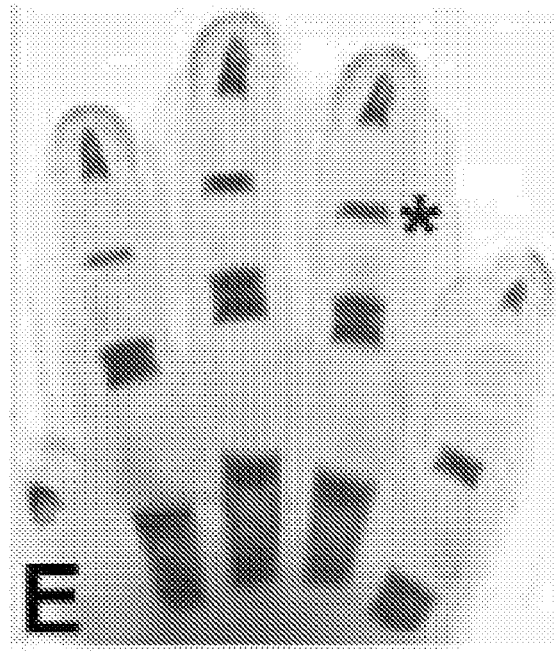
Figure 6F:
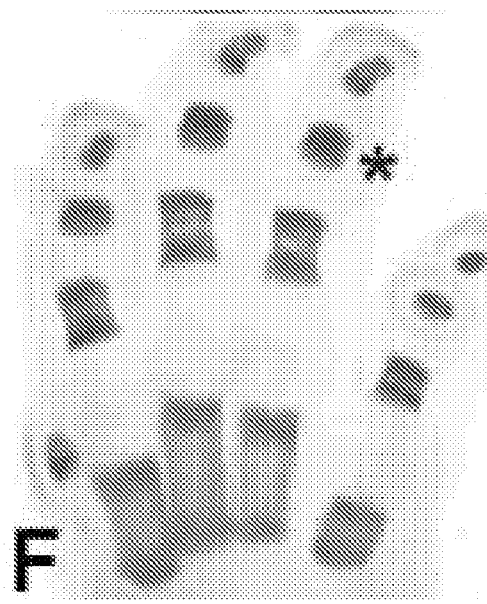
Figure 6G:
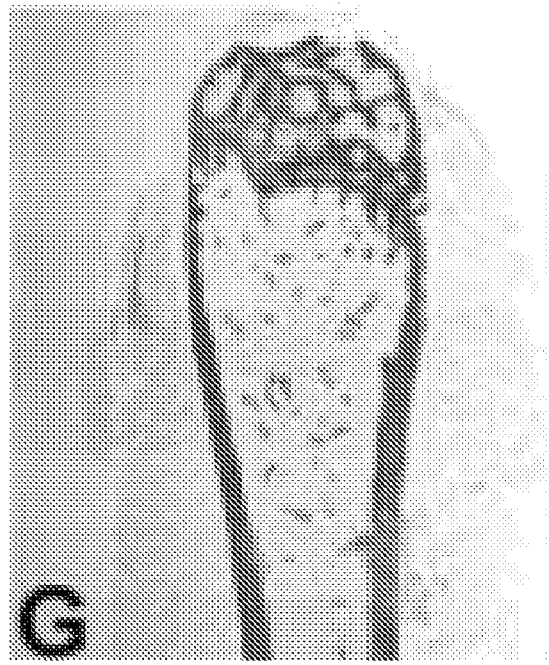
Figure 6H:
Figure 6I:
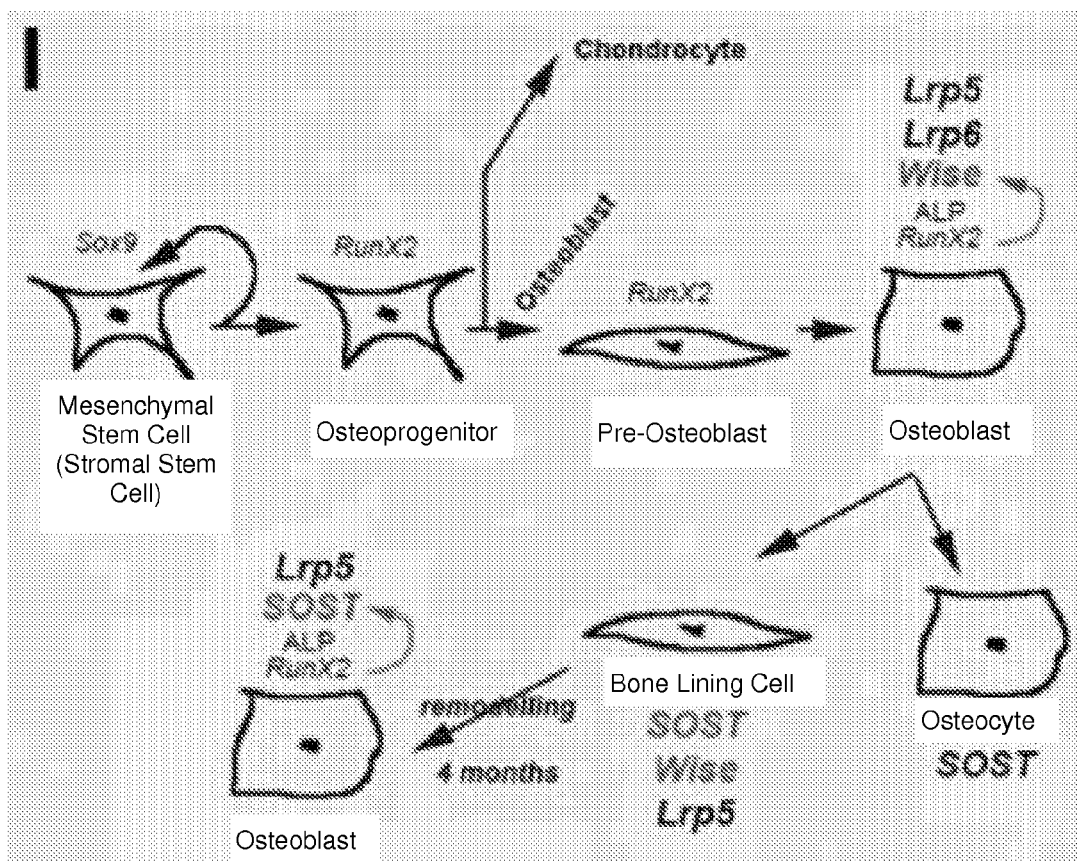
Figure 6J:
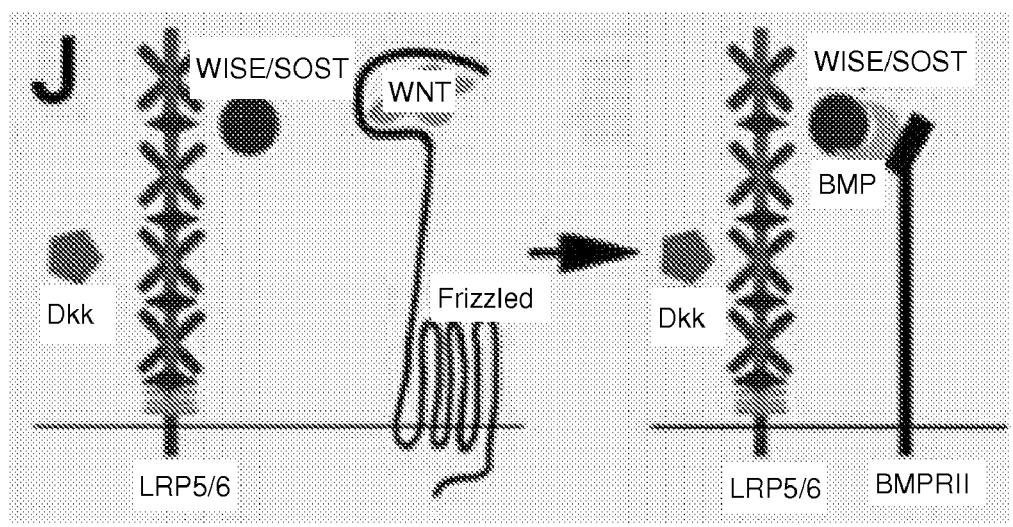

One cell type that both genes appear to affect in a similar fashion is the bone. Wise mutants have an increased alkaline phosphatase positive hypertrophic chondrocyte layer (FIGS. 5I, 5J) which results in an increase in cartilage matrix and bone deposition in the metaphysis plate (FIGS. 5G, 5H). Both SOST and Wise are expressed in hypertrophic chondrocytes, osteoblasts and bone lining cells, and SOST is also expressed in osteocytes (FIGS. 5A, 5B, 5E, 5F, 5N). However, SOST expression in early bone development (E14.5dpc) is restricted to the bone lining cells and not osteoblasts (FIG. 5B). This suggests that early bone deposition by osteoblasts is modulated by WISE. Then during bone remodeling (4 months), once the bone lining cells re-differentiate into osteoblasts, it is SOST that would modulate osteoblasts bone deposition instead of WISE, as Wise is no longer expressed (FIGS. 5E, 6I). In concurrence, Wise mutant mice have increased bone density during early prenatal bone development (under 4 months), and cease to have an affect once bone-modeling starts (4 months; FIGS. 5O, 6I). SOST mutations also leads to increased bone density, however this could be during later bone remodeling stages as Wise is absent and can not compensate for its loss after 4 months (FIGS. 5E, 5F, 6I). Thus, Wise functions to affect bone density before bone remodeling occurs by an increase in hypertrophic chondrocytes and osteoblasts (FIGS. 5A, 5G, 5J). In addition to increased chondrocytes in the growth plate of 4 month Wise mutants, we also observed thickened and extra phalanges (astericks; yellow circle, FIGS. 6A, 6B, 6E, 6F). The vertebra and long bones revealed very slight increases in cortical thickness, mostly evident in the long bones (FIGS. 6C, 6D, 6G, 6H).

Consequently, we have found a new Wise family member, SOST. Both Wise and SOST are linked to a HOX cluster further supporting HOX cluster duplication hypotheses. SOST functions like WISE to inhibit both BMP and WNT pathways, however, unlike Wise, is unable to induce En2 expression. The inability to induce En2 is very similar to other cystein knot family members, like CTGF and NOV. The phenotypes we observe in Wise mutants are also similar to that of SOST and LRP mutations, with some exceptions, ie. teeth. Interestingly, Itasaki et al. (2003) demonstrated that Wise inhibits the WNT pathway by binding to an area encompassing the first two EGF/YWTD propeller domains of LRP6. Yet, Lrp6 null mice are lethal and do not resemble phenotypes seen in Wise mutants. The autosomal recessive disorder that causes low peak bone mass, osteoporosis-pseudoglioma syndrome (OPPG), has been shown to be due to an inactivation or deletion of LRP5, and an autosomal dominant point mutation in LRP5, G171V, results in a high bone mass disorder. Furthermore. Houston and Wylie (2002) and Gong et al. (2001) have shown that Lrp5 is expressed in osteoblasts and in the retinal cell layer. Therefore, the bone density phenotypes Wise and SOST are complementary to those in LRP5 mutants. However, the Wise tooth phenotype is not seen in LRP5 or Lrp6 mutants.

Interestingly, the Runx2 null mouse develops supernumerary tooth buds, similar to those in Wise. Runx2 has been shown to be an important ossification selector gene for deciding between the osteoblast or chondrocyte lineage. Previous studies have reported normal Runx2 expression in an Lrp5 null background. Kato et al. (2002) concluded that LRP5 must affect bone density independently of Runx2. However, Runx2 acts to regulate transcription of SOST (probably Wise too; FIG. 6K), and we now report that SOST/WISE act to regulate bone deposition through binding to LRP5/6. Therefore, only one pathway exists for osteoblast differentiation-proliferation involving Runx2 and LRP5. Runx2 acts upstream to regulate transcription of SOST/Wise, which in turn bind to LRP5/6 to regulate bone deposition (FIG. 6K). Runx2 appears to function during hypertrophic chondrocytes differentiation. Wise in turn acts to induce proliferation of the hypertrophic chondrocyte layer, which leads to an increase in cartilage matrix deposition and ultimately increased bone deposition (FIG. 6I).

II. Preparation of Peptides and Nucleic Acids

As disclosed herein, proteins, peptides and nucleic acids of the present invention may be isolated from natural sources, prepared synthetically or recombinantly, or any combination of the same. Methods for isolating peptides and nucleic acids of the present invention are well known in the art. Generally any purification protocol suitable for isolating nucleic acids or proteins can be used. For example, affinity purification as discussed below in the context of antibody isolation can be used in a more general sense to isolate any peptide or protein. Nucleic acids can be purified using agarose gel electrophoresis, as is known in the art. Column chromatography techniques, precipitation protocols and other methods for separating proteins and/or nucleic acids may also be used. (see, e.g., Scopes, *Protein Purification: Principles and Practice* (1982); U.S. Pat. No. 4,673,641; Ausubel et al., supra; and Sambrook et al., supra; and Leonard et al., J. Biol. Chem. 265:10373-10382 (1990).

For example, peptides may be produced synthetically using solid phase techniques such as described in "Solid Phase Peptide Synthesis" by G. Barany and R. B. Merrifield in Peptides, Vol. 2, edited by E. Gross and J. Meienhoffer, Academic Press, New York, N.Y., pp. 100-118 (1980). Similarly, nucleic acids can also be synthesized using the solid phase techniques, such as those described in Beaucage, S. L., & Iyer, R. P. (1992) Advances in the synthesis of oligonucleotides by the phosphoramidite approach. Tetrahedron. 48, 2223-2311; and Matthes et al., *EMBO J.*, 3:801-805 (1984).

Modifications of peptides of the present invention with various amino acid mimetics or unnatural amino acids are particularly useful in increasing the stability of the peptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half life of the peptides of the present invention is conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4° C.) for 15 minutes and then spun to pellet the precipitated serum proteins. The presence of the peptides is then determined by reversed-phase HPLC using stability-specific chromatography conditions. Other useful peptide modifications known in the art include glycosylation and acetylation.

In the case of nucleic acids, existing sequences can be modified using recombinant DNA techniques well known in the art. For example, single base alterations can be made using site-directed mutagenesis techniques, such as those described in Adelman et al., DNA, 2:183, (1983).

Alternatively, nucleic acids can be amplified using PCR techniques or expression in suitable hosts (cf. Sambrook et al., Molecular Cloning: A Laboratory Manual, 1989, Cold Spring Harbor Laboratory, New York, USA). Peptides and proteins may be expressed using recombinant techniques well known in the art, e.g., by transforming suitable host cells with recombinant DNA constructs as described in Morrison, J. Bact., 132:349-351 (1977); and Clark-Curtiss & Curtiss, Methods in Enzymology, 101:347-362 (Wu et al., eds, 1983).

Peptides and nucleic acids of the present invention may also be available commercially, or may be produced commercially, given the structural and/or functional properties of the molecules desired.

The present invention also contemplates agents that antagonize binding of SOST and/or WISE to its native receptor(s) ("SOST agonist"). SOST agonosts include small organic molecules including a peptidomimetic, which is an organic molecule that mimics the structure of a peptide; or a peptoid such as a vinylogous peptoid.

Additional nonpeptide, small organic molecule SOST agonists useful in a method of the invention can be identified by screening assays as described herein.

Preferred embodiments of the present invention include SOST agonists that are preferably SOST antibodies, WISE antibodies or LRP antibodies, although the invention also contemplates inhibitory peptides and small molecular inhibitors as described above. Antibodies of the invention are preferably chimeric, more preferably humanized antibodies, ideally monoclonal antibodies preferably raised against murine proteins, most preferably murine SOST. Methods for producing such antibodies are discussed immediately below.

A. Antibody Antagonists

SOST antagonist antibodies, including anti-SOST antibodies, may be raised using as an immunogen, such as a substantially purified full length protein, such as murine SOST, but may also be a SOST, WISE or LRP protein of human, mouse or other mammalian origin. The immunogen may be prepared from natural sources or produced recombinantly, or a peptide portion of a protein, which can include a portion of the cystiene knot domain, for example, a synthetic peptide. A non-immunogenic peptide may be made immunogenic by coupling the hapten to a carrier molecule such bovine serum albumin (BSA) or keyhole limpet hemocyanin (KLH), or by expressing the peptide portion as a fusion protein. Various other carrier molecules and methods for coupling a hapten to a carrier molecule are well known in the art and described, for example, by Harlow and Lane (supra, 1988).

Particularly useful antibodies for performing methods of the invention are monoclonal antibodies that that specifically bind to LRP molecules, WISE or, most preferably, SOST. Such antibodies are particularly useful where they bind SOST with at least an order of magnitude greater affinity than they bind another protein. Methods for creating chimeric antibodies, including humanized antibodies, is discussed in greater detail below.

1. Production of Recombinant Antibody

Methods for producing both monoclonal and polyclonal antibodies from identified proteins or peptides are well known in the art. In order to prepare recombinant chimeric and humanized antibodies that may function as SOST antagonists of the present invention, the nucleic acid encoding non-human antibodies must first be isolated. This is typically done by immunizing an animal, for example a mouse, with prepared α5β1 integrin or an antigenic peptide derived therefrom. Typically mice are immunized twice intraperitoneally with approximately 50 micrograms of protein antibody per mouse. Sera from immunized mice can be tested for antibody activity by immunohistology or immunocytology on any host system expressing such polypeptide and by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymad Corp., San Francisco, Calif. Mice whose sera contain detectable active antibodies according to the invention can be sacrificed three days later and their spleens removed for fusion and hybridoma production. Positive supernatants of such hybridomas can be identified using the assays common to those of skill in the art, for example, Western blot analysis.

The nucleic acids encoding the desired antibody chains can then be isolated by, for example, using hybridoma mRNA or splenic mRNA as a template for PCR amplification of the heavy and light chain genes [Huse, et al., Science 246:1276 (1989)]. Nucleic acids for producing both antibodies and intrabodies can be derived from murine monoclonal hybridomas using this technique [Richardson J. H., et al., Proc Natl Acad Sci USA 92:3137-3141 (1995); Biocca S., et al., Biochem and Biophys Res Comm, 197:422-427 (1993) Mhashilkar, A, M., et al., EMBO J 14:1542-1551 (1995)]. These hybridomas provide a reliable source of well-characterized reagents for the construction of antibodies and are particularly useful once their epitope reactivity and affinity has been characterized. Isolation of nucleic acids from isolated cells is discussed further in Clackson, T., et al., Nature 352:624-628 (1991) (spleen) and Portolano, S., et al., supra; Barbas, C. F., et al., supra; Marks, J. D., et al., supra; Barbas, C. F., et al., Proc Natl Acad Sci USA 88:7978-7982 (1991) (human peripheral blood lymphocytes). Humanized antibodies optimally include at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

A number of methods have been described to produce recombinant antibodies, both chimeric and humanized. Controlled rearrangement of antibody domains joined through protein disulfide bonds to form chimeric antibodies may be utilized (Konieczny et al., Haematologia, 14(1):95-99, 1981). Recombinant DNA technology can also be used to construct gene fusions between DNA sequences encoding mouse antibody variable light and heavy chain domains and human antibody light and heavy chain constant domains (Morrison et al., Proc. Natl. Acad. Sci. USA, 81(21):6851-6855, 1984.).

DNA sequences encoding the antigen binding portions or complementarity determining regions (CDR's) of murine monoclonal antibodies may be grafted by molecular means into the DNA sequences encoding the frameworks of human antibody heavy and light chains (Jones et al., Nature, 321 (6069):522-525, 1986.; Riechmann et al., Nature, 332(6162): 323-327, 1988.). The expressed recombinant products are called "reshaped" or humanized antibodies, and comprise the framework of a human antibody light or heavy chain and the antigen recognition portions, CDR's, of a murine monoclonal antibody.

Other methods for producing humanized antibodies are described in U.S. Pat. Nos. 5,693,762; 5,693,761; 5,585,089; 5,639,641; 5,565,332; 5,733,743; 5,750,078; 5,502,167; 5,705,154; 5,770,403; 5,698,417; 5,693,493; 5,558,864; 4,935,496; 4,816,567; and 5,530,101, each incorporated herein by reference.

Techniques described for the production of single chain antibodies (U.S. Pat. No. 4,946,778) can be adapted to produce single chain humanized antibodies to α5β1 integrin.

2. Isolation of Antibodies

Affinity Purification

Affinity purification of an antibody pool or sera provides a practitioner with a more uniform reagent. Methods for enriching antibody granulation inhibitors using antibody affinity matrices to form an affinity column are well known in the art and available commercially (AntibodyShop, c/o Statens Serum Institut, Artillerivej 5, Bldg. P2, DK-2300 Copenhagen 5). Briefly, an antibody affinity matrix is attached to an affinity support (see e.g.; CNBR Sepharose (R), Pharmacia Biotech). A mixture comprising antibodies is then passed over the affinity matrix, to which the antibodies bind. Bound antibodies are released by techniques common to those familiar with the art, yielding a concentrated antibody pool. The enriched antibody pool can then be used for further immunological studies, some of which are described herein by way of example.

B. Small Molecule Inhibitors

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptides (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Another approach uses recombinant bacteriophage to produce large libraries. Using the "phage method" (Scott and Smith, Science 249:386-390, 1990; Cwirla, et al, Proc. Natl. Acad. Sci., 87:6378-6382, 1990; Devlin et al., Science, 49:404-406, 1990), very large libraries can be constructed ($10^6$-$10^8$ chemical entities). A second approach uses primarily chemical methods, of which the Geysen method (Geysen et al., Molecular Immunology 23:709-715, 1986; Geysen et al. J. Immunologic Method 102:259-274, 1987; and the method of Fodor et al. (Science 251:767-773, 1991) are examples. Furka et al. (14th International Congress of Biochemistry, Volume #5, Abstract FR:013, 1988; Furka, Int. J. Peptide Protein Res. 37:487-493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

III. Methods for Identifying Sost Antagonists

The present invention provides methods for identifying diagnostic and therapeutic SOST antagonists. Several exemplary methods for identifying such antagonists are described herein, including cell-based and in vitro techniques. A general method of identifying SOST antagonists involves evaluating the effects of antagonist candidates on bone deposition under controlled conditions. Preferably bone deposition is determined using x-ray techniques on live animals. Preferred animals include rodents, more preferred are primates. Hand or paw bones are particularly useful subjects for such study.

Briefly, the test animal is treated with a predetermined dose of a SOST antagonist candidate. A control animal is treated with a control solution, preferably a non-irritating buffer solution or other carrier.

When the SOST antagonist candidate is delivered in a carrier, the control solution is ideally the carrier absent the SOST antagonist candidate. Multiple doses of the SOST antagonist candidate may be applied to the test animal, preferably following a predetermined schedule of dosing. The dosing schedule may be over a period of days, more preferably over a period of weeks.

Once the dosing schedule has been completed, both test and control animals are examined to determine the level of bone deposition present. This may be accomplished by any suitable method, but is preferably performed on live animals using x-ray equipment. Methods for x-ray examination of bones in animals are well known in the art. A SOST antagonist candidate suitable for use as a SOST antagonist is identified by noting significant bone deposition in the test animal when compared to the control animal. Ideally bone deposition in the test bone(s) of the test animal should be at least 10%, more preferably 20%, most preferably 30% or 40% or more pone deposition than is present in the same bones of the control animal. Where necessary, levels of bone deposition may be calculated by determining the volume of bone deposition present in each animal. Calculations may be performed by constructing a 3-dimensional image of the bone deposition and calculating the volume from the image with the aid of e.g., computed axial tomography.

In an exemplary embodiment, intravenous injection of a SOST antagonist candidate, for example a monoclonal antibody described herein, may be made into a test animal, with a control animal receiving an equal volume of control solution without the SOST antagonist candidate. Identical dosing should be done on a weekly basis for four weeks. Suitable dosage will depend on the nature of the particular SOST antagonist candidate being tested. By way of example, in dosing it should be noted that systemic injection, either intravenously, subcutaneously or intramuscularly, may also be used. For systemic injection of a SOST antagonist candidate or a SOST antagonist, dosage should be about 5 mg/kg, preferably more preferably about 15 mg/kg, advantageously about 50 mg/kg, more advantageously about 100 mg/kg, acceptably about 200 mg/kg. dosing performed by nebulized inhalation, eye drops, or oral ingestion should be at an amount sufficient to produce blood levels of the SOST antagonist candidate similar to those reached using systemic injection. The amount of SOST antagonist candidate that must be delivered by nebulized inhalation, eye drops, or oral ingestion to attain these levels is dependent upon the nature of the inhibitor used and can be determined by routine experimentation. It is expected that, for systemic injection of the monoclonal antibody SOST antagonist candidates described herein, therapeutic levels of the antibody may be detected in the blood one week after delivery of a 15 mg/kg dose.

High Throughput Techniques

While the methods noted above can be used to identify any type of SOST antagonist, they are best suited for screening SOST antagonist candidates that are suspected as being SOST antagonists, usually through some relationship to known SOST antagonists (e.g., by belonging to the same chemical family or sharing some other structural or functional feature with a known SOST antagonist.) Moreover, novel SOST antagonists may be identified using a process known as computer, or molecular modeling, as discussed below.

Computer Modeling

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

An example of the molecular modelling system described generally above consists of the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et. al., Acta Pharmaceutica Fennica 97, 159-166 (1988); Ripka, New Scientist 54-57 (Jun. 16, 1988); McKinaly and Rossmann, Annu. Rev. Pharmacol. Toxiciol. 29, 111-122 (1989); Perry and Davies, OSAR: Quantitative Structure-Activity Relationships in Drug Design pp. 189-193 (Alan R. Liss, Inc. 1989); Lewis and Dean, Proc. R. Soc. Land. 236, 125-140 and 141-162 (1989); and, with respect to a model receptor for nucleic acid components, Askew, et al., J. Am. Chem. Soc. 111, 1082-1090 (1989). Askew et al. constructed a new molecular shape which permitted both hydrogen bonding and aromatic stacking forces to act simultaneously. Askew et al. used Kemp's triacid (Kemp et al., J. Org. Chem. 46:5140-5143 (1981)) in which a U-shaped (diaxial) relationship exists between any two carboxyl functions. Conversion of the triacid to the imide acid chloride gave an acylating agent that could be attached via amide or ester linkages to practically any available aromatic surface. The resulting structure featured an aromatic plane that could be roughly parallel to that of the atoms in the imide function; hydrogen bonding and stacking forces converged from perpendicular directions to provide a microenvironment complimentary to adenine derivatives.

Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of RNA, once that region is identified.

Screening Compound Libraries

Whether identified from existing SOST antagonists or from molecular modelling techniques, SOST antagonists generally must be modified further to enhance their therapeutic usefulness. This is typically done by creating large libraries of compounds related to the SOST antagonist, or compounds synthesized randomly, based around a core structure. In order to efficiently screen large and/or diverse libraries of SOST antagonist candidates, a high throughput screening method is necessary to at least decrease the number of candidate compounds to be screened using the assays described above. High throughput screening methods involve providing a combinatorial chemical or peptide library containing a large number of potential therapeutic compounds (potential modulator or ligand compounds). Such "combinatorial chemical libraries" or "candidate libraries" are then screened in one or more assays, as described below, to identify those library members (particular chemical species or subclasses) that are able to promote bone deposition. The compounds thus identified can serve as conventional "lead compounds" or can themselves be used as potential or actual therapeutics.

Candidate compounds of the library can be any small chemical compound, or a biological entity, such as a protein, sugar, nucleic acid or lipid, as described previously. Typically, test compounds will be small chemical molecules and peptides. The assays discussed below are designed to screen large chemical libraries by automating the assay steps and providing compounds from any convenient source to assays, which are typically run in parallel (e.g., in microtiter formats on microtiter plates or similar formats, as depicted in FIG. 5, in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

Accordingly, the present invention provides methods for high throughput screening of granulation inhibitor candidates. The initial steps of these methods allow for the efficient and rapid identification of combinatorial library members that have a high probability of being SOST antagonists. These initial steps take advantage of the observation that SOST antagonists are also LRP or SOST binding agents. Any method that determines the ability of a member of the library, termed a binding candidate, to specifically bind to SOST, WISE or an LRP protein is suitable for this initial high throughput screening. For example, competitive and non-competitive ELISA-type assays known to one of ordinary skill in the art may be utilized.

Binding candidates that are found to bind SOST, WISE or an LRP protein with acceptable specificity, e.g., with a $K_a$ for SOST, WISE or an LRP protein of at least about $10^5$ mol$^{-1}$, $10^6$ mol$^{-1}$ or greater, preferably $10^7$ mol$^{-1}$ or greater, more preferably $10^8$ mol$^{-1}$ or greater, and most preferably $10^9$ mol$^{-1}$ or greater, are SOST antagonist candidates and are screened further, as described above, to determine their ability to promote bone deposition.

A number of well-known robotic systems have been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, HewlettPackard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

IV. Therapeutic Uses

Individuals to be treated using methods of the present invention may be any individual suffering from bone loss, such as a sufferer of osteoporosis or simply an individual recovering from a broken limb. Such an individual is a vertebrate such as a mammal, including a dog, cat, horse, cow, or goat; a bird; or any other animal, particularly a commercially important animal or a domesticated animal, more particularly a human being.

Methods of the present invention are suitable for use on any individual suffering bone loss as a result of injury or disease. Some embodiments of the methods described herein are particularly suited for treatment of osteoporosis.

In therapeutic use SOST antagonists generally will be in the form of a pharmaceutical composition containing the antagonist and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters. The selection of a pharmaceutically acceptable carrier will depend, in part, on the chemical nature of the SOST antagonist, for example, whether the SOST antagonist is an antibody, a peptide or a nonpeptide, small organic molecule.

A pharmaceutically acceptable carrier may include physiologically acceptable compounds that act, for example, to stabilize the SOST antagonist or increase its absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the SOST antagonist and on its particular physio-chemical characteristics.

The methods of the present invention include application of SOST antagonists in cocktails including other medicaments, for example, antibiotics, fungicides, and anti-inflammatory agents. Alternatively, the methods may comprise sequential dosing of an afflicted individual with a SOST antagonist and one or more additional medicaments to optimize a treatment regime. In such optimized regimes, the medicaments, including the granulation inhibitor may be applied in any sequence and in any combination.

Bone loss resulting from injury or disease can occur locally, for example, in the case of a broken bone, or may be more systemic, for example in a person suffering from osteoporosis. Depending on the bone, nature of the disease or injury, one skilled in the art would select a particular route and method of administration of the SOST antagonist.

The SOST antagonists of the present invention may also be included in slow release formulations for prolonged treatment following a single dose. In one embodiment, the formulation is prepared in the form of microspheres. The microspheres may be prepared as a homogenous matrix of a SOST antagonist with a biodegradable controlled release material, with optional additional medicaments as the treatment requires. The microspheres are preferably prepared in sizes suitable for infiltration and/or injection, and injected systemically, or directly at the site of treatment.

The formulations of the invention are also suitable for administration in all body spaces/cavities, including but not limited to pleura, peritoneum, cranium, mediastinum, pericardium, bursae or bursal, epidural, intrathecal, intraocular, etc.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylate-divinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans. alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone. methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO 94/06416.

The amount of SOST antagonist administered to an individual will depend, in part, on the disease and extent of injury. Methods for determining an effective amount of an agent to administer for a diagnostic or a therapeutic procedure are well known in the art and include phase I, phase II and phase III clinical trials. Generally, an agent antagonist is administered in a dose of about 0.01 to 200 mg/kg body weight when administered systemically, and at a concentration of approximately 1 µM, when administered directly to a wound site. The total amount of SOST antagonist can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a particular SOST antagonist required to provide an effective amount to a region or regions of injury depends on many factors including the age and general health of the subject as well as the route of administration, the number of treatments to be administered, and the nature of the SOST antagonist, including whether the SOST antagonist is an antibody, a peptide, or a non-peptide small organic molecule. In view of these factors, the skilled artisan would adjust the particular dose so as to obtain an effective amount for efficaciously promoting bone deposition for therapeutic purposes.

All publications and patent applications cited in this specification are herein incorporated by reference as if each individual publication or patent application were specifically and individually indicated to be incorporated by reference.

Although the foregoing invention has been described in some detail by way of illustration and example for clarity and understanding, it will be readily apparent to one of ordinary skill in the art in light of the teachings of this invention that certain changes and modifications may be made thereto without departing from the spirit and scope of the appended claims.

As can be appreciated from the disclosure provided above, the present invention has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results.

EXAMPLES

Methods

Isolation of SOST cDNA. SOST was isolated from a mouse Day 11 cDNA library using touchdown PCR (1 cycle, denature 92° C. 2'; 5 cycles, 92° C. 1', anneal 68° C. 1', extend 72° C. 2'; 30 cycles, 92° C. 1', anneal 64° C. 1', extend 72° C. 2'; 1 cycle, extension 72° C. 10'). Forward primer, CGTGC-CTCATCTGCCTACTTGTGCA; Reverse primer, GAAGTCCTTGAGCTCCGACTGGTTGTG. 1 ul of DMSO was added to the reactions. The full length mouse SOST cDNA was created using successive PCR reactions based on GI: 13161022.

Wise Mutant Mouse (129SV/EV & C57BL6). A neoLacZ cassette containing stop codons at the 3' end was inserted into a Wise gDNA sequence isolated BAC from a 129SVEV mouse. The cassette was inserted into the first exon of Wise using SmaI and EcoRI sites. The modified BAC was then used for homologous recombination after electroporation into 129SVEV mouse ES cells. Specific integrants were selected from southern analysis using a 3' probe within exon 2 of Wise. EcoRI digests yielded either a 6.8 Kb fragment associated with homologous recombination, or a 9 Kb fragment associated with a random integration event.

Bioinformatics. Phylogenetic Tree: SOST and WISE cystein knot protein sequences were Blasted (NCBI) and all significant sequences were isolated. The cystein knots from all sequences were manually aligned using the software T-Coffee and then analyzed with Phylip bootstrap neighbor joining methods. Chromosomal location: Wise and SOST DNA sequences where Blasted against the mouse (*Mus musculus*) Ensembl database (http://www.ensembl.org/*Mus_musculus*/blastview).

*Xenopus* Assays. Capped RNA synthesis-5 ug linear DNA template (SOST, Noggin, Beta-Catenin, Wnt8, Wise) was added to the following; 5× transcription buffer (P118B promega), 0.1M DTT, 0.1M ATP, 0.1M CTP, 0.1M UTP, 0.1M GTP, 5 mM CAP (NEN 514045), Rnasin, and polymerase of choice. RNA used in Cap assays: 250 pg Noggin; SOST 300 pg, 600 pg, 900 pg; 5 pg Wnt8.[1] RNA for Ventral marginal zones: SOST 300 pg, Wnt8 100 pg, beta-Catenin 200 pg.

BMP Assay. ATDC-5 at low passage were consistently grown at subconfluency in DMEM/F12 media supplemented with 10% heat inactivated fetal calf serum, 100 units/ml penicillin, and 100 mg/ml streptomycin. In 96 well plates (Corning) inhibitors were diluted. A constant amount of BMP (R and D Systems) was added to each well and incubated for 1 hour at 37° C. ATDC-5 cells were counted and plated at $2\times10^5$ cells/ml. Heparin was added to the plate containing BMP4 at a final concentration of 2 µg/ml. L-Ascorbic Acid was added to the plate containing BMP6 at a final concentration of 50 µg/ml. Cells were then incubated for 3 days at 37° C. Cell layers were washed twice with PBS and lysed in 0.15 M NaCl, 3 mM $NaHCO_3$, and 0.1% Triton X-100 at pH 9.3. Cell layers were incubated at 37° C. for 30 mins. 20 p. 1 of each sample was incubated with 1 mg/ml of p-nitrophenyl phosphate (Sigma) in 1 M diethanolamine (Sigma) with 0.5 mM $MgCl_2$ at a pH of 9.8 and then incubated at 22° C. for 8 mins. Reaction was stopped by the addition of 0.5 N NaOH. Optical density was measured at 405 nm.

Immunoprecipitation. A 10 mm dish of 293 cells was transfected with 10 ug of LRP5, LRP6, SOST or Wise, using Fugene 6 (Roche). pCS2+LRP5 contains the extracellular portion of the human sequence between EcoRI-XbaI. pCS2+SOST contain the whole reading frame and has been modified at the 3' end to have a kozak sequence and Flag tag. Wise-Flag, and LRP6-IgG-FC are described in Itasaki et al. (2003). pCS2+ with an IgG-FC insert is the vector control. The supernatants were collected on day1, day 2, and day3. The supernatant was concentrated through an appropriate molecular weight Amicon ultra (Millipore) spin column. A protein concentration was taken on the concentrated supernatants, and 50 ug of each sample was used in each IP. Anti-Flag M2 affinity gel (Sigma) was used for the Wise and SOST IPs.

Tooth Radioactive In Situ. C57B6 J mice (Jackson Laboratories) were mated. The day of identification of a vaginal plug was considered E0.5, and the day of birth P0. Embryos were harvested at day 16.5, embedded in OCT (VWR), and quick frozen in isopentane on dry ice. 14 um cryostat sections were collected on Probe-On Plus slides and stored at −80° C. with dessicant prior to hybridization. Sections were equilibrated to room temperature, fixed in 4% paraformaldehyde in PBS for 20 min, rinsed twice in PBS with 0.1M glycine, once in PBS alone, acetylated in 0.1M triethanolamine (pH 8.0) and 0.25% acetic anhydride for 10 min, rinsed twice more in PBS, and then dehydrated. Hybridization was carried out using $^{35}$S-labeled antisense probes. Hybridization and post hybridization protocol as described by Gall et al. (1995).[23] Slides were dipped in Kodak NTB-2 liquid emulsion diluted 1:1 with distilled water, and exposed for 21-28 days at −80° C. Developed sections were then H and E stained.

X-rays & Teeth Dissections. The mice were dissected and the jaws were placed in a proteinase K solution (2×SSC, 0.2% SDS, 10 mM EDTA, and 100 ul of 10 mg/ml proteinase K) overnight at 55° C. The next day the jaws are air-dried and a digital Faxitron was used for capturing X-ray images of the mouse maxilla. The teeth where removed using tweezers.

Bone & Retinal Immunochemistry. Chick HH45 femurs were harvested and fixed in 3.5% PFA. The tissue was then processed for cryosectioning. Mouse retinas were harvested from P0 and P2.5 month. The retinas were fixed in formalin and processed for paraffin sectioning. Immunochemistry was preformed using PBS (with or without Triton) and 10% GS. The primary antibodies used were a custom made peptide antibody against chick WISE (1:100), chick PAX6 (1:10) and mouse 2H3 (1:10) from Hybridoma Bank.

Bone Density. Bone densitometry was measured using a PIXImus mouse densitometer (GE medical syetms). Bone minieral and body composition are measured using Dual Xray absorptiometry (DEXA).

TRAP and ALP. Staining was preformed on crysectioned mouse femurs. TRAP (tartrate resistant acid phosphatase) staining was done as per manufactured protocol for Sigma acid phosphatase kit (181A). Alkaline phospatase (ALP) staining was carried out for 15 minutes at RT in 100 mM Tris-maleate (pH 9.2), Naphthol As-MX phosphate and Fast red TR.

BONE ISH. Sum cryosections of mouse femurs were dried for 2 hours to overnight at room temperature. Rinse slides in 30° C. water to melt gelatin. Rinse in PBS, 2×SSC. Hybrize using 1 ug/ml dig-labelled probe in a humidified chamber containing DEPC water. Coverslip slides and incubate overnight at 65° C. Posthyb wash for 2× 10 minutes in 50% formamide, 1×SSC, 0.1% tween 20. Wash 2×MABT 10 minutes, incubate 30 minutes with blocking buffer (20% goat serum, 20% BBR, 60% MABT). Add anti-digAP 1:2000 and incubate overnight at room temp. Wash MABT 5 minutes, NTMT 10 minutes, then reveal in NTMT with NBT/BCIP. Stop reaction with PBST.

REFERENCES

1. Itasaki, N. et al. Wise, a context-dependent activator and inhibitor of Wnt signalling. *Development* 130, 4295-305 (2003).
2. Brunkow, M. E. et al. Bone dysplasia sclerosteosis results from loss of the SOST gene product, a novel cystine knot-containing protein. *Am J Hum Genet* 68, 577-89 (2001).
3. Kusu, N. et al. Sclerostin is a novel secreted osteoclast-derived bone morphogenetic protein antagonist with unique ligand specificity. *J Biol Chem* 278, 24113-7 (2003).
4. Balemans, W. et al. Increased bone density in sclerosteosis is due to the deficiency of a novel secreted protein (SOST), *Hum Mol Genet* 10, 537-43 (2001).
5. Sasai, Y. et al. *Xenopus* chordin: a novel dorsalizing factor activated by organizer-specific homeobox genes. *Cell* 79, 779-90 (1994).
6. Piccolo, S. et al. The head inducer cerberus is a multifunctional antagonist of Nodal, BMP and Wnt signals. *Nature* 397, 707-710 (1999).
7. Hsu, D. R., Economides, A. N., Wang, X., Eimon, P. M. & Harland, R. M. The *Xenopus* dorsalizing factor Gremlin identifies a novel family of secreted proteins that antagonize BMP activities. *Mol Cell* 1, 673-83 (1998).
8. Stanley, E. et al. DAN is a secreted glycoprotein related to *Xenopus* cerberus. *Mech Dev* 77, 173-84 (1998).
9. Yokouchi, Y., Vogan, K. J., Pearse, R. V., 2nd & Tabin, C. J. Antagonistic signaling by Caronte, a novel Cerberus-related gene, establishes left-right asymmetric gene expression. *Cell* 98, 573-83 (1999).
10. Laurikkala, J., Kassai, Y., Pakkasjarvi, L., Thesleff, I. & Itoh, N. Identification of a secreted BMP antagonist, ectodin, integrating BMP, FOP, and SHH signals from the tooth enamel knot. *Dev Biol* 264, 91-105 (2003).
11. Simmons, D. G. & Kennedy, T. G. Uterine sensitization-associated gene-1: a novel gene induced within the rat endometrium at the time of uterine receptivity/sensitization for the decidual cell reaction. *Biol Reprod* 67, 1638-45 (2002).
12. Winkler, D. G. et al. Osteocyte control of bone formation via sclerostin, a novel BMP antagonist. *Embo J* 22, 6267-6276 (2003).
13. Abreu, J. G., Ketpura, N. I., Reversade, B. & De Robertis, E. M. Connective-tissue growth factor (CTGF) modulates cell signalling by BMP and TGF-beta. *Nat Cell Biol* 4, 599-604 (2002).
14. Latinkic, B. V. et al. *Xenopus* Cyr61 regulates gastrulation movements and modulates Wnt signalling. *Development* 130, 2429-41 (2003).
15. Fullwood, P. et al. X linked exudative vitreoretinopathy: clinical features and genetic linkage analysis. *Br J Ophthalmol* 77, 168-70 (1993).
16. Pinson, K. I., Brennan, J., Monkley, S., Avery, B. J. & Skarnes, W. C. An LDL-receptor-related protein mediates Wnt signalling in mice. *Nature* 407, 535-8 (2000).
17. Gong, Y. et al. LDL receptor-related protein 5 (LRP5) affects bone accrual and eye development. *Cell* 107, 513-23 (2001).
18. Kato, M. et al. Cbfa1-independent decrease in osteoblast proliferation, osteopenia, and persistent embryonic eye vascularization in mice deficient in Lrp5, a Wnt coreceptor. *J Cell Biol* 157, 303-14 (2002).
19. Little, R. D. et al. A mutation in the LDL receptor-related protein 5 gene results in the autosomal dominant high-bone-mass trait. *Am J Hum Genet* 70, 11-9 (2002).
20. Aberg, T. et al. Phenotypic changes in dentition of Runx2 homozygote-null mutant mice. *J Histochem Cytochem* 52, 131-9 (2004).
21. Karsenty, G. Minireview: transcriptional control of osteoblast differentiation. *Endocrinology* 142, 2731-3 (2001).
22. Sevetson, B., Taylor, S. & Pan, Y. Cbfa1/RUNX2 directs specific expression of the sclerosteosis gene (SOST). *J Biol Chem* (2004).
23. Gall, C., Lauterborn, J. & Guthrie, K. in *Autoradiography and Correlative Imaging* (ed. W. E. Stumpf and H. F. Solomon) 379-399 (Academic Press, San Diego, 1995).
24. Kronenberg, H. M. Twist genes regulate runx2 and bone formation. *Dev Cell* 6, 317-8 (2004).

What is claimed is:

1. An isolated monoclonal antibody that specifically binds to the amino acid sequence depicted in SEQ ID NO: 18 or SEQ ID NO: 69.

2. The antibody of claim 1 wherein the antibody is a humanized antibody.

3. The isolated monoclonal antibody of claim 1, wherein the amino acid sequence is depicted in SEQ ID NO: 18.

4. The isolated monoclonal antibody of claim 3, wherein the antibody is a humanized antibody.

5. The isolated monoclonal antibody of claim 1, wherein the amino acid sequence is depicted in SEQ ID NO: 69.

6. The isolated monoclonal antibody of claim 5, wherein the antibody is a humanized antibody.

7. An isolated monoclonal antibody that specifically binds to a Sost peptide, wherein said monoclonal antibody binds to the amino acid sequence depicted in SEQ ID NO: 18 or SEQ ID NO: 69.

8. The isolated monoclonal antibody of claim 7, wherein the antibody is a humanized antibody.

9. The isolated monoclonal antibody of claim 7, wherein the amino acid sequence is depicted in SEQ ID NO: 18.

10. The isolated monoclonal antibody of claim 9, wherein the antibody is a humanized antibody.

11. The isolated monoclonal antibody of claim 7, wherein the amino acid sequence is depicted in SEQ ID NO: 69.

12. The isolated monoclonal antibody of claim 11, wherein the antibody is a humanized antibody.

13. An isolated monoclonal antibody that binds to the amino acid sequence depicted in SEQ ID NO: 18 or SEQ ID NO: 69, wherein the isolated monoclonal antibody binds to the amino acid sequence with a specific binding activity ($K_a$) of at least about $10^7$ $mol^{-1}$ or greater.

14. The isolated monoclonal antibody of claim 13, wherein the antibody is a humanized antibody.

15. The isolated monoclonal antibody of claim 13, wherein the amino acid sequence is depicted in SEQ ID NO: 18.

16. The isolated monoclonal antibody of claim 15, wherein the antibody is a humanized antibody.

17. The isolated monoclonal antibody of claim 13, wherein the amino acid sequence is depicted in SEQ ID NO: 69.

18. The isolated monoclonal antibody of claim 17, wherein the antibody is a humanized antibody.

* * * * *

SEQUENCE LISTING

<160> NUMBER OF SEQ ID NOS: 234

<210> SEQ ID NO 1
<211> LENGTH: 4131
<212> TYPE: DNA
<213> ORGANISM: Human

<400> SEQUENCE: 1

| | | | | | | |
|---|---|---|---|---|---|---|
| atgggggccg | tcctgaggag | cctcctggcc | tgcagcttct | gtgtgctcct | gagagcggcc | 60 |
| cctttgttgc | tttatgcaaa | cagacgggac | ttgcgattgg | ttgatgctac | aaatggcaaa | 120 |
| gagaatgcta | cgattgtagt | tggaggcttg | gaggatgcag | ctgcggtgga | ctttgtgttt | 180 |
| agtcatggct | tgatatactg | gagtgatgtc | agcgaagaag | ccattaaacg | aacagaattt | 240 |
| aacaaaactg | agagtgtgca | gaatgttgtt | gtttctggat | tattgtcccc | cgatgggctg | 300 |
| gcatgtgatt | ggcttggaga | aaaattgtac | tggacagatt | ctgaaactaa | tcggattgaa | 360 |
| gtttctaatt | tagatggatc | tttacgaaaa | gttttatttt | ggcaagagtt | ggatcaaccc | 420 |
| agagctattg | ccttagatcc | ttcaagtggg | ttcatgtact | ggacagactg | gggagaagtg | 480 |
| ccaaagatag | aacgtgctgg | aatggatggt | tcaagtcgct | tcattataat | aaacagtgaa | 540 |
| atttactggc | caaatggact | gactttggat | atgaagaac | aaaagcttta | ttgggcagat | 600 |
| gcaaaactta | atttcatcca | caatcaaat | ctggatggaa | caaatcggca | ggcagtggtt | 660 |
| aaaggttccc | ttccacatcc | ttttgccttg | acgttatttg | aggacatatt | gtactggact | 720 |
| gactggagca | cacactccat | tttggcttgc | aacaagtata | ctggtgaggg | tctgcgtgaa | 780 |
| atccattctg | acatcttctc | tcccatggat | atacatgcct | tcagccaaca | gaggcagcca | 840 |
| aatgccacaa | atccatgtgg | aattgacaat | ggggttgtt | cccatttgtg | tttgatgtct | 900 |
| ccagtcaagc | cttttatca | gtgtgcttgc | cccactgggg | tcaaactcct | ggagaatgga | 960 |
| aaaacctgca | agatggtgc | cacagaatta | ttgcttttag | ctcgaaggac | agacttgaga | 1020 |
| cgcatttctt | tggatacacc | agattttaca | gacattgttc | tgcagttaga | agacatccgt | 1080 |
| catgccattg | ccatagatta | cgatcctgtg | aaggctacaa | tctactggac | tgatgatgaa | 1140 |
| gtgagggcca | tacgccgttc | atttatagat | ggatctggca | gtcagtttgt | ggtcactgct | 1200 |
| caaattgccc | atcctgatgg | tattgctgtg | gactgggttg | cacgaaatct | ttattggaca | 1260 |
| gacactggca | ctgatcgaat | agaagtgaca | aggctcaatg | ggaccatgag | gaagatcttg | 1320 |
| atttcagagg | acttagagga | accccgggct | attgtgttag | atcccatggt | gggtacatg | 1380 |
| tattggactg | actggggaga | aattccgaaa | attgagcgag | cagctctgga | tggttctgac | 1440 |
| cgtgtagtat | tggttaacac | ttctcttggt | tggccaaatg | gtttagcctt | ggattatgat | 1500 |
| gaaggcaaaa | tatactgggg | agatgccaaa | acagacaaga | ttgaggttat | gaatactgat | 1560 |
| ggcactggga | cgagtactag | tggaagac | aaaattcctc | acatatttgg | atttactttg | 1620 |
| ttgggtgact | atgtttactg | gactgactgg | cagaggcgta | gcattgaaag | agttcataaa | 1680 |
| cgaagtgcag | agagggaagt | gatcatagat | cagctgcctg | acctcatggg | cctaaaggct | 1740 |
| acaaatgttc | atcgagtgat | tggttccaac | ccctgtgctg | aggaaaacgg | gggatgtagc | 1800 |
| catctctgcc | tctatagacc | tcagggcctt | cgctgtgctt | gcctattgg | ctttgaactc | 1860 |
| atcagtgaca | tgaagacctg | cattgtccca | gaggctttcc | ttttgttttc | acggagagca | 1920 |
| gatatcagac | gaatttctct | ggaaacaaac | aataataatg | tggctattcc | actcactggt | 1980 |
| gtcaaagaag | cttctgcttt | ggattttgat | gtgacagaca | accgaattta | ttggactgat | 2040 |

-continued

| | |
|---|---|
| atatcactca agaccatcag cagagccttt atgaatggca gtgcactgga acatgtggta | 2100 |
| gaattcggct tagattatcc agaaggcatg gcagtagact ggcttgggaa gaacttgtac | 2160 |
| tgggcagaca caggaacgaa tcgaattgag gtgtcaaagt tggatgggca gcaccgacaa | 2220 |
| gttttggtgt ggaaagacct agatagtccc agagctctcg cgttggaccc tgccgaagga | 2280 |
| tttatgtatt ggactgaatg gggtggaaaa cctaagatag acagagctgc aatggatgga | 2340 |
| agtgaacgta ctaccttagt tccaaatgtg gggcgggcaa acggcctaac tattgattat | 2400 |
| gctaaaagga ggctttattg gacagacctg gacaccaact taatagaatc ttcaaatatg | 2460 |
| cttgggctca accgtgaagt tatagcagat gacttgcctc atcctttttgg cttaactcag | 2520 |
| taccaagatt atatctactg gacggactgg agccgacgca gcattgagcg tgccaacaaa | 2580 |
| accagtggcc aaaaccgcac catcattcag ggccatttgg attatgtgat ggacatcctc | 2640 |
| gtctttcact catctcgaca gtcagggtgg aatgaatgtg cttccagcaa tgggcactgc | 2700 |
| tcccacctct gcttggctgt gccagttggg ggttttgttt gtggatgccc tgcccactac | 2760 |
| tctcttaatg ctgacaacag gacttgtagt gctcctacga cttttcctgct cttcagtcaa | 2820 |
| aagagtgcca tcaaccgcat ggtgattgat gaacaacaga gccccgacat catccttccc | 2880 |
| atccacagcc ttcggaatgt ccgggccatt gactatgacc cactggacaa gcaactctat | 2940 |
| tggattgact cacgacaaaa catgatccga aaggcacaag aagatggcag ccagggcttt | 3000 |
| actgtggttg tgagctcagt tccgagtcag aacctggaaa tacaacccta tgacctcagc | 3060 |
| attgatattt acagccgcta catctactgg acttgtgagg ctaccaatgt cattaatgtg | 3120 |
| acaagattag atgggagatc agttggagtg gtgctgaaag gcgagcagga cagacctcga | 3180 |
| gccattgtgg taaacccaga gaagggtat atgtattta ccaatcttca ggaaaggtct | 3240 |
| cctaaaattg aacgggctgc tttggatggg acagaacggg aggtcctctt tttcagtggc | 3300 |
| ttaagtaaac caattgcttt agcccttgat agcaggctgg gcaagctctt tgggctgat | 3360 |
| tcagatctcc ggcgaattga aagcagtgat ctctcaggtg ctaaccggat agtattagaa | 3420 |
| gactccaata tcttgcagcc tgtgggactt actgtgtttg aaaactggct ctattggatt | 3480 |
| gataaacagc agcaaatgat tgaaaaaatt gacatgacag gtcgagaggg tagaaccaaa | 3540 |
| gtccaagctc gaattgccca gcttagtgac attcatgcag taaaggagct gaaccttcaa | 3600 |
| gaatacagac agcacccttg tgctcaggat aatggtggct gttcacatat ttgtcttgta | 3660 |
| aaggggggatg gtactacaag gtgttcttgc cccatgcacc tggttctact tcaagatgag | 3720 |
| ctatcatgtg gagaacctcc aacatgttct cctcagcagt ttacttgttt cacggggggaa | 3780 |
| attgactgta tccctgtggc ttggcggtgc gatgggttta ctgaatgtga agaccacagt | 3840 |
| gatgaactca attgtcctgt atgctcagag tcccagttcc agtgtgccag tgggcagtgt | 3900 |
| attgatggtg ccctccgatg caatggagat gcaaactgcc aggacaaatc agatgagaag | 3960 |
| aactgtgaag tgctttgttt aattgatcag ttccgctgtg ccaatggtca gtgcattgga | 4020 |
| aagcacaaga gtgtgatca taatgtggat tgcagtgaca agtcagatga actggattgt | 4080 |
| tatccgactg aagaaccagc accacaggcc accaatacag ttggttctgt t | 4131 |

<210> SEQ ID NO 2
<211> LENGTH: 1377
<212> TYPE: PRT
<213> ORGANISM: Human

<400> SEQUENCE: 2

Met Gly Ala Val Leu Arg Ser Leu Leu Ala Cys Ser Phe Cys Val Leu
1               5                   10                  15

```
Leu Arg Ala Ala Pro Leu Leu Leu Tyr Ala Asn Arg Arg Asp Leu Arg
                20                  25                  30

Leu Val Asp Ala Thr Asn Gly Lys Glu Asn Ala Thr Ile Val Val Gly
            35                  40                  45

Gly Leu Glu Asp Ala Ala Val Asp Phe Val Phe Ser His Gly Leu
        50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Ser Gly Leu Leu Ser
                85                  90                  95

Pro Asp Gly Leu Ala Cys Asp Trp Leu Gly Lys Leu Tyr Trp Thr
            100                 105                 110

Asp Ser Glu Thr Asn Arg Ile Glu Val Ser Asn Leu Asp Gly Ser Leu
            115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
                180                 185                 190

Glu Gln Lys Leu Tyr Trp Ala Asp Ala Lys Leu Asn Phe Ile His Lys
            195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
    275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
    355                 360                 365

Pro Val Glu Gly Tyr Ile Tyr Trp Thr Asp Asp Glu Val Arg Ala Ile
        370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
```

```
                435                 440                 445
Arg Ala Ile Val Leu Asp Pro Met Val Gly Tyr Met Tyr Trp Thr Asp
450                 455                 460
Trp Gly Glu Ile Pro Lys Ile Glu Arg Ala Ala Leu Asp Gly Ser Asp
465                 470                 475                 480
Arg Val Val Leu Val Asn Thr Ser Leu Gly Trp Pro Asn Gly Leu Ala
                485                 490                 495
Leu Asp Tyr Asp Glu Gly Lys Ile Tyr Trp Gly Asp Ala Lys Thr Asp
                500                 505                 510
Lys Ile Glu Val Met Asn Thr Asp Gly Thr Gly Arg Arg Val Leu Val
                515                 520                 525
Glu Asp Lys Ile Pro His Ile Phe Gly Phe Thr Leu Leu Gly Asp Tyr
530                 535                 540
Val Tyr Trp Thr Asp Trp Gln Arg Arg Ser Ile Glu Arg Val His Lys
545                 550                 555                 560
Arg Ser Ala Glu Arg Glu Val Ile Ile Asp Gln Leu Pro Asp Leu Met
                565                 570                 575
Gly Leu Lys Ala Thr Asn Val His Arg Val Ile Gly Ser Asn Pro Cys
                580                 585                 590
Ala Glu Glu Asn Gly Gly Cys Ser His Leu Cys Leu Tyr Arg Pro Gln
                595                 600                 605
Gly Leu Arg Cys Ala Cys Pro Ile Gly Phe Glu Leu Ile Ser Asp Met
                610                 615                 620
Lys Thr Cys Ile Val Pro Glu Ala Phe Leu Leu Phe Ser Arg Arg Ala
625                 630                 635                 640
Asp Ile Arg Arg Ile Ser Leu Glu Thr Asn Asn Asn Asn Val Ala Ile
                645                 650                 655
Pro Leu Thr Gly Val Lys Glu Ala Ser Ala Leu Asp Phe Asp Val Thr
                660                 665                 670
Asp Asn Arg Ile Tyr Trp Thr Asp Ile Ser Leu Lys Thr Ile Ser Arg
                675                 680                 685
Ala Phe Met Asn Gly Ser Ala Leu Glu His Val Val Glu Phe Gly Leu
690                 695                 700
Asp Tyr Pro Glu Gly Met Ala Val Asp Trp Leu Gly Lys Asn Leu Tyr
705                 710                 715                 720
Trp Ala Asp Thr Gly Thr Asn Arg Ile Glu Val Ser Lys Leu Asp Gly
                725                 730                 735
Gln His Arg Gln Val Leu Val Trp Lys Asp Leu Asp Ser Pro Arg Ala
                740                 745                 750
Leu Ala Leu Asp Pro Ala Glu Gly Phe Met Tyr Trp Thr Glu Trp Gly
                755                 760                 765
Gly Lys Pro Lys Ile Asp Arg Ala Ala Met Asp Gly Ser Glu Arg Thr
                770                 775                 780
Thr Leu Val Pro Asn Val Gly Arg Ala Asn Gly Leu Thr Ile Asp Tyr
785                 790                 795                 800
Ala Lys Arg Arg Leu Tyr Trp Thr Asp Leu Asp Thr Asn Leu Ile Glu
                805                 810                 815
Ser Ser Asn Met Leu Gly Leu Asn Arg Glu Val Ile Ala Asp Asp Leu
                820                 825                 830
Pro His Pro Phe Gly Leu Thr Gln Tyr Gln Asp Tyr Ile Tyr Trp Thr
                835                 840                 845
Asp Trp Ser Arg Arg Ser Ile Glu Arg Ala Asn Lys Thr Ser Gly Gln
                850                 855                 860
```

-continued

```
Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
        915                 920                 925

Cys Ser Ala Pro Thr Thr Phe Leu Leu Phe Ser Gln Lys Ser Ala Ile
    930                 935                 940

Asn Arg Met Val Ile Asp Glu Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
                980                 985                 990

Gln Glu Asp Gly Ser Gln Gly Phe Thr Val Val Val Ser Ser Val Pro
            995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Ile Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
    1085                1090                1095

Ser Gly Leu Ser Lys Pro Ile Ala Leu Ala Leu Asp Ser Arg Leu
    1100                1105                1110

Gly Lys Leu Phe Trp Ala Asp Ser Asp Leu Arg Arg Ile Glu Ser
    1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

Gln His Pro Cys Ala Gln Asp Asn Gly Gly Cys Ser His Ile Cys
    1205                1210                1215

Leu Val Lys Gly Asp Gly Thr Thr Arg Cys Ser Cys Pro Met His
    1220                1225                1230

Leu Val Leu Leu Gln Asp Glu Leu Ser Cys Gly Glu Pro Pro Thr
    1235                1240                1245

Cys Ser Pro Gln Gln Phe Thr Cys Phe Thr Gly Glu Ile Asp Cys
    1250                1255                1260

Ile Pro Val Ala Trp Arg Cys Asp Gly Phe Thr Glu Cys Glu Asp
    1265                1270                1275
```

| His | Ser | Asp | Glu | Leu | Asn | Cys | Pro | Val | Cys | Ser | Glu | Ser | Gln | Phe |
| | 1280 | | | | 1285 | | | | 1290 | | | | | |

| Gln | Cys | Ala | Ser | Gly | Gln | Cys | Ile | Asp | Gly | Ala | Leu | Arg | Cys | Asn |
| 1295 | | | | | 1300 | | | | | 1305 | | | | |

| Gly | Asp | Ala | Asn | Cys | Gln | Asp | Lys | Ser | Asp | Glu | Lys | Asn | Cys | Glu |
| 1310 | | | | | 1315 | | | | | 1320 | | | | |

| Val | Leu | Cys | Leu | Ile | Asp | Gln | Phe | Arg | Cys | Ala | Asn | Gly | Gln | Cys |
| 1325 | | | | | 1330 | | | | | 1335 | | | | |

| Ile | Gly | Lys | His | Lys | Lys | Cys | Asp | His | Asn | Val | Asp | Cys | Ser | Asp |
| 1340 | | | | | 1345 | | | | | 1350 | | | | |

| Lys | Ser | Asp | Glu | Leu | Asp | Cys | Tyr | Pro | Thr | Glu | Glu | Pro | Ala | Pro |
| 1355 | | | | | 1360 | | | | | 1365 | | | | |

| Gln | Ala | Thr | Asn | Thr | Val | Gly | Ser | Val |
| 1370 | | | | | 1375 | | | |

<210> SEQ ID NO 3
<211> LENGTH: 4842
<212> TYPE: DNA
<213> ORGANISM: Human

<400> SEQUENCE: 3

```
atggggccg tcctgaggag cctcctggcc tgcagcttct gtgtgctcct gagagcggcc      60
cctttgttgc tttatgcaaa cagacgggac ttgcgattgg ttgatgctac aaatggcaaa     120
gagaatgcta cgattgtagt tggaggcttg gaggatgcag ctgcggtgga ctttgtgttt     180
agtcatggct tgatatactg gagtgatgtc agcgaagaag ccattaaacg aacagaattt     240
aacaaaactg agagtgtgca gaatgttgtt gtttctggat tatttgtccc cgatgggctg     300
gcatgtgatt ggcttggaga aaaattgtac tggacagatt ctgaaactaa tcggattgaa     360
gtttctaatt tagatggatc tttacgaaaa gttttatttt ggcaagagtt ggatcaaccc     420
agagctattg ccttagatcc ttcaagtggg ttcatgtact ggacagactg gggagaagtg     480
ccaaagatag aacgtgctgg aatggatggt tcaagtcgct tcattataat aaacagtgaa     540
atttactggc caaatggact gactttggat tatgaagaac aaaagcttta ttgggcagat     600
gcaaaactta atttcatcca caatcaaat ctggatggaa caaatcggca ggcagtggtt     660
aaaggttccc ttccacatcc ttttgccttg acgttatttg aggacatatt gtactggact     720
gactggagca cacactccat tttggcttgc aacaagtata ctggtgaggg tctgcgtgaa     780
atccattctg acatcttctc tcccatggat atacatgcct tcagccaaca gaggcagcca     840
aatgccacaa atccatgtgg aattgacaat gggggttgtt cccatttgtg tttgatgtct     900
ccagtcaagc ttttttatca gtgtgcttgc cccactgggg tcaaactcct ggagaatgga     960
aaaacctgca agatggtgc cacagaatta ttgcttttag ctcgaaggac agacttgaga    1020
cgcatttctt tggatacacc agattttaca gacattgttc tgcagttaga agacatccgt    1080
catgccattg ccatagatta cgatcctgtg aaggctaca tctactggac tgatgatgaa    1140
gtgagggcca tacgccgttc atttatagat ggatctggca gtcagtttgt ggtcactgct    1200
caaattgccc atcctgatgg tattgctgtg gactggggttg cacgaaatct ttattggaca    1260
gacactggca ctgatcgaat agaagtgaca aggctcaatg gaccatgag gaagatcttg    1320 atttcagagg acttagagga accccgggct attgtgttag atcccatggt tgggtacatg    1380
tattggactg actggggaga aattccgaaa attgagcgag cagctctgga tggttctgac    1440
cgtgtagtat tggttaacac ttctcttggt tggccaaatg gtttagcctt ggattatgat    1500
```

| | |
|---|---|
| gaaggcaaaa tatactgggg agatgccaaa acagacaaga ttgaggttat gaatactgat | 1560 |
| ggcactggga gacgagtact agtggaagac aaaattcctc acatatttgg atttactttg | 1620 |
| ttgggtgact atgtttactg gactgactgg cagaggcgta gcattgaaag agttcataaa | 1680 |
| cgaagtgcag agagggaagt gatcatagat cagctgcctg acctcatggg cctaaaggct | 1740 |
| acaaatgttc atcgagtgat tggttccaac ccctgtgctg aggaaaacgg gggatgtagc | 1800 |
| catctctgcc tctatagacc tcagggcctt cgctgtgctt gccctattgg ctttgaactc | 1860 |
| atcagtgaca tgaagacctg cattgtccca gaggctttcc ttttgttttc acggagagca | 1920 |
| gatatcagac gaatttctct ggaaacaaac aataataatg tggctattcc actcactggt | 1980 |
| gtcaaagaag cttctgcttt ggattttgat gtgacagaca accgaattta ttggactgat | 2040 |
| atatcactca agaccatcag cagagccttt atgaatggca gtgcactgga acatgtggta | 2100 |
| gaattcggct tagattatcc agaaggcatg gcagtagact ggcttgggaa gaacttgtac | 2160 |
| tgggcagaca caggaacgaa tcgaattgag gtgtcaaagt tggatgggca gcaccgacaa | 2220 |
| gttttggtgt ggaaagacct agatagtccc agagctctcg cgttggaccc tgccgaagga | 2280 |
| tttatgtatt ggactgaatg gggtggaaaa cctaagatag acagagctgc aatggatgga | 2340 |
| agtgaacgta ctaccttagt tccaaatgtg gggcgggcaa acggcctaac tattgattat | 2400 |
| gctaaaagga ggctttattg gacagacctg gacaccaact aatagaatc ttcaaatatg | 2460 |
| cttgggctca accgtgaagt tatagcagat gacttgcctc atccttttgg cttaactcag | 2520 |
| taccaagatt atatctactg gacggactgg agccgacgca gcattgagcg tgccaacaaa | 2580 |
| accagtggcc aaaaccgcac catcattcag ggccatttgg attatgtgat ggacatcctc | 2640 |
| gtctttcact catctcgaca gtcagggtgg aatgaatgtg cttccagcaa tgggcactgc | 2700 |
| tcccacctct gcttggctgt gccagttggg ggttttgttt gtggatgccc tgcccactac | 2760 |
| tctcttaatg ctgacaacag gacttgtagt gctcctacga cttcctgct cttcagtcaa | 2820 |
| aagagtgcca tcaaccgcat ggtgattgat gaacaacaga gccccgacat catccttccc | 2880 |
| atccacagcc ttcggaatgt ccgggccatt gactatgacc cactggacaa gcaactctat | 2940 |
| tggattgact cacgacaaaa catgatccga aaggcacaag aagatggcag ccagggcttt | 3000 |
| actgtggttg tgagctcagt tccgagtcag aacctggaaa tacaacccta tgacctcagc | 3060 |
| attgatattt acagccgcta catctactgg acttgtgagg ctaccaatgt cattaatgtg | 3120 |
| acaagattag atgggagatc agttggagtg gtgctgaaag gcgagcagga cagacctcga | 3180 |
| gccattgtgg taaacccaga gaaagggtat atgtattta ccaatcttca ggaaaggtct | 3240 |
| cctaaaattg aacgggctgc tttggatggg acagaacggg aggtcctctt tttcagtggc | 3300 |
| ttaagtaaac caattgcttt agcccttgat agcaggctgg gcaagctctt tgggctgat | 3360 |
| tcagatctcc ggcgaattga aagcagtgat ctctcaggtg ctaaccggat agtattagaa | 3420 |
| gactccaata tcttgcagcc tgtgggactt actgtgtttg aaaactggct ctattggatt | 3480 |
| gataaacagc agcaaatgat tgaaaaaatt gacatgacag gtcgagaggg tagaaccaaa | 3540 |
| gtccaagctc gaattgccca gcttagtgac attcatgcag taaaggagct gaaccttcaa | 3600 |
| gaatacagac agcacccttg tgctcaggat aatggtggct gttcacatat ttgtcttgta | 3660 |
| aaggggggatg gtactacaag gtgttcttgc cccatgcacc tggttctact tcaagatgag | 3720 |
| ctatcatgtg gagaacctcc aacatgttct cctcagcagt ttacttgttt cacggggggaa | 3780 |
| attgactgta tccctgtggc ttggcggtgc gatgggttta ctgaatgtga agaccacagt | 3840 |
| gatgaactca attgtcctgt atgctcagag tcccagttcc agtgtgccag tgggcagtgt | 3900 |

-continued

```
attgatggtg ccctccgatg caatggagat gcaaactgcc aggacaaatc agatgagaag   3960
aactgtgaag tgctttgttt aattgatcag ttccgctgtg ccaatggtca gtgcattgga   4020
aagcacaaga gtgtgatca taatgtggat tgcagtgaca agtcagatga actggattgt   4080
tatccgactg aagaaccagc accacaggcc accaatacag ttggttctgt tattggcgta   4140
attgtcacca ttttgtgtc tggaactgta tactttatct gccagaggat gttgtgtcca   4200
cgtatgaagg gagatgggga aactatgact aatgactatg tagttcatgg accagcttct   4260
gtgcctcttg gttatgtgcc acacccaagt tctttgtcag gatctcttcc aggaatgtct   4320
cgaggtaaat caatgatcag ctccctcagt atcatggggg gaagcagtgg acccccctat   4380
gaccgagccc atgttacagg agcatcatca agtagttctt caagcaccaa aggcacttac   4440
ttccctgcaa ttttgaaccc tccaccatcc ccagccacag agcgatcaca ttacactatg   4500
gaatttggat attcttcaaa cagtccttcc actcataggt catacagcta caggccatat   4560
agctaccggc actttgcacc ccccaccaca ccctgcagca cagatgtttg tgacagtgac   4620
tatgctccta gtcggagaat gacctcagtg gcaacagcca agggctatac cagtgacttg   4680
aactatgatt cagaacctgt gcccccacct cccacacccc gaagccaata cttgtcagca   4740
gaggagaact atgaaagctg cccaccttct ccatacacag agaggagcta ttctcatcac   4800
ctctacccac cgccaccctc tccctgtaca gactcctcct ga                     4842
```

<210> SEQ ID NO 4
<211> LENGTH: 1613
<212> TYPE: PRT
<213> ORGANISM: Human

<400> SEQUENCE: 4

```
Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
                20                  25                  30

Leu Val Asp Ala Thr Asn Gly Lys Glu Asn Ala Thr Ile Val Val Gly
            35                  40                  45

Gly Leu Glu Asp Ala Ala Ala Val Asp Phe Val Phe Ser His Gly Leu
        50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Ser Gly Leu Leu Ser
                85                  90                  95

Pro Asp Gly Leu Ala Cys Asp Trp Leu Gly Glu Lys Leu Tyr Trp Thr
                100                 105                 110

Asp Ser Glu Thr Asn Arg Ile Glu Val Ser Asn Leu Asp Gly Ser Leu
            115                 120                 125

Arg Lys Val Leu Phe Trp Gln Glu Leu Asp Gln Pro Arg Ala Ile Ala
        130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
```

```
                210                 215                 220
Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
        275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Ala Arg Arg
            325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
        355                 360                 365

Pro Val Glu Gly Tyr Ile Tyr Trp Thr Asp Asp Glu Val Arg Ala Ile
    370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
            405                 410                 415

Leu Tyr Trp Thr Asp Thr Gly Thr Asp Arg Ile Glu Val Thr Arg Leu
        420                 425                 430

Asn Gly Thr Met Arg Lys Ile Leu Ile Ser Glu Asp Leu Glu Glu Pro
    435                 440                 445

Arg Ala Ile Val Leu Asp Pro Met Val Gly Tyr Met Tyr Trp Thr Asp
        450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
            485                 490                 495

Leu Asp Tyr Asp Glu Gly Lys Ile Tyr Trp Gly Asp Ala Lys Thr Asp
        500                 505                 510

Lys Ile Glu Val Met Asn Thr Asp Gly Thr Gly Arg Arg Val Leu Val
    515                 520                 525

Glu Asp Lys Ile Pro His Ile Phe Gly Phe Thr Leu Leu Gly Asp Tyr
530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
            565                 570                 575

Gly Leu Lys Ala Thr Asn Val His Arg Val Ile Gly Ser Asn Pro Cys
        580                 585                 590

Ala Glu Glu Asn Gly Gly Cys Ser His Leu Cys Leu Tyr Arg Pro Gln
    595                 600                 605

Gly Leu Arg Cys Ala Cys Pro Ile Gly Phe Glu Leu Ile Ser Asp Met
    610                 615                 620

Lys Thr Cys Ile Val Pro Glu Ala Phe Leu Leu Phe Ser Arg Arg Ala
625                 630                 635                 640
```

-continued

Asp Ile Arg Arg Ile Ser Leu Glu Thr Asn Asn Asn Val Ala Ile
            645                 650                 655

Pro Leu Thr Gly Val Lys Glu Ala Ser Ala Leu Asp Phe Asp Val Thr
        660                 665                 670

Asp Asn Arg Ile Tyr Trp Thr Asp Ile Ser Leu Lys Thr Ile Ser Arg
    675                 680                 685

Ala Phe Met Asn Gly Ser Ala Leu Glu His Val Glu Phe Gly Leu
690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
            740                 745                 750

Leu Ala Leu Asp Pro Ala Glu Gly Phe Met Tyr Trp Thr Glu Trp Gly
        755                 760                 765

Gly Lys Pro Lys Ile Asp Arg Ala Ala Met Asp Gly Ser Glu Arg Thr
    770                 775                 780

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
                805                 810                 815

Ser Ser Asn Met Leu Gly Leu Asn Arg Glu Val Ile Ala Asp Asp Leu
            820                 825                 830

Pro His Pro Phe Gly Leu Thr Gln Tyr Gln Asp Tyr Ile Tyr Trp Thr
        835                 840                 845

Asp Trp Ser Arg Arg Ser Ile Glu Arg Ala Asn Lys Thr Ser Gly Gln
    850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
        915                 920                 925

Cys Ser Ala Pro Thr Thr Phe Leu Leu Phe Ser Gln Lys Ser Ala Ile
    930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
            980                 985                 990

Gln Glu Asp Gly Ser Gln Gly Phe Thr Val Val Val Ser Ser Val Pro
        995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Ile Val Val Asn Pro Glu Lys
    1055                1060                1065

```
Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
    1085                1090                1095

Ser Gly Leu Ser Lys Pro Ile Ala Leu Ala Leu Asp Ser Arg Leu
    1100                1105                1110

Gly Lys Leu Phe Trp Ala Asp Ser Asp Leu Arg Arg Ile Glu Ser
    1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

Gln His Pro Cys Ala Gln Asp Asn Gly Gly Cys Ser His Ile Cys
    1205                1210                1215

Leu Val Lys Gly Asp Gly Thr Thr Arg Cys Ser Cys Pro Met His
    1220                1225                1230

Leu Val Leu Leu Gln Asp Glu Leu Ser Cys Gly Glu Pro Pro Thr
    1235                1240                1245

Cys Ser Pro Gln Gln Phe Thr Cys Phe Thr Gly Glu Ile Asp Cys
    1250                1255                1260

Ile Pro Val Ala Trp Arg Cys Asp Gly Phe Thr Glu Cys Glu Asp
    1265                1270                1275

His Ser Asp Glu Leu Asn Cys Pro Val Cys Ser Glu Ser Gln Phe
    1280                1285                1290

Gln Cys Ala Ser Gly Gln Cys Ile Asp Gly Ala Leu Arg Cys Asn
    1295                1300                1305

Gly Asp Ala Asn Cys Gln Asp Lys Ser Asp Glu Lys Asn Cys Glu
    1310                1315                1320

Val Leu Cys Leu Ile Asp Gln Phe Arg Cys Ala Asn Gly Gln Cys
    1325                1330                1335

Ile Gly Lys His Lys Lys Cys Asp His Asn Val Asp Cys Ser Asp
    1340                1345                1350

Lys Ser Asp Glu Leu Asp Cys Tyr Pro Thr Glu Glu Pro Ala Pro
    1355                1360                1365

Gln Ala Thr Asn Thr Val Gly Ser Val Ile Gly Val Ile Val Thr
    1370                1375                1380

Ile Phe Val Ser Gly Thr Val Tyr Phe Ile Cys Gln Arg Met Leu
    1385                1390                1395

Cys Pro Arg Met Lys Gly Asp Gly Glu Thr Met Thr Asn Asp Tyr
    1400                1405                1410

Val Val His Gly Pro Ala Ser Val Pro Leu Gly Tyr Val Pro His
    1415                1420                1425

Pro Ser Ser Leu Ser Gly Ser Leu Pro Gly Met Ser Arg Gly Lys
    1430                1435                1440

Ser Met Ile Ser Ser Leu Ser Ile Met Gly Gly Ser Ser Gly Pro
    1445                1450                1455

Pro Tyr Asp Arg Ala His Val Thr Gly Ala Ser Ser Ser Ser Ser
```

-continued

```
       1460            1465            1470

Ser  Ser  Thr  Lys  Gly  Thr  Tyr  Phe  Pro  Ala  Ile  Leu  Asn  Pro  Pro
     1475                1480                1485

Pro  Ser  Pro  Ala  Thr  Glu  Arg  Ser  His  Tyr  Thr  Met  Glu  Phe  Gly
     1490                1495                1500

Tyr  Ser  Ser  Asn  Ser  Pro  Ser  Thr  His  Arg  Ser  Tyr  Ser  Tyr  Arg
     1505                1510                1515

Pro  Tyr  Ser  Tyr  Arg  His  Phe  Ala  Pro  Pro  Thr  Thr  Pro  Cys  Ser
     1520                1525                1530

Thr  Asp  Val  Cys  Asp  Ser  Asp  Tyr  Ala  Pro  Ser  Arg  Arg  Met  Thr
     1535                1540                1545

Ser  Val  Ala  Thr  Ala  Lys  Gly  Tyr  Thr  Ser  Asp  Leu  Asn  Tyr  Asp
     1550                1555                1560

Ser  Glu  Pro  Val  Pro  Pro  Pro  Thr  Pro  Arg  Ser  Gln  Tyr  Leu
     1565                1570                1575

Ser  Ala  Glu  Glu  Asn  Tyr  Glu  Ser  Cys  Pro  Pro  Ser  Pro  Tyr  Thr
     1580                1585                1590

Glu  Arg  Ser  Tyr  Ser  His  His  Leu  Tyr  Pro  Pro  Pro  Ser  Pro
     1595                1600                1605

Cys  Thr  Asp  Ser  Ser
     1610

<210> SEQ ID NO 5
<211> LENGTH: 4161
<212> TYPE: DNA
<213> ORGANISM: Human

<400> SEQUENCE: 5
atggaggcag cgccgcccgg gccgccgtgg ccgctgctgc tgctgctgct gctgctgctg      60
gcgctgtgcg gctgcccggc ccccgccgcg gcctcgccgc tcctgctatt tgccaaccgc     120
cgggacgtac ggctggtgga cgccggcgga gtcaagctgg agtccaccat cgtggtcagc     180
ggcctggagg atgcggccgc agtggacttc cagttttcca agggagccgt gtactggaca     240
gacgtgagcg aggaggccat caagcagacc tacctgaacc agacggggc cgccgtgcag     300 aacgtggtca tctccggcct ggtctctccc gacggcctcg cctgcgactg ggtgggcaag     360
aagctgtact ggacggactc agagaccaac cgcatcgagg tggccaacct caatggcaca     420
tcccggaagg tgctcttctg gcaggacctt gaccagccga gggccatcgc cttggacccc     480
gctcacgggt acatgtactg gacagactgg ggtgagacgc cccggattga gcggcaggg     540 atggatggca gcacccggaa gatcattgtg gactcggaca tttactggcc caatggactg     600
accatcgacc tggaggagca gaagctctac tgggctgacg ccaagctcag cttcatccac     660
cgtgccaacc tggacggctc gttccggcag aaggtggtgg agggcagcct gacgcacccc     720
ttcgccctga cgctctccgg ggacactctg tactggacag actggcagac ccgctccatc     780
catgcctgca caagcgcac tggggggaag aggaaggaga tcctgagtgc cctctactca     840
cccatggaca tccaggtgct gagccaggag cggcagcctt cttccacac tgctgtgag     900 aggacaatg gcggctgctc ccacctgtgc ctgctgtccc aagcgagcc tttctacaca     960 tgcgcctgcc ccacgggtgt gcagctgcag gacaacggca ggacgtgtaa ggcaggagcc    1020
gaggaggtgc tgctgctggc ccggcgacg gacctacgga ggatctcgct ggacacgccg    1080
gactttaccg acatcgtgct gcaggtggac gacatccggc acgccattgc catcgactac    1140
gacccgctag agggctatgt ctactggaca gatgacgagg tgcgggccat cgcagggcg    1200
```

-continued

```
tacctggacg ggtctggggc gcagacgctg gtcaacaccg agatcaacga ccccgatggc   1260
atcgcggtcg actgggtggc ccgaaacctc tactggaccg acacgggcac ggaccgcatc   1320
gaggtgacgc gcctcaacgg cacctcccgc aagatcctgg tgtcggagga cctggacgag   1380
ccccgagcca tcgcactgca ccccgtgatg ggcctcatgt actggacaga ctggggagag   1440
aaccctaaaa tcgagtgtgc caacttggat gggcaggagc ggcgtgtgct ggtcaatgcc   1500
tccctcgggt ggcccaacgg cctggccctg acctgcagg aggggaagct ctactgggga   1560
gacgccaaga cagacaagat cgaggtgatc aatgttgatg ggacgaagag gcggaccctc   1620
ctggaggaca agctcccgca cattttcggg ttcacgctgc tgggggactt catctactgg   1680
actgactggc agcgccgcag catcgagcgg gtgcacaagg tcaaggccag ccgggacgtc   1740
atcattgacc agctgcccga cctgatgggg ctcaaagctg tgaatgtggc caaggtcgtc   1800
ggaaccaacc cgtgtgcgga caggaacggg gggtgcagcc acctgtgctt cttcacaccc   1860
cacgcaaccc ggtgtggctg ccccatcggc ctggagctgc tgagtgacat gaagacctgc   1920
atcgtgcctg aggccttctt ggtcttcacc agcagagccg ccatccacag gatctccctc   1980
gagaccaata caacgacgt ggccatcccg ctcacgggcg tcaaggaggc ctcagccctg   2040
gactttgatg tgtccaacaa ccacatctac tggacagacg tcagcctgaa gaccatcagc   2100
cgcgccttca tgaacgggag ctcggtggag cacgtggtgg agtttggcct tgactacccc   2160
gagggcatgg ccgttgactg gatgggcaag aacctctact gggccgacac tgggaccaac   2220
agaatcgaag tggcgcggct ggacgggcag ttccggcaag tcctcgtgtg gagggacttg   2280
gacaacccga ggtcgctggc cctggatccc accaagggct acatctactg gaccgagtgg   2340
ggcggcaagc cgaggatcgt gcgggccttc atggacggga ccaactgcat gacgctggtg   2400
gacaaggtgg gccgggccaa cgacctcacc attgactacg ctgaccagcg cctctactgg   2460
accgacctgg acaccaacat gatcgagtcg tccaacatgc tgggtcagga gcgggtcgtg   2520
attgccgacg atctcccgca cccgttcggt ctgacgcagt acagcgatta tatctactgg   2580
acagactgga atctgcacag cattgagcgg gccgacaaga ctagcggccg gaaccgcacc   2640
ctcatccagg gccacctgga cttcgtgatg gacatcctgg tgttccactc ctcccgccag   2700
gatggcctca atgactgtat gcacaacaac gggcagtgtg ggcagctgtg ccttgccatc   2760
cccggcggcc accgctgcgg ctgcgcctca cactacaccc tggaccccag cagccgcaac   2820
tgcagcccgc ccaccaccct cttgctgttc agccagaaat ctgccatcag tcggatgatc   2880
ccggacgacc agcacagccc ggatctcatc ctgcccctgc atggactgag gaacgtcaaa   2940
gccatcgact atgacccact ggacaagttc atctactggg tggatgggcg ccagaacatc   3000
aagcgagcca aggacgacgg gacccagccc tttgttttga cctctctgag ccaaggccaa   3060
aacccagaca ggcagcccca cgacctcagc atcgacatct acagccggac actgttctgg   3120
acgtgcgagg ccaccaatac catcaacgtc cacaggctga cgggggaagc catgggggtg   3180
gtgctgcgtg ggaccgcga caagcccagg gccatcgtcg tcaacgcgga gcgagggtac   3240
ctgtacttca ccaacatgca ggaccgggca gccaagatcg aacgcgcagc cctgacggc   3300 accgagcgcg aggtcctctt caccaccggc ctcatccgcc ctgtggccct ggtggtagac   3360
aacacactgg gcaagctgtt ctgggtggac gcggacctga gcgcattga gagctgtgac   3420 ctgtcagggg ccaaccgcct gaccctggag gacgccaaca tcgtgcagcc tctgggcctg   3480
accatccttg gcaagcatct ctactggatc gaccgcagc agcagatgat cgagcgtgtg   3540
gagaagacca ccgggacaa gcggactcgc atccagggcc gtgtcgccca cctcactggc   3600
```

```
atccatgcag tggaggaagt cagcctggag gagttctcag cccacccatg tgcccgtgac    3660
aatggtggct gctcccacat ctgtattgcc aagggtgatg ggacaccacg gtgctcatgc    3720
ccagtccacc tcgtgctcct gcagaacctg ctgacctgtg agagccgcc cacctgctcc     3780 ccggaccagt ttgcatgtgc cacaggggag atcgactgta tccccggggc ctggcgctgt    3840
gacggctttc ccgagtgcga tgaccagagc gacgaggagg ctgccccgt gtgctccgcc     3900 gcccagttcc cctgcgcgcg gggtcagtgt gtggacctgc cctgcgctg cgacggcgag     3960 gcagactgtc aggaccgctc agacgaggcg gactgtgacg ccatctgcct gcccaaccag    4020
ttccggtgtg cgagcggcca gtgtgtcctc atcaaacagc agtgcgactc cttccccgac    4080
tgtatcgacg gctccgacga gctcatgtgt gaaatcacca agccgccctc agacgacagc    4140
ccggcccaca gcagtgccat c                                               4161
```

<210> SEQ ID NO 6
<211> LENGTH: 1383
<212> TYPE: PRT
<213> ORGANISM: Human

<400> SEQUENCE: 6

```
Met Glu Ala Ala Pro Gly Pro Pro Trp Pro Leu Leu Leu Leu
1               5                   10                  15

Leu Leu Leu Ala Leu Cys Gly Cys Pro Ala Pro Ala Ala Ser
            20                  25                  30

Pro Leu Leu Leu Phe Ala Asn Arg Arg Asp Val Arg Leu Val Asp Ala
            35                  40                  45

Gly Gly Val Lys Leu Glu Ser Thr Ile Val Val Ser Gly Leu Glu Asp
    50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
            100                 105                 110

Leu Ala Cys Asp Trp Val Gly Lys Lys Leu Tyr Trp Thr Asp Ser Glu
        115                 120                 125

Thr Asn Arg Ile Glu Val Ala Asn Leu Asn Gly Thr Ser Arg Lys Val
    130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
            180                 185                 190

Asp Ile Tyr Trp Pro Asn Gly Leu Thr Ile Asp Leu Glu Glu Gln Lys
        195                 200                 205

Leu Tyr Trp Ala Asp Ala Lys Leu Ser Phe Ile His Arg Ala Asn Leu
    210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
            260                 265                 270

Glu Ile Leu Ser Ala Leu Tyr Ser Pro Met Asp Ile Gln Val Leu Ser
```

|  |  |  |  | 275 |  |  |  | 280 |  |  |  | 285 |  |  |
|--|--|--|--|--|--|--|--|--|--|--|--|--|--|--|
| Gln | Glu | Arg | Gln | Pro | Phe | Phe | His | Thr | Arg | Cys | Glu | Glu | Asp | Asn | Gly |
|  |  |  |  | 290 |  |  |  | 295 |  |  |  | 300 |  |  |  |
| Gly | Cys | Ser | His | Leu | Cys | Leu | Leu | Ser | Pro | Ser | Glu | Pro | Phe | Tyr | Thr |
| 305 |  |  |  |  | 310 |  |  |  |  | 315 |  |  |  |  | 320 |
| Cys | Ala | Cys | Pro | Thr | Gly | Val | Gln | Leu | Gln | Asp | Asn | Gly | Arg | Thr | Cys |
|  |  |  |  | 325 |  |  |  |  | 330 |  |  |  |  | 335 |  |
| Lys | Ala | Gly | Ala | Glu | Val | Leu | Leu | Leu | Ala | Arg | Arg | Thr | Asp | Leu |  |
|  |  |  | 340 |  |  |  |  | 345 |  |  |  |  | 350 |  |  |
| Arg | Arg | Ile | Ser | Leu | Asp | Thr | Pro | Asp | Phe | Thr | Asp | Ile | Val | Leu | Gln |
|  |  |  | 355 |  |  |  |  | 360 |  |  |  |  | 365 |  |  |
| Val | Asp | Asp | Ile | Arg | His | Ala | Ile | Ala | Ile | Asp | Tyr | Asp | Pro | Leu | Glu |
|  | 370 |  |  |  |  | 375 |  |  |  |  | 380 |  |  |  |  |
| Gly | Tyr | Val | Tyr | Trp | Thr | Asp | Asp | Glu | Val | Arg | Ala | Ile | Arg | Arg | Ala |
| 385 |  |  |  |  | 390 |  |  |  |  | 395 |  |  |  |  | 400 |
| Tyr | Leu | Asp | Gly | Ser | Gly | Ala | Gln | Thr | Leu | Val | Asn | Thr | Glu | Ile | Asn |
|  |  |  |  | 405 |  |  |  |  | 410 |  |  |  |  | 415 |  |
| Asp | Pro | Asp | Gly | Ile | Ala | Val | Asp | Trp | Val | Ala | Arg | Asn | Leu | Tyr | Trp |
|  |  |  | 420 |  |  |  |  | 425 |  |  |  |  | 430 |  |  |
| Thr | Asp | Thr | Gly | Thr | Asp | Arg | Ile | Glu | Val | Thr | Arg | Leu | Asn | Gly | Thr |
|  |  | 435 |  |  |  |  | 440 |  |  |  |  | 445 |  |  |  |
| Ser | Arg | Lys | Ile | Leu | Val | Ser | Glu | Asp | Leu | Asp | Glu | Pro | Arg | Ala | Ile |
|  | 450 |  |  |  |  | 455 |  |  |  |  | 460 |  |  |  |  |
| Ala | Leu | His | Pro | Val | Met | Gly | Leu | Met | Tyr | Trp | Thr | Asp | Trp | Gly | Glu |
| 465 |  |  |  |  | 470 |  |  |  |  | 475 |  |  |  |  | 480 |
| Asn | Pro | Lys | Ile | Glu | Cys | Ala | Asn | Leu | Asp | Gly | Gln | Glu | Arg | Arg | Val |
|  |  |  |  | 485 |  |  |  |  | 490 |  |  |  |  | 495 |  |
| Leu | Val | Asn | Ala | Ser | Leu | Gly | Trp | Pro | Asn | Gly | Leu | Ala | Leu | Asp | Leu |
|  |  |  | 500 |  |  |  |  | 505 |  |  |  |  | 510 |  |  |
| Gln | Glu | Gly | Lys | Leu | Tyr | Trp | Gly | Asp | Ala | Lys | Thr | Asp | Lys | Ile | Glu |
|  |  |  | 515 |  |  |  |  | 520 |  |  |  |  | 525 |  |  |
| Val | Ile | Asn | Val | Asp | Gly | Thr | Lys | Arg | Arg | Thr | Leu | Leu | Glu | Asp | Lys |
|  | 530 |  |  |  |  | 535 |  |  |  |  | 540 |  |  |  |  |
| Leu | Pro | His | Ile | Phe | Gly | Phe | Thr | Leu | Leu | Gly | Asp | Phe | Ile | Tyr | Trp |
| 545 |  |  |  |  | 550 |  |  |  |  | 555 |  |  |  |  | 560 |
| Thr | Asp | Trp | Gln | Arg | Arg | Ser | Ile | Glu | Arg | Val | His | Lys | Val | Lys | Ala |
|  |  |  |  | 565 |  |  |  |  | 570 |  |  |  |  | 575 |  |
| Ser | Arg | Asp | Val | Ile | Ile | Asp | Gln | Leu | Pro | Asp | Leu | Met | Gly | Leu | Lys |
|  |  |  | 580 |  |  |  |  | 585 |  |  |  |  | 590 |  |  |
| Ala | Val | Asn | Val | Ala | Lys | Val | Val | Gly | Thr | Asn | Pro | Cys | Ala | Asp | Arg |
|  |  |  | 595 |  |  |  |  | 600 |  |  |  |  | 605 |  |  |
| Asn | Gly | Gly | Cys | Ser | His | Leu | Cys | Phe | Phe | Thr | Pro | His | Ala | Thr | Arg |
|  | 610 |  |  |  |  | 615 |  |  |  |  | 620 |  |  |  |  |
| Cys | Gly | Cys | Pro | Ile | Gly | Leu | Glu | Leu | Leu | Ser | Asp | Met | Lys | Thr | Cys |
| 625 |  |  |  |  | 630 |  |  |  |  | 635 |  |  |  |  | 640 |
| Ile | Val | Pro | Glu | Ala | Phe | Leu | Val | Phe | Thr | Ser | Arg | Ala | Ala | Ile | His |
|  |  |  |  | 645 |  |  |  |  | 650 |  |  |  |  | 655 |  |
| Arg | Ile | Ser | Leu | Glu | Thr | Asn | Asn | Asn | Asp | Val | Ala | Ile | Pro | Leu | Thr |
|  |  |  | 660 |  |  |  |  | 665 |  |  |  |  | 670 |  |  |
| Gly | Val | Lys | Glu | Ala | Ser | Ala | Leu | Asp | Phe | Asp | Val | Ser | Asn | Asn | His |
|  |  | 675 |  |  |  |  | 680 |  |  |  |  | 685 |  |  |  |
| Ile | Tyr | Trp | Thr | Asp | Val | Ser | Leu | Lys | Thr | Ile | Ser | Arg | Ala | Phe | Met |
|  | 690 |  |  |  |  | 695 |  |  |  |  | 700 |  |  |  |  |

-continued

```
Asn Gly Ser Ser Val Glu His Val Val Glu Phe Gly Leu Asp Tyr Pro
705                 710                 715                 720

Glu Gly Met Ala Val Asp Trp Met Gly Lys Asn Leu Tyr Trp Ala Asp
            725                 730                 735

Thr Gly Thr Asn Arg Ile Glu Val Ala Arg Leu Asp Gly Gln Phe Arg
        740                 745                 750

Gln Val Leu Val Trp Arg Asp Leu Asp Asn Pro Arg Ser Leu Ala Leu
    755                 760                 765

Asp Pro Thr Lys Gly Tyr Ile Tyr Trp Thr Glu Trp Gly Gly Lys Pro
770                 775                 780

Arg Ile Val Arg Ala Phe Met Asp Gly Thr Asn Cys Met Thr Leu Val
785                 790                 795                 800

Asp Lys Val Gly Arg Ala Asn Asp Leu Thr Ile Asp Tyr Ala Asp Gln
            805                 810                 815

Arg Leu Tyr Trp Thr Asp Leu Asp Thr Asn Met Ile Glu Ser Ser Asn
        820                 825                 830

Met Leu Gly Gln Glu Arg Val Val Ile Ala Asp Asp Leu Pro His Pro
    835                 840                 845

Phe Gly Leu Thr Gln Tyr Ser Asp Tyr Ile Tyr Trp Thr Asp Trp Asn
850                 855                 860

Leu His Ser Ile Glu Arg Ala Asp Lys Thr Ser Gly Arg Asn Arg Thr
865                 870                 875                 880

Leu Ile Gln Gly His Leu Asp Phe Val Met Asp Ile Leu Val Phe His
            885                 890                 895

Ser Ser Arg Gln Asp Gly Leu Asn Asp Cys Met His Asn Asn Gly Gln
        900                 905                 910

Cys Gly Gln Leu Cys Leu Ala Ile Pro Gly Gly His Arg Cys Gly Cys
    915                 920                 925

Ala Ser His Tyr Thr Leu Asp Pro Ser Ser Arg Asn Cys Ser Pro Pro
930                 935                 940

Thr Thr Phe Leu Leu Phe Ser Gln Lys Ser Ala Ile Ser Arg Met Ile
945                 950                 955                 960

Pro Asp Asp Gln His Ser Pro Asp Leu Ile Leu Pro Leu His Gly Leu
            965                 970                 975

Arg Asn Val Lys Ala Ile Asp Tyr Asp Pro Leu Asp Lys Phe Ile Tyr
        980                 985                 990

Trp Val Asp Gly Arg Gln Asn Ile Lys Arg Ala Lys Asp Asp Gly Thr
    995                 1000                1005

Gln Pro Phe Val Leu Thr Ser Leu Ser Gln Gly Gln Asn Pro Asp
1010                1015                1020

Arg Gln Pro His Asp Leu Ser Ile Asp Ile Tyr Ser Arg Thr Leu
1025                1030                1035

Phe Trp Thr Cys Glu Ala Thr Asn Thr Ile Asn Val His Arg Leu
1040                1045                1050

Ser Gly Glu Ala Met Gly Val Val Leu Arg Gly Asp Arg Asp Lys
1055                1060                1065

Pro Arg Ala Ile Val Val Asn Ala Glu Arg Gly Tyr Leu Tyr Phe
1070                1075                1080

Thr Asn Met Gln Asp Arg Ala Ala Lys Ile Glu Arg Ala Ala Leu
1085                1090                1095

Asp Gly Thr Glu Arg Glu Val Leu Phe Thr Thr Gly Leu Ile Arg
1100                1105                1110

Pro Val Ala Leu Val Val Asp Asn Thr Leu Gly Lys Leu Phe Trp
1115                1120                1125
```

```
Val Asp Ala Asp Leu Lys Arg Ile Glu Ser Cys Asp Leu Ser Gly
    1130                1135                1140

Ala Asn Arg Leu Thr Leu Glu Asp Ala Asn Ile Val Gln Pro Leu
    1145                1150                1155

Gly Leu Thr Ile Leu Gly Lys His Leu Tyr Trp Ile Asp Arg Gln
    1160                1165                1170

Gln Gln Met Ile Glu Arg Val Glu Lys Thr Thr Gly Asp Lys Arg
    1175                1180                1185

Thr Arg Ile Gln Gly Arg Val Ala His Leu Thr Gly Ile His Ala
    1190                1195                1200

Val Glu Glu Val Ser Leu Glu Glu Phe Ser Ala His Pro Cys Ala
    1205                1210                1215

Arg Asp Asn Gly Gly Cys Ser His Ile Cys Ile Ala Lys Gly Asp
    1220                1225                1230

Gly Thr Pro Arg Cys Ser Cys Pro Val His Leu Val Leu Leu Gln
    1235                1240                1245

Asn Leu Leu Thr Cys Gly Glu Pro Pro Thr Cys Ser Pro Asp Gln
    1250                1255                1260

Phe Ala Cys Ala Thr Gly Glu Ile Asp Cys Ile Pro Gly Ala Trp
    1265                1270                1275

Arg Cys Asp Gly Phe Pro Glu Cys Asp Asp Gln Ser Asp Glu Glu
    1280                1285                1290

Gly Cys Pro Val Cys Ser Ala Ala Gln Phe Pro Cys Ala Arg Gly
    1295                1300                1305

Gln Cys Val Asp Leu Arg Leu Arg Cys Asp Gly Glu Ala Asp Cys
    1310                1315                1320

Gln Asp Arg Ser Asp Glu Ala Asp Cys Asp Ala Ile Cys Leu Pro
    1325                1330                1335

Asn Gln Phe Arg Cys Ala Ser Gly Gln Cys Val Leu Ile Lys Gln
    1340                1345                1350

Gln Cys Asp Ser Phe Pro Asp Cys Ile Asp Gly Ser Asp Glu Leu
    1355                1360                1365

Met Cys Glu Ile Thr Lys Pro Pro Ser Asp Ser Pro Ala His
    1370                1375                1380

<210> SEQ ID NO 7
<211> LENGTH: 4161
<212> TYPE: DNA
<213> ORGANISM: Mouse

<400> SEQUENCE: 7
atggaggcag cgccgcccgg gccgccgtgg ccgctgctgc tgctgctgct gctgctgctg      60
gcgctgtgcg gctgcccggc cccgccgcg gcctcgccgc tcctgctatt tgccaaccgc     120
cgggacgtac ggctggtgga cgccggcgga gtcaagctgg agtccaccat cgtggtcagc     180
ggcctggagg atgcggccgc agtggacttc agttttcca agggagccgt gtactggaca     240
gacgtgagcg aggaggccat caagcagacc tacctgaacc agacggggc cgccgtgcag     300 aacgtggtca tctccggcct ggtctctccc gacggcctcg cctgcgactg ggtgggcaag     360
aagctgtact ggacggactc agagaccaac cgcatcgagg tggccaacct caatggcaca     420
tcccggaagg tgctcttctg caggaccttt gaccagccga gggccatcgc cttggacccc     480
gctcacgggt acatgtactg gacagactgg ggtgagacgc ccggattga gcgggcaggg     540 atggatggca gcaccccgaa gatcattgtg gactcggaca tttactggcc caatggactg     600
```

```
accatcgacc tggaggagca gaagctctac tgggctgacg ccaagctcag cttcatccac    660
cgtgccaacc tggacggctc gttccggcag aaggtggtgg agggcagcct gacgcacccc    720
ttcgccctga cgctctccgg ggacactctg tactggacag actggcagac ccgctccatc    780
catgcctgca acaagcgcac tgggggaag aggaaggaga tcctgagtgc cctctactca    840
cccatggaca tccaggtgct gagccaggag cggcagcctt tcttccacac tcgctgtgag    900
gaggacaatg gcggctgctc ccacctgtgc ctgctgtccc aagcgagcc tttctacaca    960
tgcgcctgcc ccacgggtgt gcagctgcag acaacggca ggacgtgtaa ggcaggagcc   1020
gaggaggtgc tgctgctggc ccggcggacg gacctacgga ggatctcgct ggacacgccg   1080
gactttaccg acatcgtgct gcaggtggac gacatccggc acgccattgc catcgactac   1140
gacccgctag agggctatgt ctactggaca gatgacgagg tgcgggccat ccgcagggcg   1200
tacctggacg ggtctggggc gcagacgctg gtcaacaccg agatcaacga ccccgatggc   1260
atcgcggtcg actgggtggc ccgaaacctc tactggaccg acacgggcac ggaccgcatc   1320
gaggtgacgc gcctcaacgg cacctcccgc aagatcctgg tgtcggagga cctggacgag   1380
ccccgagcca tcgcactgca ccccgtgatg ggcctcatgt actggacaga ctggggagag   1440
aaccctaaaa tcgagtgtgc caacttggat gggcaggagc ggcgtgtgct ggtcaatgcc   1500
tccctcgggt ggcccaacgg cctggccctg acctgcagg aggggaagct ctactgggga   1560
gacgccaaga cagacaagat cgaggtgatc aatgttgatg ggacgaagag gcggaccctc   1620
ctggaggaca agctcccgca cattttcggg ttcacgctgc tgggggactt catctactgg   1680
actgactggc agcgccgcag catcgagcgg gtgcacaagg tcaaggccag ccgggacgtc   1740
atcattgacc agctgcccga cctgatgggg ctcaaagctg tgaatgtggc caaggtcgtc   1800
ggaaccaacc cgtgtgcgga caggaacggg gggtgcagcc acctgtgctt cttcacaccc   1860
cacgcaaccc ggtgtggctg ccccatcggc ctggagctgc tgagtgacat gaagacctgc   1920
atcgtgcctg aggccttctt ggtcttcacc agcagagccg ccatccacag gatctccctc   1980
gagaccaata caacgacgt ggccatcccg ctcacgggcg tcaaggaggc ctcagccctg   2040
gactttgatg tgtccaacaa ccacatctac tggacagacg tcagcctgaa gaccatcagc   2100
cgcgccttca tgaacgggag ctcggtggag cacgtggtgg agtttggcct tgactacccc   2160
gagggcatgg ccgttgactg gatgggcaag aacctctact gggccgacac tgggaccaac   2220
agaatcgaag tggcgcggct ggacgggcag ttccggcaag tcctcgtgtg agggacttg   2280
gacaacccga ggtcgctggc cctggatccc accaagggct acatctactg gaccgagtgg   2340
ggcggcaagc cgaggatcgt gcgggccttc atggacggga ccaactgcat gacgctggtg   2400
gacaaggtgg ccgggccaa cgacctcacc attgactacg ctgaccagcg cctctactgg   2460
accgacctgg acaccaacat gatcgagtcg tccaacatgc tgggtcagga gcgggtcgtg   2520
attgccgacg atctcccgca cccgttcggt ctgacgcagt acagcgatta tatctactgg   2580
acagactgga atctgcacag cattgagcgg gccgacaaga ctagcggccg gaaccgcacc   2640
ctcatccagg gccacctgga cttcgtgatg gacatcctgg tgttccactc ctcccgccag   2700
gatggcctca atgactgtat gcacaacaac gggcagtgtg ggcagctgtg ccttgccatc   2760
cccgcggcc accgctgcgg ctgcgcctca cactacaccc tggaccccag cagccgcaac   2820
tgcagcccgc ccaccacctt cttgctgttc agccagaaat ctgccatcag tcggatgatc   2880
ccggacgacc agcacagccc ggatctcatc ctgcccctgc atggactgag gaacgtcaaa   2940
gccatcgact atgacccact ggacaagttc atctactggg tggatgggcg ccagaacatc   3000
```

```
aagcgagcca aggacgacgg gacccagccc tttgttttga cctctctgag ccaaggccaa    3060
aacccagaca ggcagcccca cgacctcagc atcgacatct acagccggac actgttctgg    3120
acgtgcgagg ccaccaatac catcaacgtc cacaggctga gcggggaagc catgggggtg    3180
gtgctgcgtg gggaccgcga caagcccagg gccatcgtcg tcaacgcgga gcagggtac     3240 ctgtacttca ccaacatgca ggaccgggca gccaagatcg aacgcgcagc cctggacggc    3300
accgagcgcg aggtcctctt caccaccggc ctcatccgcc ctgtggccct ggtggtagac    3360
aacacactgg gcaagctgtt ctgggtggac gcggacctga agcgcattga gagctgtgac    3420
ctgtcagggg ccaaccgcct gaccctggag gacgccaaca tcgtgcagcc tctgggcctg    3480
accatccttg gcaagcatct ctactggatc gaccgccagc agcagatgat cgagcgtgtg    3540
gagaagacca ccggggacaa gcggactcgc atccagggcc gtgtcgccca cctcactggc    3600
atccatgcag tggaggaagt cagcctggag gagttctcag cccacccatg tgcccgtgac    3660
aatggtggct gctcccacat ctgtattgcc aagggtgatg ggacaccacg gtgctcatgc    3720
ccagtccacc tcgtgctcct gcagaacctg ctgacctgtg gagagccgcc cacctgctcc    3780
ccggaccagt ttgcatgtgc cacaggggag atcgactgta tccccggggc ctggcgctgt    3840
gacggctttc ccgagtgcga tgaccagagc gacgaggagg gctgccccgt gtgctccgcc    3900
gcccagttcc cctgcgcgcg gggtcagtgt gtggacctgc cctgcgctg cgacggcgag    3960 gcagactgtc aggaccgctc agacgaggcg gactgtgacg ccatctgcct gcccaaccag    4020
ttccggtgtg cgagcggcca gtgtgtcctc atcaaacagc agtgcgactc cttccccgac    4080
tgtatcgacg gctccgacga gctcatgtgt gaaatcacca agccgccctc agacgacagc    4140
ccggcccaca gcagtgccat c                                              4161
```

<210> SEQ ID NO 8
<211> LENGTH: 1373
<212> TYPE: PRT
<213> ORGANISM: Mouse

<400> SEQUENCE: 8

```
Met Gly Ala Val Leu Arg Ser Leu Leu Ala Cys Ser Phe Cys Val Leu
1               5                   10                  15

Leu Arg Ala Ala Pro Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Val Asp Phe Val Phe Gly His Gly Leu
    50                  55                  60

Ile Tyr Trp Ser Asp Val Ser Glu Glu Ala Ile Lys Arg Thr Glu Phe
65                  70                  75                  80

Asn Lys Ser Glu Ser Val Gln Asn Val Val Ser Gly Leu Leu Ser
                85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Val Ile
                165                 170                 175
```

```
Ile Asn Thr Glu Ile Tyr Trp Pro Asn Gly Leu Thr Leu Asp Tyr Gln
            180                 185                 190

Glu Arg Lys Leu Tyr Trp Ala Asp Ala Lys Leu Asn Phe Ile His Lys
            195                 200                 205

Ser Asn Leu Asp Gly Thr Asn Arg Gln Ala Val Val Lys Gly Ser Leu
210                 215                 220

Pro His Pro Phe Ala Leu Thr Leu Phe Glu Asp Thr Leu Tyr Trp Thr
225                 230                 235                 240

Asp Trp Asn Thr His Ser Ile Leu Ala Cys Asn Lys Tyr Thr Gly Glu
                245                 250                 255

Gly Leu Arg Glu Ile His Ser Asn Ile Phe Ser Pro Met Asp Ile His
            260                 265                 270

Ala Phe Ser Gln Gln Arg Gln Pro Asn Ala Thr Asn Pro Cys Gly Ile
            275                 280                 285

Asp Asn Gly Gly Cys Ser His Leu Cys Leu Met Ser Pro Val Lys Pro
            290                 295                 300

Phe Tyr Gln Cys Ala Cys Pro Thr Gly Val Lys Leu Met Glu Asn Gly
305                 310                 315                 320

Lys Thr Cys Lys Asp Gly Ala Thr Glu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
            355                 360                 365

Pro Val Glu Gly Tyr Ile Tyr Trp Thr Asp Asp Glu Val Arg Ala Ile
            370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
            405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
            435                 440                 445

Arg Ala Ile Val Leu Asp Pro Met Val Gly Tyr Met Tyr Trp Thr Asp
450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
            485                 490                 495

Leu Asp Tyr Asp Glu Gly Thr Ile Tyr Trp Gly Asp Ala Lys Thr Asp
            500                 505                 510

Lys Ile Glu Val Met Asn Thr Asp Gly Thr Gly Arg Arg Val Leu Val
            515                 520                 525

Glu Asp Lys Ile Pro His Ile Phe Gly Phe Thr Leu Leu Gly Asp Tyr
530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Ser Val His Arg Val Ile Gly Ser Asn Pro Cys
            580                 585                 590

Ala Glu Asp Asn Gly Gly Cys Ser His Leu Cys Leu Tyr Arg Pro Gln
```

-continued

```
            595                 600                 605
Gly Leu Arg Cys Ala Cys Pro Ile Gly Phe Glu Leu Ile Gly Asp Met
    610                 615                 620
Lys Thr Cys Ile Val Pro Glu Ala Phe Leu Leu Phe Ser Arg Arg Ala
625                 630                 635                 640
Asp Ile Arg Arg Ile Ser Leu Glu Thr Asn Asn Asn Val Ala Ile
                    645                 650                 655
Pro Leu Thr Gly Val Lys Glu Ala Ser Ala Leu Asp Phe Asp Val Thr
                660                 665                 670
Asp Asn Arg Ile Tyr Trp Thr Asp Ile Ser Leu Lys Thr Ile Ser Arg
        675                 680                 685
Ala Phe Met Asn Gly Ser Ala Leu Glu His Val Val Glu Phe Gly Leu
    690                 695                 700
Asp Tyr Pro Glu Gly Met Ala Val Asp Trp Leu Gly Lys Asn Leu Tyr
705                 710                 715                 720
Trp Ala Asp Thr Gly Thr Asn Arg Ile Glu Val Ser Lys Leu Asp Gly
                725                 730                 735
Gln His Arg Gln Val Leu Val Trp Lys Asp Leu Asp Ser Pro Arg Ala
            740                 745                 750
Leu Ala Leu Asp Pro Ala Glu Gly Phe Met Tyr Trp Thr Glu Trp Gly
        755                 760                 765
Gly Lys Pro Lys Ile Asp Arg Ala Ala Met Asp Gly Ser Glu Arg Thr
    770                 775                 780
Thr Leu Val Pro Asn Val Gly Arg Ala Asn Gly Leu Thr Ile Asp Tyr
785                 790                 795                 800
Ala Lys Arg Arg Leu Tyr Trp Thr Asp Leu Asp Thr Asn Leu Ile Glu
                805                 810                 815
Ser Ser Asp Met Leu Gly Leu Asn Arg Glu Val Ile Ala Asp Asp Leu
            820                 825                 830
Pro His Pro Phe Gly Leu Thr Gln Tyr Gln Asp Tyr Ile Tyr Trp Thr
        835                 840                 845
Asp Trp Ser Arg Arg Ser Ile Glu Arg Ala Asn Lys Thr Ser Gly Gln
    850                 855                 860
Asn Arg Thr Ile Ile Gln Gly His Leu Asp Tyr Val Met Asp Ile Leu
865                 870                 875                 880
Val Phe His Ser Ser Arg Gln Ala Gly Trp Asn Glu Cys Ala Ser Ser
                885                 890                 895
Asn Gly His Cys Ser His Leu Cys Leu Ala Val Pro Val Gly Gly Phe
            900                 905                 910
Val Cys Gly Cys Pro Ala His Tyr Ser Leu Asn Ala Asp Asn Arg Thr
        915                 920                 925
Cys Ser Ala Pro Ser Thr Phe Leu Leu Phe Ser Gln Lys Ser Ala Ile
    930                 935                 940
Asn Arg Met Val Ile Asp Glu Gln Gln Ser Pro Asp Ile Ile Leu Pro
945                 950                 955                 960
Ile His Ser Leu Arg Asn Val Arg Ala Ile Asp Tyr Asp Pro Leu Asp
                965                 970                 975
Lys Gln Leu Tyr Trp Ile Asp Ser Arg Gln Asn Ser Ile Arg Lys Ala
            980                 985                 990
His Glu Asp Gly Gly Gln Gly Phe Asn Val Val Ala Asn Ser Val Ala
        995                 1000                1005
Asn Gln Asn Leu Glu Ile Gln Pro Tyr Asp Leu Ser Ile Asp Ile
    1010                1015                1020
```

Tyr Ser Arg Tyr Ile Tyr Trp Thr Cys Glu Ala Thr Asn Val Ile
1025                1030                1035

Asp Val Thr Arg Leu Asp Gly Arg Ser Val Gly Val Val Leu Lys
1040                1045                1050

Gly Glu Gln Asp Arg Pro Arg Ala Ile Val Val Asn Pro Glu Lys
1055                1060                1065

Gly Tyr Met Tyr Phe Thr Asn Leu Gln Glu Arg Ser Pro Lys Ile
1070                1075                1080

Glu Arg Ala Ala Leu Asp Gly Thr Glu Arg Glu Val Leu Phe Phe
1085                1090                1095

Ser Gly Leu Ser Lys Pro Ile Ala Leu Ala Leu Asp Ser Lys Leu
1100                1105                1110

Gly Lys Leu Phe Trp Ala Asp Ser Asp Leu Arg Arg Ile Glu Ser
1115                1120                1125

Ser Asp Leu Ser Gly Ala Asn Arg Ile Val Leu Glu Asp Ser Asn
1130                1135                1140

Ile Leu Gln Pro Val Gly Leu Thr Val Phe Glu Asn Trp Leu Tyr
1145                1150                1155

Trp Ile Asp Lys Gln Gln Gln Met Ile Glu Lys Ile Asp Met Thr
1160                1165                1170

Gly Arg Glu Gly Arg Thr Lys Val Gln Ala Arg Ile Ala Gln Leu
1175                1180                1185

Ser Asp Ile His Ala Val Lys Glu Leu Asn Leu Gln Glu Tyr Arg
1190                1195                1200

Gln His Pro Cys Ala Gln Asp Asn Gly Gly Cys Ser His Ile Cys
1205                1210                1215

Leu Val Lys Gly Asp Gly Thr Thr Arg Cys Ser Cys Pro Met His
1220                1225                1230

Leu Val Leu Leu Gln Asp Glu Leu Ser Cys Gly Glu Pro Pro Thr
1235                1240                1245

Cys Ser Pro Gln Gln Phe Thr Cys Phe Thr Gly Asp Ile Asp Cys
1250                1255                1260

Ile Pro Val Ala Trp Arg Cys Asp Gly Phe Thr Glu Cys Glu Asp
1265                1270                1275

His Ser Asp Glu Leu Asn Cys Pro Val Cys Ser Glu Ser Gln Phe
1280                1285                1290

Gln Cys Ala Ser Gly Gln Cys Ile Asp Gly Ala Leu Arg Cys Asn
1295                1300                1305

Gly Asp Ala Asn Cys Gln Asp Lys Ser Asp Glu Lys Asn Cys Glu
1310                1315                1320

Val Leu Cys Leu Ile Asp Gln Phe Arg Cys Ala Asn Gly Gln Cys
1325                1330                1335

Val Gly Lys His Lys Lys Cys Asp His Ser Val Asp Cys Ser Asp
1340                1345                1350

Arg Ser Asp Glu Leu Asp Cys Tyr Pro Thr Glu Glu Pro Ala Pro
1355                1360                1365

Gln Ala Thr Asn Thr
1370

<210> SEQ ID NO 9
<211> LENGTH: 4842
<212> TYPE: DNA
<213> ORGANISM: Mouse

<400> SEQUENCE: 9

-continued

| | |
|---|---|
| atgggggccg tgctgaggag cctcctggcc tgcagcttct gcgtgctgct gagagcggcc | 60 |
| cctttgttgc tttatgcaaa cagacgggac ttgagattgg ttgatgctac aaatggcaaa | 120 |
| gagaatgcaa cgattgtagt tggaggcttg gaggatgcag ctgcggtgga ctttgtgttt | 180 |
| ggtcatggct tgatatactg gagtgatgtc agcgaagaag ccattaaacg aacagaattt | 240 |
| aacaaaagtg aaagtgtaca gaatgttgtt gtttctggat tattgtcccc ggatgggctg | 300 |
| gcatgtgatt ggcttggaga aaaattgtac tggacagatt ctgaaactaa tcgtattgaa | 360 |
| gtttctaatt tagatggatc tttacgaaaa gttttatttt ggcaagagtt ggatcaaccc | 420 |
| agagctattg ccttagatcc atcaagtggg ttcatgtact ggacagactg gggagaagtg | 480 |
| ccaaagatag aacgggctgg gatggatggc tcaagtcgct tcgttataat aaacacggag | 540 |
| atttactggc aaacggact gactctggat tatcaggagc ggaagcttta ctgggccgat | 600 |
| gcaaaactta atttcatcca taaatcaaac ctggatggaa caaaccggca ggcagtggtt | 660 |
| aaaggttccc ttccacatcc ttttgccttg acgttatttg aggacacatt gtactggact | 720 |
| gactggaata cacactctat tttggcttgc aacaaatata ctggcgaggg tctgcgtgaa | 780 |
| attcattcta acatcttctc tcccatggat atacatgctt tcagccaaca gaggcagcca | 840 |
| aatgctacaa atccatgtgg aattgataat ggtggttgtt cccatttgtg tttgatgtct | 900 |
| ccagtcaagc cttttatca gtgtgcttgc ccaactgggg tcaagctgat ggagaatgga | 960 |
| aagacctgca aagatggtgc cactgaacta ttgctgttag cccgacggac agacttgagg | 1020 |
| cgaatttctt tggatacacc cgattttact gacattgttc tgcagttaga agatatccgg | 1080 |
| catgccattg ccatagacta tgaccctgta gaaggctaca tatactggac agatgacgaa | 1140 |
| gtgagggcta ccgtcgctc cttcatagat ggatctggca gtcagtttgt ggtcacggcc | 1200 |
| cagattgctc atcctgatgg tattgctgtt gactgggttg caaggaacct gtactggaca | 1260 |
| gacactggca cggatcgtat agaagtgaca aggctcaatg ggaccatgag gaagatcttg | 1320 |
| atttcagagg acttagagga gccccgggct atcgtgttag atcccatggt tgggtacatg | 1380 |
| tattggacag actggggaga atcccaaaa atagagcgag ctgctctgga cggatctgac | 1440 |
| cgagtagttc ttgtcaacac ttcccttggt tggccaaacg gcttagccct ggattatgat | 1500 |
| gaaggcacaa tactggggg agatgccaaa acagacaaaa ttgaggttat gaataccgat | 1560 |
| ggcaccggga ggcgagtgct ggtggaagac aagatccctc acatatttgg gtttaccttg | 1620 |
| ctgggtgact atgtttactg gactgactgg cagaggcgga gcatcgagag agtacacaaa | 1680 |
| cggagcgcag agagggaagt catcatagac cagctgccag acctcatggg actgaaggcc | 1740 |
| acaagtgttc acagagtcat tggttctaac ccctgtgctg aggacaatgg aggatgtagc | 1800 |
| catctttgcc tgtacaggcc tcaggggctt cgatgcgcct gtcccattgg ctttgagctc | 1860 |
| atcggtgaca tgaagacatg cattgtcccc gaggctttcc ttctgttctc gaggagagcg | 1920 |
| gatatcagac gcatatcttt ggaaacaaac aacaacaatg tggccattcc tctcactggt | 1980 |
| gtcaaagaag cctctgcttt ggattttgat gtcacagaca acaggattta ctggactgat | 2040 |
| atatcactga agactattag cagagccttt atgaatggca gtgcactgga acatgtggta | 2100 |
| gagtttggct tagattatcc agaaggcatg gcagtggact ggcttgggaa gaacttatac | 2160 |
| tgggcagaca caggaacaaa tcgcattgag gtatcaaagt tggacggaca gcaccgacag | 2220 |
| gttttggtat ggaaagacct tgacagtcct cgagctctgg cactggatcc tgctgaaggg | 2280 |
| tttatgtatt ggactgagtg ggggaggcaag cctaagattg acagggctgc tatggatgga | 2340 |
| agtgaacgca ctacattagt tccaaatgta ggccgagcaa atggtctcac catcgactat | 2400 |

```
gctaaaaggc ggctttactg gacagacctg gacactaacc taatagaatc ctcagatatg   2460
ctcggactca accgtgaagt tatagcagat gacttgcctc atcctttTgg cttaactcag   2520
taccaagatt acatctactg gacagactgg agccgacgca gcattgaacg tgccaacaaa   2580
accagtggcc aaaaccgcac catcatccag ggccatttgg actatgtgat ggacatcctg   2640
gtcttccact cttcccggca ggcagggtgg aatgagtgtg cctccagcaa cgggcactgc   2700
tcccacctct gcttggctgt gcccgtcgga ggttttgtgt gtggatgccc tgcccactac   2760
tccctgaatg ctgacaacag gacctgcagt gctcccagca ccttcctgct cttcagtcag   2820
aagagcgcca tcaaccgcat ggtgattgat gaacaacaga gccctgacat catccttcct   2880
atccacagcc ttcggaacgt ccgggccatt gactatgacc ctttggacaa gcagctctac   2940
tggattgact ctcgacaaaa ctccatacga aaggcacatg aagatggtgg ccagggtttt   3000
aatgtagttg caaactcggt cgcaaatcag aaccttgaaa tacagcccta tgatctcagc   3060
attgatattt atagccgtta catctactgg acctgtgaag ctaccaatgt cattgatgtg   3120
acgagattag atggacgatc agttggagtg gttctaaaag gcgagcaaga cagacctcga   3180
gccattgtgg taaaccccga gaagggtat  atgtatttta ccaatcttca ggaaagatct   3240
cctaaaattg aacgggctgc attggatggt acagaacgag aggtcctctt tttcagtggc   3300
ttaagtaaac caattgcttt ggctcttgat agcaagctgg gcaagctctt ctgggctgac   3360
tcagatctcc ggcgaattga aagcagtgat ctctcaggtg ccaacaggat cgtgctagaa   3420
gactctaata tattcagcc tgtgggcctg accgtgtttg aaaactggct ctattggatt   3480
gataaacagc agcagatgat tgaaaaaatt gacatgactg gtcgagaagg aagaaccaag   3540
gtccaggctc gaattgctca gctgagtgac atccatgcag taaaggagct gaaccttcag   3600
gagtacagac agcacccttg tgcccaggat aatggtggct gttcacatat ctgccttgta   3660
aaaggagatg gtacgacaag atgctcctgc cccatgcact tagttctgct tcaggatgag   3720
ctgtcctgtg gagagcctcc aacgtgttct cctcagcagt ttacctgctt cactggggac   3780
attgactgca tccctgtggc ttggcggtgt gatgggttca ctgagtgcga agaccacagc   3840
gatgaactca attgtcccgt gtgctcagag tctcagttcc agtgtgccag cgggcagtgc   3900
attgatggtg cccttcgatg caatggcgat gcgaactgcc aggacaaatc agatgagaag   3960
aactgtgaag tgctttgttt aattgatcag ttccgctgtg ccaatggtca gtgcgttgga   4020
aagcacaaga atgtgaccca cagtgtggac tgcagtgaca gatctgacga gctggactgt   4080
tatccaactg aggagccagc accacaagcc accaacacag ttggttccgt tattggagta   4140
attgtcacca ttttttgtgtc tggaaccata tactttatct gccagaggat gctgtgtcct   4200
cgtatgaagg gagacgggga gaccatgact aacgactatg tggttcacag cccggcgtct   4260
gtgccccttg gttatgttcc tcacccaagc tctctctctg gatctcttcc aggaatgtct   4320
cgaggcaaat caatgatcag ttccctcagt atcatggggg gaagcagtgg ccccccctat   4380
gatcgagcgc acgtcacggg agcctcctca gcagttctt  ccagtaccaa aggcacttat   4440
ttccctgcaa ttttgaaccc accaccatcc cctgccacag aaagatccca ttataccatg   4500
gaatttggtt attcttccaa cagtccttcc acacataggt cctacagcta taggccgtac   4560
agctaccggc actttgcacc gcccaccaca ccctgcagca ctgatgtctg tgacagtgac   4620
tatgctccta gccggaggat gacctcggtg gcaacagcca agggctacac cagtgacgtg   4680
aactatgact cagaacctgt gccccccaccg cccacacccc gaagccagta cttgtcagcg   4740
gaggagaact atgaaagctg ccccccttcc ccatacacgg agaggagtta ctcccaccac   4800
```
ctctacccgc caccaccctc ccctgcacg gactcctcct ga       4842

<210> SEQ ID NO 10
<211> LENGTH: 1613
<212> TYPE: PRT
<213> ORGANISM: Mouse

<400> SEQUENCE: 10

```
Met Gly Ala Val Leu Arg Ser Leu Leu Ala Cys Ser Phe Cys Val Leu
1               5                   10                  15

Leu Arg Ala Ala Pro Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Val Asp Phe Val Phe Gly His Gly Leu
    50                  55                  60

Ile Tyr Trp Ser Asp Val Ser Glu Glu Ala Ile Lys Arg Thr Glu Phe
65                  70                  75                  80

Asn Lys Ser Glu Ser Val Gln Asn Val Val Ser Gly Leu Leu Ser
                85                  90                  95

Pro Asp Gly Leu Ala Cys Asp Trp Leu Gly Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Val Ile
                165                 170                 175

Ile Asn Thr Glu Ile Tyr Trp Pro Asn Gly Leu Thr Leu Asp Tyr Gln
            180                 185                 190

Glu Arg Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Thr Leu Tyr Trp Thr
225                 230                 235                 240

Asp Trp Asn Thr His Ser Ile Leu Ala Cys Asn Lys Tyr Thr Gly Glu
                245                 250                 255

Gly Leu Arg Glu Ile His Ser Asn Ile Phe Ser Pro Met Asp Ile His
            260                 265                 270

Ala Phe Ser Gln Gln Arg Gln Pro Asn Ala Thr Asn Pro Cys Gly Ile
        275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Met Glu Asn Gly
305                 310                 315                 320

Lys Thr Cys Lys Asp Gly Ala Thr Glu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
        355                 360                 365

Pro Val Glu Gly Tyr Ile Tyr Trp Thr Asp Asp Glu Val Arg Ala Ile
```

-continued

```
                   370                 375                 380
Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
                420                 425                 430

Asn Gly Thr Met Arg Lys Ile Leu Ile Ser Glu Asp Leu Glu Glu Pro
                435                 440                 445

Arg Ala Ile Val Leu Asp Pro Met Val Gly Tyr Met Tyr Trp Thr Asp
                450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Thr Ile Tyr Trp Gly Asp Ala Lys Thr Asp
                500                 505                 510

Lys Ile Glu Val Met Asn Thr Asp Gly Thr Gly Arg Arg Val Leu Val
                515                 520                 525

Glu Asp Lys Ile Pro His Ile Phe Gly Phe Thr Leu Leu Gly Asp Tyr
530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Ser Val His Arg Val Ile Gly Ser Asn Pro Cys
                580                 585                 590

Ala Glu Asp Asn Gly Gly Cys Ser His Leu Cys Leu Tyr Arg Pro Gln
                595                 600                 605

Gly Leu Arg Cys Ala Cys Pro Ile Gly Phe Glu Leu Ile Gly Asp Met
                610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Val Ala Ile
                645                 650                 655

Pro Leu Thr Gly Val Lys Glu Ala Ser Ala Leu Asp Phe Asp Val Thr
                660                 665                 670

Asp Asn Arg Ile Tyr Trp Thr Asp Ile Ser Leu Lys Thr Ile Ser Arg
                675                 680                 685

Ala Phe Met Asn Gly Ser Ala Leu Glu His Val Val Glu Phe Gly Leu
690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
                740                 745                 750

Leu Ala Leu Asp Pro Ala Glu Gly Phe Met Tyr Trp Thr Glu Trp Gly
                755                 760                 765

Gly Lys Pro Lys Ile Asp Arg Ala Ala Met Asp Gly Ser Glu Arg Thr
                770                 775                 780

Thr Leu Val Pro Asn Val Gly Arg Ala Asn Gly Leu Thr Ile Asp Tyr
785                 790                 795                 800
```

-continued

```
Ala Lys Arg Arg Leu Tyr Trp Thr Asp Leu Asp Thr Asn Leu Ile Glu
            805                 810                 815

Ser Ser Asp Met Leu Gly Leu Asn Arg Glu Val Ile Ala Asp Asp Leu
            820                 825                 830

Pro His Pro Phe Gly Leu Thr Gln Tyr Gln Asp Tyr Ile Tyr Trp Thr
            835                 840                 845

Asp Trp Ser Arg Arg Ser Ile Glu Arg Ala Asn Lys Thr Ser Gly Gln
            850                 855                 860

Asn Arg Thr Ile Ile Gln Gly His Leu Asp Tyr Val Met Asp Ile Leu
865                 870                 875                 880

Val Phe His Ser Ser Arg Gln Ala Gly Trp Asn Glu Cys Ala Ser Ser
            885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
            915                 920                 925

Cys Ser Ala Pro Ser Thr Phe Leu Leu Phe Ser Gln Lys Ser Ala Ile
            930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
            965                 970                 975

Lys Gln Leu Tyr Trp Ile Asp Ser Arg Gln Asn Ser Ile Arg Lys Ala
            980                 985                 990

His Glu Asp Gly Gly Gln Gly Phe  Asn Val Val Ala Asn  Ser Val Ala
            995                 1000                1005

Asn Gln  Asn Leu Glu Ile Gln  Pro Tyr Asp Leu Ser  Ile Asp Ile
       1010                1015                1020

Tyr Ser  Arg Tyr Ile Tyr Trp  Thr Cys Glu Ala Thr  Asn Val Ile
       1025                1030                1035

Asp Val  Thr Arg Leu Asp Gly  Arg Ser Val Gly Val  Val Leu Lys
       1040                1045                1050

Gly Glu  Gln Asp Arg Pro Arg  Ala Ile Val Val Asn  Pro Glu Lys
       1055                1060                1065

Gly Tyr  Met Tyr Phe Thr Asn  Leu Gln Glu Arg Ser  Pro Lys Ile
       1070                1075                1080

Glu Arg  Ala Ala Leu Asp Gly  Thr Glu Arg Glu Val  Leu Phe Phe
       1085                1090                1095

Ser Gly  Leu Ser Lys Pro Ile  Ala Leu Ala Leu Asp  Ser Lys Leu
       1100                1105                1110

Gly Lys  Leu Phe Trp Ala Asp  Ser Asp Leu Arg Arg  Ile Glu Ser
       1115                1120                1125

Ser Asp  Leu Ser Gly Ala Asn  Arg Ile Val Leu Glu  Asp Ser Asn
       1130                1135                1140

Ile Leu  Gln Pro Val Gly Leu  Thr Val Phe Glu Asn  Trp Leu Tyr
       1145                1150                1155

Trp Ile  Asp Lys Gln Gln Gln  Met Ile Glu Lys Ile  Asp Met Thr
       1160                1165                1170

Gly Arg  Glu Gly Arg Thr Lys  Val Gln Ala Arg Ile  Ala Gln Leu
       1175                1180                1185

Ser Asp  Ile His Ala Val Lys  Glu Leu Asn Leu Gln  Glu Tyr Arg
       1190                1195                1200

Gln His  Pro Cys Ala Gln Asp  Asn Gly Gly Cys Ser  His Ile Cys
       1205                1210                1215
```

```
Leu Val Lys Gly Asp Gly Thr  Thr Arg Cys Ser Cys  Pro Met His
    1220            1225                 1230

Leu Val Leu Leu Gln Asp Glu  Leu Ser Cys Gly Glu  Pro Pro Thr
    1235            1240                 1245

Cys Ser Pro Gln Gln Phe Thr  Cys Phe Thr Gly Asp  Ile Asp Cys
    1250            1255                 1260

Ile Pro Val Ala Trp Arg Cys  Asp Gly Phe Thr Glu  Cys Glu Asp
    1265            1270                 1275

His Ser Asp Glu Leu Asn Cys  Pro Val Cys Ser Glu  Ser Gln Phe
    1280            1285                 1290

Gln Cys Ala Ser Gly Gln Cys  Ile Asp Gly Ala Leu  Arg Cys Asn
    1295            1300                 1305

Gly Asp Ala Asn Cys Gln Asp  Lys Ser Asp Glu Lys  Asn Cys Glu
    1310            1315                 1320

Val Leu Cys Leu Ile Asp Gln  Phe Arg Cys Ala Asn  Gly Gln Cys
    1325            1330                 1335

Val Gly Lys His Lys Lys Cys  Asp His Ser Val Asp  Cys Ser Asp
    1340            1345                 1350

Arg Ser Asp Glu Leu Asp Cys  Tyr Pro Thr Glu Glu  Pro Ala Pro
    1355            1360                 1365

Gln Ala Thr Asn Thr Val Gly  Ser Val Ile Gly Val  Ile Val Thr
    1370            1375                 1380

Ile Phe Val Ser Gly Thr Ile  Tyr Phe Ile Cys Gln  Arg Met Leu
    1385            1390                 1395

Cys Pro Arg Met Lys Gly Asp  Gly Glu Thr Met Thr  Asn Asp Tyr
    1400            1405                 1410

Val Val His Ser Pro Ala Ser  Val Pro Leu Gly Tyr  Val Pro His
    1415            1420                 1425

Pro Ser Ser Leu Ser Gly Ser  Leu Pro Gly Met Ser  Arg Gly Lys
    1430            1435                 1440

Ser Met Ile Ser Ser Leu Ser  Ile Met Gly Gly Ser  Ser Gly Pro
    1445            1450                 1455

Pro Tyr Asp Arg Ala His Val  Thr Gly Ala Ser Ser  Ser Ser Ser
    1460            1465                 1470

Ser Ser Thr Lys Gly Thr Tyr  Phe Pro Ala Ile Leu  Asn Pro Pro
    1475            1480                 1485

Pro Ser Pro Ala Thr Glu Arg  Ser His Tyr Thr Met  Glu Phe Gly
    1490            1495                 1500

Tyr Ser Ser Asn Ser Pro Ser  Thr His Arg Ser Tyr  Ser Tyr Arg
    1505            1510                 1515

Pro Tyr Ser Tyr Arg His Phe  Ala Pro Pro Thr Thr  Pro Cys Ser
    1520            1525                 1530

Thr Asp Val Cys Asp Ser Asp  Tyr Ala Pro Ser Arg  Arg Met Thr
    1535            1540                 1545

Ser Val Ala Thr Ala Lys Gly  Tyr Thr Ser Asp Val  Asn Tyr Asp
    1550            1555                 1560

Ser Glu Pro Val Pro Pro Pro  Pro Thr Pro Arg Ser  Gln Tyr Leu
    1565            1570                 1575

Ser Ala Glu Glu Asn Tyr Glu  Ser Cys Pro Pro Ser  Pro Tyr Thr
    1580            1585                 1590

Glu Arg Ser Tyr Ser His His  Leu Tyr Pro Pro Pro  Pro Ser Pro
    1595            1600                 1605

Cys Thr Asp Ser Ser
```

1610

<210> SEQ ID NO 11
<211> LENGTH: 4161
<212> TYPE: DNA
<213> ORGANISM: Mouse

<400> SEQUENCE: 11

| | |
|---|---|
| atggaaacgg cgccgacccg ggcccctccg ccgccgccgc cgccgctgct gctgctggtg | 60 |
| ctgtactgca gcttggtccc cgccgcggcc tcaccgctcc tgttgtttgc caaccgccgg | 120 |
| gatgtgcggc tagtggatgc cggcggagtg aagctggagt ccaccattgt ggccagtggc | 180 |
| ctggaggatg cagctgctgt agacttccag ttctccaagg gtgctgtgta ctggacagat | 240 |
| gtgagcgagg aggccatcaa acagacctac ctgaaccaga ctggagctgc tgcacagaac | 300 |
| attgtcatct cgggcctcgt gtcacctgat ggcctggcct gtgactgggt tggcaagaag | 360 |
| ctgtactgga cggactccga gaccaaccgc attgaggttg ccaacctcaa tgggacgtcc | 420 |
| cgtaaggttc tcttctggca ggacctggac cagccaaggg ccattgccct ggatcctgca | 480 |
| catgggtaca tgtactggac tgactggggg gaagcacccc ggatcgagcg ggcagggatg | 540 |
| gatggcagta cccggaagat cattgtagac tccgacattt actggcccaa tgggctgacc | 600 |
| atcgacctgg aggaacagaa gctgtactgg gccgatgcca agctcagctt catccaccgt | 660 |
| gccaacctgg acggctcctt ccggcagaag gtggtggagg cagcctcac tcacccttt | 720 |
| gccctgacac tctctgggga cacactctac tggacagact ggcagacccg ctccatccac | 780 |
| gcctgcaaca agtggacagg ggagcagagg aaggagatcc ttagtgctct gtactcaccc | 840 |
| atggacatcc aagtgctgag ccaggagcgg cagcctcccct tccacacacc atgcgaggag | 900 |
| gacaacggtg gctgttccca cctgtgcctg ctgtccccga gggagccttt ctactcctgt | 960 |
| gcctgcccca ctggtgtgca gttgcaggac aatggcaaga cgtgcaagac aggggctgag | 1020 |
| gaagtgctgc tgctggctcg gaggacagac ctgaggagga tctctctgga cacccctgac | 1080 |
| ttcacagaca tagtgctgca ggtgggcgac atccggcatg ccattgccat tgactacgat | 1140 |
| cccctggagg gctacgtgta ctggaccgat gatgaggtgc gggctatccg cagggcgtac | 1200 |
| ctagatggct caggtgcgca gacacttgtg aacactgaga tcaatgaccc cgatggcatt | 1260 |
| gctgtggact gggtcgcccg gaacctctac tggacagata caggcactga cagaattgag | 1320 |
| gtgactcgcc tcaacggcac ctcccgaaag atcctggtat ctgaggacct ggacgaaccg | 1380 |
| cgagccattg tgttgcaccc tgtgatgggc ctcatgtact ggacagactg ggggagaac | 1440 |
| cccaaaatcg aatgcgccaa cctagatggg agagatcggc atgtcctggt gaacacctcc | 1500 |
| cttgggtggc caatggact ggccctggac ctgcaggagg caagctgta ctgggggat | 1560 |
| gccaaaactg ataaaatcga ggtgatcaac atagacggga caaagcggaa gaccctgctt | 1620 |
| gaggacaagc tccacacat tttgggttc acactgctgg ggacttcat ctactggacc | 1680 |
| gactggcaga gacgcagtat tgaaagggtc cacaaggtca aggccagccg ggatgtcatc | 1740 |
| attgatcaac tccccgacct gatgggactc aaagccgtga atgtggccaa ggttgtcgga | 1800 |
| accaacccat gtgcggatgg aaatggaggg tgcagccatc tgtgcttctt cacccccacgt | 1860 |
| gccaccaagt gtgctgccc cattggcctg gagctgttga gtgacatgaa gacctgcata | 1920 |
| atccccgagg ccttcctggt attcaccagc agagccacca tccacaggat ctccctggag | 1980 |
| actaacaaca cgatgtggc tatcccactc acgggtgtca agaggcctc tgcactggac | 2040 |
| tttgatgtgt ccaacaatca catctactgg actgatgtta gcctcaagac gatcagccga | 2100 |

```
gccttcatga atgggagctc agtggagcac gtgattgagt ttggcctcga ctaccctgaa    2160
ggaatggctg tggactggat gggcaagaac ctctattggg cggacacagg gaccaacagg    2220
attgaggtgg cccggctgga tgggcagttc cggcaggtgc ttgtgtggag agaccttgac    2280
aaccccaggt ctctggctct ggatcctact aaaggctaca tctactggac tgagtggggt    2340
ggcaagccaa ggattgtgcg ggccttcatg gatgggacca attgtatgac actggtagac    2400
aaggtgggcc gggccaacga cctcaccatt gattatgccg accagcgact gtactggact    2460
gacctggaca ccaacatgat tgagtcttcc aacatgctgg gtcaggagcg catggtgata    2520
gctgacgatc tgccctaccc gtttggcctg actcaatata gcgattacat ctactggact    2580
gactggaacc tgcatagcat tgaacgggcg acaagacca gtgggcggaa ccgcaccctc     2640
atccagggtc acctggactt cgtcatggac atcctggtgt ccactcctc ccgtcaggat     2700 ggcctcaacg actgcgtgca cagcaatggc cagtgtgggc agctgtgcct cgccatcccc    2760
ggaggccacc gctgtggctg tgcttcacac tacacgctgg accccagcag ccgcaactgc    2820
agcccgccct ccaccttctt gctgttcagc cagaaatttg ccatcagccg gatgatcccc    2880
gatgaccagc tcagcccgga ccttgtccta ccccttcatg ggctgaggaa cgtcaaagcc    2940
atcaactatg acccgctgga caagttcatc tactgggtgg acgggcgcca gaacatcaag    3000
agggccaagg acgacggtac ccagccctcc atgctgacct ctcccagcca aagcctgagc    3060
ccagacagac agccacacga cctcagcatt gacatctaca gccggacact gttctggacc    3120
tgtgaggcca ccaacactat caatgtccac cggctggatg gggatgccat gggagtggtg    3180
cttcgagggg accgtgacaa gccaagggcc attgctgtca atgctgagcg agggtacatg    3240
tactttacca acatgcagga ccatgctgcc aagatcgagc gagcctccct ggatggcaca    3300
gagcgggagg tcctcttcac cacaggcctc atccgtcccg tggcccttgt ggtggacaat    3360
gctctgggca gctcttctg ggtggatgcc gacctaaagc gaatcgaaag ctgtgacctc    3420
tctggggcca accgcctgac cctggaagat gccaacatcg tacagccagt aggtctgaca    3480
gtgctgggca gcacctcta ctggatcgac cgccagcagc agatgatcga gcgcgtggag    3540
aagaccactg ggacaagcg gactagggtt cagggccgtg tcacccacct gacaggcatc    3600
catgccgtgg aggaagtcag cctggaggag ttctcagccc atccttgtgc ccgagacaat    3660
ggcggctgct cccacatctg tatcgccaag ggtgatggaa caccgcgctg ctcgtgccct    3720
gtccacctgg tgctcctgca gaacctgctg acttgtggtg agcctcctac ctgctcccct    3780
gatcagtttg catgtaccac tggtgagatc gactgcatcc ccggagcctg gcgctgtgac    3840
ggcttccctg agtgtgctga ccagagtgat gaagaaggct gcccagtgtg ctccgcctct    3900 cagttccccct gcgctcgagg ccagtgtgtg gacctgcgt tacgctgcga cggtgaggcc    3960
gactgccagg atcgctctga tgaagctaac tgcgatgctg tctgtctgcc caatcagttc    4020
cggtgcacca gcgccagtg tgtcctcatc aagcaacagt gtgactcctt ccccgactgt    4080
gctgatgggt ctgatgagct catgtgtgaa atcaacaagc caccctctga tgacatccca    4140
gcccacagca gtgccattgg g                                              4161
```

<210> SEQ ID NO 12
<211> LENGTH: 1384
<212> TYPE: PRT
<213> ORGANISM: Mouse

<400> SEQUENCE: 12

```
Met Glu Thr Ala Pro Thr Arg Ala Pro Pro Pro Pro Pro Pro Pro Leu
1               5                   10                  15
```

Leu Leu Leu Val Leu Tyr Cys Ser Leu Val Pro Ala Ala Ser Pro
                20              25              30

Leu Leu Leu Phe Ala Asn Arg Arg Asp Val Arg Leu Val Asp Ala Gly
                35              40              45

Gly Val Lys Leu Glu Ser Thr Ile Val Ala Ser Gly Leu Glu Asp Ala
        50              55              60

Ala Ala Val Asp Phe Gln Phe Ser Lys Gly Ala Val Tyr Trp Thr Asp
65              70              75              80

Val Ser Glu Glu Ala Ile Lys Gln Thr Tyr Leu Asn Gln Thr Gly Ala
                85              90              95

Ala Ala Gln Asn Ile Val Ile Ser Gly Leu Val Ser Pro Asp Gly Leu
                100             105             110

Ala Cys Asp Trp Val Gly Lys Lys Leu Tyr Trp Thr Asp Ser Glu Thr
                115             120             125

Asn Arg Ile Glu Val Ala Asn Leu Asn Gly Thr Ser Arg Lys Val Leu
                130             135             140

Phe Trp Gln Asp Leu Asp Gln Pro Arg Ala Ile Ala Leu Asp Pro Ala
145             150             155             160

His Gly Tyr Met Tyr Trp Thr Asp Trp Gly Ala Pro Arg Ile Glu
                165             170             175

Arg Ala Gly Met Asp Gly Ser Thr Arg Lys Ile Ile Val Asp Ser Asp
                180             185             190

Ile Tyr Trp Pro Asn Gly Leu Thr Ile Asp Leu Glu Glu Gln Lys Leu
                195             200             205

Tyr Trp Ala Asp Ala Lys Leu Ser Phe Ile His Arg Ala Asn Leu Asp
                210             215             220

Gly Ser Phe Arg Gln Lys Val Val Glu Gly Ser Leu Thr His Pro Phe
225             230             235             240

Ala Leu Thr Leu Ser Gly Asp Thr Leu Tyr Trp Thr Asp Trp Gln Thr
                245             250             255

Arg Ser Ile His Ala Cys Asn Lys Trp Thr Gly Glu Gln Arg Lys Glu
                260             265             270

Ile Leu Ser Ala Leu Tyr Ser Pro Met Asp Ile Gln Val Leu Ser Gln
                275             280             285

Glu Arg Gln Pro Pro Phe His Thr Pro Cys Glu Glu Asp Asn Gly Gly
                290             295             300

Cys Ser His Leu Cys Leu Leu Ser Pro Arg Glu Pro Phe Tyr Ser Cys
305             310             315             320

Ala Cys Pro Thr Gly Val Gln Leu Gln Asp Asn Gly Lys Thr Cys Lys
                325             330             335

Thr Gly Ala Glu Glu Val Leu Leu Leu Ala Arg Arg Thr Asp Leu Arg
                340             345             350

Arg Ile Ser Leu Asp Thr Pro Asp Phe Thr Asp Ile Val Leu Gln Val
                355             360             365

Gly Asp Ile Arg His Ala Ile Ala Ile Asp Tyr Asp Pro Leu Glu Gly
                370             375             380

Tyr Val Tyr Trp Thr Asp Asp Glu Val Arg Ala Ile Arg Arg Ala Tyr
385             390             395             400

Leu Asp Gly Ser Gly Ala Gln Thr Leu Val Asn Thr Glu Ile Asn Asp
                405             410             415

Pro Asp Gly Ile Ala Val Asp Trp Val Ala Arg Asn Leu Tyr Trp Thr
                420             425             430

Asp Thr Gly Thr Asp Arg Ile Glu Val Thr Arg Leu Asn Gly Thr Ser

```
                    435                 440                 445
Arg Lys Ile Leu Val Ser Glu Asp Leu Asp Glu Pro Arg Ala Ile Val
450                 455                 460

Leu His Pro Val Met Gly Leu Met Tyr Trp Thr Asp Trp Gly Glu Asn
465                 470                 475                 480

Pro Lys Ile Glu Cys Ala Asn Leu Asp Gly Arg Asp Arg His Val Leu
                    485                 490                 495

Val Asn Thr Ser Leu Gly Trp Pro Asn Gly Leu Ala Leu Asp Leu Gln
                500                 505                 510

Glu Gly Lys Leu Tyr Trp Gly Asp Ala Lys Thr Asp Lys Ile Glu Val
            515                 520                 525

Ile Asn Ile Asp Gly Thr Lys Arg Lys Thr Leu Leu Glu Asp Lys Leu
530                 535                 540

Pro His Ile Phe Gly Phe Thr Leu Leu Gly Asp Phe Ile Tyr Trp Thr
545                 550                 555                 560

Asp Trp Gln Arg Arg Ser Ile Glu Arg Val His Lys Val Lys Ala Ser
                565                 570                 575

Arg Asp Val Ile Ile Asp Gln Leu Pro Asp Leu Met Gly Leu Lys Ala
                580                 585                 590

Val Asn Val Ala Lys Val Val Gly Thr Asn Pro Cys Ala Asp Gly Asn
            595                 600                 605

Gly Gly Cys Ser His Leu Cys Phe Phe Thr Pro Arg Ala Thr Lys Cys
610                 615                 620

Gly Cys Pro Ile Gly Leu Glu Leu Leu Ser Asp Met Lys Thr Cys Ile
625                 630                 635                 640

Ile Pro Glu Ala Phe Leu Val Phe Thr Ser Arg Ala Thr Ile His Arg
                645                 650                 655

Ile Ser Leu Glu Thr Asn Asn Asn Asp Val Ala Ile Pro Leu Thr Gly
                660                 665                 670

Val Lys Glu Ala Ser Ala Leu Asp Phe Asp Val Ser Asn Asn His Ile
            675                 680                 685

Tyr Trp Thr Asp Val Ser Leu Lys Thr Ile Ser Arg Ala Phe Met Asn
690                 695                 700

Gly Ser Ser Val Glu His Val Ile Glu Phe Gly Leu Asp Tyr Pro Glu
705                 710                 715                 720

Gly Met Ala Val Asp Trp Met Gly Lys Asn Leu Tyr Trp Ala Asp Thr
                725                 730                 735

Gly Thr Asn Arg Ile Glu Val Ala Arg Leu Asp Gly Gln Phe Arg Gln
                740                 745                 750

Val Leu Val Trp Arg Asp Leu Asp Asn Pro Arg Ser Leu Ala Leu Asp
            755                 760                 765

Pro Thr Lys Gly Tyr Ile Tyr Trp Thr Glu Trp Gly Gly Lys Pro Arg
770                 775                 780

Ile Val Arg Ala Phe Met Asp Gly Thr Asn Cys Met Thr Leu Val Asp
785                 790                 795                 800

Lys Val Gly Arg Ala Asn Asp Leu Thr Ile Asp Tyr Ala Asp Gln Arg
                805                 810                 815

Leu Tyr Trp Thr Asp Leu Asp Thr Asn Met Ile Glu Ser Ser Asn Met
                820                 825                 830

Leu Gly Gln Glu Arg Met Val Ile Ala Asp Asp Leu Pro Tyr Pro Phe
            835                 840                 845

Gly Leu Thr Gln Tyr Ser Asp Tyr Ile Tyr Trp Thr Asp Trp Asn Leu
850                 855                 860
```

-continued

```
His Ser Ile Glu Arg Ala Asp Lys Thr Ser Gly Arg Asn Arg Thr Leu
865                 870                 875                 880

Ile Gln Gly His Leu Asp Phe Val Met Asp Ile Leu Val Phe His Ser
                885                 890                 895

Ser Arg Gln Asp Gly Leu Asn Asp Cys Val His Ser Asn Gly Gln Cys
            900                 905                 910

Gly Gln Leu Cys Leu Ala Ile Pro Gly Gly His Arg Cys Gly Cys Ala
        915                 920                 925

Ser His Tyr Thr Leu Asp Pro Ser Ser Arg Asn Cys Ser Pro Pro Ser
    930                 935                 940

Thr Phe Leu Leu Phe Ser Gln Lys Phe Ala Ile Ser Arg Met Ile Pro
945                 950                 955                 960

Asp Asp Gln Leu Ser Pro Asp Leu Val Leu Pro Leu His Gly Leu Arg
                965                 970                 975

Asn Val Lys Ala Ile Asn Tyr Asp Pro Leu Asp Lys Phe Ile Tyr Trp
            980                 985                 990

Val Asp Gly Arg Gln Asn Ile Lys Arg Ala Lys Asp Asp Gly Thr Gln
        995                 1000                1005

Pro Ser Met Leu Thr Ser Pro Ser Gln Ser Leu Ser Pro Asp Arg
    1010                1015                1020

Gln Pro His Asp Leu Ser Ile Asp Ile Tyr Ser Arg Thr Leu Phe
    1025                1030                1035

Trp Thr Cys Glu Ala Thr Asn Thr Ile Asn Val His Arg Leu Asp
    1040                1045                1050

Gly Asp Ala Met Gly Val Val Leu Arg Gly Asp Arg Asp Lys Pro
    1055                1060                1065

Arg Ala Ile Ala Val Asn Ala Glu Arg Gly Tyr Met Tyr Phe Thr
    1070                1075                1080

Asn Met Gln Asp His Ala Ala Lys Ile Glu Arg Ala Ser Leu Asp
    1085                1090                1095

Gly Thr Glu Arg Glu Val Leu Phe Thr Thr Gly Leu Ile Arg Pro
    1100                1105                1110

Val Ala Leu Val Val Asp Asn Ala Leu Gly Lys Leu Phe Trp Val
    1115                1120                1125

Asp Ala Asp Leu Lys Arg Ile Glu Ser Cys Asp Leu Ser Gly Ala
    1130                1135                1140

Asn Arg Leu Thr Leu Glu Asp Ala Asn Ile Val Gln Pro Val Gly
    1145                1150                1155

Leu Thr Val Leu Gly Arg His Leu Tyr Trp Ile Asp Arg Gln Gln
    1160                1165                1170

Gln Met Ile Glu Arg Val Glu Lys Thr Thr Gly Asp Lys Arg Thr
    1175                1180                1185

Arg Val Gln Gly Arg Val Thr His Leu Thr Gly Ile His Ala Val
    1190                1195                1200

Glu Glu Val Ser Leu Glu Glu Phe Ser Ala His Pro Cys Ala Arg
    1205                1210                1215

Asp Asn Gly Gly Cys Ser His Ile Cys Ile Ala Lys Gly Asp Gly
    1220                1225                1230

Thr Pro Arg Cys Ser Cys Pro Val His Leu Val Leu Leu Gln Asn
    1235                1240                1245

Leu Leu Thr Cys Gly Glu Pro Pro Thr Cys Ser Pro Asp Gln Phe
    1250                1255                1260

Ala Cys Thr Thr Gly Glu Ile Asp Cys Ile Pro Gly Ala Trp Arg
    1265                1270                1275
```

```
Cys Asp Gly Phe Pro Glu Cys Ala Asp Gln Ser Asp Glu Glu Gly
    1280            1285                1290
Cys Pro Val Cys Ser Ala Ser Gln Phe Pro Cys Ala Arg Gly Gln
    1295            1300                1305
Cys Val Asp Leu Arg Leu Arg Cys Asp Gly Glu Ala Asp Cys Gln
    1310            1315                1320
Asp Arg Ser Asp Glu Ala Asn Cys Asp Ala Val Cys Leu Pro Asn
    1325            1330                1335
Gln Phe Arg Cys Thr Ser Gly Gln Cys Val Leu Ile Lys Gln Gln
    1340            1345                1350
Cys Asp Ser Phe Pro Asp Cys Ala Asp Gly Ser Asp Glu Leu Met
    1355            1360                1365
Cys Glu Ile Asn Lys Pro Pro Ser Asp Asp Ile Pro Ala His Ser
    1370            1375                1380
Ser

<210> SEQ ID NO 13
<211> LENGTH: 4845
<212> TYPE: DNA
<213> ORGANISM: Mouse

<400> SEQUENCE: 13
atggaaacgg cgccgacccg ggcccctccg ccgccgccgc cgccgctgct gctgctggtg      60
ctgtactgca gcttggtccc cgccgcggcc tcaccgctcc tgttgttttgc aaccgccgg     120 gatgtgcggc tagtggatgc cggcggagtg aagctggagt ccaccattgt ggccagtggc    180
ctggaggatg cagctgctgt agacttccag ttctccaagg gtgctgtgta ctggacagat    240
gtgagcgagg aggccatcaa acagacctac ctgaaccaga ctggagctgc tgcacagaac    300
attgtcatct cgggcctcgt gtcacctgat ggcctggcct gtgactgggt tgcaagaag     360 ctgtactgga cggactccga gaccaaccgc attgaggttg ccaacctcaa tgggacgtcc    420
cgtaaggttc tcttctggca ggacctggac cagccaaggg ccattgccct ggatcctgca    480
catgggtaca tgtactggac tgactggggg gaagcacccc ggatcgagcg ggcagggatg    540
gatggcagta cccggaagat cattgtagac tccgacattt actggcccaa tgggctgacc    600
atcgacctgg aggaacagaa gctgtactgg gccgatgcca agctcagctt catccaccgt    660
gccaacctgg acggctcctt ccggcagaag gtggtggagg gcagcctcac tcaccctttt    720
gccctgacac tctctgggga cacactctac tggacagact ggcagacccg ctccatccac    780
gcctgcaaca gtggacagg ggagcagagg aaggagatcc ttagtgctct gtactcaccc    840
atggacatcc aagtgctgag ccaggagcgg cagcctccct tccacacacc atgcgaggag    900
gacaacggtg gctgttccca cctgtgcctg ctgtccccga gggagccttt ctactcctgt    960
gcctgcccca ctggtgtgca gttgcaggac aatggcaaga cgtgcaagac aggggctgag   1020
gaagtgctgc tgctggctcg gaggacagac ctgaggagga tctctctgga caccctgac   1080 ttcacagaca tagtgctgca ggtgggcgac atccggcatg ccattgccat tgactacgat   1140 ccctggagg gctacgtgta ctggaccgat gatgaggtgc gggctatccg cagggcgtac   1200
ctagatggct caggtgcgca gacacttgtg aacactgaga tcaatgaccc cgatggcatt   1260
gctgtggact gggtcgcccg gaacctctac tggacagata caggcactga cagaattgag   1320
gtgactcgcc tcaacggcac ctcccgaaag atcctggtat ctgaggacct ggacgaaccg   1380
cgagccattg tgttgcaccc tgtgatgggc ctcatgtact ggacagactg gggggagaac   1440
```

```
cccaaaatcg aatgcgccaa cctagatggg agagatcggc atgtcctggt gaacacctcc    1500
cttgggtggc ccaatggact ggccctggac ctgcaggagg gcaagctgta ctgggggat     1560 gccaaaactg ataaaatcga ggtgatcaac atagacggga caaagcggaa gaccctgctt    1620
gaggacaagc tcccacacat ttttgggttc acactgctgg gggacttcat ctactggacc    1680
gactggcaga gacgcagtat tgaaagggtc cacaaggtca aggccagccg ggatgtcatc    1740
attgatcaac tccccgacct gatgggactc aaagccgtga atgtggccaa ggttgtcgga    1800
accaacccat gtgcggatgg aaatggaggg tgcagccatc tgtgcttctt caccccacgt    1860
gccaccaagt gtggctgccc cattggcctg gagctgttga gtgacatgaa gacctgcata    1920
atccccgagg ccttcctggt attcaccagc agagccacca tccacaggat ctccctggag    1980
actaacaaca cgatgtggc tatcccactc acgggtgtca agaggcctc tgcactggac      2040 tttgatgtgt ccaacaatca catctactgg actgatgtta gcctcaagac gatcagccga    2100
gccttcatga atgggagctc agtggagcac gtgattgagt ttggcctcga ctaccctgaa    2160
ggaatggctg tggactggat gggcaagaac ctctattggg cggacacagg gaccaacagg    2220
attgaggtgg cccggctgga tgggcagttc cggcaggtgc ttgtgtggag agaccttgac    2280
aaccccaggt ctctggctct ggatcctact aaaggctaca tctactggac tgagtggggt    2340
ggcaagccaa ggattgtgcg ggccttcatg gatgggacca attgtatgac actggtagac    2400
aaggtgggcc gggccaacga cctcaccatt gattatgccg accagcgact gtactggact    2460
gacctggaca ccaacatgat tgagtcttcc aacatgctgg gtcaggagcg catggtgata    2520
gctgacgatc tgccctaccc gtttggcctg actcaatata gcgattacat ctactggact    2580
gactggaacc tgcatagcat tgaacgggcg gacaagacca gtgggcggaa ccgcacccte    2640 atccagggtc acctggactt cgtcatggac atcctggtgt tccactcctc ccgtcaggat    2700
ggcctcaacg actgcgtgca cagcaatggc cagtgtgggc agctgtgcct cgccatcccc    2760
ggaggccacc gctgtggctg tgcttcacac tacacgctgg accccagcag ccgcaactgc    2820
agcccgccct ccaccttctt gctgttcagc cagaaatttg ccatcagccg gatgatcccc    2880
gatgaccagc tcagcccgga ccttgtccta ccccttcatg ggctgaggaa cgtcaaagcc    2940
atcaactatg accccgctgga caagttcatc tactgggtgg acgggcgcca gaacatcaag    3000
agggccaagg acgacggtac ccagcccctcc atgctgacct ctcccagcca aagcctgagc    3060
ccagacagac agccacacga cctcagcatt gacatctaca gccggacact gttctggacc    3120
tgtgaggcca ccaacactat caatgtccac cggctggatg gggatgccat gggagtggtg    3180
cttcgagggg accgtgacaa gccaagggcc attgctgtca atgctgagcg agggtacatg    3240
tactttacca acatgcagga ccatgctgcc aagatcgagc gagcctccct ggatggcaca    3300
gagcgggagg tcctcttcac cacaggcctc atccgtcccg tggcccttgt ggtggacaat    3360
gctctgggca gctcttctg gtggatgcc gacctaaagc gaatcgaaag ctgtgacctc     3420
tctggggcca accgcctgac cctggaagat gccaacatcg tacagccagt aggtctgaca    3480
gtgctgggca gcaccctcta ctggatcgac cgccagcagc agatgatcga gcgcgtggag    3540
aagaccactg ggacaagcg gactagggtt cagggccgtg tcacccacct gacaggcatc     3600
catgccgtgg aggaagtcag cctggaggag ttctcagccc atccttgtgc ccagacaat    3660 ggcggctgct cccacatctg tatcgccaag ggtgatggaa caccgcgctg ctcgtgccct    3720
gtccacctgg tgctcctgca gaacctgctg acttgtggtg agcctcctac ctgctcccct    3780
gatcagtttg catgtaccac tggtgagatc gactgcatcc ccggagcctg gcgctgtgac    3840
```

-continued

```
ggcttccctg agtgtgctga ccagagtgat gaagaaggct gcccagtgtg ctccgcctct    3900
cagttcccct gcgctcgagg ccagtgtgtg gacctgcgt tacgctgcga cggtgaggcc     3960
gactgccagg atcgctctga tgaagctaac tgcgatgctg tctgtctgcc caatcagttc    4020
cggtgcacca gcggccagtg tgtcctcatc aagcaacagt gtgactcctt ccccgactgt    4080
gctgatgggt ctgatgagct catgtgtgaa atcaacaagc accctctga tgacatccca     4140 gcccacagca gtgccattgg gcccgtcatt ggtatcatcc tctccctctt cgtcatgggc    4200
ggggtctact ttgtctgcca gcgtgtgatg tgccagcgct acacaggggc cagtgggccc    4260
tttccccacg agtatgttgg tggagcccct catgtgcctc tcaacttcat agccccaggt    4320
ggctcacagc acggtccctt cccaggcatc ccgtgcagca agtccgtgat gagctccatg    4380
agcctggtgg gggggcgcgg cagcgtgccc ctctatgacc ggaatcacgt cactggggcc    4440
tcatccagca gctcgtccag cacaaaggcc acactatatc cgccgatcct gaacccaccc    4500
ccgtccccgg ccacagaccc ctctctctac aacgtggacg tgttttattc ttcaggcatc    4560
ccggccaccg ctagaccata caggccctac gtcattcgag gtatggcacc cccaacaaca    4620
ccgtgcagca cagatgtgtg tgacagtgac tacagcatca gtcgctggaa gagcagcaaa    4680
tactacctgg acttgaattc ggactcagac ccctaccccc cccgcccac ccccacagc     4740 cagtacctat ctgcagagga cagctgccca ccctcaccag gcactgagag gagttactgc    4800
cacctcttcc cgcccccacc gtccccctgc acggactcgt cctga                   4845
```

<210> SEQ ID NO 14
<211> LENGTH: 1614
<212> TYPE: PRT
<213> ORGANISM: Mouse

<400> SEQUENCE: 14

```
Met Glu Thr Ala Pro Thr Arg Ala Pro Pro Pro Pro Pro Pro Leu
1               5                   10                  15

Leu Leu Leu Val Leu Tyr Cys Ser Leu Val Pro Ala Ala Ser Pro
                20                  25                  30

Leu Leu Leu Phe Ala Asn Arg Arg Asp Val Arg Leu Val Asp Ala Gly
            35                  40                  45

Gly Val Lys Leu Glu Ser Thr Ile Val Ala Ser Gly Leu Glu Asp Ala
50                  55                  60

Ala Ala Val Asp Phe Gln Phe Ser Lys Gly Ala Val Tyr Trp Thr Asp
65                  70                  75                  80

Val Ser Glu Glu Ala Ile Lys Gln Thr Tyr Leu Asn Gln Thr Gly Ala
                85                  90                  95

Ala Ala Gln Asn Ile Val Ile Ser Gly Leu Val Ser Pro Asp Gly Leu
                100                 105                 110

Ala Cys Asp Trp Val Gly Lys Lys Leu Tyr Trp Thr Asp Ser Glu Thr
            115                 120                 125

Asn Arg Ile Glu Val Ala Asn Leu Asn Gly Thr Ser Arg Lys Val Leu
130                 135                 140

Phe Trp Gln Asp Leu Asp Gln Pro Arg Ala Ile Ala Leu Asp Pro Ala
145                 150                 155                 160

His Gly Tyr Met Tyr Trp Thr Asp Trp Gly Glu Ala Pro Arg Ile Glu
                165                 170                 175

Arg Ala Gly Met Asp Gly Ser Thr Arg Lys Ile Ile Val Asp Ser Asp
                180                 185                 190

Ile Tyr Trp Pro Asn Gly Leu Thr Ile Asp Leu Glu Glu Gln Lys Leu
            195                 200                 205
```

```
Tyr Trp Ala Asp Ala Lys Leu Ser Phe Ile His Arg Ala Asn Leu Asp
    210                 215                 220

Gly Ser Phe Arg Gln Lys Val Val Glu Gly Ser Leu Thr His Pro Phe
225                 230                 235                 240

Ala Leu Thr Leu Ser Gly Asp Thr Leu Tyr Trp Thr Asp Trp Gln Thr
                    245                 250                 255

Arg Ser Ile His Ala Cys Asn Lys Trp Thr Gly Glu Gln Arg Lys Glu
                260                 265                 270

Ile Leu Ser Ala Leu Tyr Ser Pro Met Asp Ile Gln Val Leu Ser Gln
            275                 280                 285

Glu Arg Gln Pro Pro Phe His Thr Pro Cys Glu Glu Asp Asn Gly Gly
        290                 295                 300

Cys Ser His Leu Cys Leu Leu Ser Pro Arg Glu Pro Phe Tyr Ser Cys
305                 310                 315                 320

Ala Cys Pro Thr Gly Val Gln Leu Gln Asp Asn Gly Lys Thr Cys Lys
                    325                 330                 335

Thr Gly Ala Glu Glu Val Leu Leu Ala Arg Arg Thr Asp Leu Arg
                340                 345                 350

Arg Ile Ser Leu Asp Thr Pro Asp Phe Thr Asp Ile Val Leu Gln Val
            355                 360                 365

Gly Asp Ile Arg His Ala Ile Ala Ile Asp Tyr Asp Pro Leu Glu Gly
370                 375                 380

Tyr Val Tyr Trp Thr Asp Asp Glu Val Arg Ala Ile Arg Arg Ala Tyr
385                 390                 395                 400

Leu Asp Gly Ser Gly Ala Gln Thr Leu Val Asn Thr Glu Ile Asn Asp
                    405                 410                 415

Pro Asp Gly Ile Ala Val Asp Trp Val Ala Arg Asn Leu Tyr Trp Thr
                420                 425                 430

Asp Thr Gly Thr Asp Arg Ile Glu Val Thr Arg Leu Asn Gly Thr Ser
            435                 440                 445

Arg Lys Ile Leu Val Ser Glu Asp Leu Asp Glu Pro Arg Ala Ile Val
450                 455                 460

Leu His Pro Val Met Gly Leu Met Tyr Trp Thr Asp Trp Gly Glu Asn
465                 470                 475                 480

Pro Lys Ile Glu Cys Ala Asn Leu Asp Gly Arg Asp Arg His Val Leu
                    485                 490                 495

Val Asn Thr Ser Leu Gly Trp Pro Asn Gly Leu Ala Leu Asp Leu Gln
                500                 505                 510

Glu Gly Lys Leu Tyr Trp Gly Asp Ala Lys Thr Asp Lys Ile Glu Val
            515                 520                 525

Ile Asn Ile Asp Gly Thr Lys Arg Lys Thr Leu Leu Glu Asp Lys Leu
530                 535                 540

Pro His Ile Phe Gly Phe Thr Leu Leu Gly Asp Phe Ile Tyr Trp Thr
545                 550                 555                 560

Asp Trp Gln Arg Arg Ser Ile Glu Arg Val His Lys Val Lys Ala Ser
                    565                 570                 575

Arg Asp Val Ile Ile Asp Gln Leu Pro Asp Leu Met Gly Leu Lys Ala
                580                 585                 590

Val Asn Val Ala Lys Val Val Gly Thr Asn Pro Cys Ala Asp Gly Asn
            595                 600                 605

Gly Gly Cys Ser His Leu Cys Phe Phe Thr Pro Arg Ala Thr Lys Cys
610                 615                 620

Gly Cys Pro Ile Gly Leu Glu Leu Leu Ser Asp Met Lys Thr Cys Ile
```

-continued

```
              625                 630                 635                 640
Ile Pro Glu Ala Phe Leu Val Phe Thr Ser Arg Ala Thr Ile His Arg
                645                 650                 655

Ile Ser Leu Glu Thr Asn Asn Asn Asp Val Ala Ile Pro Leu Thr Gly
            660                 665                 670

Val Lys Glu Ala Ser Ala Leu Asp Phe Asp Val Ser Asn Asn His Ile
            675                 680                 685

Tyr Trp Thr Asp Val Ser Leu Lys Thr Ile Ser Arg Ala Phe Met Asn
    690                 695                 700

Gly Ser Ser Val Glu His Val Ile Glu Phe Gly Leu Asp Tyr Pro Glu
705                 710                 715                 720

Gly Met Ala Val Asp Trp Met Gly Lys Asn Leu Tyr Trp Ala Asp Thr
                725                 730                 735

Gly Thr Asn Arg Ile Glu Val Ala Arg Leu Asp Gly Gln Phe Arg Gln
                740                 745                 750

Val Leu Val Trp Arg Asp Leu Asp Asn Pro Arg Ser Leu Ala Leu Asp
            755                 760                 765

Pro Thr Lys Gly Tyr Ile Tyr Trp Thr Glu Trp Gly Gly Lys Pro Arg
    770                 775                 780

Ile Val Arg Ala Phe Met Asp Gly Thr Asn Cys Met Thr Leu Val Asp
785                 790                 795                 800

Lys Val Gly Arg Ala Asn Asp Leu Thr Ile Asp Tyr Ala Asp Gln Arg
                805                 810                 815

Leu Tyr Trp Thr Asp Leu Asp Thr Asn Met Ile Glu Ser Ser Asn Met
                820                 825                 830

Leu Gly Gln Glu Arg Met Val Ile Ala Asp Asp Leu Pro Tyr Pro Phe
            835                 840                 845

Gly Leu Thr Gln Tyr Ser Asp Tyr Ile Tyr Trp Thr Asp Trp Asn Leu
    850                 855                 860

His Ser Ile Glu Arg Ala Asp Lys Thr Ser Gly Arg Asn Arg Thr Leu
865                 870                 875                 880

Ile Gln Gly His Leu Asp Phe Val Met Asp Ile Leu Val Phe His Ser
                885                 890                 895

Ser Arg Gln Asp Gly Leu Asn Asp Cys Val His Ser Asn Gly Gln Cys
            900                 905                 910

Gly Gln Leu Cys Leu Ala Ile Pro Gly Gly His Arg Cys Gly Cys Ala
            915                 920                 925

Ser His Tyr Thr Leu Asp Pro Ser Ser Arg Asn Cys Ser Pro Pro Ser
    930                 935                 940

Thr Phe Leu Leu Phe Ser Gln Lys Phe Ala Ile Ser Arg Met Ile Pro
945                 950                 955                 960

Asp Asp Gln Leu Ser Pro Asp Leu Val Leu Pro Leu His Gly Leu Arg
                965                 970                 975

Asn Val Lys Ala Ile Asn Tyr Asp Pro Leu Asp Lys Phe Ile Tyr Trp
            980                 985                 990

Val Asp Gly Arg Gln Asn Ile Lys  Arg Ala Lys Asp  Gly Thr Gln
            995                 1000                1005

Pro Ser  Met Leu Thr Ser Pro  Ser Gln Ser Leu Ser  Pro Asp Arg
    1010                1015                1020

Gln Pro  His Asp Leu Ser Ile  Asp Ile Tyr Ser Arg  Thr Leu Phe
    1025                1030                1035

Trp Thr  Cys Glu Ala Thr Asn  Thr Ile Asn Val His  Arg Leu Asp
    1040                1045                1050
```

-continued

Gly Asp Ala Met Gly Val Val Leu Arg Gly Asp Arg Asp Lys Pro
1055                1060                1065

Arg Ala Ile Ala Val Asn Ala Glu Arg Gly Tyr Met Tyr Phe Thr
1070                1075                1080

Asn Met Gln Asp His Ala Ala Lys Ile Glu Arg Ala Ser Leu Asp
1085                1090                1095

Gly Thr Glu Arg Glu Val Leu Phe Thr Thr Gly Leu Ile Arg Pro
1100                1105                1110

Val Ala Leu Val Val Asp Asn Ala Leu Gly Lys Leu Phe Trp Val
1115                1120                1125

Asp Ala Asp Leu Lys Arg Ile Glu Ser Cys Asp Leu Ser Gly Ala
1130                1135                1140

Asn Arg Leu Thr Leu Glu Asp Ala Asn Ile Val Gln Pro Val Gly
1145                1150                1155

Leu Thr Val Leu Gly Arg His Leu Tyr Trp Ile Asp Arg Gln Gln
1160                1165                1170

Gln Met Ile Glu Arg Val Glu Lys Thr Thr Gly Asp Lys Arg Thr
1175                1180                1185

Arg Val Gln Gly Arg Val Thr His Leu Thr Gly Ile His Ala Val
1190                1195                1200

Glu Glu Val Ser Leu Glu Glu Phe Ser Ala His Pro Cys Ala Arg
1205                1210                1215

Asp Asn Gly Gly Cys Ser His Ile Cys Ile Ala Lys Gly Asp Gly
1220                1225                1230

Thr Pro Arg Cys Ser Cys Pro Val His Leu Val Leu Leu Gln Asn
1235                1240                1245

Leu Leu Thr Cys Gly Glu Pro Pro Thr Cys Ser Pro Asp Gln Phe
1250                1255                1260

Ala Cys Thr Thr Gly Glu Ile Asp Cys Ile Pro Gly Ala Trp Arg
1265                1270                1275

Cys Asp Gly Phe Pro Glu Cys Ala Asp Gln Ser Asp Glu Glu Gly
1280                1285                1290

Cys Pro Val Cys Ser Ala Ser Gln Phe Pro Cys Ala Arg Gly Gln
1295                1300                1305

Cys Val Asp Leu Arg Leu Arg Cys Asp Gly Glu Ala Asp Cys Gln
1310                1315                1320

Asp Arg Ser Asp Glu Ala Asn Cys Asp Ala Val Cys Leu Pro Asn
1325                1330                1335

Gln Phe Arg Cys Thr Ser Gly Gln Cys Val Leu Ile Lys Gln Gln
1340                1345                1350

Cys Asp Ser Phe Pro Asp Cys Ala Asp Gly Ser Asp Glu Leu Met
1355                1360                1365

Cys Glu Ile Asn Lys Pro Pro Ser Asp Asp Ile Pro Ala His Ser
1370                1375                1380

Ser Ala Ile Gly Pro Val Ile Gly Ile Ile Leu Ser Leu Phe Val
1385                1390                1395

Met Gly Gly Val Tyr Phe Val Cys Gln Arg Val Met Cys Gln Arg
1400                1405                1410

Tyr Thr Gly Ala Ser Gly Pro Phe Pro His Glu Tyr Val Gly Gly
1415                1420                1425

Ala Pro His Val Pro Leu Asn Phe Ile Ala Pro Gly Gly Ser Gln
1430                1435                1440

His Gly Pro Phe Pro Gly Ile Pro Cys Ser Lys Ser Val Met Ser
1445                1450                1455

```
Ser Met Ser Leu Val Gly Gly Arg Gly Ser Val Pro Leu Tyr Asp
    1460            1465                1470

Arg Asn His Val Thr Gly Ala Ser Ser Ser Ser Ser Ser Ser Thr
    1475            1480                1485

Lys Ala Thr Leu Tyr Pro Pro Ile Leu Asn Pro Pro Pro Ser Pro
    1490            1495                1500

Ala Thr Asp Pro Ser Leu Tyr Asn Val Asp Val Phe Tyr Ser Ser
    1505            1510                1515

Gly Ile Pro Ala Thr Ala Arg Pro Tyr Arg Pro Tyr Val Ile Arg
    1520            1525                1530

Gly Met Ala Pro Pro Thr Thr Pro Cys Ser Thr Asp Val Cys Asp
    1535            1540                1545

Ser Asp Tyr Ser Ile Ser Arg Trp Lys Ser Ser Lys Tyr Tyr Leu
    1550            1555                1560

Asp Leu Asn Ser Asp Ser Asp Pro Tyr Pro Pro Pro Thr Pro
    1565            1570                1575

His Ser Gln Tyr Leu Ser Ala Glu Asp Ser Cys Pro Pro Ser Pro
    1580            1585                1590

Gly Thr Glu Arg Ser Tyr Cys His Leu Phe Pro Pro Pro Pro Ser
    1595            1600                1605

Pro Cys Thr Asp Ser Ser
    1610

<210> SEQ ID NO 15
<211> LENGTH: 14
<212> TYPE: PRT
<213> ORGANISM: Human

<400> SEQUENCE: 15

Glu Asn Asn Lys Thr Met Asn Arg Ala Glu Asn Gly Gly Arg
1               5                   10

<210> SEQ ID NO 16
<211> LENGTH: 16
<212> TYPE: PRT
<213> ORGANISM: Human

<400> SEQUENCE: 16

His Pro Phe Glu Thr Lys Asp Val Ser Glu Tyr Ser Cys Arg Glu Leu
1               5                   10                  15

<210> SEQ ID NO 17
<211> LENGTH: 17
<212> TYPE: PRT
<213> ORGANISM: Human

<400> SEQUENCE: 17

Arg Glu Leu His Phe Thr Arg Tyr Val Thr Asp Gly Pro Cys Arg Ser
1               5                   10                  15
Ala

<210> SEQ ID NO 18
<211> LENGTH: 12
<212> TYPE: PRT
<213> ORGANISM: Human

<400> SEQUENCE: 18

Leu Cys Pro Gly Gly Glu Ala Pro Arg Ala Arg Lys
1               5                   10
```

```
<210> SEQ ID NO 19
<211> LENGTH: 615
<212> TYPE: DNA
<213> ORGANISM: Mouse

<400> SEQUENCE: 19
atgcagccct cactagcccc gtgcctcatc tgcctacttg tgcacgctgc cttctgtgct      60
gtggagggcc aggggtggca agccttcagg aatgatgcca cagaggtcat cccagggctt     120
ggagagtacc ccgagcctac tcctgagaac aaccagacca tgaaccgggc ggagaatggt     180
ggcagacctc cccaccatcc ctatgacgcc aaagatgtgt ccgagtacag ctgccgcgag     240
ctgcactaca cccgcttcct gacagacggc ccatgccgca gcgccaagcc ggtcaccgag     300
ttggtgtgct ccggccagtg cggccccgcg cggctgctgc ccaacgccat cgggcgcgtg     360
aagtggtggc gcccgaacgg accggatttc cgctgcatcc cggatcgcta ccgcgcgcag     420
cgggtgcagc tgctgtgccc cggggcgcg gcgccacgct cgcgcaaggt gcgtctggtg      480
gcctcgtgca agtgcaagcg ccccacccgc ttccacaacc agtcggagct caaggacttc     540
gggccggaga ccgcgcggcc gcagaagggt cgcaagccgc ggcccggcgc ccggggagcc     600
aaagccaacc aggcg                                                    615

<210> SEQ ID NO 20
<211> LENGTH: 203
<212> TYPE: PRT
<213> ORGANISM: Mouse

<400> SEQUENCE: 20

Met Gln Pro Ser Leu Ala Pro Cys Leu Ile Cys Leu Val His Ala
1               5                   10                  15

Ala Phe Cys Ala Val Glu Gly Gln Gly Trp Gln Ala Phe Arg Asn Asp
            20                  25                  30

Ala Thr Glu Val Ile Pro Gly Leu Gly Glu Tyr Pro Glu Pro Pro
        35                  40                  45

Glu Asn Asn Gln Thr Met Asn Arg Ala Glu Asn Gly Gly Arg Pro Pro
    50                  55                  60

His His Pro Tyr Asp Ala Lys Asp Val Ser Glu Tyr Ser Cys Arg Glu
65                  70                  75                  80

Leu His Tyr Thr Arg Phe Leu Thr Asp Gly Pro Cys Arg Ser Ala Lys
                85                  90                  95

Pro Val Thr Glu Leu Val Cys Ser Gly Gln Cys Gly Pro Ala Arg Leu
            100                 105                 110

Leu Pro Asn Ala Ile Gly Arg Val Lys Trp Trp Arg Pro Asn Gly Pro
        115                 120                 125

Asp Phe Arg Cys Ile Pro Asp Arg Tyr Arg Ala Gln Arg Val Gln Leu
    130                 135                 140

Leu Cys Pro Gly Gly Ala Ala Pro Arg Ser Arg Lys Val Arg Leu Val
145                 150                 155                 160

Ala Ser Cys Lys Cys Lys Arg Leu Thr Arg Phe His Asn Gln Ser Glu
                165                 170                 175

Leu Lys Asp Phe Gly Pro Glu Thr Ala Arg Pro Gln Lys Gly Arg Lys
            180                 185                 190

Pro Arg Pro Gly Ala Arg Gly Ala Lys Ala Asn
        195                 200

<210> SEQ ID NO 21
<211> LENGTH: 203
```

```
<212> TYPE: PRT
<213> ORGANISM: Artificial
<220> FEATURE:
<223> OTHER INFORMATION: Wise/SOST Peptides

<400> SEQUENCE: 21

Met Gln Pro Ser Leu Ala Pro Cys Leu Ile Cys Leu Leu Val His Ala
1               5                   10                  15

Ala Phe Cys Ala Val Glu Gly Gln Gly Trp Gln Ala Phe Arg Asn Asp
            20                  25                  30

Ala Thr Glu Val Ile Pro Gly Leu Gly Glu Tyr Pro Glu Pro Pro Pro
        35                  40                  45

Glu Asn Asn Gln Thr Met Asn Arg Ala Glu Asn Gly Gly Arg Pro Pro
    50                  55                  60

His His Pro Tyr Asp Ala Lys Asp Val Ser Glu Tyr Ser Cys Arg Glu
65                  70                  75                  80

Leu His Tyr Thr Arg Phe Leu Thr Asp Gly Pro Cys Arg Ser Ala Lys
                85                  90                  95

Pro Val Thr Glu Leu Val Cys Ser Gly Gln Cys Gly Pro Ala Arg Leu
            100                 105                 110

Leu Pro Asn Ala Ile Gly Arg Val Lys Trp Trp Arg Pro Asn Gly Pro
        115                 120                 125

Asp Phe Arg Cys Ile Pro Asp Arg Tyr Arg Ala Gln Arg Val Gln Leu
    130                 135                 140

Leu Cys Pro Gly Gly Ala Ala Pro Arg Ser Arg Lys Val Arg Leu Val
145                 150                 155                 160

Ala Ser Cys Lys Cys Lys Arg Leu Thr Arg Phe His Asn Gln Ser Glu
                165                 170                 175

Leu Lys Asp Phe Gly Pro Glu Thr Ala Arg Pro Gln Lys Gly Arg Lys
            180                 185                 190

Pro Arg Pro Gly Ala Arg Gly Ala Lys Ala Asn
        195                 200

<210> SEQ ID NO 22
<211> LENGTH: 14
<212> TYPE: PRT
<213> ORGANISM: Artificial
<220> FEATURE:
<223> OTHER INFORMATION: Wise/SOST Peptides

<400> SEQUENCE: 22

Leu Asn Asn Lys Thr Met Asn Arg Ala Glu Asn Gly Gly Arg
1               5                   10

<210> SEQ ID NO 23
<211> LENGTH: 14
<212> TYPE: PRT
<213> ORGANISM: Artificial
<220> FEATURE:
<223> OTHER INFORMATION: Wise/SOST Peptides

<400> SEQUENCE: 23

Ser Ser Asn Ser Thr Met Asn Gln Ala Arg Asn Gly Gly Arg
1               5                   10

<210> SEQ ID NO 24
<211> LENGTH: 14
<212> TYPE: PRT
<213> ORGANISM: Artificial
<220> FEATURE:
<223> OTHER INFORMATION: Wise/SOST Peptides
```

```
<400> SEQUENCE: 24

Ala Asn Ser Ser Ala Leu Asn Gln Ala Arg Asn Gly Gly Arg
1               5                   10

<210> SEQ ID NO 25
<211> LENGTH: 14
<212> TYPE: PRT
<213> ORGANISM: Artificial
<220> FEATURE:
<223> OTHER INFORMATION: Wise/SOST Peptides

<400> SEQUENCE: 25

Ala Asn Ser Ser Thr Leu Asn Gln Ala Arg Asn Gly Gly Arg
1               5                   10

<210> SEQ ID NO 26
<211> LENGTH: 14
<212> TYPE: PRT
<213> ORGANISM: Artificial
<220> FEATURE:
<223> OTHER INFORMATION: Wise/SOST Peptides

<400> SEQUENCE: 26

Ser Ser Ser Asn Gly Gly Asn Arg Ala Lys Ser Gly Gly Arg
1               5                   10

<210> SEQ ID NO 27
<211> LENGTH: 14
<212> TYPE: PRT
<213> ORGANISM: Artificial
<220> FEATURE:
<223> OTHER INFORMATION: Wise/SOST Peptides

<400> SEQUENCE: 27

Ala Ser Ser Asn Ala Gly Asn Arg Ala Lys Ser Gly Ala Arg
1               5                   10

<210> SEQ ID NO 28
<211> LENGTH: 14
<212> TYPE: PRT
<213> ORGANISM: Artificial
<220> FEATURE:
<223> OTHER INFORMATION: Wise/SOST Peptides

<400> SEQUENCE: 28

Ser Asn Asn Asn Thr Met Asn Gln Ala Lys His Gly Gly Arg
1               5                   10

<210> SEQ ID NO 29
<211> LENGTH: 14
<212> TYPE: PRT
<213> ORGANISM: Artificial
<220> FEATURE:
<223> OTHER INFORMATION: Wise/SOST Peptides

<400> SEQUENCE: 29

Glu Asn Asn Gln Thr Met Asn Arg Ala Glu Asn Gly Gly Arg
1               5                   10

<210> SEQ ID NO 30
<211> LENGTH: 16
<212> TYPE: PRT
<213> ORGANISM: Artificial
<220> FEATURE:
<223> OTHER INFORMATION: Wise/SOST Peptides

<400> SEQUENCE: 30
```

His Pro Phe Glu Thr Lys Asp Ala Ser Glu Tyr Ser Cys Arg Glu Leu
1               5                   10                  15

<210> SEQ ID NO 31
<211> LENGTH: 16
<212> TYPE: PRT
<213> ORGANISM: Artificial
<220> FEATURE:
<223> OTHER INFORMATION: Wise/SOST Peptides

<400> SEQUENCE: 31

His Pro Tyr Asp Ala Lys Gly Val Ser Glu Tyr Ser Cys Arg Glu Leu
1               5                   10                  15

<210> SEQ ID NO 32
<211> LENGTH: 16
<212> TYPE: PRT
<213> ORGANISM: Artificial
<220> FEATURE:
<223> OTHER INFORMATION: Wise/SOST Peptides

<400> SEQUENCE: 32

His Pro Tyr Asp Thr Lys Asp Val Ser Glu Tyr Ser Cys Arg Glu Leu
1               5                   10                  15

<210> SEQ ID NO 33
<211> LENGTH: 16
<212> TYPE: PRT
<213> ORGANISM: Artificial
<220> FEATURE:
<223> OTHER INFORMATION: Wise/SOST Peptides

<400> SEQUENCE: 33

Gln Ala Pro Asp Pro Asn Asp Val Ser Asp Phe Ser Cys Arg Glu Met
1               5                   10                  15

<210> SEQ ID NO 34
<211> LENGTH: 16
<212> TYPE: PRT
<213> ORGANISM: Artificial
<220> FEATURE:
<223> OTHER INFORMATION: Wise/SOST Peptides

<400> SEQUENCE: 34

Thr Gly Leu Asp Arg Asn Thr Arg Val Gln Val Gly Cys Arg Glu Leu
1               5                   10                  15

<210> SEQ ID NO 35
<211> LENGTH: 16
<212> TYPE: PRT
<213> ORGANISM: Artificial
<220> FEATURE:
<223> OTHER INFORMATION: Wise/SOST Peptides

<400> SEQUENCE: 35

Thr Gly Leu Asp Arg Asn Ser Arg Val Gln Val Gly Cys Arg Glu Leu
1               5                   10                  15

<210> SEQ ID NO 36
<211> LENGTH: 16
<212> TYPE: PRT
<213> ORGANISM: Artificial
<220> FEATURE:
<223> OTHER INFORMATION: Wise/SOST Peptides

<400> SEQUENCE: 36

Thr Gly Ser Asp Arg Asn Asn Arg Val Gln Val Gly Cys Arg Glu Leu
1               5                   10                  15

```
<210> SEQ ID NO 37
<211> LENGTH: 16
<212> TYPE: PRT
<213> ORGANISM: Artificial
<220> FEATURE:
<223> OTHER INFORMATION: Wise/SOST Peptides

<400> SEQUENCE: 37

Ser Ala Met Asp Arg Thr Asn Pro His Gln Val Gly Cys Arg Glu Leu
1               5                   10                  15

<210> SEQ ID NO 38
<211> LENGTH: 16
<212> TYPE: PRT
<213> ORGANISM: Artificial
<220> FEATURE:
<223> OTHER INFORMATION: Wise/SOST Peptides

<400> SEQUENCE: 38

Ser Ala Leu Asp Arg Thr Asn His His Gln Val Gly Cys Arg Glu Leu
1               5                   10                  15

<210> SEQ ID NO 39
<211> LENGTH: 16
<212> TYPE: PRT
<213> ORGANISM: Artificial
<220> FEATURE:
<223> OTHER INFORMATION: Wise/SOST Peptides

<400> SEQUENCE: 39

Thr Ser Ser Val Thr Tyr Ser Ala Ser Glu Leu Ser Cys Arg Glu Leu
1               5                   10                  15

<210> SEQ ID NO 40
<211> LENGTH: 16
<212> TYPE: PRT
<213> ORGANISM: Artificial
<220> FEATURE:
<223> OTHER INFORMATION: Wise/SOST Peptides

<400> SEQUENCE: 40

Thr Ser Thr Val Ser Tyr Ser Ala Ser Glu Leu Ser Cys Arg Glu Leu
1               5                   10                  15

<210> SEQ ID NO 41
<211> LENGTH: 17
<212> TYPE: PRT
<213> ORGANISM: Artificial
<220> FEATURE:
<223> OTHER INFORMATION: Wise/SOST Peptides

<400> SEQUENCE: 41

Arg Glu Leu Arg Ser Thr Lys Tyr Ile Ser Asp Gly Gln Cys Thr Ser
1               5                   10                  15

Ile

<210> SEQ ID NO 42
<211> LENGTH: 16
<212> TYPE: PRT
<213> ORGANISM: Artificial
<220> FEATURE:
<223> OTHER INFORMATION: Wise/SOST Peptodes

<400> SEQUENCE: 42

Lys Thr Gln Pro Leu Lys Gln Thr Ile His Glu Asp Gly Cys Asn Ser
1               5                   10                  15
```

<210> SEQ ID NO 43
<211> LENGTH: 17
<212> TYPE: PRT
<213> ORGANISM: Artificial
<220> FEATURE:
<223> OTHER INFORMATION: Wise/SOST Peptides

<400> SEQUENCE: 43

Arg Glu Leu Arg Ser Thr Arg Tyr Val Thr Asp Gly Ser Cys Arg Ser
1               5                   10                  15

Ala

<210> SEQ ID NO 44
<211> LENGTH: 17
<212> TYPE: PRT
<213> ORGANISM: Artificial
<220> FEATURE:
<223> OTHER INFORMATION: Wise/SOST Peptides

<400> SEQUENCE: 44

Arg Glu Met Arg Ile Thr Arg Tyr Val Thr Glu Gly Pro Cys Arg Ser
1               5                   10                  15

Leu

<210> SEQ ID NO 45
<211> LENGTH: 17
<212> TYPE: PRT
<213> ORGANISM: Artificial
<220> FEATURE:
<223> OTHER INFORMATION: Wise/SOST Peptides

<400> SEQUENCE: 45

Arg Glu Leu His Tyr Thr Arg Phe Leu Thr Asp Gly Pro Cys Arg Ser
1               5                   10                  15

Ala

<210> SEQ ID NO 46
<211> LENGTH: 15
<212> TYPE: PRT
<213> ORGANISM: Artificial
<220> FEATURE:
<223> OTHER INFORMATION: Wise/SOST Peptides

<400> SEQUENCE: 46

Glu Leu Val Cys Ser Gly Gln Cys Gly Pro Ala Arg Leu Leu Pro
1               5                   10                  15

<210> SEQ ID NO 47
<211> LENGTH: 15
<212> TYPE: PRT
<213> ORGANISM: Artificial
<220> FEATURE:
<223> OTHER INFORMATION: Wise/SOST Peptides

<400> SEQUENCE: 47

Glu Leu Val Cys Ser Gly Gln Cys Val Pro Ser His Leu Leu Pro
1               5                   10                  15

<210> SEQ ID NO 48
<211> LENGTH: 15
<212> TYPE: PRT
<213> ORGANISM: Artificial
<220> FEATURE:
<223> OTHER INFORMATION: Wise/SOST Peptides

```
<400> SEQUENCE: 48

Glu Leu Val Cys Ser Gly Gln Cys Leu Pro Ala His Leu Met Pro
1               5                   10                  15

<210> SEQ ID NO 49
<211> LENGTH: 15
<212> TYPE: PRT
<213> ORGANISM: Artificial
<220> FEATURE:
<223> OTHER INFORMATION: Wise/SOST Peptides

<400> SEQUENCE: 49

Glu Leu Val Cys Thr Gly Gln Cys Leu Pro Ala Gln Met Leu Pro
1               5                   10                  15

<210> SEQ ID NO 50
<211> LENGTH: 15
<212> TYPE: PRT
<213> ORGANISM: Artificial
<220> FEATURE:
<223> OTHER INFORMATION: Wise/SOST Peptides

<400> SEQUENCE: 50

Glu Leu Val Cys Ala Gly Glu Cys Leu Pro Leu Pro Ile Leu Pro
1               5                   10                  15

<210> SEQ ID NO 51
<211> LENGTH: 15
<212> TYPE: PRT
<213> ORGANISM: Artificial
<220> FEATURE:
<223> OTHER INFORMATION: Wise/SOST Peptides

<400> SEQUENCE: 51

Glu Leu Val Cys Ala Gly Glu Cys Leu Pro Leu Pro Leu Leu Pro
1               5                   10                  15

<210> SEQ ID NO 52
<211> LENGTH: 15
<212> TYPE: PRT
<213> ORGANISM: Artificial
<220> FEATURE:
<223> OTHER INFORMATION: Wise/SOST Peptides

<400> SEQUENCE: 52

Glu Leu Val Cys Ala Gly Glu Cys Leu Pro Leu Pro Val Leu Pro
1               5                   10                  15

<210> SEQ ID NO 53
<211> LENGTH: 15
<212> TYPE: PRT
<213> ORGANISM: Artificial
<220> FEATURE:
<223> OTHER INFORMATION: Wise/SOST Peptides

<400> SEQUENCE: 53

Glu Leu Val Cys Ser Gly Gln Cys Gly Pro Ala Arg Leu Leu Pro
1               5                   10                  15

<210> SEQ ID NO 54
<211> LENGTH: 15
<212> TYPE: PRT
<213> ORGANISM: Artificial
<220> FEATURE:
<223> OTHER INFORMATION: Wise/SOST Peptides

<400> SEQUENCE: 54
```

```
Glu Leu Val Cys Ala Gly Glu Cys Leu Pro Leu Ser Val Leu Pro
1               5                   10                  15
```

<210> SEQ ID NO 55
<211> LENGTH: 15
<212> TYPE: PRT
<213> ORGANISM: Artificial
<220> FEATURE:
<223> OTHER INFORMATION: Wise/SOST Peptides

<400> SEQUENCE: 55

```
Glu Leu Val Cys Ser Gly Gln Cys Gly Pro Ala Arg Leu Leu Pro
1               5                   10                  15
```

<210> SEQ ID NO 56
<211> LENGTH: 21
<212> TYPE: PRT
<213> ORGANISM: Artificial
<220> FEATURE:
<223> OTHER INFORMATION: Wise/SOST Peptides

<400> SEQUENCE: 56

```
Asn Ala Ile Gly Arg Gly Lys Trp Trp Arg Pro Ser Gly Pro Asp Phe
1               5                   10                  15

Arg Cys Ile Pro Asp
            20
```

<210> SEQ ID NO 57
<211> LENGTH: 25
<212> TYPE: PRT
<213> ORGANISM: Artificial
<220> FEATURE:
<223> OTHER INFORMATION: Wise/SOST Peptides

<400> SEQUENCE: 57

```
Asn Trp Ile Gly Gly Gly Tyr Gly Thr Lys Tyr Trp Ser Arg Arg Ser
1               5                   10                  15

Ser Gln Glu Trp Arg Cys Val Asn Asp
            20                  25
```

<210> SEQ ID NO 58
<211> LENGTH: 25
<212> TYPE: PRT
<213> ORGANISM: Artificial
<220> FEATURE:
<223> OTHER INFORMATION: Wise Peptides

<400> SEQUENCE: 58

```
Asn Trp Ile Gly Gly Gly Tyr Gly Thr Lys Tyr Trp Ser Arg Arg Ser
1               5                   10                  15

Ser Gln Glu Trp Arg Cys Val Asn Asp
            20                  25
```

<210> SEQ ID NO 59
<211> LENGTH: 21
<212> TYPE: PRT
<213> ORGANISM: Artificial
<220> FEATURE:
<223> OTHER INFORMATION: Wise Peptides

<400> SEQUENCE: 59

```
Asn Ala Ile Gly Arg Gly Lys Trp Trp Arg Pro Ser Gly Pro Asp Phe
1               5                   10                  15

Arg Cys Ile Pro Asp
            20
```

```
<210> SEQ ID NO 60
<211> LENGTH: 25
<212> TYPE: PRT
<213> ORGANISM: Artificial
<220> FEATURE:
<223> OTHER INFORMATION: Wise Peptides

<400> SEQUENCE: 60

Asn Trp Ile Gly Gly Gly Tyr Gly Thr Lys Tyr Trp Ser Arg Arg Ser
1               5                   10                  15

Ser Gln Glu Trp Arg Cys Val Asn Asp
            20                  25

<210> SEQ ID NO 61
<211> LENGTH: 25
<212> TYPE: PRT
<213> ORGANISM: Artificial
<220> FEATURE:
<223> OTHER INFORMATION: Wise/SOST Peptides

<400> SEQUENCE: 61

Asn Trp Ile Gly Gly Gly Tyr Gly Thr Lys Tyr Trp Ser Arg Arg Gly
1               5                   10                  15

Ser Gln Glu Trp Arg Cys Val Asn Asp
            20                  25

<210> SEQ ID NO 62
<211> LENGTH: 24
<212> TYPE: PRT
<213> ORGANISM: Artificial
<220> FEATURE:
<223> OTHER INFORMATION: Wise/SOST Peptides

<400> SEQUENCE: 62

Asn Trp Ile Gly Gly Tyr Gly Lys Lys Ser Trp Asn Arg Arg Asn Ser
1               5                   10                  15

Gln Glu Trp Arg Cys Val Asn Asp
            20

<210> SEQ ID NO 63
<211> LENGTH: 21
<212> TYPE: PRT
<213> ORGANISM: Artificial
<220> FEATURE:
<223> OTHER INFORMATION: Wise/SOST Peptides

<400> SEQUENCE: 63

Asn Thr Ile Gly Arg Gly Lys Trp Trp Arg Ser Asn Thr Ser Glu Tyr
1               5                   10                  15

Arg Cys Ile Pro Ala
            20

<210> SEQ ID NO 64
<211> LENGTH: 21
<212> TYPE: PRT
<213> ORGANISM: Artificial
<220> FEATURE:
<223> OTHER INFORMATION: Wise/SOST Peptides

<400> SEQUENCE: 64

Asn Thr Ile Gly Arg Ala Lys Trp Trp Arg Ser Ser Thr Ser Glu Tyr
1               5                   10                  15

Arg Cys Val Pro Ala
            20
```

```
<210> SEQ ID NO 65
<211> LENGTH: 21
<212> TYPE: PRT
<213> ORGANISM: Artificial
<220> FEATURE:
<223> OTHER INFORMATION: Wise/SOST Peptides

<400> SEQUENCE: 65

Asn Ser Ile Gly Arg Gly Lys Trp Trp Arg Gln Asn Ser Pro Asp Tyr
1               5                   10                  15

Arg Cys Ile Pro Ala
            20

<210> SEQ ID NO 66
<211> LENGTH: 21
<212> TYPE: PRT
<213> ORGANISM: Artificial
<220> FEATURE:
<223> OTHER INFORMATION: Wise/SOST Peptides

<400> SEQUENCE: 66

Asn Ala Ile Gly Arg Val Lys Trp Trp Arg Pro Asn Gly Pro Asp Phe
1               5                   10                  15

Arg Cys Ile Pro Asp
            20

<210> SEQ ID NO 67
<211> LENGTH: 21
<212> TYPE: PRT
<213> ORGANISM: Artificial
<220> FEATURE:
<223> OTHER INFORMATION: Wise/SOST Peptides

<400> SEQUENCE: 67

Asn Ala Ile Gly Arg Gly Lys Trp Trp Arg Pro Ser Gly Pro Asp Phe
1               5                   10                  15

Arg Cys Ile Pro Asp
            20

<210> SEQ ID NO 68
<211> LENGTH: 13
<212> TYPE: PRT
<213> ORGANISM: Artificial
<220> FEATURE:
<223> OTHER INFORMATION: Wise/SOST Peptides

<400> SEQUENCE: 68

Leu Leu Cys Pro Gly Gly Ala Ala Pro Arg Ala Arg Lys
1               5                   10

<210> SEQ ID NO 69
<211> LENGTH: 13
<212> TYPE: PRT
<213> ORGANISM: Artificial
<220> FEATURE:
<223> OTHER INFORMATION: Wise/SOST Peptides

<400> SEQUENCE: 69

Leu Leu Cys Pro Gly Gly Glu Ala Pro Arg Ala Arg Lys
1               5                   10

<210> SEQ ID NO 70
<211> LENGTH: 12
<212> TYPE: PRT
<213> ORGANISM: Artificial
<220> FEATURE:
```

<223> OTHER INFORMATION: Wise/SOST Peptides

<400> SEQUENCE: 70

Leu Gln Cys Gln Asp Gly Ser Thr Arg Thr Tyr Lys
1               5                   10

<210> SEQ ID NO 71
<211> LENGTH: 12
<212> TYPE: PRT
<213> ORGANISM: Artificial
<220> FEATURE:
<223> OTHER INFORMATION: Wise/SOST Peptides

<400> SEQUENCE: 71

Leu Gln Cys Glu Asp Gly Thr Thr Arg Thr Tyr Lys
1               5                   10

<210> SEQ ID NO 72
<211> LENGTH: 12
<212> TYPE: PRT
<213> ORGANISM: Artificial
<220> FEATURE:
<223> OTHER INFORMATION: Wise/SOST Peptides

<400> SEQUENCE: 72

Leu Gln Cys Pro Asn Gly Asn Thr Arg Thr Tyr Lys
1               5                   10

<210> SEQ ID NO 73
<211> LENGTH: 12
<212> TYPE: PRT
<213> ORGANISM: Artificial
<220> FEATURE:
<223> OTHER INFORMATION: Wise/SOST Peptides

<400> SEQUENCE: 73

Leu Arg Cys Pro Asn Gly Asn Thr Arg Thr Tyr Lys
1               5                   10

<210> SEQ ID NO 74
<211> LENGTH: 12
<212> TYPE: PRT
<213> ORGANISM: Artificial
<220> FEATURE:
<223> OTHER INFORMATION: Wise/SOST Peptides

<400> SEQUENCE: 74

Met Ala Cys Pro Glu Asp Glu Thr Arg Thr Tyr Lys
1               5                   10

<210> SEQ ID NO 75
<211> LENGTH: 13
<212> TYPE: PRT
<213> ORGANISM: Artificial
<220> FEATURE:
<223> OTHER INFORMATION: Wise/SOST Peptides

<400> SEQUENCE: 75

Leu Leu Cys Pro Gly Gly Ala Ala Pro Arg Ser Arg Lys
1               5                   10

<210> SEQ ID NO 76
<211> LENGTH: 11
<212> TYPE: PRT
<213> ORGANISM: Artificial
<220> FEATURE:
<223> OTHER INFORMATION: Wise/SOST Peptides

```
<400> SEQUENCE: 76

Asp Thr Gly Thr Asp Arg Ile Glu Val Thr Arg
1               5                   10

<210> SEQ ID NO 77
<211> LENGTH: 11
<212> TYPE: PRT
<213> ORGANISM: Artificial
<220> FEATURE:
<223> OTHER INFORMATION: Wise/SOST Peptides

<400> SEQUENCE: 77

Asp Thr Val Thr Asp Arg Ile Glu Val Cys Arg
1               5                   10

<210> SEQ ID NO 78
<211> LENGTH: 11
<212> TYPE: PRT
<213> ORGANISM: Artificial
<220> FEATURE:
<223> OTHER INFORMATION: Wise/SOST Peptides
<220> FEATURE:
<221> NAME/KEY: misc_feature
<222> LOCATION: (4)..(4)
<223> OTHER INFORMATION: Xaa can be any naturally occurring amino acid

<400> SEQUENCE: 78

Asp Thr Val Xaa Asp Arg Ile Glu Val Cys Arg
1               5                   10

<210> SEQ ID NO 79
<211> LENGTH: 11
<212> TYPE: PRT
<213> ORGANISM: Artificial
<220> FEATURE:
<223> OTHER INFORMATION: Wise/SOST Peptides

<400> SEQUENCE: 79

Asp Ala Gly Thr Asp Arg Ile Glu Val Ala Asn
1               5                   10

<210> SEQ ID NO 80
<211> LENGTH: 11
<212> TYPE: PRT
<213> ORGANISM: Artificial
<220> FEATURE:
<223> OTHER INFORMATION: Wise/SOST Peptides

<400> SEQUENCE: 80

Asp Ala Gly Thr Asp Arg Ile Glu Val Ala Asn
1               5                   10

<210> SEQ ID NO 81
<211> LENGTH: 11
<212> TYPE: PRT
<213> ORGANISM: Artificial
<220> FEATURE:
<223> OTHER INFORMATION: Wise/SOST Peptides

<400> SEQUENCE: 81

Asn Lys Ile Thr Gln Thr Ile Glu Ile Ile Arg
1               5                   10

<210> SEQ ID NO 82
<211> LENGTH: 11
<212> TYPE: PRT
<213> ORGANISM: Artificial
<220> FEATURE:
```

<223> OTHER INFORMATION: Wise/SOST Peptides

<400> SEQUENCE: 82

Asp Arg Gly Arg Ser Leu Ile Glu Gly Ser Asp
1               5                   10

<210> SEQ ID NO 83
<211> LENGTH: 546
<212> TYPE: DNA
<213> ORGANISM: Dog

<400> SEQUENCE: 83

```
atgcagctct ctcttgctct gtgtctcgtc tgcttgctgg tgcatgcagc cttccgtgca      60
gtggagggcc aggggtggca ggccttcaag aacgatgcca cagaaatcat ccccgagctg     120
ggcgagtacc ccgagcctcc accagagctg gagaacaaca agaccatgaa ccgggcggag     180
aacggagggc ggccccctca ccatcccttt gagaccaaag acgcatccga gtacagctgc     240
cgcgagctgc acttcacccg ctacgtgacg gacgggccgt gccgcagcgc caagccggtc     300
accgagctgg tgtgctcggg ccagtgcggc ccgcgcgcc tgctgcccaa cgccatcggc     360
cgcggcaagt ggtggcgccc gagcgggccc gacttccgct gcatccccga ccgctaccgc     420
gcgcagcggg tgcagctgct gttgcgcctg gtggcctcgt gcaagtgcaa gcgactcacc     480
cgcttccaca accagtccga gctcaaggac ttcgggcccg aggccgcgcg gccgcagaag     540
ggccga                                                                546
```

<210> SEQ ID NO 84
<211> LENGTH: 642
<212> TYPE: DNA
<213> ORGANISM: Chimp

<400> SEQUENCE: 84

```
atgcagctcc cactggccct gtgtctcgtc tgcctgctgg tacacacagc cttccgtgta      60
gtggagggcc aggggtggca ggcgttcaag aatgatgcca cggaaatcat ccccgagctc     120
ggagagtacc ccgagcctcc accggagctg gagaacaaca agaccatgaa ccgggcggag     180
aacggagggc ggcctcccca ccacccctt gagaccaaag acgtgtccga gtacagctgc     240
cgcgagctgc acttcacccg ctacgtgacc gatgggccgt gccgcagcgc caagccggtc     300
accgagctgg tgtgctccgg ccagtgcggc ccggcgcgcc tgctgcccaa cgccatcggc     360
cgcggcaagt ggtggcgacc tagtgggccc gacttccgct gcatccccga ccgctaccgc     420
gcgcagcgcg tgcagctgct gtgtcccggt ggtgcggcgc cgcgcgcgcg caaggtgcgc     480
ctggtggcct cgtgcaagtg caagcgcctc acccgcttcc acaaccagtc ggagctcaag     540
gacttcggga ccgaggccgc tcggccgcag aagggccgga agccgcggcc ccgcgcccgg     600
agcgccaaag ccaaccaggc cgagctggag aacgcctact ag                        642
```

<210> SEQ ID NO 85
<211> LENGTH: 13
<212> TYPE: PRT
<213> ORGANISM: Chick

<400> SEQUENCE: 85

Ser Asn Asn Asn Thr Met Asn Gln Ala Lys Gly Gly Arg
1               5                   10

<210> SEQ ID NO 86
<211> LENGTH: 15
<212> TYPE: PRT

<213> ORGANISM: Chick

<400> SEQUENCE: 86

Ala Pro Asp Pro Asn Asp Val Ser Asp Phe Ser Cys Arg Glu Met
1               5                   10                  15

<210> SEQ ID NO 87
<211> LENGTH: 27
<212> TYPE: PRT
<213> ORGANISM: Chick

<400> SEQUENCE: 87

Arg Glu Met Arg Ile Thr Arg Tyr Val Thr Glu Gly Pro Cys Arg Ser
1               5                   10                  15

Leu Lys Pro Val Lys Glu Leu Val Cys Ser Gly
            20                  25

<210> SEQ ID NO 88
<211> LENGTH: 641
<212> TYPE: DNA
<213> ORGANISM: Chick

<400> SEQUENCE: 88
atgcagatct cctgggctgt gtgctctgtc tgcgtcctca tccaaatcgc atcccgggca      60
ctggagggtg gcaagtgttc aaaaatgatg cgacagaaat catccccgag atcaccgaaa     120
acacagagac cccaatggag cagatttaca gcaacaacaa cacgatgaac caggcaaagc     180 acggggaag gcacatacag caagctccgg accctaatga tgtctccgac ttcagctgca     240
gagagatgcg catcacccgc tacgtgacgg aggggccgtg ccgcagcctg aagcccgtga     300
aggagctggt gtgctcgggg cagtgcgtcc atcccacct cctgcccaac tccatcggca     360
gagggaagtg gtggaggcag aactccccgg attaccgctg catcccggct cacacccgca     420
cgcagcgcat ccagatggcg tgtcccgagg atgagactcg gacttacaaa ttccgagctg     480
tcacagcctg caaatgcaag cgctacactc ggtaccacaa ccagtccgag ctgaaggact     540
ttgggaagga cccctccagg cagcagaaga caagaagtc gcgtctgtcc cgagccagga     600
gcagcaaacc gaaccagcac gagctggaaa acgcctatta g                        641

<210> SEQ ID NO 89
<211> LENGTH: 555
<212> TYPE: DNA
<213> ORGANISM: Fugu

<400> SEQUENCE: 89
tggaaggtgc tgaagaacga cgccacagag atttaccgg actaccggga gcggagtccg      60
cacgagccga tgacgcaggc ggcgaacagc agcagtaacg gcgggaaccg cgcgaagagc     120
ggcgggagaa gcacgagctc ggtgacctac agtgcctcgg agctgagctg cagggagctg     180
cgttccaccc gctacgtcac cgatggatct tgccgcagcg ccaaacccat caaggagctg     240
gtgtgctcgg gccagtgcct gccagcgcac ctcatgccca acaccatcgg ccgcggcaag     300
tggtggcgga gcaacacctc ggagtaccgc tgcatcccgg ctcactccag gaccaggagg     360
atccagctgc agtgccccaa cggcaacact cggacttaca aaatccgcat agtgacctcc     420
tgcaagtgta agcggttcag ggctcaccac aaccagtcgg aggccaagga ggtcctgagg     480
aggcagcgga gcaagaagcg cacgtctcaa ggacggagca aaaacaacac gcctttgatt     540
gacaattcat actga                                                     555

<210> SEQ ID NO 90
<211> LENGTH: 618
<212> TYPE: DNA
<213> ORGANISM: Mouse
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t

<400> SEQUENCE: 90

```
atgcttcctc ctgccattca tctctctctc attcccctgc tctgcatcct gatgagaaac    60
tgtttggctt ttaaaaatga tgccacagaa atcctttatt cacatgtggt taaacctgtc   120
ccggcacacc ccagcagcaa cagcaccctg aatcaagcca ggaatggagg caggcatttc   180
agtagcactg gactggatcg aaacagtcga gttcaagtgg gctgcaggga actgcggtcc   240
accaaataca tttcggacgg ccagtgcacc agcatcagcc ctntgaagga gctggtgtgc   300
gcgggcgagt gcttgcccct gccggtgctt cccaactgga tcggaggagg ctatggaaca   360
aagtactgga gccggaggag ctntcaggag tggcggtgtg tcaacgacaa gacgcgcacc   420
cagaggatcc agctgcagtg tcaggacggc agcacgcgca cctacaaaat caccgtggtc   480
acggcgtgca agtgcaagag gtacacccgt cagcacaacg agtccagcca caactttgaa   540
agcgtgtcgc ccgccaagcc cgcccagcac acagagagc ggaagagagc cagcaaatcc   600
agcaagcaca gtctgagc                                                 618
```

<210> SEQ ID NO 91
<211> LENGTH: 14
<212> TYPE: PRT
<213> ORGANISM: Mouse

<400> SEQUENCE: 91

```
Ser Ser Asn Ser Thr Leu Asn Gln Ala Arg Asn Gly Gly Arg
1               5                   10
```

<210> SEQ ID NO 92
<211> LENGTH: 621
<212> TYPE: DNA
<213> ORGANISM: Human

<400> SEQUENCE: 92

```
atgcttcctc ctgccattca tctctctctc attcccctgc tctgcatcct gatgaaaaac    60
tgtttggctt ttaaaaatga tgccacagaa atcctttatt cacatgtggt taaacctgtt   120
tcagcacacc ccagcagcaa cagcaccttg aatcaagcca ggaatggagg caggcacttc   180
agtagcacgg gactggatcg aaatagtcga gttcaagtgg gctgcaggga actgcggtcc   240
accaaataca tctcggatgg ccagtgcacc agcatcagcc tctgaagga gctggtgtgc    300
gcgggtgagt gcttgccctt gccagtgctt cccaactgga tcggaggagg ctacggaaca   360
aagtactgga gccggagggg ctcccaggag tggcggtgtg tcaacgacaa gacgcgcacc   420
cagagaatcc agctgcagtg tcaggacggc agcacacgca cctacaaaat caccgtggtc   480
acagcgtgca agtgcaagag gtacacccgg cagcacaacg agtccagcca caactttgaa   540
agcgtgtctc ccgccaagcc cgcccagcac acagagagc ggaagagagc cagcaaatcc   600
agcaagcaca gtctgagcta g                                             621
```

<210> SEQ ID NO 93

<211> LENGTH: 15
<212> TYPE: PRT
<213> ORGANISM: Human

<400> SEQUENCE: 93

Pro Ser Ser Asn Ser Thr Leu Asn Gln Ala Arg Asn Gly Gly Arg
1               5                   10                  15

<210> SEQ ID NO 94
<211> LENGTH: 642
<212> TYPE: DNA
<213> ORGANISM: Xenopus Leavis

<400> SEQUENCE: 94

```
atggttgtct caaggctcca gtgctgcatg ctctaccttg cgtgtattct catagaaagc      60
tgcgtgtctt ttaagaatga cgctacagaa atcctgtatt cccacgtgga taaacatatc     120
caagatagtg caaacagcag cacccctgaat caggctagaa atggaggaag aaatgctgca    180
aactctgcac tggacagaac aaatcaccat caggttggat gcagagagct gagatctacc     240
aagtacatct cggatggaca gtgcaccagt atccagcctt tgaaagaact ggtctgtgct     300
ggagagtgtc ttcctctttc tattttggcc cactggatcg ggggtggcta cgggctgaaa     360
tattggagtc gaagaagttc ccaggaatgg agatgtgtca atgacaagac ccgcactcag     420
cgtatccagt tacagtgtga ggatggcact actagaaacct acaaagtcac agtggttact    480
tcctgcaagt gcaagagata caccagacag cacaatgaat ccagccataa ctaccaagga     540
gcttctccca ttaaacccgt tcactctcac caacatcatc actccccacca caaccgtgat    600 aagaaaagac taatcaagat gtccaagcac attcctagct ag                       642
```

<210> SEQ ID NO 95
<211> LENGTH: 14
<212> TYPE: PRT
<213> ORGANISM: Xenopus Leavis

<400> SEQUENCE: 95

Arg Ser Thr Lys Tyr Ile Ser Asp Gly Gln Cys Thr Ser Ile
1               5                   10

<210> SEQ ID NO 96
<211> LENGTH: 642
<212> TYPE: DNA
<213> ORGANISM: Xenopus tropicalis

<400> SEQUENCE: 96

```
atggtcgtct caaggctcca atgctgcatg ttatactttg catgcatttt catagaaagc      60
tgcatgtctt ttaagaacga tgccacagaa atcctgtatt cccatgtgga taaaaacatc    120
caagagagtg ccaacagcag tgccctgaac caggctagga atggaggaag acacacggct    180
aactctgcca tggacaggac aaatccccat caagttggat gcaggagct gagatctaca     240 aagtacatct cagatgggca gtgcaccagt atccagcctt tgaaagaact ggtctgtgct    300
ggagagtgtc ttcctcttcc tattttgccc aactggatcg ggggtggcta tgggctgaag    360
tactggagtc ggagaagctc tcaggaatgg agatgtgtca atgacaagac tcgcactcag    420
cgtatccagt tgcagtgtga ggatggcacg actagaaacct acaaagtcac ggtggtaact    480
tcctgcaagt gcaagaggta caccaggcag cacaacgaat ccagccataa ctacgaagga     540
gcttctccaa tgaaacccat tcactctctc caacatcatc actccccacca caaccgtgat    600 aagaaaagac taatcaagat gtccaagcac attcctagct ag                       642
```

<210> SEQ ID NO 97
<211> LENGTH: 621
<212> TYPE: DNA
<213> ORGANISM: Chick

<400> SEQUENCE: 97

```
atgcttctct ccgccattca cttctacggc ttactcctag cttgcacctt cacgagaagc      60
tactcggctt tcaagaacga tgccactgag atactttatt cccacgtcgt aaacctgcc     120
cctgcgagcc cgagcagcaa cagcacgttg aaccaagcca ggaacggagg gaggcactac     180
gccggcacgg gctccgaccg taacaatcgc gttcaagttg gctgccggga actgcgatct     240
accaagtaca tctcagacgg ccagtgcacc agcatcaatc ccctgaagga gctggtgtgt     300
gctggcgaat gcctcccctt gccgctcctg cccaactgga ttggaggagg ttatggaacc     360
aagtactgga gcagacggag ctcgcaagag tggagatgtg tcaatgacaa aactcgcacc     420
cagaggatcc agctgcagtg ccaggatgga agtataagaa cctacaaaat aactgtggtc     480
acggcctgca agtgcaagcg atacaccagg cagcacaacg agtccagcca aactttgag     540
ggaacctctc aagcaaagcc tgtccagcat cacaaagaga gaaaaagagc cagtaaatcc     600
agcaaacata gtacaagtta g                                               621
```

<210> SEQ ID NO 98
<211> LENGTH: 15
<212> TYPE: PRT
<213> ORGANISM: Chick

<400> SEQUENCE: 98

Gly Ser Asp Arg Asn Asn Arg Val Gln Val Gly Cys Arg Glu Leu
1               5                   10                  15

<210> SEQ ID NO 99
<211> LENGTH: 621
<212> TYPE: DNA
<213> ORGANISM: Dog

<400> SEQUENCE: 99

```
atgcttcctc ctgccattca tctctctctc attcccctgc tctgcatcct gatgaaaaac      60
tgtttggctt ttaaaaatga tgccacagaa atcctttatt cacatgtggt taaacctgtt     120
tcagcacacc ccagcagcaa cagcaccttg aatcaagcca ggaatggagg caggcacttc     180
agtagcacgg gactggatcg aaatagtcga gttcaagtgg ctgcaggga actgcggtcc     240
accaaataca tctcggatgg ccagtgcacc agcatcagcc tctgaagga gctggtgtgc     300
gcgggtgagt gcttgccctt gccagtgctt cccaactgga tcggaggagg ctacggaaca     360
aagtactgga gccggagggg ctcccaggag tggcggtgtg tcaacgacaa gacgcgcacc     420
cagagaatcc agctgcagtg tcaggacggc agcacacgca cctacaaaat caccgtggtc     480
acagcgtgca agtgcaagag gtacacccgg cagcacaacg agtccagcca aactttgaa     540
agcgtgtctc ccgccaagcc cgcccagcac cacagagagc ggaagagagc cagcaaatcc     600
agcaagcaca gtctgagcta g                                               621
```

<210> SEQ ID NO 100
<211> LENGTH: 625
<212> TYPE: DNA
<213> ORGANISM: Rat

<400> SEQUENCE: 100

```
atgcttcctc ctgccattca tctctctctc attcccctgc tctgcatcct gatgaaaaac      60
```

```
tgtttggctt ttaaaaatga tgccacagaa atcctttatt cacatgtggt taaacctgtt    120
tcagcacacc ccagcagcaa cagcaccttg aatcaagcca ggaatggagg caggcacttc    180
agtagcacgg gactggatcg aaatagtcga gttcaagtgg gctgcaggga actgcggtcc    240
accaaataca tctcggatgg ccagtgcacc agcatcagcc tctgaagga gctggtgtgc    300 gcgggtgagt gcttgccctt gccagtgctt cccaactgga tcggaggagg ctacggaaca    360
aagtactgga gccggaggag ctcccaggag tggcggtgtg tcaacgacaa gacgcgcacc    420
cagagaatcc agctgcagtg tcaggacggc agcacacgca cctacaaaat caccgtggtc    480
acagcgtgca agtgcaagag gtacacccgg cagcacaacg agtccagcca caactttgaa    540
agcgtgtctc ccgccaagcc cgcccagcac cacagagagc ggaagagagc cagcaaatcc    600
agcaagcaca gtctgagcta gagct                                         625
```

```
<210> SEQ ID NO 101
<211> LENGTH: 14
<212> TYPE: PRT
<213> ORGANISM: Zebrafish

<400> SEQUENCE: 101

Thr His Asp Arg Glu Arg Ile Pro Val Gly Cys Arg Glu Leu
1               5                   10
```

```
<210> SEQ ID NO 102
<211> LENGTH: 608
<212> TYPE: DNA
<213> ORGANISM: Zebrafish

<400> SEQUENCE: 102
cagagttgaa gcacatctct ccattggccg tgggtcatta cgcatcgcca tgtatataaa     60
cgcaccagag tcgtgcaatt tcatggtttt attttgcttt ttaataagga gtggtttgac    120
tttgaagaac gatgctacgg agattttcta ctcgcatgtg gtcagtcccg ttcaggatgc    180
gcagagcaac gcgtctctca accgcgcgcg ctccggagga agaggcttca gcacgcacga    240
cagagaacga atcccagtag gctgcagaga gctccgatcc accaagtaca tctcagatgg    300
ccagtgcacc agcataaacc ctgtgaaaga gctggtgtgc acaggacagt gcctccccgc    360
tcagatgctg cccaattgga ttggaggata cggcaagaag tcctggaacc gccggaacag    420
tcaggaatgg cgctgtgtaa atgacaagac ccgaactcag cggattcagc tccagtgcca    480
ggatggcagc accaggacct acaagatcac agtggtgacc tcctgcaaat gcaaacgata    540
ctcgcggcaa cacaatgaat caggagttaa gtctgaggga tactctcata gccagatcaa    600
aaaacaga                                                            608
```

```
<210> SEQ ID NO 103
<211> LENGTH: 12
<212> TYPE: PRT
<213> ORGANISM: Fugu

<400> SEQUENCE: 103

Thr Tyr Ser Ala Ser Glu Leu Ser Cys Arg Glu Leu
1               5                   10
```

```
<210> SEQ ID NO 104
<211> LENGTH: 576
<212> TYPE: DNA
<213> ORGANISM: Fugu

<400> SEQUENCE: 104
```

```
tgctgcaccg ccgcgcgcgg atggaaggtg ctgaagaacg acgccacaga gattttaccg      60
gactaccggg agcggagtcc gcacgagccg atgacgcagg cggcgaacag cagcagtaac     120
ggcgggaacc gcgcgaagag cggcgggaga agcacgagct cggtgaccta cagtgcctcg     180
gagctgagct gcagggagct gcgttccacc cgctacgtca ccgatggatc ttgccgcagc     240
gccaaaccca tcaaggagct ggtgtgctcg ggccagtgcc tgccagcgca cctcatgccc     300
aacaccatcg gccgcggcaa gtggtggcgg agcaacacct cggagtaccg ctgcatcccg     360
gctcactcca ggaccaggag gatccagctg cagtgcccca acggcaacac tcggacttac     420
aaaatccgca tagtgacctc ctgcaagtgt aagcggttca gggctcacca caaccagtcg     480
gaggccaagg aggtcctgag gaggcagcgg agcaagaagc gcacgtctca aggacggagc     540
aaaaacaaca cgcctttgat tgacaattca tactga                               576
```

<210> SEQ ID NO 105
<211> LENGTH: 16
<212> TYPE: PRT
<213> ORGANISM: Pan troglodytes chimp

<400> SEQUENCE: 105

```
His Pro Ser Ser Asn Ser Thr Leu Asn Gln Ala Arg Asn Gly Gly Arg
1               5                   10                  15
```

<210> SEQ ID NO 106
<211> LENGTH: 618
<212> TYPE: DNA
<213> ORGANISM: Pan troglodytes chimp

<400> SEQUENCE: 106

```
atgcttcctc ctgccattca tttctatctc cttccccttg catgcatcct aatgaaaagc      60
tgtttggctt ttaaaaatga tgccacagaa atcctttatt cacatgtggt taaacctgtt     120
ccagcacacc ccagcagcaa cagcacgttg aatcaagcca gaaatggagg caggcatttc     180
agtaacactg gactggatcg gaacactcgg gttcaagtgg gttgccggga actgcgttcc     240
accaaataca tctctgatgg ccagtgcacc agcatcagcc tctgaagga gctggtgtgt      300 gctggtgagt gcttgcccct gccagtgctc cctaactgga ttggaggagg ctatggaaca     360
aagtactgga gcaggaggag ctcccaggag tggcggtgtg tcaatgacaa aacccgtacc     420
cagagaatcc agctgcagtg ccaagatggc agcacacgca cctacaaaat cacagtagtc     480
actgcctgca gtgcaagag gtacacccgg cagcacaacg agtccagtca caactttgag      540
agcatgtcac ctgccaagcc agtccagcat cacagagagc ggaaaagagc cagcaaatcc     600
agcaagcaca gcatgagt                                                   618
```

<210> SEQ ID NO 107
<211> LENGTH: 633
<212> TYPE: DNA
<213> ORGANISM: Tetradon fish

<400> SEQUENCE: 107

```
atgcaggtgt ctctggtcct cctcgtgtcc agctcggcgc tcgtgctgct gcagggatgc      60
tgcgccgccg cgcgcggctg gaaggcgctg aagaacgacg ccaccgaggt tttagcggac     120
gaccgcgagc ggagcccgca cgagcccgcc gcgcacgcgg ccaacgccag cagtaacgcg     180
ggaaaccggg cgaagagcgg cgcgaggagc acgagcacgc tgtcctacag tgcctcggag     240
ctaagctgca gggagctgcg ctccacccgt tacgtcaccg atgggtcctg ccgcagcgcc     300
```

```
aaacccatca aagagctggt gtgctcgggc cagtgcctgc cggcgcacct catgcccaac    360
accattggcc gggccaagtg gtggcggagc agcacctcgg agtaccgctg cgtcccggct    420
cactccaggc ccaggaggat ccagctgcgc tgccccaacg gcaacactcg gacttacaaa    480
atccgcacgg tgacctcctg caagtgcaag aggttccggg ctcaccacaa ccagtcggag    540
gccaaggagg tcccgaggag gcaacgcacc aagaagcggc catcccgagg ccgcagcaag    600
aaccccacgc ctttgattga caattcctac tga                                633

<210> SEQ ID NO 108
<211> LENGTH: 621
<212> TYPE: DNA
<213> ORGANISM: Pongo pygmaeus

<400> SEQUENCE: 108
atgcttcctc ccgccattca tttctatctc cttccccttg catgcatcct aatgaaaagc     60
tgtttggctt ttaaaaatga tgccacagaa atcctttatt cacatgtggt taaacctgtt    120
ccagcacacc ccagcagcaa cagcacgttg aatcaagcca gaatggagg caggcatttc     180 agtaacactg gactggatcg gaacactcgg gttcaagtgg gttgccggga actgcgttcc    240
accaaataca tctctgatgg ccagtgcacc agcatcagcc ctctgaagga gctggtgtgt    300
gctggcgagt gcttgcccct gtcagtgctc cctaactgga ttggaggagg ttatggaaca    360
aagtactgga gcaggaggag ctcccaggag tggcggtgcg tcaatgacaa aacccgtacc    420
cagagaatcc agctgcagtg ccaagatggc agcacacgca cctacaaaat cacagtagtc    480
actgcctgca gtgcaagag gtacacccgg cagcacaacg agtccagtca aactttgag     540 agcatgtcac ctgccaagcc agtccagcat cacagagagc ggaaaagagc cagcaaatcc    600
agcaagcaca gcatgagtta g                                             621

<210> SEQ ID NO 109
<211> LENGTH: 15
<212> TYPE: PRT
<213> ORGANISM: Artificial
<220> FEATURE:
<223> OTHER INFORMATION: LRP 5/6 Peptides

<400> SEQUENCE: 109

Leu Phe Ala Asn Arg Arg Asp Val Arg Leu Val Asp Ala Gly Gly
1               5                  10                  15

<210> SEQ ID NO 110
<211> LENGTH: 8
<212> TYPE: PRT
<213> ORGANISM: Artificial
<220> FEATURE:
<223> OTHER INFORMATION: LTRP 5/6 Peptides

<400> SEQUENCE: 110

Tyr Trp Thr Asp Val Ser Glu Glu
1               5

<210> SEQ ID NO 111
<211> LENGTH: 19
<212> TYPE: PRT
<213> ORGANISM: Artificial
<220> FEATURE:
<223> OTHER INFORMATION: LRP 5/6 Peptides

<400> SEQUENCE: 111

Lys Leu Tyr Trp Thr Asp Ser Glu Thr Asn Arg Ile Glu Val Ala Asn
1               5                  10                  15
```

Leu Asn Gly

<210> SEQ ID NO 112
<211> LENGTH: 7
<212> TYPE: PRT
<213> ORGANISM: Artificial
<220> FEATURE:
<223> OTHER INFORMATION: LRP 5/6 Peptides

<400> SEQUENCE: 112

Leu Phe Trp Gln Asp Leu Asp
1               5

<210> SEQ ID NO 113
<211> LENGTH: 23
<212> TYPE: PRT
<213> ORGANISM: Artificial
<220> FEATURE:
<223> OTHER INFORMATION: LRP 5/6 Peptides

<400> SEQUENCE: 113

Thr Asp Trp Gly Glu Thr Pro Arg Ile Glu Arg Ala Gly Met Asp Gly
1               5                   10                  15

Ser Thr Arg Lys Ile Ile Val
            20

<210> SEQ ID NO 114
<211> LENGTH: 11
<212> TYPE: PRT
<213> ORGANISM: Artificial
<220> FEATURE:
<223> OTHER INFORMATION: LRP 5/6 Peptides

<400> SEQUENCE: 114

His Ala Cys Asn Lys Arg Thr Gly Gly Lys Arg
1               5                   10

<210> SEQ ID NO 115
<211> LENGTH: 15
<212> TYPE: PRT
<213> ORGANISM: Artificial
<220> FEATURE:
<223> OTHER INFORMATION: LRP 5/6 Peptides

<400> SEQUENCE: 115

Thr Gly Val Gln Leu Gln Asp Asn Gly Arg Thr Cys Lys Ala Gly
1               5                   10                  15

<210> SEQ ID NO 116
<211> LENGTH: 19
<212> TYPE: PRT
<213> ORGANISM: Artificial
<220> FEATURE:
<223> OTHER INFORMATION: LRP 5/6 Peptides

<400> SEQUENCE: 116

Glu Val Leu Leu Leu Ala Arg Arg Thr Asp Leu Arg Arg Ile Ser Leu
1               5                   10                  15

Asp Thr Pro

<210> SEQ ID NO 117
<211> LENGTH: 14
<212> TYPE: PRT
<213> ORGANISM: Artificial
<220> FEATURE:
<223> OTHER INFORMATION: LRP 5/6 Peptides -continued

<400> SEQUENCE: 117

Tyr Trp Thr Asp Asp Glu Val Arg Ala Ile Arg Arg Ala Tyr
1               5                   10

<210> SEQ ID NO 118
<211> LENGTH: 10
<212> TYPE: PRT
<213> ORGANISM: Artificial
<220> FEATURE:
<223> OTHER INFORMATION: LRP 5/6 Peptides

<400> SEQUENCE: 118

Val Asn Thr Glu Ile Asn Asp Pro Asp Gly
1               5                   10

<210> SEQ ID NO 119
<211> LENGTH: 29
<212> TYPE: PRT
<213> ORGANISM: Artificial
<220> FEATURE:
<223> OTHER INFORMATION: LRP 5/6 Peptides

<400> SEQUENCE: 119

Tyr Trp Thr Asp Thr Gly Thr Asp Arg Ile Glu Val Thr Arg Leu Asn
1               5                   10                  15

Gly Thr Ser Arg Lys Ile Leu Val Ser Glu Asp Leu Asp
            20                  25

<210> SEQ ID NO 120
<211> LENGTH: 20
<212> TYPE: PRT
<213> ORGANISM: LRP 5/6 Peptides

<400> SEQUENCE: 120

Thr Asp Trp Gln Arg Arg Ser Ile Glu Arg Val His Lys Val Lys Ala
1               5                   10                  15

Ser Arg Asp Val
            20

<210> SEQ ID NO 121
<211> LENGTH: 11
<212> TYPE: PRT
<213> ORGANISM: Artificial
<220> FEATURE:
<223> OTHER INFORMATION: LRP 5/6 Peptides

<400> SEQUENCE: 121

Asn Val Asp Gly Thr Lys Arg Arg Thr Leu Leu
1               5                   10

<210> SEQ ID NO 122
<211> LENGTH: 109
<212> TYPE: PRT
<213> ORGANISM: Artificial
<220> FEATURE:
<223> OTHER INFORMATION: LRP 5/6 Peptides

<400> SEQUENCE: 122

Pro Glu Pro Pro Pro Glu Leu Glu Asn Asn Lys Thr Met Asn Arg Ala
1               5                   10                  15

Glu Asn Gly Gly Arg Pro Pro His His Pro Phe Glu Thr Lys Asp Val
            20                  25                  30

Ser Glu Tyr Ser Cys Arg Glu Leu His Phe Thr Arg Tyr Val Thr Asp
        35                  40                  45

Gly Pro Cys Arg Ser Ala Lys Pro Val Thr Glu Leu Val Cys Ser Gly
    50                  55                  60

Gln Cys Gly Pro Ala Arg Leu Leu Pro Asn Ala Ile Gly Arg Gly Lys
65                  70                  75                  80

Trp Trp Arg Pro Ser Gly Pro Asp Phe Arg Cys Ile Pro Asp Arg Tyr
                85                  90                  95

Arg Ala Gln Arg Val Gln Leu Leu Cys Pro Gly Gly Glu
            100                 105

<210> SEQ ID NO 123
<211> LENGTH: 56
<212> TYPE: PRT
<213> ORGANISM: Artificial
<220> FEATURE:
<223> OTHER INFORMATION: LRP 5/6 Peptides

<400> SEQUENCE: 123

Pro Glu Pro Pro Glu Leu Glu Asn Asn Lys Thr Met Asn Arg Ala
1               5                   10                  15

Glu Asn Gly Gly Arg Pro Pro His Pro Phe Glu Thr Lys Asp Val
            20                  25                  30

Ser Glu Tyr Ser Cys Arg Glu Leu His Phe Thr Arg Tyr Val Thr Asp
        35                  40                  45

Gly Pro Cys Arg Ser Ala Lys Pro
    50                  55

<210> SEQ ID NO 124
<211> LENGTH: 53
<212> TYPE: PRT
<213> ORGANISM: Artificial
<220> FEATURE:
<223> OTHER INFORMATION: LRP 5/6 Peptides

<400> SEQUENCE: 124

Val Thr Glu Leu Val Cys Ser Gly Gln Cys Gly Pro Ala Arg Leu Leu
1               5                   10                  15

Pro Asn Ala Ile Gly Arg Gly Lys Trp Trp Arg Pro Ser Gly Pro Asp
            20                  25                  30

Phe Arg Cys Ile Pro Asp Arg Tyr Arg Ala Gln Arg Val Gln Leu Leu
        35                  40                  45

Cys Pro Gly Gly Glu
    50

<210> SEQ ID NO 125
<211> LENGTH: 24
<212> TYPE: PRT
<213> ORGANISM: Artificial
<220> FEATURE:
<223> OTHER INFORMATION: LRP 5/6 Peptides

<400> SEQUENCE: 125

Gly Phe Met Tyr Trp Thr Asp Trp Gly Glu Val Pro Lys Ile Glu Arg
1               5                   10                  15

Ala Gly Met Asp Gly Ser Ser Arg
            20

<210> SEQ ID NO 126
<211> LENGTH: 13
<212> TYPE: PRT
<213> ORGANISM: Artificial
<220> FEATURE:
<223> OTHER INFORMATION: LRP 5/6 Peptides

```
<400> SEQUENCE: 126

Pro Lys Ile Glu Arg Ala Gly Met Asp Gly Ser Ser Arg
1               5                   10

<210> SEQ ID NO 127
<211> LENGTH: 18
<212> TYPE: PRT
<213> ORGANISM: Artificial
<220> FEATURE:
<223> OTHER INFORMATION: LRP 5/6 Peptides

<400> SEQUENCE: 127

Ala Ala Pro Leu Leu Leu Tyr Ala Asn Arg Arg Asp Leu Arg Leu Val
1               5                   10                  15

Asp Ala

<210> SEQ ID NO 128
<211> LENGTH: 17
<212> TYPE: PRT
<213> ORGANISM: Artificial
<220> FEATURE:
<223> OTHER INFORMATION: LRP 5/6 Peptides

<400> SEQUENCE: 128

Thr Ile Val Val Gly Gly Leu Glu Asp Ala Ala Val Asp Phe Val
1               5                   10                  15

Phe

<210> SEQ ID NO 129
<211> LENGTH: 14
<212> TYPE: PRT
<213> ORGANISM: Artificial
<220> FEATURE:
<223> OTHER INFORMATION: LRP 5/6 Peptides

<400> SEQUENCE: 129

Gly Leu Ile Tyr Trp Ser Asp Val Ser Glu Glu Ala Ile Lys
1               5                   10

<210> SEQ ID NO 130
<211> LENGTH: 40
<212> TYPE: PRT
<213> ORGANISM: Artificial
<220> FEATURE:
<223> OTHER INFORMATION: LRP 5/6 Peptides

<400> SEQUENCE: 130

Ser Val Gln Asn Val Val Val Ser Gly Leu Leu Ser Pro Asp Gly Leu
1               5                   10                  15

Ala Cys Asp Trp Leu Gly Glu Lys Leu Tyr Trp Thr Asp Ser Glu Thr
            20                  25                  30

Asn Arg Ile Glu Val Ser Asn Leu
        35                  40

<210> SEQ ID NO 131
<211> LENGTH: 19
<212> TYPE: PRT
<213> ORGANISM: Artificial
<220> FEATURE:
<223> OTHER INFORMATION: LRP 5/6 Peptides

<400> SEQUENCE: 131

Gln Asn Val Val Val Ser Gly Leu Leu Ser Pro Asp Gly Leu Ala Cys
1               5                   10                  15
```

Asp Trp Leu

<210> SEQ ID NO 132
<211> LENGTH: 20
<212> TYPE: PRT
<213> ORGANISM: Artificial
<220> FEATURE:
<223> OTHER INFORMATION: LRP 5/6 Peptides

<400> SEQUENCE: 132

Lys Leu Tyr Trp Thr Asp Ser Glu Thr Asn Arg Ile Glu Val Ser Asn
1               5                   10                  15

Leu Asp Gly Ser
            20

<210> SEQ ID NO 133
<211> LENGTH: 19
<212> TYPE: PRT
<213> ORGANISM: Artificial
<220> FEATURE:
<223> OTHER INFORMATION: LRP 5/6 Peptides

<400> SEQUENCE: 133

Arg Lys Val Leu Phe Trp Gln Glu Leu Asp Gln Pro Arg Ala Ile Ala
1               5                   10                  15

Leu Asp Pro

<210> SEQ ID NO 134
<211> LENGTH: 20
<212> TYPE: PRT
<213> ORGANISM: Artificial
<220> FEATURE:
<223> OTHER INFORMATION: LRP 5/6 Peptides

<400> SEQUENCE: 134

Met Tyr Trp Thr Asp Trp Gly Glu Val Pro Lys Ile Glu Arg Ala Gly
1               5                   10                  15

Met Asp Gly Ser
            20

<210> SEQ ID NO 135
<211> LENGTH: 8
<212> TYPE: PRT
<213> ORGANISM: Artificial
<220> FEATURE:
<223> OTHER INFORMATION: LRP 5/6 Peptides

<400> SEQUENCE: 135

Ile Tyr Trp Pro Asn Gly Leu Thr
1               5

<210> SEQ ID NO 136
<211> LENGTH: 9
<212> TYPE: PRT
<213> ORGANISM: Artificial
<220> FEATURE:
<223> OTHER INFORMATION: LRP 5/6 Peptides

<400> SEQUENCE: 136

Lys Leu Tyr Trp Ala Asp Ala Lys Leu
1               5

<210> SEQ ID NO 137
<211> LENGTH: 13
<212> TYPE: PRT

```
<213> ORGANISM: Artificial
<220> FEATURE:
<223> OTHER INFORMATION: LRP 5/6 Peptides

<400> SEQUENCE: 137

Phe Ile His Lys Ser Asn Leu Asp Gly Thr Asn Arg Gln
1               5                   10

<210> SEQ ID NO 138
<211> LENGTH: 14
<212> TYPE: PRT
<213> ORGANISM: Artificial
<220> FEATURE:
<223> OTHER INFORMATION: LRP 5/6 Peptides

<400> SEQUENCE: 138

Val Val Lys Gly Ser Leu Pro His Pro Phe Ala Leu Thr Leu
1               5                   10

<210> SEQ ID NO 139
<211> LENGTH: 21
<212> TYPE: PRT
<213> ORGANISM: Artificial
<220> FEATURE:
<223> OTHER INFORMATION: LRP 5/6 Peptides

<400> SEQUENCE: 139

Asp Thr Leu Tyr Trp Thr Asp Trp Asn Thr His Ser Ile Leu Ala Cys
1               5                   10                  15

Asn Lys Tyr Thr Gly
            20

<210> SEQ ID NO 140
<211> LENGTH: 13
<212> TYPE: PRT
<213> ORGANISM: Artificial
<220> FEATURE:
<223> OTHER INFORMATION: LRP 5/6 Peptides

<400> SEQUENCE: 140

Arg Glu Ile His Ser Asn Ile Phe Ser Pro Met Asp Ile
1               5                   10

<210> SEQ ID NO 141
<211> LENGTH: 21
<212> TYPE: PRT
<213> ORGANISM: Artificial
<220> FEATURE:
<223> OTHER INFORMATION: LRP 5/6 Peptides

<400> SEQUENCE: 141

Ser Asp Arg Asn Asn Arg Val Gln Val Gly Cys Arg Glu Leu Arg Ser
1               5                   10                  15

Thr Lys Tyr Ile Ser
            20

<210> SEQ ID NO 142
<211> LENGTH: 21
<212> TYPE: PRT
<213> ORGANISM: Artificial
<220> FEATURE:
<223> OTHER INFORMATION: LRP 5/6 Peptides

<400> SEQUENCE: 142

Pro Glu Pro Pro Glu Leu Glu Asn Asn Lys Thr Met Asn Arg Ala
1               5                   10                  15
```

```
Glu Asn Gly Gly Arg
            20

<210> SEQ ID NO 143
<211> LENGTH: 32
<212> TYPE: PRT
<213> ORGANISM: Artificial
<220> FEATURE:
<223> OTHER INFORMATION: LRP 5/6 Peptides

<400> SEQUENCE: 143

Asn Gly Gly Arg Pro Pro His His Pro Phe Glu Thr Lys Asp Val Ser
1               5                   10                  15

Glu Tyr Ser Cys Arg Glu Leu His Phe Thr Arg Tyr Val Thr Asp Gly
            20                  25                  30

<210> SEQ ID NO 144
<211> LENGTH: 8
<212> TYPE: PRT
<213> ORGANISM: Artificial
<220> FEATURE:
<223> OTHER INFORMATION: LRP 5/6 Peptides

<400> SEQUENCE: 144

Asn Asn Lys Thr Met Asn Arg Ala
1               5

<210> SEQ ID NO 145
<211> LENGTH: 5
<212> TYPE: PRT
<213> ORGANISM: Artificial
<220> FEATURE:
<223> OTHER INFORMATION: LRP 5/6 Peptides

<400> SEQUENCE: 145

Thr Met Asn Arg Ala
1               5

<210> SEQ ID NO 146
<211> LENGTH: 8
<212> TYPE: PRT
<213> ORGANISM: Artificial
<220> FEATURE:
<223> OTHER INFORMATION: LRP 5/6 Peptides

<400> SEQUENCE: 146

Gly Gly Arg Pro Pro His His Pro
1               5

<210> SEQ ID NO 147
<211> LENGTH: 9
<212> TYPE: PRT
<213> ORGANISM: Artificial
<220> FEATURE:
<223> OTHER INFORMATION: LRP 5/6 Peptides

<400> SEQUENCE: 147

His His Pro Phe Glu Thr Lys Asp Val
1               5

<210> SEQ ID NO 148
<211> LENGTH: 10
<212> TYPE: PRT
<213> ORGANISM: Artificial
<220> FEATURE:
<223> OTHER INFORMATION: LRP 5/6 Peptides

<400> SEQUENCE: 148
```

```
Asp Val Ser Glu Tyr Ser Cys Arg Glu Leu
1               5                  10

<210> SEQ ID NO 149
<211> LENGTH: 17
<212> TYPE: PRT
<213> ORGANISM: Artificial
<220> FEATURE:
<223> OTHER INFORMATION: LRP 5/6 Peptides

<400> SEQUENCE: 149

Cys Arg Glu Leu His Phe Thr Arg Tyr Val Thr Asp Gly Pro Cys Arg
1               5                  10                  15

Ser

<210> SEQ ID NO 150
<211> LENGTH: 7
<212> TYPE: PRT
<213> ORGANISM: Artificial
<220> FEATURE:
<223> OTHER INFORMATION: LRP 5/6 Peptides

<400> SEQUENCE: 150

Thr Arg Tyr Val Thr Asp Gly
1               5

<210> SEQ ID NO 151
<211> LENGTH: 5
<212> TYPE: PRT
<213> ORGANISM: Artificial
<220> FEATURE:
<223> OTHER INFORMATION: LRP 5/6 Peptides

<400> SEQUENCE: 151

Tyr Val Thr Asp Gly
1               5

<210> SEQ ID NO 152
<211> LENGTH: 6
<212> TYPE: PRT
<213> ORGANISM: Artificial
<220> FEATURE:
<223> OTHER INFORMATION: LRP 5/6 Peptides

<400> SEQUENCE: 152

Asp Gly Pro Cys Arg Ser
1               5

<210> SEQ ID NO 153
<211> LENGTH: 12
<212> TYPE: PRT
<213> ORGANISM: Artificial
<220> FEATURE:
<223> OTHER INFORMATION: LRP 5/6 Peptides

<400> SEQUENCE: 153

Leu Pro Asn Ala Ile Gly Arg Gly Lys Trp Trp Arg
1               5                  10

<210> SEQ ID NO 154
<211> LENGTH: 8
<212> TYPE: PRT
<213> ORGANISM: Artificial
<220> FEATURE:
<223> OTHER INFORMATION: LRP 5/6 Peptides

<400> SEQUENCE: 154
```

```
Pro Asn Trp Ile Gly Gly Gly Tyr
1               5

<210> SEQ ID NO 155
<211> LENGTH: 11
<212> TYPE: PRT
<213> ORGANISM: Artificial
<220> FEATURE:
<223> OTHER INFORMATION: LRP 5/6 Peptides

<400> SEQUENCE: 155

Thr Leu Asn Gln Ala Arg Asn Gly Gly Arg His
1               5                   10

<210> SEQ ID NO 156
<211> LENGTH: 5
<212> TYPE: PRT
<213> ORGANISM: Artificial
<220> FEATURE:
<223> OTHER INFORMATION: LRP 5/6 Peptides

<400> SEQUENCE: 156

Gly Leu Asp Arg Asn
1               5

<210> SEQ ID NO 157
<211> LENGTH: 13
<212> TYPE: PRT
<213> ORGANISM: Artificial
<220> FEATURE:
<223> OTHER INFORMATION: LRP 5/6 Peptides

<400> SEQUENCE: 157

Cys Arg Glu Leu Arg Ser Thr Lys Tyr Ile Ser Asp Gly
1               5                   10

<210> SEQ ID NO 158
<211> LENGTH: 15
<212> TYPE: PRT
<213> ORGANISM: Artificial
<220> FEATURE:
<223> OTHER INFORMATION: LRP 5/6 Peptides

<400> SEQUENCE: 158

Leu Phe Ala Asn Arg Arg Asp Val Arg Leu Val Asp Ala Gly Gly
1               5                   10                  15

<210> SEQ ID NO 159
<211> LENGTH: 8
<212> TYPE: PRT
<213> ORGANISM: Artificial
<220> FEATURE:
<223> OTHER INFORMATION: LRP 5/6 Peptides

<400> SEQUENCE: 159

Tyr Trp Thr Asp Val Ser Glu Glu
1               5

<210> SEQ ID NO 160
<211> LENGTH: 19
<212> TYPE: PRT
<213> ORGANISM: Artificial
<220> FEATURE:
<223> OTHER INFORMATION: LRP 5/6 Peptides

<400> SEQUENCE: 160

Lys Leu Tyr Trp Thr Asp Ser Glu Thr Asn Arg Ile Glu Val Ala Asn
```

```
                   1               5                  10                  15

Leu Asn Gly

<210> SEQ ID NO 161
<211> LENGTH: 7
<212> TYPE: PRT
<213> ORGANISM: Artificial
<220> FEATURE:
<223> OTHER INFORMATION: LRP 5/6 Peptides

<400> SEQUENCE: 161

Leu Phe Trp Gln Asp Leu Asp
1               5

<210> SEQ ID NO 162
<211> LENGTH: 23
<212> TYPE: PRT
<213> ORGANISM: Artificial
<220> FEATURE:
<223> OTHER INFORMATION: LRP 5/6 Peptides

<400> SEQUENCE: 162

Thr Asp Trp Gly Glu Thr Pro Arg Ile Glu Arg Ala Gly Met Asp Gly
1               5                  10                  15

Ser Thr Arg Lys Ile Ile Val
            20

<210> SEQ ID NO 163
<211> LENGTH: 11
<212> TYPE: PRT
<213> ORGANISM: Artificial
<220> FEATURE:
<223> OTHER INFORMATION: LRP 5/6 Peptides

<400> SEQUENCE: 163

His Ala Cys Asn Lys Arg Thr Gly Gly Lys Arg
1               5                  10

<210> SEQ ID NO 164
<211> LENGTH: 15
<212> TYPE: PRT
<213> ORGANISM: Artificial
<220> FEATURE:
<223> OTHER INFORMATION: LRP 5/6 Peptides

<400> SEQUENCE: 164

Thr Gly Val Gln Leu Gln Asp Asn Gly Arg Thr Cys Lys Ala Gly
1               5                  10                  15

<210> SEQ ID NO 165
<211> LENGTH: 19
<212> TYPE: PRT
<213> ORGANISM: Artificial
<220> FEATURE:
<223> OTHER INFORMATION: LRP 5/6 Peptides

<400> SEQUENCE: 165

Glu Val Leu Leu Leu Ala Arg Arg Thr Asp Leu Arg Arg Ile Ser Leu
1               5                  10                  15

Asp Thr Pro

<210> SEQ ID NO 166
<211> LENGTH: 14
<212> TYPE: PRT
<213> ORGANISM: Artificial
<220> FEATURE:
```

<223> OTHER INFORMATION: LRP 5/6 Peptides

<400> SEQUENCE: 166

Tyr Trp Thr Asp Asp Glu Val Arg Ala Ile Arg Arg Ala Tyr
1               5                   10

<210> SEQ ID NO 167
<211> LENGTH: 10
<212> TYPE: PRT
<213> ORGANISM: Artificial
<220> FEATURE:
<223> OTHER INFORMATION: LRP 5/6 Peptides

<400> SEQUENCE: 167

Val Asn Thr Glu Ile Asn Asp Pro Asp Gly
1               5                   10

<210> SEQ ID NO 168
<211> LENGTH: 29
<212> TYPE: PRT
<213> ORGANISM: Artificial
<220> FEATURE:
<223> OTHER INFORMATION: LRP 5/6 Peptides

<400> SEQUENCE: 168

Tyr Trp Thr Asp Thr Gly Thr Asp Arg Ile Glu Val Thr Arg Leu Asn
1               5                   10                  15

Gly Thr Ser Arg Lys Ile Leu Val Ser Glu Asp Leu Asp
            20                  25

<210> SEQ ID NO 169
<211> LENGTH: 20
<212> TYPE: PRT
<213> ORGANISM: Artificial
<220> FEATURE:
<223> OTHER INFORMATION: LRP 5/6 Peptides

<400> SEQUENCE: 169

Thr Asp Trp Gln Arg Arg Ser Ile Glu Arg Val His Lys Val Lys Ala
1               5                   10                  15

Ser Arg Asp Val
            20

<210> SEQ ID NO 170
<211> LENGTH: 11
<212> TYPE: PRT
<213> ORGANISM: Artificial
<220> FEATURE:
<223> OTHER INFORMATION: LRP 5/6 Peptides

<400> SEQUENCE: 170

Asn Val Asp Gly Thr Lys Arg Arg Thr Leu Leu
1               5                   10

<210> SEQ ID NO 171
<211> LENGTH: 109
<212> TYPE: PRT
<213> ORGANISM: Artificial
<220> FEATURE:
<223> OTHER INFORMATION: LRP 5/6 Peptides

<400> SEQUENCE: 171

Pro Glu Pro Pro Glu Leu Glu Asn Asn Lys Thr Met Asn Arg Ala
1               5                   10                  15

Glu Asn Gly Gly Arg Pro Pro His His Pro Phe Glu Thr Lys Asp Val
            20                  25                  30

Ser Glu Tyr Ser Cys Arg Glu Leu His Phe Thr Arg Tyr Val Thr Asp
                35                  40                  45

Gly Pro Cys Arg Ser Ala Lys Pro Val Thr Glu Leu Val Cys Ser Gly
    50                  55                  60

Gln Cys Gly Pro Ala Arg Leu Leu Pro Asn Ala Ile Gly Arg Gly Lys
65                  70                  75                  80

Trp Trp Arg Pro Ser Gly Pro Asp Phe Arg Cys Ile Pro Asp Arg Tyr
                85                  90                  95

Arg Ala Gln Arg Val Gln Leu Leu Cys Pro Gly Gly Glu
                100                 105

<210> SEQ ID NO 172
<211> LENGTH: 56
<212> TYPE: PRT
<213> ORGANISM: Artificial
<220> FEATURE:
<223> OTHER INFORMATION: LRP 5/6 Peptides

<400> SEQUENCE: 172

Pro Glu Pro Pro Pro Glu Leu Glu Asn Asn Lys Thr Met Asn Arg Ala
1               5                   10                  15

Glu Asn Gly Gly Arg Pro Pro His Pro Phe Glu Thr Lys Asp Val
                20                  25                  30

Ser Glu Tyr Ser Cys Arg Glu Leu His Phe Thr Arg Tyr Val Thr Asp
                35                  40                  45

Gly Pro Cys Arg Ser Ala Lys Pro
    50                  55

<210> SEQ ID NO 173
<211> LENGTH: 53
<212> TYPE: PRT
<213> ORGANISM: Artificial
<220> FEATURE:
<223> OTHER INFORMATION: LRP 5/6 Peptides

<400> SEQUENCE: 173

Val Thr Glu Leu Val Cys Ser Gly Gln Cys Gly Pro Ala Arg Leu Leu
1               5                   10                  15

Pro Asn Ala Ile Gly Arg Gly Lys Trp Trp Arg Pro Ser Gly Pro Asp
                20                  25                  30

Phe Arg Cys Ile Pro Asp Arg Tyr Arg Ala Gln Arg Val Gln Leu Leu
                35                  40                  45

Cys Pro Gly Gly Glu
    50

<210> SEQ ID NO 174
<211> LENGTH: 18
<212> TYPE: PRT
<213> ORGANISM: Artificial
<220> FEATURE:
<223> OTHER INFORMATION: LRP 5/6 Peptides

<400> SEQUENCE: 174

Ala Ala Pro Leu Leu Leu Tyr Ala Asn Arg Arg Asp Leu Arg Leu Val
1               5                   10                  15

Asp Ala

<210> SEQ ID NO 175
<211> LENGTH: 17
<212> TYPE: PRT
<213> ORGANISM: Artificial

```
<220> FEATURE:
<223> OTHER INFORMATION: LRP 5/6 Peptides

<400> SEQUENCE: 175

Thr Ile Val Val Gly Gly Leu Glu Asp Ala Ala Ala Val Asp Phe Val
1               5                   10                  15

Phe

<210> SEQ ID NO 176
<211> LENGTH: 14
<212> TYPE: PRT
<213> ORGANISM: Artificial
<220> FEATURE:
<223> OTHER INFORMATION: LRP 5/6 Peptides

<400> SEQUENCE: 176

Gly Leu Ile Tyr Trp Ser Asp Val Ser Glu Glu Ala Ile Lys
1               5                   10

<210> SEQ ID NO 177
<211> LENGTH: 40
<212> TYPE: PRT
<213> ORGANISM: Artificial
<220> FEATURE:
<223> OTHER INFORMATION: LRP 5/6 Peptides

<400> SEQUENCE: 177

Ser Val Gln Asn Val Val Val Ser Gly Leu Leu Ser Pro Asp Gly Leu
1               5                   10                  15

Ala Cys Asp Trp Leu Gly Glu Lys Leu Tyr Trp Thr Asp Ser Glu Thr
            20                  25                  30

Asn Arg Ile Glu Val Ser Asn Leu
        35                  40

<210> SEQ ID NO 178
<211> LENGTH: 19
<212> TYPE: PRT
<213> ORGANISM: Artificial
<220> FEATURE:
<223> OTHER INFORMATION: LRP 5/6 Peptides

<400> SEQUENCE: 178

Gln Asn Val Val Val Ser Gly Leu Leu Ser Pro Asp Gly Leu Ala Cys
1               5                   10                  15

Asp Trp Leu

<210> SEQ ID NO 179
<211> LENGTH: 20
<212> TYPE: PRT
<213> ORGANISM: Artificial
<220> FEATURE:
<223> OTHER INFORMATION: LRP 5/6 Peptides

<400> SEQUENCE: 179

Lys Leu Tyr Trp Thr Asp Ser Glu Thr Asn Arg Ile Glu Val Ser Asn
1               5                   10                  15

Leu Asp Gly Ser
            20

<210> SEQ ID NO 180
<211> LENGTH: 19
<212> TYPE: PRT
<213> ORGANISM: Artificial
<220> FEATURE:
<223> OTHER INFORMATION: LRP 5/6 Peptides
```

<400> SEQUENCE: 180

Arg Lys Val Leu Phe Trp Gln Glu Leu Asp Gln Pro Arg Ala Ile Ala
1               5                   10                  15
Leu Asp Pro

<210> SEQ ID NO 181
<211> LENGTH: 20
<212> TYPE: PRT
<213> ORGANISM: Artificial
<220> FEATURE:
<223> OTHER INFORMATION: LRP 5/6 Peptides

<400> SEQUENCE: 181

Met Tyr Trp Thr Asp Trp Gly Glu Val Pro Lys Ile Glu Arg Ala Gly
1               5                   10                  15
Met Asp Gly Ser
            20

<210> SEQ ID NO 182
<211> LENGTH: 8
<212> TYPE: PRT
<213> ORGANISM: Artificial
<220> FEATURE:
<223> OTHER INFORMATION: LRP 5/6 Peptides

<400> SEQUENCE: 182

Ile Tyr Trp Pro Asn Gly Leu Thr
1               5

<210> SEQ ID NO 183
<211> LENGTH: 9
<212> TYPE: PRT
<213> ORGANISM: Artificial
<220> FEATURE:
<223> OTHER INFORMATION: LRP 5/6 Peptides

<400> SEQUENCE: 183

Lys Leu Tyr Trp Ala Asp Ala Lys Leu
1               5

<210> SEQ ID NO 184
<211> LENGTH: 13
<212> TYPE: PRT
<213> ORGANISM: Artificial
<220> FEATURE:
<223> OTHER INFORMATION: LRP 5/6 Peptides

<400> SEQUENCE: 184

Phe Ile His Lys Ser Asn Leu Asp Gly Thr Asn Arg Gln
1               5                   10

<210> SEQ ID NO 185
<211> LENGTH: 14
<212> TYPE: PRT
<213> ORGANISM: Artificial
<220> FEATURE:
<223> OTHER INFORMATION: LRP 5/6 Peptides

<400> SEQUENCE: 185

Val Val Lys Gly Ser Leu Pro His Pro Phe Ala Leu Thr Leu
1               5                   10

<210> SEQ ID NO 186
<211> LENGTH: 21
<212> TYPE: PRT

```
<213> ORGANISM: Artificial
<220> FEATURE:
<223> OTHER INFORMATION: LRP 5/6 Peptides

<400> SEQUENCE: 186

Asp Thr Leu Tyr Trp Thr Asp Trp Asn Thr His Ser Ile Leu Ala Cys
1               5                   10                  15

Asn Lys Tyr Thr Gly
            20

<210> SEQ ID NO 187
<211> LENGTH: 13
<212> TYPE: PRT
<213> ORGANISM: Artificial
<220> FEATURE:
<223> OTHER INFORMATION: LRP 5/6 Peptides

<400> SEQUENCE: 187

Arg Glu Ile His Ser Asn Ile Phe Ser Pro Met Asp Ile
1               5                   10

<210> SEQ ID NO 188
<211> LENGTH: 10
<212> TYPE: PRT
<213> ORGANISM: Artificial
<220> FEATURE:
<223> OTHER INFORMATION: LRP 5/6 Peptides

<400> SEQUENCE: 188

Asp Asn Gly Gly Cys Ser His Leu Cys Leu
1               5                   10

<210> SEQ ID NO 189
<211> LENGTH: 11
<212> TYPE: PRT
<213> ORGANISM: Artificial
<220> FEATURE:
<223> OTHER INFORMATION: LRP 5/6 Peptides

<400> SEQUENCE: 189

Pro Phe Tyr Gln Cys Ala Cys Pro Thr Gly Val
1               5                   10

<210> SEQ ID NO 190
<211> LENGTH: 25
<212> TYPE: PRT
<213> ORGANISM: Artificial
<220> FEATURE:
<223> OTHER INFORMATION: LRP 5/6 Peptides

<400> SEQUENCE: 190

Leu Leu Leu Ala Arg Arg Thr Asp Leu Arg Arg Ile Ser Leu Asp Thr
1               5                   10                  15

Pro Asp Phe Thr Asp Ile Val Leu Gln
            20                  25

<210> SEQ ID NO 191
<211> LENGTH: 12
<212> TYPE: PRT
<213> ORGANISM: Artificial
<220> FEATURE:
<223> OTHER INFORMATION: LRP 5/6 Peptides

<400> SEQUENCE: 191

Asp Ile Arg His Ala Ile Ala Ile Asp Tyr Asp Pro
1               5                   10
```

```
<210> SEQ ID NO 192
<211> LENGTH: 16
<212> TYPE: PRT
<213> ORGANISM: Artificial
<220> FEATURE:
<223> OTHER INFORMATION: LRP 5/6 Peptides

<400> SEQUENCE: 192

Glu Gly Tyr Ile Tyr Trp Thr Asp Asp Glu Val Arg Ala Ile Arg Arg
1               5                   10                  15

<210> SEQ ID NO 193
<211> LENGTH: 31
<212> TYPE: PRT
<213> ORGANISM: Artificial
<220> FEATURE:
<223> OTHER INFORMATION: LRP 5/6 Peptides

<400> SEQUENCE: 193

Pro Asp Gly Ile Ala Val Asp Trp Val Ala Arg Asn Leu Tyr Trp Thr
1               5                   10                  15

Asp Thr Gly Thr Asp Arg Ile Glu Val Thr Arg Leu Asn Gly Thr
            20                  25                  30

<210> SEQ ID NO 194
<211> LENGTH: 15
<212> TYPE: PRT
<213> ORGANISM: Artificial
<220> FEATURE:
<223> OTHER INFORMATION: LRP 5/6 Peptides

<400> SEQUENCE: 194

Arg Lys Ile Leu Ile Ser Glu Asp Leu Glu Glu Pro Arg Ala Ile
1               5                   10                  15

<210> SEQ ID NO 195
<211> LENGTH: 8
<212> TYPE: PRT
<213> ORGANISM: Artificial
<220> FEATURE:
<223> OTHER INFORMATION: LRP 5/6 Peptides

<400> SEQUENCE: 195

Met Tyr Trp Thr Asp Trp Gly Glu
1               5

<210> SEQ ID NO 196
<211> LENGTH: 10
<212> TYPE: PRT
<213> ORGANISM: Artificial
<220> FEATURE:
<223> OTHER INFORMATION: LRP 5/6 Peptides

<400> SEQUENCE: 196

Pro Lys Ile Glu Arg Ala Ala Leu Asp Gly
1               5                   10

<210> SEQ ID NO 197
<211> LENGTH: 16
<212> TYPE: PRT
<213> ORGANISM: Artificial
<220> FEATURE:
<223> OTHER INFORMATION: LRP 5/6 Peptides

<400> SEQUENCE: 197

Val Leu Val Asn Thr Ser Leu Gly Trp Pro Asn Gly Leu Ala Leu Asp
1               5                   10                  15
```

<210> SEQ ID NO 198
<211> LENGTH: 12
<212> TYPE: PRT
<213> ORGANISM: Artificial
<220> FEATURE:
<223> OTHER INFORMATION: LRP 5/6 Peptides

<400> SEQUENCE: 198

Tyr Trp Gly Asp Ala Lys Thr Asp Lys Ile Glu Val
1               5                   10

<210> SEQ ID NO 199
<211> LENGTH: 32
<212> TYPE: PRT
<213> ORGANISM: Artificial
<220> FEATURE:
<223> OTHER INFORMATION: LRP 5/6 Peptides

<400> SEQUENCE: 199

Glu Asp Lys Ile Pro His Ile Phe Gly Phe Thr Leu Leu Gly Asp Tyr
1               5                   10                  15

Val Tyr Trp Thr Asp Trp Gln Arg Arg Ser Ile Glu Arg Val His Lys
            20                  25                  30

<210> SEQ ID NO 200
<211> LENGTH: 24
<212> TYPE: PRT
<213> ORGANISM: Artificial
<220> FEATURE:
<223> OTHER INFORMATION: LRP 5/6 Peptides

<400> SEQUENCE: 200

Gly Phe Met Tyr Trp Thr Asp Trp Gly Glu Val Pro Lys Ile Glu Arg
1               5                   10                  15

Ala Gly Met Asp Gly Ser Ser Arg
            20

<210> SEQ ID NO 201
<211> LENGTH: 13
<212> TYPE: PRT
<213> ORGANISM: Artificial
<220> FEATURE:
<223> OTHER INFORMATION: LRP 5/6 Peptides

<400> SEQUENCE: 201

Pro Lys Ile Glu Arg Ala Gly Met Asp Gly Ser Ser Arg
1               5                   10

<210> SEQ ID NO 202
<211> LENGTH: 10
<212> TYPE: PRT
<213> ORGANISM: Artificial
<220> FEATURE:
<223> OTHER INFORMATION: LRP 5/6 Peptides

<400> SEQUENCE: 202

Asp Asn Gly Gly Cys Ser His Leu Cys Leu
1               5                   10

<210> SEQ ID NO 203
<211> LENGTH: 11
<212> TYPE: PRT
<213> ORGANISM: Artificial
<220> FEATURE:
<223> OTHER INFORMATION: LRP 5/6 Peptides -continued

```
<400> SEQUENCE: 203

Pro Phe Tyr Gln Cys Ala Cys Pro Thr Gly Val
1               5                   10

<210> SEQ ID NO 204
<211> LENGTH: 25
<212> TYPE: PRT
<213> ORGANISM: Artificial
<220> FEATURE:
<223> OTHER INFORMATION: LRP 5/6 Peptides

<400> SEQUENCE: 204

Leu Leu Leu Ala Arg Arg Thr Asp Leu Arg Arg Ile Ser Leu Asp Thr
1               5                   10                  15

Pro Asp Phe Thr Asp Ile Val Leu Gln
            20                  25

<210> SEQ ID NO 205
<211> LENGTH: 12
<212> TYPE: PRT
<213> ORGANISM: Artificial
<220> FEATURE:
<223> OTHER INFORMATION: LRP 5/6 Peptides

<400> SEQUENCE: 205

Asp Ile Arg His Ala Ile Ala Ile Asp Tyr Asp Pro
1               5                   10

<210> SEQ ID NO 206
<211> LENGTH: 16
<212> TYPE: PRT
<213> ORGANISM: Artificial
<220> FEATURE:
<223> OTHER INFORMATION: LRP 5/6 Peptides

<400> SEQUENCE: 206

Glu Gly Tyr Ile Tyr Trp Thr Asp Asp Glu Val Arg Ala Ile Arg Arg
1               5                   10                  15

<210> SEQ ID NO 207
<211> LENGTH: 31
<212> TYPE: PRT
<213> ORGANISM: Artificial
<220> FEATURE:
<223> OTHER INFORMATION: LRP 5/6 Peptides

<400> SEQUENCE: 207

Pro Asp Gly Ile Ala Val Asp Trp Val Ala Arg Asn Leu Tyr Trp Thr
1               5                   10                  15

Asp Thr Gly Thr Asp Arg Ile Glu Val Thr Arg Leu Asn Gly Thr
            20                  25                  30

<210> SEQ ID NO 208
<211> LENGTH: 15
<212> TYPE: PRT
<213> ORGANISM: Artificial
<220> FEATURE:
<223> OTHER INFORMATION: LRP 5/6 Peptides

<400> SEQUENCE: 208

Arg Lys Ile Leu Ile Ser Glu Asp Leu Glu Glu Pro Arg Ala Ile
1               5                   10                  15

<210> SEQ ID NO 209
<211> LENGTH: 8
<212> TYPE: PRT
```

```
<213> ORGANISM: Artificial
<220> FEATURE:
<223> OTHER INFORMATION: LRP 5/6 Peptides

<400> SEQUENCE: 209

Met Tyr Trp Thr Asp Trp Gly Glu
1               5

<210> SEQ ID NO 210
<211> LENGTH: 10
<212> TYPE: PRT
<213> ORGANISM: Artificial
<220> FEATURE:
<223> OTHER INFORMATION: LRP 5/6 Peptides

<400> SEQUENCE: 210

Pro Lys Ile Glu Arg Ala Ala Leu Asp Gly
1               5                   10

<210> SEQ ID NO 211
<211> LENGTH: 16
<212> TYPE: PRT
<213> ORGANISM: Artificial
<220> FEATURE:
<223> OTHER INFORMATION: LRP 5/6 Peptides

<400> SEQUENCE: 211

Val Leu Val Asn Thr Ser Leu Gly Trp Pro Asn Gly Leu Ala Leu Asp
1               5                   10                  15

<210> SEQ ID NO 212
<211> LENGTH: 12
<212> TYPE: PRT
<213> ORGANISM: Artificial
<220> FEATURE:
<223> OTHER INFORMATION: LRP 5/6 Peptides

<400> SEQUENCE: 212

Tyr Trp Gly Asp Ala Lys Thr Asp Lys Ile Glu Val
1               5                   10

<210> SEQ ID NO 213
<211> LENGTH: 32
<212> TYPE: PRT
<213> ORGANISM: Artificial
<220> FEATURE:
<223> OTHER INFORMATION: LRP 5/6 Peptides

<400> SEQUENCE: 213

Glu Asp Lys Ile Pro His Ile Phe Gly Phe Thr Leu Leu Gly Asp Tyr
1               5                   10                  15

Val Tyr Trp Thr Asp Trp Gln Arg Arg Ser Ile Glu Arg Val His Lys
            20                  25                  30

<210> SEQ ID NO 214
<211> LENGTH: 21
<212> TYPE: PRT
<213> ORGANISM: Artificial
<220> FEATURE:
<223> OTHER INFORMATION: LRP 5/6 Peptides

<400> SEQUENCE: 214

Ser Asp Arg Asn Asn Arg Val Gln Val Gly Cys Arg Glu Leu Arg Ser
1               5                   10                  15

Thr Lys Tyr Ile Ser
            20
```

```
<210> SEQ ID NO 215
<211> LENGTH: 206
<212> TYPE: PRT
<213> ORGANISM: Mus musculus
<220> FEATURE:
<221> NAME/KEY: misc_feature
<222> LOCATION: (128)..(128)
<223> OTHER INFORMATION: Xaa can be any naturally occurring amino acid

<400> SEQUENCE: 215

Met Leu Pro Pro Ala Ile His Leu Ser Leu Ile Pro Leu Leu Cys Ile
1               5                   10                  15

Leu Met Arg Asn Cys Leu Ala Phe Lys Asn Asp Ala Thr Glu Ile Leu
            20                  25                  30

Tyr Ser His Val Val Lys Pro Val Pro Ala His Pro Ser Ser Asn Ser
        35                  40                  45

Thr Leu Asn Gln Ala Arg Asn Gly Gly Arg His Phe Ser Ser Thr Gly
    50                  55                  60

Leu Asp Arg Asn Ser Arg Val Gln Val Gly Cys Arg Glu Leu Arg Ser
65                  70                  75                  80

Thr Lys Tyr Ile Ser Asp Gly Gln Cys Thr Ser Ile Ser Pro Lys Lys
                85                  90                  95

Glu Leu Val Cys Ala Gly Glu Cys Leu Pro Leu Pro Val Leu Pro Asn
            100                 105                 110

Trp Ile Gly Gly Gly Tyr Gly Thr Lys Tyr Trp Ser Arg Arg Ser Xaa
        115                 120                 125

Gln Glu Trp Arg Cys Val Asn Asp Lys Thr Arg Thr Gln Arg Ile Gln
    130                 135                 140

Leu Gln Cys Gln Asp Gly Ser Thr Arg Thr Tyr Lys Ile Thr Val Val
145                 150                 155                 160

Thr Ala Cys Lys Cys Lys Arg Tyr Thr Arg Gln His Asn Glu Ser Ser
                165                 170                 175

His Asn Phe Glu Ser Val Ser Pro Ala Lys Pro Ala Gln His His Arg
            180                 185                 190

Glu Arg Lys Arg Ala Ser Lys Ser Ser Lys His Ser Leu Ser
        195                 200                 205

<210> SEQ ID NO 216
<211> LENGTH: 211
<212> TYPE: PRT
<213> ORGANISM: Mus musculus

<400> SEQUENCE: 216

Met Gln Pro Ser Leu Ala Pro Cys Leu Ile Cys Leu Leu Val His Ala
1               5                   10                  15

Ala Phe Cys Ala Val Glu Gly Gln Gly Trp Gln Ala Phe Arg Asn Asp
            20                  25                  30

Ala Thr Glu Val Ile Pro Gly Leu Gly Glu Tyr Pro Gly Pro Pro
        35                  40                  45

Glu Asn Asn Gln Thr Met Asn Arg Ala Glu Asn Gly Gly Arg Pro Pro
    50                  55                  60

His His Pro Tyr Asp Ala Lys Asp Val Ser Glu Tyr Ser Cys Arg Glu
65                  70                  75                  80

Leu His Tyr Thr Arg Phe Leu Thr Asp Gly Pro Cys Arg Ser Ala Lys
                85                  90                  95

Pro Val Thr Glu Leu Val Cys Ser Gly Gln Cys Gly Pro Ala Arg Leu
            100                 105                 110
```

```
Leu Pro Asn Ala Ile Gly Arg Val Lys Trp Trp Arg Pro Asn Gly Pro
        115                 120                 125

Asp Phe Arg Cys Ile Pro Asp Arg Tyr Arg Ala Gln Arg Val Gln Leu
130                 135                 140

Leu Cys Pro Gly Gly Ala Ala Pro Arg Ser Arg Lys Val Arg Leu Val
145                 150                 155                 160

Ala Ser Cys Lys Cys Lys Arg Leu Thr Arg Phe His Asn Gln Ser Glu
                165                 170                 175

Leu Lys Asp Phe Gly Pro Glu Thr Ala Arg Pro Gln Lys Gly Arg Lys
            180                 185                 190

Pro Arg Pro Gly Ala Arg Gly Ala Lys Ala Asn Gln Ala Glu Leu Glu
        195                 200                 205

Asn Ala Tyr
    210

<210> SEQ ID NO 217
<211> LENGTH: 81
<212> TYPE: PRT
<213> ORGANISM: Artificial
<220> FEATURE:
<223> OTHER INFORMATION: Synthetic Construct

<400> SEQUENCE: 217

Cys Lys Thr Gln Pro Leu Arg Gln Thr Val Ser Glu Glu Gly Cys Arg
1               5                   10                  15

Ser Arg Thr Ile Leu Asn Arg Phe Cys Tyr Gly Gln Cys Asn Ser Phe
            20                  25                  30

Tyr Ile Pro Arg His Val Lys Lys Glu Glu Asp Ser Cys Ala Phe Cys
        35                  40                  45

Lys Pro Gln Arg Val Thr Ser Val Ile Val Glu Leu Glu Cys Pro Gly
    50                  55                  60

Leu Asp Pro Pro Phe Arg Ile Lys Lys Ile Gln Lys Val Lys Cys Arg
65                  70                  75                  80

Cys

<210> SEQ ID NO 218
<211> LENGTH: 78
<212> TYPE: PRT
<213> ORGANISM: Artificial
<220> FEATURE:
<223> OTHER INFORMATION: Synthetic Construct

<400> SEQUENCE: 218

Cys Arg Thr Leu Pro Phe Ser Gln Ser Val Ala His Glu Ser Cys Glu
1               5                   10                  15

Lys Val Ile Val Gln Asn Asn Leu Cys Phe Gly Lys Cys Ser Ser Phe
            20                  25                  30

His Val Pro Gly Pro Asp Asp Arg Leu Tyr Thr Phe Cys Cys Leu Pro
        35                  40                  45

Thr Lys Phe Ser Met Lys His Phe Asp Leu Asn Cys Thr Ser Ser Val
    50                  55                  60

Pro Val Val Lys Lys Val Asn Ile Val Glu Glu Cys Asn Cys
65                  70                  75

<210> SEQ ID NO 219
<211> LENGTH: 80
<212> TYPE: PRT
<213> ORGANISM: Artificial
<220> FEATURE:
<223> OTHER INFORMATION: Synthetic Construct
```

-continued

```
<400> SEQUENCE: 219

Cys Arg Thr Val Pro Phe Asn Gln Thr Ile Ala His Glu Asp Cys Gln
1               5                   10                  15

Lys Val Val Gln Asn Asn Leu Cys Phe Gly Lys Cys Ser Ser Ile
            20                  25                  30

Arg Phe Pro Gly Glu Gly Ala Asp Ala His Ser Phe Cys Ser His Cys
            35                  40                  45

Ser Pro Thr Lys Phe Thr Thr Val His Leu Met Leu Asn Cys Thr Ser
        50                  55                  60

Pro Thr Pro Val Val Lys Met Val Met Gln Val Glu Glu Cys Gln Cys
65                  70                  75                  80

<210> SEQ ID NO 220
<211> LENGTH: 82
<212> TYPE: PRT
<213> ORGANISM: Artificial
<220> FEATURE:
<223> OTHER INFORMATION: Synthetic Construct

<400> SEQUENCE: 220

Cys Arg Glu Leu His Tyr Thr Arg Phe Leu Thr Asp Gly Pro Cys Arg
1               5                   10                  15

Ser Ala Lys Pro Val Thr Glu Leu Val Cys Ser Gly Gln Cys Gly Pro
            20                  25                  30

Ala Arg Leu Leu Pro Asn Ala Ile Gly Arg Val Lys Trp Asn Gly Pro
            35                  40                  45

Cys Ile Pro Asp Arg Tyr Arg Ala Gln Arg Val Gln Leu Leu Cys Pro
        50                  55                  60

Gly Gly Ala Ala Pro Arg Ser Arg Lys Val Arg Leu Val Ala Ser Cys
65                  70                  75                  80

Lys Cys

<210> SEQ ID NO 221
<211> LENGTH: 81
<212> TYPE: PRT
<213> ORGANISM: Artificial
<220> FEATURE:
<223> OTHER INFORMATION: Synthetic Construct
<220> FEATURE:
<221> NAME/KEY: misc_feature
<222> LOCATION: (21)..(21)
<223> OTHER INFORMATION: Xaa can be any naturally occurring amino acid

<400> SEQUENCE: 221

Cys Arg Glu Leu Arg Ser Thr Lys Tyr Ile Ser Asp Gly Gln Cys Thr
1               5                   10                  15

Ser Ile Ser Pro Xaa Lys Glu Leu Val Cys Ala Gly Glu Cys Leu Pro
            20                  25                  30

Leu Pro Val Leu Pro Asn Trp Ile Gly Gly Gly Tyr Gly Trp Ser Arg
            35                  40                  45

Cys Val Asn Asp Lys Thr Arg Thr Gln Arg Ile Gln Leu Gln Cys Gln
        50                  55                  60

Asp Gly Ser Thr Arg Thr Tyr Lys Ile Thr Val Val Thr Ala Cys Lys
65                  70                  75                  80

Cys

<210> SEQ ID NO 222
<211> LENGTH: 70
<212> TYPE: PRT
```

```
<213> ORGANISM: Artificial
<220> FEATURE:
<223> OTHER INFORMATION: Synthetic Construct

<400> SEQUENCE: 222

Cys Leu Arg Thr Lys Lys Ser Leu Lys Ala Ile His Leu Gln Phe Lys
1               5                   10                  15

Asn Cys Thr Ser Leu His Thr Tyr Lys Pro Arg Phe Cys Gly Val Cys
            20                  25                  30

Ser Asp Gly Arg Cys Cys Thr Pro His Asn Thr Lys Thr Ile Gln Ala
        35                  40                  45

Glu Phe Gln Cys Ser Pro Gly Gln Ile Val Lys Lys Pro Val Met Val
    50                  55                  60

Ile Gly Thr Cys Thr Cys
65                  70

<210> SEQ ID NO 223
<211> LENGTH: 70
<212> TYPE: PRT
<213> ORGANISM: Artificial
<220> FEATURE:
<223> OTHER INFORMATION: Synthetic Construct

<400> SEQUENCE: 223

Cys Ser Lys Thr Lys Lys Ser Pro Glu Pro Val Arg Phe Thr Tyr Ala
1               5                   10                  15

Gly Cys Leu Ser Val Lys Lys Tyr Arg Pro Lys Tyr Cys Gly Ser Cys
            20                  25                  30

Val Asp Gly Arg Cys Cys Thr Pro Gln Leu Thr Arg Thr Val Lys Met
        35                  40                  45

Arg Phe Arg Cys Glu Asp Gly Glu Thr Phe Ser Lys Asn Val Met Met
    50                  55                  60

Ile Gln Ser Cys Lys Cys
65                  70

<210> SEQ ID NO 224
<211> LENGTH: 70
<212> TYPE: PRT
<213> ORGANISM: Artificial
<220> FEATURE:
<223> OTHER INFORMATION: Synthetic Construct

<400> SEQUENCE: 224

Cys Thr Lys Thr Lys Lys Ser Pro Ser Pro Val Arg Phe Thr Tyr Ala
1               5                   10                  15

Gly Cys Ser Ser Val Lys Lys Tyr Arg Pro Lys Tyr Cys Gly Ser Cys
            20                  25                  30

Val Asp Gly Arg Cys Cys Thr Pro Gln Gln Thr Arg Thr Val Lys Ile
        35                  40                  45

Arg Phe Arg Cys Asp Asp Gly Glu Thr Phe Thr Lys Ser Val Met Met
    50                  55                  60

Ile Gln Ser Cys Arg Cys
65                  70

<210> SEQ ID NO 225
<211> LENGTH: 70
<212> TYPE: PRT
<213> ORGANISM: Artificial
<220> FEATURE:
<223> OTHER INFORMATION: Synthetic Construct

<400> SEQUENCE: 225
```

```
Cys Ile Arg Thr Pro Lys Ile Ala Lys Pro Val Lys Phe Glu Leu Ser
1               5                   10                  15

Gly Cys Thr Ser Val Lys Thr Tyr Arg Ala Lys Phe Cys Gly Val Cys
                20                  25                  30

Thr Asp Gly Arg Cys Cys Thr Pro His Arg Thr Thr Thr Leu Pro Val
            35                  40                  45

Glu Phe Lys Cys Pro Asp Gly Glu Ile Met Lys Lys Asn Met Met Phe
        50                  55                  60

Ile Lys Thr Cys Ala Cys
65              70
```

<210> SEQ ID NO 226
<211> LENGTH: 83
<212> TYPE: PRT
<213> ORGANISM: Artificial
<220> FEATURE:
<223> OTHER INFORMATION: Synthetic Construct

<400> SEQUENCE: 226

```
Cys Asn Asp Ile Thr Ala Arg Leu Gln Tyr Val Lys Val Gly Ser Cys
1               5                   10                  15

Lys Ser Glu Val Glu Val Asp Ile His Tyr Cys Gln Gly Lys Cys Ala
                20                  25                  30

Ser Lys Ala Met Tyr Ser Ile Asp Ile Asn Asp Val Gln Asp Gln Cys
            35                  40                  45

Ser Cys Cys Ser Pro Thr Arg Thr Glu Pro Met Gln Val Ala Leu His
        50                  55                  60

Cys Thr Asn Gly Ser Val Val Tyr His Glu Val Leu Asn Ala Met Glu
65                  70                  75                  80

Cys Lys Cys
```

<210> SEQ ID NO 227
<211> LENGTH: 77
<212> TYPE: PRT
<213> ORGANISM: Artificial
<220> FEATURE:
<223> OTHER INFORMATION: Synthetic Construct

<400> SEQUENCE: 227

```
Cys Lys Pro Ser Pro Val Asn Val Thr Val Arg Tyr Asn Gly Cys Thr
1               5                   10                  15

Ile Lys Val Glu Met Ala Arg Cys Val Gly Glu Cys Lys Lys Thr Val
                20                  25                  30

Thr Tyr Asp Tyr Asp Ile Phe Gln Leu Lys Asn Cys Cys Gln Glu Glu
            35                  40                  45

Asp Tyr Glu Phe Arg Asp Ile Val Leu Asp Cys Pro Asp Gly Ser Thr
        50                  55                  60

Leu Pro Tyr Arg Tyr Arg His Ile Thr Ala Cys Ser Cys
65                  70                  75
```

<210> SEQ ID NO 228
<211> LENGTH: 79
<212> TYPE: PRT
<213> ORGANISM: Artificial
<220> FEATURE:
<223> OTHER INFORMATION: Synthetic Construct

<400> SEQUENCE: 228

```
Cys Ser Thr Val Pro Val Thr Thr Glu Val Ser Tyr Ala Gly Cys Thr
1               5                   10                  15
```

```
Lys Thr Val Leu Met Asn His Cys Ser Gly Ser Cys Gly Thr Phe Val
            20                  25                  30

Met Tyr Ser Ala Lys Ala Gln Ala Leu Asp His Cys Ser Cys Cys Lys
            35                  40                  45

Glu Glu Lys Thr Ser Gln Arg Glu Val Val Leu Ser Cys Pro Asn Gly
50                  55                  60

Gly Ser Leu Thr His Thr Tyr Thr His Ile Glu Ser Cys Gln Cys
65                  70                  75

<210> SEQ ID NO 229
<211> LENGTH: 79
<212> TYPE: PRT
<213> ORGANISM: Artificial
<220> FEATURE:
<223> OTHER INFORMATION: Synthetic Construct

<400> SEQUENCE: 229

Cys Gln Val His Val Asn Ala Thr Val Leu Arg Tyr Lys Gly Cys Glu
1               5                   10                  15

Thr Glu Val Asn Ile Thr Phe Cys Glu Gly Ser Cys Ser Gly Ile Ser
            20                  25                  30

Lys Tyr Ser Met Glu Ala Gln Ala Met Glu Arg Cys Thr Cys Cys Gln
            35                  40                  45

Glu Ser Lys Val His Asp Val Ala Val Thr Met Gln Cys Pro Asp Gly
50                  55                  60

Thr Val Ile Gln His Thr Tyr Thr His Ile Asp Glu Cys Asn Cys
65                  70                  75

<210> SEQ ID NO 230
<211> LENGTH: 81
<212> TYPE: PRT
<213> ORGANISM: Artificial
<220> FEATURE:
<223> OTHER INFORMATION: Synthetic Construct

<400> SEQUENCE: 230

Cys Ala Val Tyr His Gln His Gln Val Leu Gln Gln Ser Cys Arg
1               5                   10                  15

Ser Ala Gly Pro Val Arg Leu Thr Tyr Cys Gln Gly Asn Cys Gly Asp
            20                  25                  30

Thr Ala Ser Met Tyr Ser Pro Glu Ala Asn Ala Val Glu Cys Lys Cys
            35                  40                  45

Cys Gln Glu Leu Gln Val Ala Leu Arg Asn Val Thr Leu His Cys Pro
50                  55                  60

Asp Gly Ser Ser Arg Ala Phe Ser Tyr Thr Val Glu Lys Cys Gly
65                  70                  75                  80

Cys

<210> SEQ ID NO 231
<211> LENGTH: 81
<212> TYPE: PRT
<213> ORGANISM: Artificial
<220> FEATURE:
<223> OTHER INFORMATION: Synthetic Construct

<400> SEQUENCE: 231

Cys Thr Val His Gln Arg Gln Gln Ile Ile Arg Gln Gln Asn Cys Ser
1               5                   10                  15

Ser Glu Gly Pro Val Ser Ile Ser Tyr Cys Gln Gly Asn Cys Gly Asp
            20                  25                  30
```

Ser Ile Ser Met Tyr Ser Leu Glu Ala Asn Lys Val Glu Cys Glu Cys
                35                  40                  45

Cys Gln Glu Leu Gln Thr Ser Gln Arg Asn Val Thr Leu Arg Cys Asp
         50                  55                  60

Asp Gly Ser Ser Gln Thr Phe Ser Tyr Thr Gln Val Glu Lys Cys Gly
 65                  70                  75                  80

Cys

<210> SEQ ID NO 232
<211> LENGTH: 71
<212> TYPE: PRT
<213> ORGANISM: Artificial
<220> FEATURE:
<223> OTHER INFORMATION: Synthetic Construct

<400> SEQUENCE: 232

Cys Arg Gly Asp Pro Val Arg Asp Phe His Arg Val Gln Arg Gly Tyr
 1               5                   10                  15

Ala Cys Gln Thr Thr Arg Pro Leu Ser Trp Val Glu Cys Arg Gly Ala
                20                  25                  30

Cys Pro Gly Gln Gly Cys Cys Gln Gly Leu Arg Leu Lys Arg Arg Lys
             35                  40                  45

Leu Thr Phe Glu Cys Ser Asp Gly Thr Ser Phe Ala Glu Glu Val Glu
         50                  55                  60

Lys Pro Thr Lys Cys Gly Cys
 65                  70

<210> SEQ ID NO 233
<211> LENGTH: 71
<212> TYPE: PRT
<213> ORGANISM: Artificial
<220> FEATURE:
<223> OTHER INFORMATION: Synthetic Construct

<400> SEQUENCE: 233

Cys Glu Gly Glu Ala Val Arg Asp Tyr Tyr Gln Lys Gln Gly Tyr
 1               5                   10                  15

Ala Cys Gln Thr Thr Lys Lys Val Ser Arg Leu Glu Cys Arg Gly Gly
                20                  25                  30

Cys Ala Gly Gly Gln Cys Cys Gly Pro Leu Arg Ser Lys Arg Arg Lys
             35                  40                  45

Tyr Ser Phe Glu Cys Thr Asp Gly Ser Ser Phe Val Asp Glu Val Glu
         50                  55                  60

Lys Val Val Lys Cys Gly Cys
 65                  70

<210> SEQ ID NO 234
<211> LENGTH: 70
<212> TYPE: PRT
<213> ORGANISM: Artificial
<220> FEATURE:
<223> OTHER INFORMATION: Synthetic Construct

<400> SEQUENCE: 234

Cys Met Gly Glu Ile Val Arg Glu Ala Ile Arg Arg Gln Lys Asp Tyr
 1               5                   10                  15

Ala Cys Ala Thr Ala Ser Lys Val Pro Ile Met Glu Cys Arg Gly Gly
                20                  25                  30

Cys Gly Ser Gln Cys Cys Gln Pro Ile Arg Ser Lys Arg Lys Tyr
             35                  40                  45

```
Val Phe Gln Cys Thr Asp Gly Ser Ser Phe Val Glu Glu Val Glu Arg
    50                  55                  60

His Leu Glu Cys Gly Cys
65                  70
```